(12) United States Patent
Jin

(10) Patent No.: US 11,085,051 B2
(45) Date of Patent: Aug. 10, 2021

(54) CONTROLLING FUNGAL PATHOGENS BY DISABLING THEIR SMALL RNA PATHWAYS USING RNAI-BASED STRATEGY

(71) Applicant: The Regents of the University of California, Oakland, CA (US)

(72) Inventor: Hailing Jin, Riverside, CA (US)

(73) Assignee: The Regents of the University of California, Oakland, CA (US)

(*) Notice: Subject to any disclaimer, the term of this patent is extended or adjusted under 35 U.S.C. 154(b) by 45 days.

(21) Appl. No.: 15/569,740

(22) PCT Filed: Apr. 27, 2016

(86) PCT No.: PCT/US2016/029560
§ 371 (c)(1),
(2) Date: Oct. 26, 2017

(87) PCT Pub. No.: WO2016/176324
PCT Pub. Date: Nov. 3, 2016

(65) Prior Publication Data
US 2018/0142253 A1    May 24, 2018

Related U.S. Application Data

(63) Continuation-in-part of application No. 14/809,063, filed on Jul. 24, 2015.

(60) Provisional application No. 62/153,440, filed on Apr. 27, 2015, provisional application No. 62/028,776, filed on Jul. 24, 2014, provisional application No. 62/153,440, filed on Apr. 27, 2015.

(51) Int. Cl.
*C12N 15/82*      (2006.01)
*C12N 15/113*     (2010.01)

(52) U.S. Cl.
CPC ........ *C12N 15/8282* (2013.01); *C12N 15/113* (2013.01); *C12N 15/8218* (2013.01); *C12N 2310/14* (2013.01)

(58) Field of Classification Search
CPC ................................................ C12N 15/8282
USPC ........................................................ 800/279
See application file for complete search history.

(56) References Cited

U.S. PATENT DOCUMENTS

| | | | |
|---|---|---|---|
| 6,353,155 B1 | 3/2002 | Kloeti et al. | |
| 6,495,133 B1 | 12/2002 | Xue | |
| 6,653,535 B1 | 11/2003 | Tarczynski | |
| 7,834,243 B2 | 11/2010 | Schweizer | |
| 8,148,604 B2 | 4/2012 | Niblett | |
| 8,865,968 B2 | 10/2014 | Van De Craen et al. | |
| 2003/0221211 A1 | 11/2003 | Rottmann | |
| 2004/0029283 A1 | 2/2004 | Fillatti | |
| 2008/0022423 A1* | 1/2008 | Roberts | C12N 15/8282 800/279 |
| 2009/0300796 A1 | 12/2009 | Raemaekers et al. | |
| 2011/0061128 A1 | 3/2011 | Roberts et al. | |
| 2011/0119788 A1 | 5/2011 | Rodriguez Baixauli et al. | |
| 2014/0283211 A1 | 9/2014 | Crawford et al. | |
| 2015/0089688 A1 | 3/2015 | Jacobs et al. | |
| 2015/0203865 A1 | 7/2015 | Jin | |
| 2016/0032314 A1 | 2/2016 | Jin | |

FOREIGN PATENT DOCUMENTS

| | | |
|---|---|---|
| EP | 1888754 | 5/2011 |
| EP | 2698379 A1 | 2/2014 |
| WO | 2012/155109 A1 | 11/2012 |
| WO | 2013/025670 A1 | 2/2013 |
| WO | 2014/033723 A1 | 3/2014 |

OTHER PUBLICATIONS

Nicolas et al Fungal Genet Biol., 2007, 44: 504-516.*
Kadotani et al J Biol Chem., 2004, 279: 44467-44474.*
Bernstein et al PNAS, 2012, 109: 523-528.*
Segers et al PNAS, 2007, 104:12902-12906.*
Drinnenberg et al Science, 2009, 326: 544-550.*
Catalanotto et al Mol Cell Biol., 2004, 24(6): 2536-2545.*
UniProt M7U4R4_BOTF1, published May 29, 2013, see sequence in Final Office Action dated Sep. 10, 2018 for U.S. Appl. No. 14/809,063.
UniProt M7U651_BOTF1, published May 29, 2013, see sequence in Final Office Action dated Sep. 10, 2018 for U.S. Appl. No. 14/809,063.
UniProt G2WQ29_VERDV, published online Nov. 16, 2011, see sequence in Final Office Action dated Sep. 10, 2018 for U.S. Appl. No. 14/809,063.
UniProt G2XA42_VERDV, published online Nov. 16, 2011, see sequence in Final Office Action dated Sep. 10, 2018 for U.S. Appl. No. 14/809,063.
U.S. Appl. No. 14/809,063, "Final Office Action," dated Sep. 10, 2018, 43 pages.
Yoshinari et al., "Effects on RNAi of the Tight Structure, Sequence and Position of the Targeted Region", Nucleic Acids Research, vol. 32, Issue 2, Jan. 16, 2004, pp. 691-699.
Amselem et al., "Genomic Analysis of the Necrotrophic Fungal Pathogens *Sclerotinia sclerotiorum* and *Botrytis cinerea*" PLoS Genetics, Aug. 2011, vol. 7, Issue 8, e1002230, pp. 1-27.
Chen et al., "Characterization of RNA silencing components in the plant pathogenic fungus *Fusarium graminearum*," www.nature.com/ Scientific Reports, Published Jul. 27, 2015, 5:12500, DOI:10.1038/ srep12500, pp. 1-13.

(Continued)

*Primary Examiner* — Li Zheng

(74) *Attorney, Agent, or Firm* — Kilpatrick Townsend & Stockton LLP

(57) ABSTRACT

The present invention relates to methods of increasing pathogen resistance in a plant or a part of a plant. In one aspect, the method comprises contacting the plant or the part of the plant with a double-stranded RNA or a small RNA duplex that targets a fungal dicer-like (DCL) gene, wherein the plant or the part of the plant has increased resistance to a fungal pathogen compared to a control plant or control plant part that has not been contacted with the double-stranded RNA or small RNA duplex.

23 Claims, 26 Drawing Sheets
Specification includes a Sequence Listing.

(56) References Cited

OTHER PUBLICATIONS

Starkel, "Host Induced Gene Silencing—strategies for the improvement of resistance against *Cercospora beticola* in sugar beet (*B. vulgaris* L.) and against *Fusarium graminearum* in wheat (*T. aestivum* L.) and maize (*Z. mays* L.)," Thesis submitted 2011 to the Biology Dept, the Faculty of Mathematics, Informatics and Natural Sciences, University of Hamburg, pp. 1-130.
EP16787063.3, Extended European Search Report, dated Sep. 7, 2018, 9 pages.
GenBank XM_001551139, 2008.
GenBank XP_001551189, 2008.
U.S. Appl. No. 14/809,063 , "Non-Final Office Action", dated Nov. 16, 2017, 37 pages.
Bernstein et al., "*Candida albicans* Dicer (CaDcr1) is required for efficient ribosomal and spliceosomal RNA maturation," PNAS, 2012, 109:523-528.
Catalanotto et al., "Redundancy of the Two Dicer Genes in Transgene-Induced Posttranscriptional Gene Silencing in *Neurospora crassa*," Mol Cell Biol., 2004, 24(6):2536-2545.
Drinnenberg et al., "RNAi in Budding Yeast," Science, 2009, 326:544-550.
Kadotani et al., "One of the Two Dicer-like Proteins in the Filamentous Fungi *Magnaporthe oryzae* Genome Is Responsible for Hairpin RNA-triggered RNA Silencing and Related Small Interfering RNA Accumulation," J Biol Chern., 2004, 279 (43):44467-44474.
Nicolas et al., "Mutants defective in a *Mucor circinelloides* dicer-like gene are not compromised in siRNA silencing but display developmental defects," Fungal Genet Biol., 2007, 44:504-516.
Segers et al., "Evidence that RNA silencing functions as an antiviral defense mechanism in fungi," PNAS, 2007, 104 (31):12902-12906.
Wang et al., "Pathogen small RNAs: a new class of effectors for pathogen attacks," Molecular Plant Pathology, 2015, 16(3):219-223.
Weiberg et al., "Conversations between kingdoms: small RNAs," Current Opinion in Biotechnology, 2015, 32:207-215.
Weiberg et al., "Fungal Small RNAs Suppress Plant Immunity by Hijacking Host RNA Interference Pathways," Science, 2013, 342(6154):118-123.
Weiberg et al., "Small RNAs: A New Paradigm in Plant-Microbe Interactions, " Ann. Rev. Phytopathol., 2014, 52:495-516.
Yang et al., "Roles of small RNAs in plant disease resistance," J. Integrative Plant Biology, Oct. 2014, 56(10):962-970.
Ashida H. et al., "Shigella deploy multiple countermeasures against host innate immune responses" *Curr. Opin. Microbiol.* 14, 16-23 (2011).
Bozkurt T.O. et al., "oomycetes, effectors, and all that jazz" *Curr. Opin. Plant Biol.* 15, 483-492 (2012).
Dean et al., "the top 10 fungal pathogens in molecular plant pathology," *Mol Plant Pathol* (2012) 13(4):414-430.
Deleris et al., "Hierarchical Action and Inhibition of Plant Dicer-Like Proteins in Antiviral Defense," *Science*, Jun. 1, 2006, vol. 313, No. 5783, 7 pages.
Ellendorff U. et al., "RNA Silencing Is Required For *Arabidopsis* Defence Against Verticillium Wilt Disease" *J. Exp. Bot.* 60, 591 (2009).
Gan et al., "Bacterially expressed dsRNA protects maize against SCMV infection," *Plant Cell Reports* 29(11):1261-1268 (2010).
Govindarajulu et al., "Host-induced gene silencing inhibits the biotrophic pathogen causing downy mildew of lettuce," *Plant Biotechnology Journal* (2015) 13(7):875-883.
Hilbi H. et al., "Secretive Bacterial Pathogens and the Secretory Pathway" *Traffic* 13, 1187 (2012).
Jiang N, Yan Y, Janbon G, Pan J, Zhu X."Identification and functional demonstration of miRNAs in the fungus *Cryptococcus neoformans*" *PLoS One.* 2012; 7:e52734.
Katiyar-Agarwal S, Jin H., "Role of small RNAs in host-microbe interactions" *Annu Rev Phytopathol.* 2010; 48:225-226.
Lee HC et al. "Diverse pathways generate microRNA-like RNAs and Dicer-independent small interfering RNAs in fungi" *Mol Cell.* 2010; 38:803-814.
Lu et al., "RNA silencing in plants by the expression of siRNA duplexes," *Nucleic Acids Res.* 32(21):e171 (2004).
Mi S.J. et al., "Sorting of Small RNAs into *Arabidopsis* Argonaute Complexes Is Directed by the 50 Terminal Nucleotide" *Cell* 133, 116 (2008).
Montgomery T.A. et al., "Specificity of ARGONAUTE7-miR390 Interaction and Dual Functionality in TAS3 Trans-Acting siRNA Formation" *Cell* 133, 128 (2008).
Nowara et al., "HIGS: Host-Induced Gene Silencing in the Obligate Biotrophic Fungal Pathogen *Blumeria graminis*," *Plant Cell* (2010) 22(9):3130-3141.
Nunes CC et al. "Diverse and tissue-enriched small RNAs in the plant pathogenic fungus, *Magnaporthe oryzae*" *MBC Genomics.* 2011; 12:288.
Nunes et al., "Host-induced gene silencing: a tool for understanding fungal host interaction and for developing novel disease control strategies," *Mol Plant Pathol* (2012) 13(5):519-529.
Qutob D, Patrick Chapman B, Gijzen M., "Transgenerational gene silencing causes gain of virulence in a plant pathogen" *Nature Comm.* 2013; 4:1349.
Rafiqi M. et al., "Challenges and progress towards understanding the role of effectors in plant-fungal interactions" *Curr. Opin. Plant Biol.* 15, 477-482 (2012).
Raman V et al. "Physiological stressors and invasive plant infections alter the small RNA transcriptome of the rice blast fungus, *Magnaporthe oryzae*" *MBC Genomics.* 2011; 14:326.
Ruiz-Ferrer V, Voinnet O. "Roles of plant small RNAs in biotic stress responses" *Annu Rev Plant Biol.* 2009, 60:485-510.
Tang et al., "Construction of short tandem target mimic (STTM) to block the functions of plant and animal microRNAs" *Methods* 58:118-125 (2012).
Wessner B, Gryadunov-Masutti L, Tschan H, Bachl N, Roth E. "Is there a role for microRNAs in exercise immunology? A synopsis of current literature and future developments" *Exerc Immunol Rev.* 2010;16:22-29.
Yan et al., "Effective Small RNA Destruction by the Expression of a Short Tandem Target Mimic in *Arabidopsis*" *Plant Cell* 24:415-427 (2012).
Zhang X et al. "*Arabidopsis* Argonaute 2 regulates innate immunity via miRNA393(*)-mediated silencing of a Golgi-localized SNARE gene, MEMB12" *Mol Cell.* 2011; 42:356-366.
Zhou J et al., "Identification of microRNA-like RNAs in a plant pathogenic fungus *Sclerotinia sclerotiorum* by high-throughput sequencing" *Mol Gen Genet.* 2012;287-282.
PCT/US2016/029560, "International Search Report and Written Opinion", dated Jul. 14, 2016, pp. 1-9.

\* cited by examiner

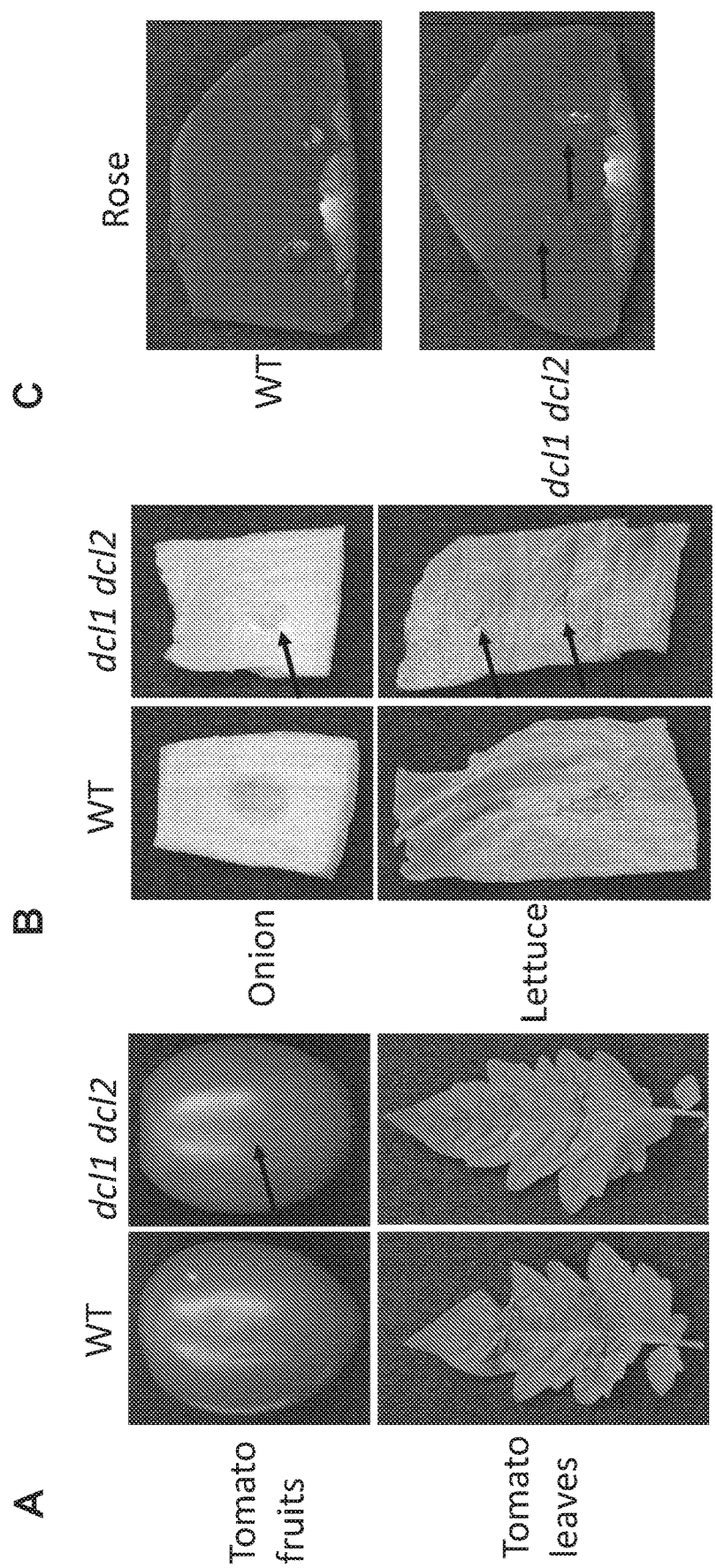

Absolute sRNA numbers at different genomic regions

|  |  | WT | dcl1dcl2 | ratio |
|---|---|---|---|---|
| IGR | S | 2,034,017 | 3,818,294 | 1.88 |
| Coding gene | S | 6,797,713 | 7,057,318 | 1.04 |
|  | AS |  |  |  |
| LTR | S | 32,889,611 | 13,316,060 | 0.41 |
|  | AS | 23,557 | 3,892 | 0.16 |
|  |  |  |  |  |
| Total | S | 41,977,871 | 24,199,411 |  |
| rRNA | S | 38,989,023 | 14,619,918 | 0.52 |
|  | AS | 75903 | 39387 | 0.37 |
| Total |  | 39,064,926 | 14,695,305 |  |
| tRNA | S | 2,919,709 | 14,029,210 | 4.81 |
|  | AS | 14,865 | 4,558 | 0.31 |
| Total |  | 2,934,574 | 14,033,768 |  |
| Absolute |  | 83,977,371 | 52,892,484 |  |

FIG. 6
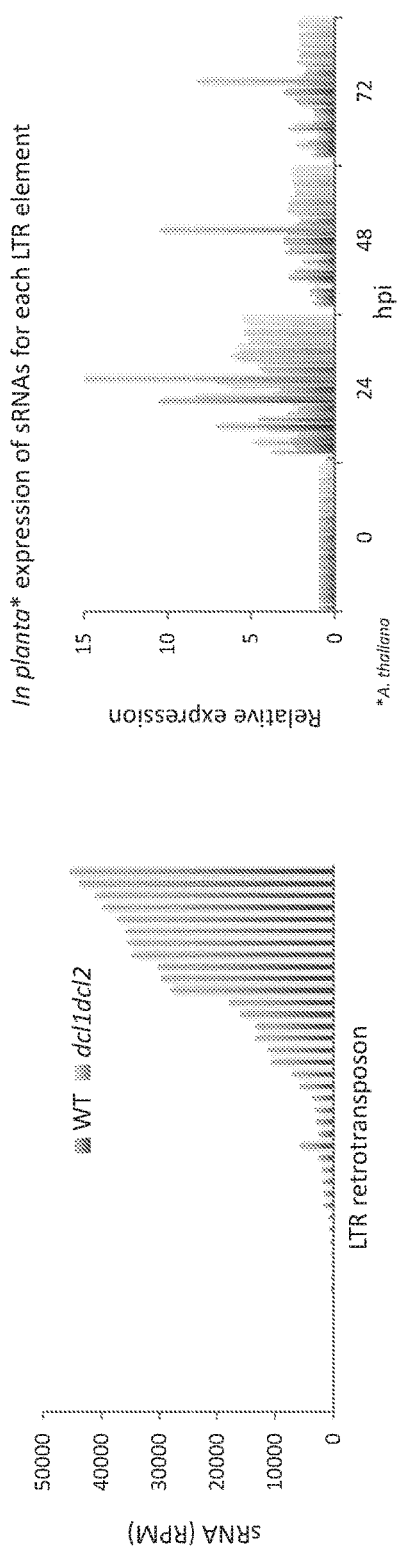
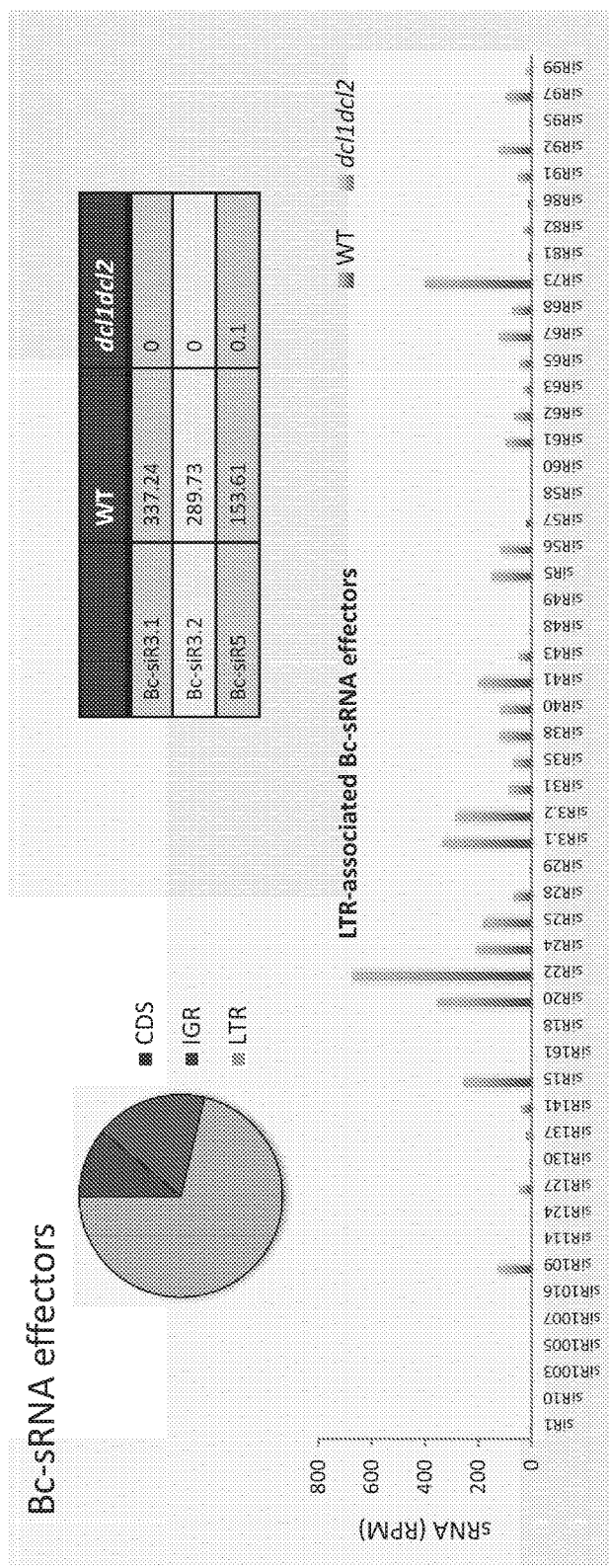

FIG. 19A-D
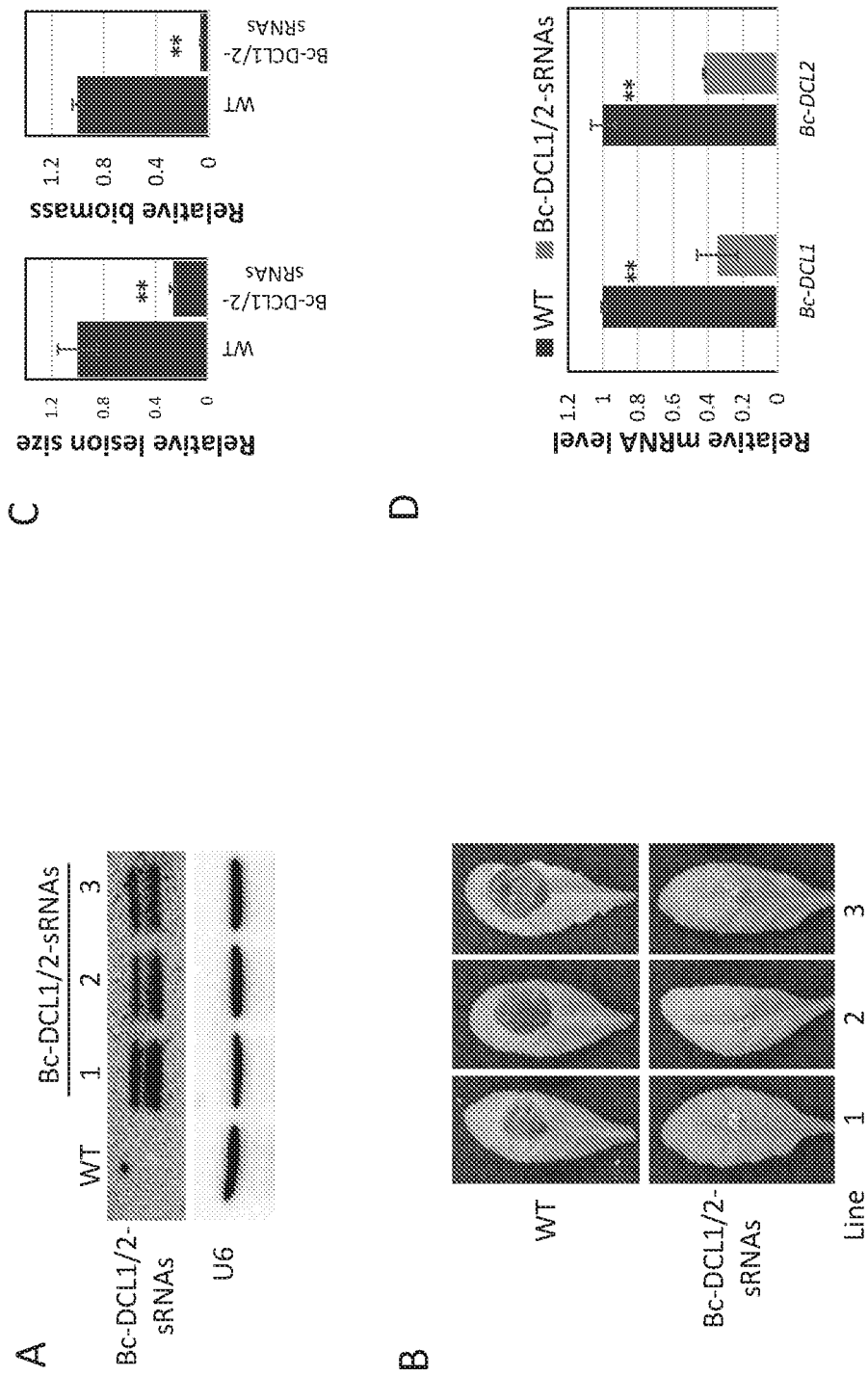

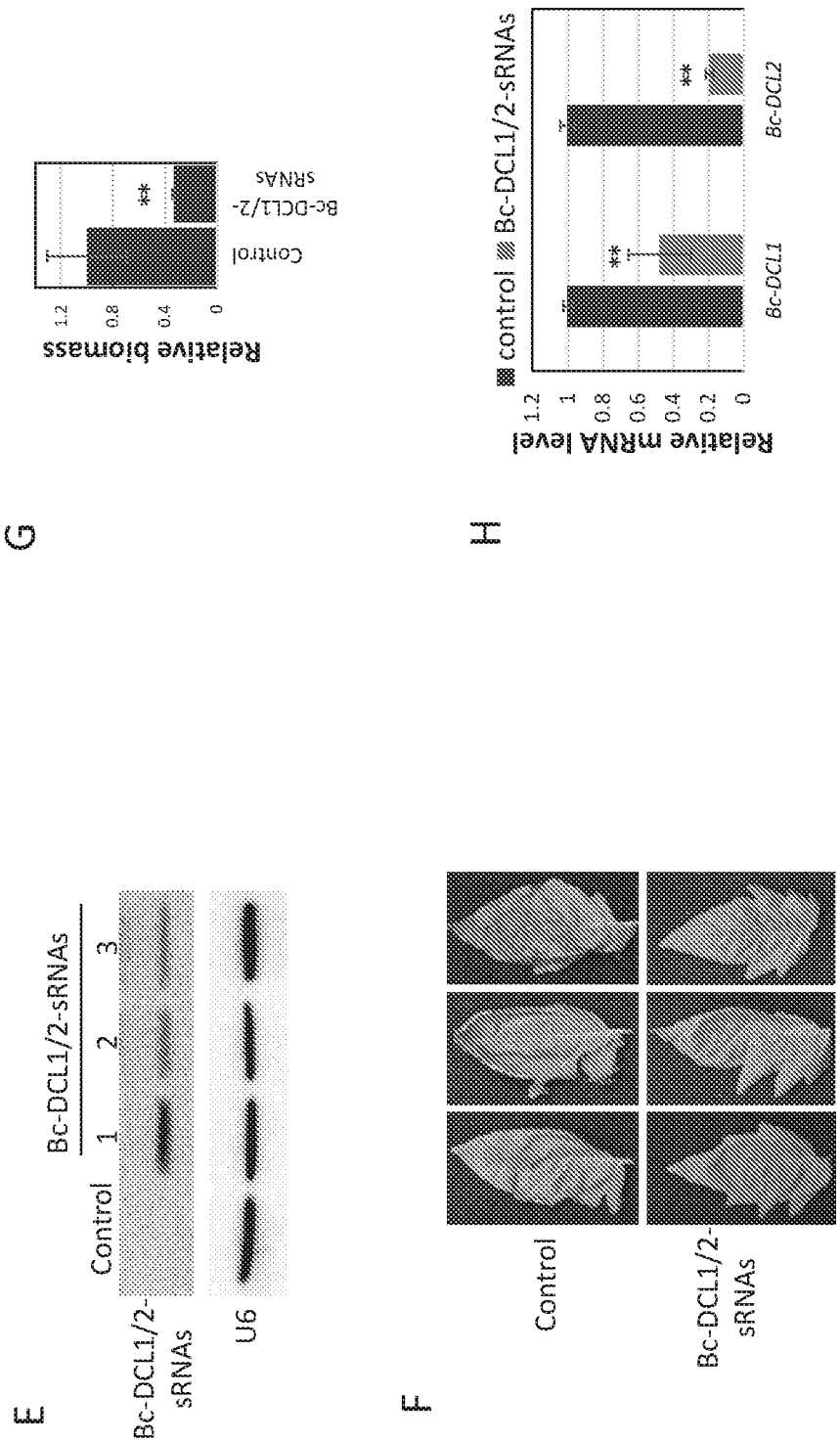
FIG. 19E-H

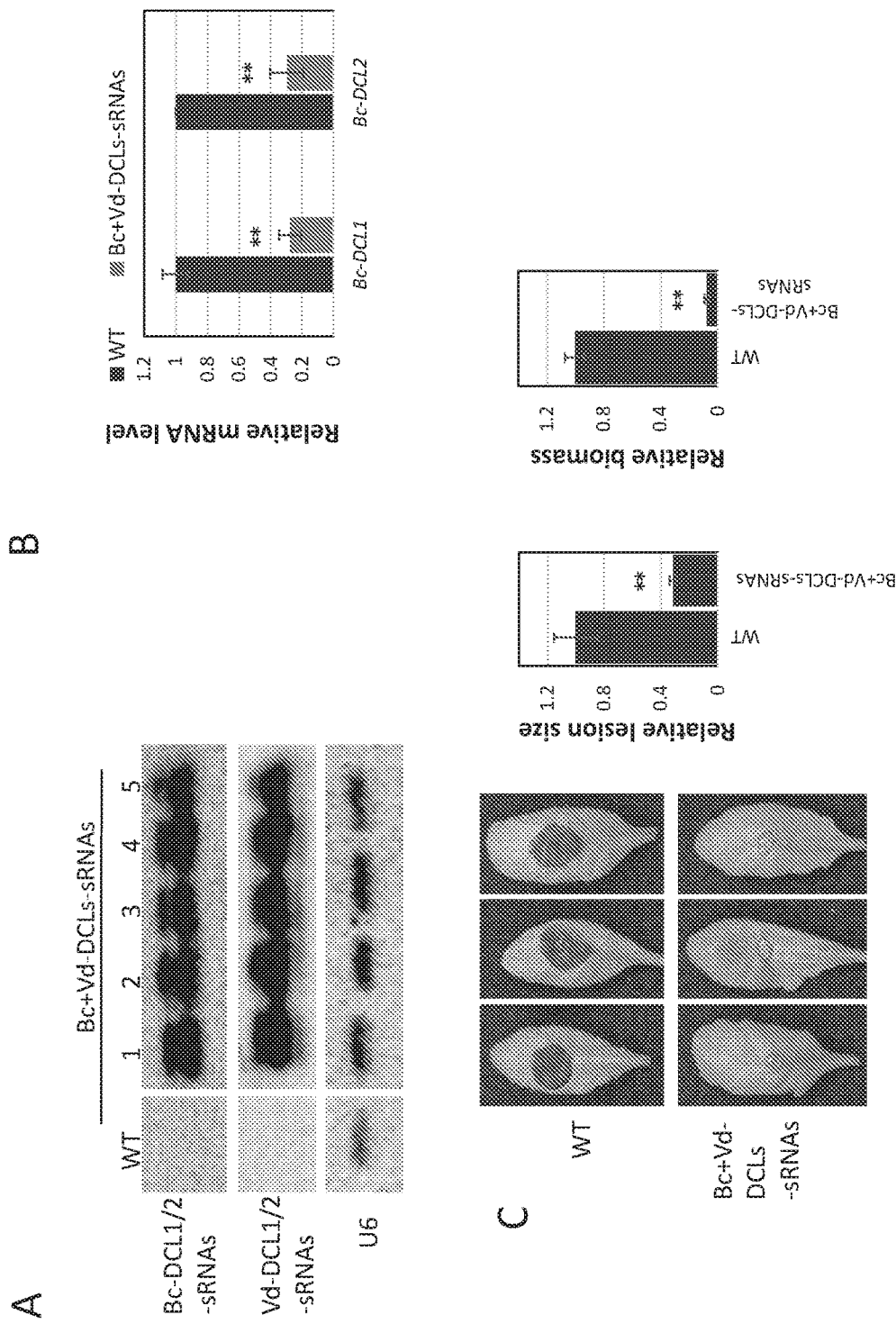
FIG. 23A-C

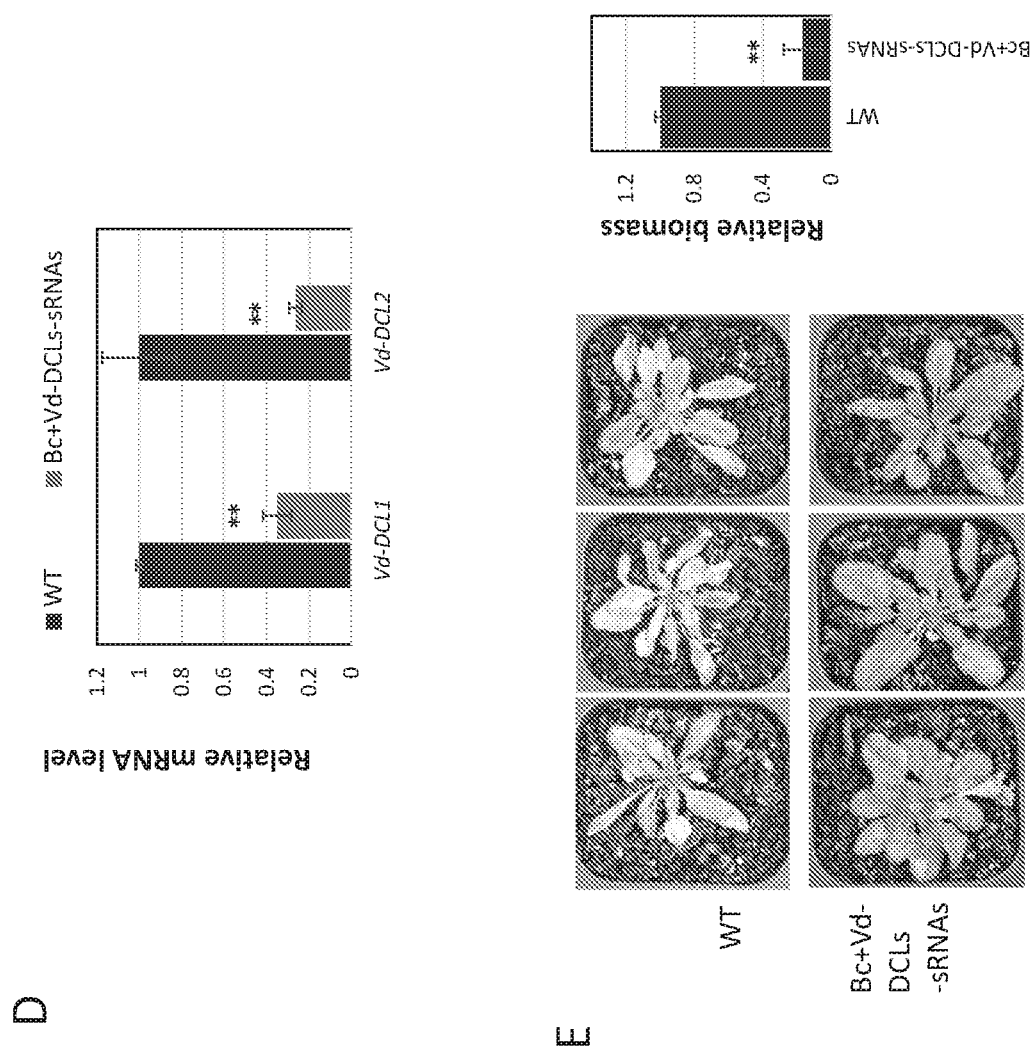
FIG. 23D-E

SEQUENCE LISTING

<160> NUMBER OF SEQ ID NOS: 66

<210> SEQ ID NO 1
<211> LENGTH: 5529
<212> TYPE: DNA
<213> ORGANISM: Botrytis cinerea

<400> SEQUENCE: 1

```
atgacgagag acgcagcagc agcaaaaagt ctctaccatt ggcgaagaaa aggcgtcact      60
ccttcagccg aagaggatct tctatcgttt gatgatattg ttactgccgt tccacctaca     120
atcttgtctt cgtctgtcgc tccatatact tctcgagata agataccttc tgcatctggc     180
aacggagatg ctatagcaga tgttagcagt ggttacctca acaggctac cgtatcttct      240
cattctgctc aagtccgatc atcttcaaac ggcaatcaag gtgatgccaa agttctccc      300
tctctttcac ctgatagtaa actggaattc atctttgggc ctcctttaag ggagccagag     360
aagccattct ttaataaatc ttcttattcg tttcgagatt cgagagggtt gagcagaaat     420
cgggcttctt cttctatgga aaattcgaga actctcgatc caaagatact caaaccagtt     480
atcatcaata atcaccaggg cgaatgcttc aagaggctt ccagaacagg tatacctcag      540
gctgatactt ttgataaatc ttcccttgct aagactgcgg atatggattt gtcaccagtt     600
tctcaccatg cggatgtgct tgcgacgacg gtcactgcac agcattctgc aatagccgcc     660
cagaacgcag ctcaaagctc taagatgcca ggtcctgaag cttttttact tgccgaaaag     720
gacgaggcag gttctcccgt tgttatatca ctgggttctg caaaccaaat tccttctgga     780
aacatttctt tgcagcttga ttcaccatct ctggaaaacc attctccaaa tgtgacccca     840
atcaacaaag tccctacacc attcgcactt tctacaagga caaccgatga cgttttcgca     900
gaacttaggc ggccttttgca tccccaagct attcagagcc agattgatat caagacttcc     960
tcttgtgttg atagttataa cacgaatgat gagattctag acaacaatca aggttccaat    1020
caaaagatc tgcatgttgt tgaaaaggat aaggaagagg aagaggaaga ggatatgaac    1080
caagccatac ccgatatcaa acgtatctca gcacgaaaac aaaagaacgc tgccatattt    1140
gacgtttttc ttaaggaagc taccaaacta ccaaagacga aaaagacttc acatgcgaat    1200
gatgaagcaa ttcagtctac taggtggttg attgaccaag cagaaaaaca gcatattata    1260
gaaagtccca gggactatca acttgaattg tttgagaagg caaagaaaca gaacattata    1320
gctgtacttg atacaggatc tggcaagaca ttcattgcag ttctcttact tcggtggatc    1380
atagaccaag agcttgaaga tagagctatt ggcaagcctc atcgtgtttc attcttcctg    1440
tggaagaaac gactggatac gaatatggtc attgtctgca ctgcagaaat tttgcgccaa    1500
tgcctgcacc attcgtttgt tacaatggct caaataaatc tgctaatttt cgatgaagcc    1560
caccatgcaa agaaggatca tccttatgct aggattatta agattttta tcgcaatgac    1620
acggaaaagg atatcgctct gcctaaaata tttgggatga cagcatcacc ggtagatgct    1680
agagataatg tcaagaaagc tgcggaagaa cttgaaggtt tgctacacag tcaaatatgt    1740
actgcagaag atcccagctt gctgcagtac tcaatcaaag gtaaacctga gactcttgcc    1800
tactatgatc ccttgggccc gaaattcaat actcctcttt atcttcaaat gctcccgctt    1860
ctaaaagaca atcctatctt tcggaagcca tttgtatttg gacagaagc cagtagaact     1920
ctaggatctt ggtgtgttga ccagatctgg actttctgtc ttcaagaaga agagtctaag    1980
aaactacaag caaggacgga gcaggcgcat cataagaaga gagtcccgga gccacttgaa    2040
gtgctagaga aacgcaagga acaacttgaa caagccaaat ccattgtcga aaatcacact    2100
ttcgagccac cacactttgc atcaagatta ttggatgatt tcacaacaaa agttcactat    2160
tcgaataatt tatctactaa agtcgttgct ctcttgagta ttctcaaaga tcgtttccaa    2220
cgacccacca atgacaagtg tattgtatttt gtcaaagaaa gatacaccgc acgccttcta    2280
gcctcacttc tctccacacc tgaagctggg acaccattct tgaaggctgc accgctggtt    2340
```

```
ggtactacgt ctgcttcagc cggggaaatg catatcacat ttagatcaca aactcttact   2400
atgcacaact ttcgcaatgg taaaatcaac tgccttatcg caacatcagt tgctgaagaa   2460
ggtcttgaca ttcctgactg taacctcgtt gtcagattcg atttgtacaa tacagtcatt   2520
cagtacattc aatctagagg tcgtgctagg catatcaatt caaggtacta ccatatggta   2580
gagagccaca acgaggaaca gattcgtaca atcaagaggt tttgaagcat gagaaaatg    2640 ctaaagcttt ttgcttctgc tcttccagaa gatcgaaaat tgaccggaaa caacttcaat   2700
atggattact tcctcagaaa agaacgaggc cacagaattt accctgtccc gaatagtgac   2760
gcaaaactta cttacagaat gagcttaacg gtcctatctg ccttcgttga ctcacttcct   2820
cgagccccag agtcggttct tcgagtggat tatgtcgtca caactgtcga taagcagttt   2880
atctgtgagg ccattttgcc agaagaagca cccatacgcg gagcaattgg tcggccagca   2940
acaactaaac aagtggccaa atgctcagca gcctttgaaa cttgtgtgat tctgcaccag   3000
aaaggataca tcaacgacta cctactttct acatttaaaa gatcagcaca catgatgaga   3060
aatgcacttt tggctgtgga tggaaagaag caagaagctt atgatatgca gactaaacca   3120
actttatggt cttcgaaagg gaaacaaggc atattttata tgactgtctt gtctctcaaa   3180
tctccagata atcttgacag agcatctcag ccattgggct tactgacaag atcacccttg   3240
cctgatttgc cagaatttgt tcttcatttc ggagcagggc gaaactctcc aacctcgtgc   3300
gtacctctcg cttcctcaat tacgctcgaa aaaaacaagc ttgaccaagt taatatgttc   3360
accctatgtt tattccaaga tgtgttcagt aaagcataca aatcagatcc ggatagtatg   3420
ccatactttc tggttcctat caactgcctg aatgctattg tcgactggaa atcacaaaac   3480
ccaatgtcaa taatcgattg ggagacagtt gaatatgtcc aagacttcga gaataagcaa   3540
gctgataagc catgggagca caagccatgg ttaggaaagc ctgacgatta tttcaaagac   3600
aaattcataa ctgatccctt tgacgggtct cgaaaattgt ggtccgttgg aatcacaaaa   3660
gaatacagac cattggatcc agtcccacca aacacggcgc ccaggaaggg agctagaaag   3720
aacaatagta atatcatgga gtatagttgt agtctctggg caaaggctag agcaaaacga   3780
acttttgatg aagaacagcc tgttattgaa gcaacctaca tttcacttcg gagaaatttg   3840
cttgatgaat tgatggaggt gagctcgag acttcaaaga agagttttat tattttagaa   3900
ccattgaagg tatcacctct tccaactacc gtgggtgcaa tggcctatct tttacctgca   3960
attattcatc gagttgagtc atatctcatt gctcttgaag caacagactt gttacatctt   4020
gatatccgtc ctgatcttgc gctagaggct gttaccaagg attccgacaa ttctggagag   4080
catggtgagg aacagacaaa ctttcaacgt ggaatgggca ataattatga acgattggaa   4140
tttcttgggg actgcttctt gaagatggga acgtcaatat ctctatacgg tctaaatcct   4200
gatagtgatg aattccgcta ccatgttgat cgtatgtgtc tgatttgcaa caaaaatctg   4260
ttcaatacgc ctttgaaatt agagctttac aaatacattc ggtcggcagc cttcaaccga   4320
cgagcttggt atcccgaagg ccccgaatta ttaagaggaa agacagccac ggcaccaaat   4380
acccacaagc tcggcgataa gtcagttgca gatgtttgtg aagcaatgat tggagctgct   4440
ttactaagcc accacgaaag caagtccatg gataatgcgg ttcgcgccgt tactgaagtt   4500
gtcaatagtg acaaccacaa tgctgttgta tggtctgatt attacaaatt gtatgagaaa   4560
ccaaaatggc aaactgctac agctacagct gcacaaatag atatggcaag acaagttgaa   4620
atgaaacatc catatcattt caaacaccca cgcctgttaa gatcagcttt catccatccg   4680
```

-continued

```
gcatacttgt tcatctatga acaaattcct tgttatcaac gtctcgaatt tttgggtgat    4740
tcgctactcg atatggcatg tgtcaacttc cttttttcaca accacccaac aaaagatcct    4800
```

```
gcatacttgt tcatctatga acaaattcct tgttatcaac gtctcgaatt tttgggtgat    4740
tcgctactcg atatggcatg tgtcaacttc ctttttcaca accacccaac aaaagatcct    4800
cagtggctca ctgagcacaa gatggctata gtatccaatc agtttcttgg agctctttgt    4860
gtcaaattag gcttccacaa acatctactg acactcgatt ctcaagttca aaaaatgatt    4920
gcagattact cctcagatat caatgaagct ctcattcaag ccaaaacgga cgcaaagaga    4980
gtcggcaaag tagaagatga ttacgctcgt gattattgga ttgccgtccg tcaacctcct    5040
aaatgtcttc ccgatattgt agaagcattc attggtgcca tttttgtcga ctctgagtat    5100
gactacggtg aagttgagaa gttctttgaa atgcatatca gatggtactt tgaggatatg    5160
ggcatctacg ataccctatgc taacaagcac ccaaccactt tccttactaa tttcttgcaa    5220
aagaacatgg gatgtgagga ctgggcacca gttagtaagg aagtacctgg agaggatggt    5280
agaaagaatg ttgtagtttg cggggtcatc atacacaata aggtggtatc aactgccact    5340
gccgaaagta tgagatatgc tagggtcgga gcagcgagga atgccttgag aaaattggag    5400
ggaatgagtg tccgagaatt cagggatgaa tacgggtgct catgtgaagg tgatgttgtt    5460
gatgaagagg gcaatattga atttgttgaa cgtgaagacg ggatggaggg gatcggtatg    5520
ggatattga                                                            5529
```

<210> SEQ ID NO 2
<211> LENGTH: 1842
<212> TYPE: PRT
<213> ORGANISM: Botrytis cinerea

<400> SEQUENCE: 2

```
Met Thr Arg Asp Ala Ala Ala Lys Ser Leu Tyr His Trp Arg Arg
1               5

```
Gln Ser Ser Lys Met Pro Gly Pro Glu Ala Phe Leu Leu Ala Glu Lys
225                 230                 235                 240

Asp Glu Ala Gly Ser Pro Val Val Ile Ser Leu Gly Ser Ala Asn Gln
            245                 250                 255

Ile Pro Ser Gly Asn Ile Ser Leu Gln Leu Asp Ser Pro Ser Leu Glu
                260                 265                 270

Asn His Ser Pro Asn Val Thr Pro Ile Asn Lys Val Pro Thr Pro Phe
            275                 280                 285

Ala Leu Ser Thr Arg Thr Thr Asp Asp Val Phe Ala Glu Leu Arg Arg
290                 295                 300

Pro Leu His Pro Gln Ala Ile Gln Ser Gln Ile Asp Ile Lys Thr Ser
305                 310                 315                 320

Ser Cys Val Asp Ser Tyr Asn Thr Asn Asp Glu Ile Leu Asp Asn Asn
                325                 330                 335

Gln Gly Ser Asn Gln Lys Asp Leu His Val Val Glu Lys Asp Lys Glu
            340                 345                 350

Glu Glu Glu Glu Glu Asp Met Asn Gln Ala Ile Pro Asp Ile Lys Arg
            355                 360                 365

Ile Ser Ala Arg Lys Gln Lys Asn Ala Ala Ile Phe Asp Val Phe Leu
370                 375                 380

Lys Glu Ala Thr Lys Leu Pro Lys Thr Glu Lys Thr Ser His Ala Asn
385                 390                 395                 400

Asp Glu Ala Ile Gln Ser Thr Arg Trp Leu Ile Asp Gln Ala Glu Lys
                405                 410                 415

Gln His Ile Ile Glu Ser Pro Arg Asp Tyr Gln Leu Glu Leu Phe Glu
            420                 425                 430

Lys Ala Lys Lys Gln Asn Ile Ile Ala Val Leu Asp Thr Gly Ser Gly
            435                 440                 445

Lys Thr Phe Ile Ala Val Leu Leu Leu Arg Trp Ile Ile Asp Gln Glu
450                 455                 460

Leu Glu Asp Arg Ala Ile Gly Lys Pro His Arg Val Ser Phe Phe Leu
465                 470                 475                 480

Trp Lys Lys Arg Leu Asp Thr Asn Met Val Ile Val Cys Thr Ala Glu
                485                 490                 495

Ile Leu Arg Gln Cys Leu His His Ser Phe Val Thr Met Ala Gln Ile
            500                 505                 510

Asn Leu Leu Ile Phe Asp Glu Ala His His Ala Lys Lys Asp His Pro
            515                 520                 525

Tyr Ala Arg Ile Ile Lys Asp Phe Tyr Arg Asn Asp Thr Glu Lys Asp
530                 535                 540

Ile Ala Leu Pro Lys Ile Phe Gly Met Thr Ala Ser Pro Val Asp Ala
545                 550                 555                 560

Arg Asp Asn Val Lys Lys Ala Ala Glu Glu Leu Glu Gly Leu Leu His
                565                 570                 575

Ser Gln Ile Cys Thr Ala Glu Asp Pro Ser Leu Leu Gln Tyr Ser Ile
            580                 585                 590

Lys Gly Lys Pro Glu Thr Leu Ala Tyr Tyr Asp Pro Leu Gly Pro Lys
            595                 600                 605

Phe Asn Thr Pro Leu Tyr Leu Gln Met Leu Pro Leu Leu Lys Asp Asn
610                 615                 620

Pro Ile Phe Arg Lys Pro Phe Val Phe Gly Thr Glu Ala Ser Arg Thr
625                 630                 635                 640
```

-continued

Leu Gly Ser Trp Cys Val Asp Gln Ile Trp Thr Phe Cys Leu Gln Glu
                645                 650                 655

Glu Glu Ser Lys Lys Leu Gln Ala Arg Thr Glu Gln Ala His His Lys
        660                 665                 670

Lys Arg Val Pro Glu Pro Leu Glu Val Leu Glu Lys Arg Lys Glu Gln
                675                 680                 685

Leu Glu Gln Ala Lys Ser Ile Val Glu Asn His Thr Phe Glu Pro Pro
        690                 695                 700

His Phe Ala Ser Arg Leu Leu Asp Asp Phe Thr Thr Lys Val His Tyr
705                 710                 715                 720

Ser Asn Asn Leu Ser Thr Lys Val Val Ala Leu Leu Ser Ile Leu Lys
                725                 730                 735

Asp Arg Phe Gln Arg Pro Thr Asn Asp Lys Cys Ile Val Phe Val Lys
                740                 745                 750

Glu Arg Tyr Thr Ala Arg Leu Leu Ala Ser Leu Leu Ser Thr Pro Glu
        755                 760                 765

Ala Gly Thr Pro Phe Leu Lys Ala Ala Pro Leu Val Gly Thr Thr Ser
        770                 775                 780

Ala Ser Ala Gly Glu Met His Ile Thr Phe Arg Ser Gln Thr Leu Thr
785                 790                 795                 800

Met His Asn Phe Arg Asn Gly Lys Ile Asn Cys Leu Ile Ala Thr Ser
                805                 810                 815

Val Ala Glu Glu Gly Leu Asp Ile Pro Asp Cys Asn Leu Val Val Arg
        820                 825                 830

Phe Asp Leu Tyr Asn Thr Val Ile Gln Tyr Ile Gln Ser Arg Gly Arg
        835                 840                 845

Ala Arg His Ile Asn Ser Arg Tyr Tyr His Met Val Glu Ser His Asn
850                 855                 860

Glu Glu Gln Ile Arg Thr Ile Lys Glu Val Leu Lys His Glu Lys Met
865                 870                 875                 880

Leu Lys Leu Phe Ala Ser Ala Leu Pro Glu Asp Arg Lys Leu Thr Gly
                885                 890                 895

Asn Asn Phe Asn Met Asp Tyr Phe Leu Arg Lys Glu Arg Gly His Arg
        900                 905                 910

Ile Tyr Pro Val Pro Asn Ser Asp Ala Lys Leu Thr Tyr Arg Met Ser
        915                 920                 925

Leu Thr Val Leu Ser Ala Phe Val Asp Ser Leu Pro Arg Ala Pro Glu
        930                 935                 940

Ser Val Leu Arg Val Asp Tyr Val Val Thr Thr Val Asp Lys Gln Phe
945                 950                 955                 960

Ile Cys Glu Ala Ile Leu Pro Glu Ala Pro Ile Arg Gly Ala Ile
                965                 970                 975

Gly Arg Pro Ala Thr Thr Lys Gln Val Ala Lys Cys Ser Ala Ala Phe
                980                 985                 990

Glu Thr Cys Val Ile Leu His Gln Lys Gly Tyr Ile Asn Asp Tyr Leu
        995                 1000                1005

Leu Ser Thr Phe Lys Arg Ser Ala His Met Met Arg Asn Ala Leu
        1010                1015                1020

Leu Ala Val Asp Gly Lys Lys Gln Glu Ala Tyr Asp Met Gln Thr
        1025                1030                1035

Lys Pro Thr Leu Trp Ser Ser Lys Gly Lys Gln Gly Ile Phe Tyr
        1040                1045                1050

Met Thr Val Leu Ser Leu Lys Ser Pro Asp Asn Leu Asp Arg Ala

```
                  1055                1060                1065
Ser  Gln  Pro  Leu  Gly  Leu  Leu  Thr  Arg  Ser  Pro  Leu  Pro  Asp  Leu
          1070                1075                1080

Pro  Glu  Phe  Val  Leu  His  Phe  Gly  Ala  Gly  Arg  Asn  Ser  Pro  Thr
          1085                1090                1095

Ser  Cys  Val  Pro  Leu  Ala  Ser  Ser  Ile  Thr  Leu  Glu  Lys  Asn  Lys
          1100                1105                1110

Leu  Asp  Gln  Val  Asn  Met  Phe  Thr  Leu  Cys  Leu  Phe  Gln  Asp  Val
          1115                1120                1125

Phe  Ser  Lys  Ala  Tyr  Lys  Ser  Asp  Pro  Asp  Ser  Met  Pro  Tyr  Phe
          1130                1135                1140

Leu  Val  Pro  Ile  Asn  Cys  Leu  Asn  Ala  Ile  Val  Asp  Trp  Lys  Ser
          1145                1150                1155

Gln  Asn  Pro  Met  Ser  Ile  Ile  Asp  Trp  Glu  Thr  Val  Glu  Tyr  Val
          1160                1165                1170

Gln  Asp  Phe  Glu  Asn  Lys  Gln  Ala  Asp  Lys  Pro  Trp  Glu  His  Lys
          1175                1180                1185

Pro  Trp  Leu  Gly  Lys  Pro  Asp  Asp  Tyr  Phe  Lys  Asp  Lys  Phe  Ile
          1190                1195                1200

Thr  Asp  Pro  Phe  Asp  Gly  Ser  Arg  Lys  Leu  Trp  Ser  Val  Gly  Ile
          1205                1210                1215

Thr  Lys  Glu  Tyr  Arg  Pro  Leu  Asp  Pro  Val  Pro  Pro  Asn  Thr  Ala
          1220                1225                1230

Pro  Arg  Lys  Gly  Ala  Arg  Lys  Asn  Asn  Ser  Asn  Ile  Met  Glu  Tyr
          1235                1240                1245

Ser  Cys  Ser  Leu  Trp  Ala  Lys  Ala  Arg  Ala  Lys  Arg  Thr  Phe  Asp
          1250                1255                1260

Glu  Glu  Gln  Pro  Val  Ile  Glu  Ala  Thr  Tyr  Ile  Ser  Leu  Arg  Arg
          1265                1270                1275

Asn  Leu  Leu  Asp  Glu  Phe  Asp  Gly  Gly  Glu  Leu  Glu  Thr  Ser  Lys
          1280                1285                1290

Lys  Ser  Phe  Ile  Ile  Leu  Glu  Pro  Leu  Lys  Val  Ser  Pro  Leu  Pro
          1295                1300                1305

Thr  Thr  Val  Gly  Ala  Met  Ala  Tyr  Leu  Leu  Pro  Ala  Ile  Ile  His
          1310                1315                1320

Arg  Val  Glu  Ser  Tyr  Leu  Ile  Ala  Leu  Glu  Ala  Thr  Asp  Leu  Leu
          1325                1330                1335

His  Leu  Asp  Ile  Arg  Pro  Asp  Leu  Ala  Leu  Glu  Ala  Val  Thr  Lys
          1340                1345                1350

Asp  Ser  Asp  Asn  Ser  Gly  Glu  His  Gly  Glu  Gln  Thr  Asn  Phe
          1355                1360                1365

Gln  Arg  Gly  Met  Gly  Asn  Asn  Tyr  Glu  Arg  Leu  Glu  Phe  Leu  Gly
          1370                1375                1380

Asp  Cys  Phe  Leu  Lys  Met  Gly  Thr  Ser  Ile  Ser  Leu  Tyr  Gly  Leu
          1385                1390                1395

Asn  Pro  Asp  Ser  Asp  Glu  Phe  Arg  Tyr  His  Val  Asp  Arg  Met  Cys
          1400                1405                1410

Leu  Ile  Cys  Asn  Lys  Asn  Leu  Phe  Asn  Thr  Ala  Leu  Lys  Leu  Glu
          1415                1420                1425

Leu  Tyr  Lys  Tyr  Ile  Arg  Ser  Ala  Ala  Phe  Asn  Arg  Arg  Ala  Trp
          1430                1435                1440

Tyr  Pro  Glu  Gly  Pro  Glu  Leu  Leu  Arg  Gly  Lys  Thr  Ala  Thr  Ala
          1445                1450                1455
```

-continued

Pro Asn Thr His Lys Leu Gly Asp Lys Ser Val Ala Asp Val Cys
1460                1465                1470

Glu Ala Met Ile Gly Ala Ala Leu Leu Ser His His Glu Ser Lys
1475                1480                1485

Ser Met Asp Asn Ala Val Arg Ala Val Thr Glu Val Val Asn Ser
1490                1495                1500

Asp Asn His Asn Ala Val Val Trp Ser Asp Tyr Tyr Lys Leu Tyr
1505                1510                1515

Glu Lys Pro Lys Trp Gln Thr Ala Thr Ala Ala Gln Ile
1520                1525                1530

Asp Met Ala Arg Gln Val Glu Met Lys His Pro Tyr His Phe Lys
1535                1540                1545

His Pro Arg Leu Leu Arg Ser Ala Phe Ile His Pro Ala Tyr Leu
1550                1555                1560

Phe Ile Tyr Glu Gln Ile Pro Cys Tyr Gln Arg Leu Glu Phe Leu
1565                1570                1575

Gly Asp Ser Leu Leu Asp Met Ala Cys Val Asn Phe Leu Phe His
1580                1585                1590

Asn His Pro Thr Lys Asp Pro Gln Trp Leu Thr Glu His Lys Met
1595                1600                1605

Ala Ile Val Ser Asn Gln Phe Leu Gly Ala Leu Cys Val Lys Leu
1610                1615                1620

Gly Phe His Lys His Leu Leu Thr Leu Asp Ser Gln Val Gln Lys
1625                1630                1635

Met Ile Ala Asp Tyr Ser Ser Asp Ile Asn Glu Ala Leu Ile Gln
1640                1645                1650

Ala Lys Thr Asp Ala Lys Arg Val Gly Lys Val Glu Asp Asp Tyr
1655                1660                1665

Ala Arg Asp Tyr Trp Ile Ala Val Arg Gln Pro Pro Lys Cys Leu
1670                1675                1680

Pro Asp Ile Val Glu Ala Phe Ile Gly Ala Ile Phe Val Asp Ser
1685                1690                1695

Glu Tyr Asp Tyr Gly Glu Val Glu Lys Phe Phe Glu Met His Ile
1700                1705                1710

Arg Trp Tyr Phe Glu Asp Met Gly Ile Tyr Asp Thr Tyr Ala Asn
1715                1720                1725

Lys His Pro Thr Thr Phe Leu Thr Asn Phe Leu Gln Lys Asn Met
1730                1735                1740

Gly Cys Glu Asp Trp Ala Pro Val Ser Lys Glu Val Pro Gly Glu
1745                1750                1755

Asp Gly Arg Lys Asn Val Val Val Cys Gly Val Ile Ile His Asn
1760                1765                1770

Lys Val Val Ser Thr Ala Thr Ala Glu Ser Met Arg Tyr Ala Arg
1775                1780                1785

Val Gly Ala Ala Arg Asn Ala Leu Arg Lys Leu Glu Gly Met Ser
1790                1795                1800

Val Arg Glu Phe Arg Asp Glu Tyr Gly Cys Ser Cys Glu Gly Asp
1805                1810                1815

Val Val Asp Glu Glu Gly Asn Ile Glu Phe Val Glu Arg Glu Asp
1820                1825                1830

Gly Met Glu Gly Ile Gly Met Gly Tyr
1835                1840

<210> SEQ ID NO 3
<211> LENGTH: 4197
<212> TYPE: DNA
<213> ORGANISM: Botrytis cinerea

<400> SEQUENCE: 3
atggaataca cttcggaacc tgacactgac ccggatacac gcggtagcct tatcgatggt 60
cgagatggga ttgaagggga tcttattgct ttgacgtctg ggaacgact taatgagact 120 gtagaggatt tatgtagtga ctcatcagga ttgattgttg agaatgaaga tgatgataac 180
agcgcagggg agaagggaga gattgtgata gtaacaccaa gaacatacca actggaaatg 240
ttggaagaga gtttgaaaag gaatgtcatc gttgcgatgg atacaggaag tggcaagaca 300
catgtggccg ttctccgaat actagcggaa cttgagcgga tgaagcctgg caagataata 360
tggtttcttg cgcctaccgt tgcgctctgt gctcagcatc acgaatatct ccagctgaat 420
attccctctg ttttgatcaa aatgcttatt ggtgctgatg gtgtggatcg atggacagag 480
cagagacagt gggatacggt cttgaaggat gtcaaggtag tcgtatcttc ctatcaagtt 540
cttctagatg cccttacaca cggattcgta cgcatggggc gtctgtcctt gatcattttt 600
gatgaagcac ataattgtgt aaataaagcg ccaggggcta aaattatgaa atctttctat 660
catccgtata aatcgatatt cccacttccc cacattctgg gcctctcggc cagccctgtc 720
atgagatcca gtccacaatc tttaagtgat atcgaggaga ctttggatgc catttgctgc 780
acgccaaaaa tacatcgagc agatcttcgc cttcgagtaa agctaccact tctatctatt 840
atctactata ccccagagtc aaatatcatc gtgacgaaaa ctgtggcgag cctgagaaag 900
attgtgcaaa gtctcaacat tttcgaagac ccctacgttt tgacactaaa aaggagtgat 960
agcgaaaaaa gtcaacgtga gctggcgaaa gtactcaaga gttttaagac atatagtcaa 1020
acccaattaa agtcaatcga caaaactagc aacgagatta ttcttgtaga gctaggccca 1080
tgggctgcag attactatat ctcaacagtg gtgacgagat acttgaaggc aatgtcggca 1140
aaggacactt tcattgttga agattcacca gctgccgaga agctatatat tgccaaggct 1200
ctcagacaag tcgaaatctc tccttcaact ctctcagata caggcaaaat ttctaacaag 1260
gttgaaaagc tactggggat aattgcgcaa cagaagcctc ccttttccgc tattatattt 1320
gtccaagaaa gagccacggt gtctgtgcta gcccatctat tatcgcatca tccattgaca 1380
aaggatcgtt ttaagattgg aaccatggtt ggcacatcct taaatggcaa gcgtacagac 1440
caaataggag agcttgtcga tgttaatcaa caaaaagaca ctttgtcaag tttcaagcgt 1500
ggaaaaattg atatccttat agctacaaat gtattggaag agggaattga tgttcctgcc 1560
tgtaatctag tgatctgctt tagtaaacca gcaaacctca aatctttcgt acaaagacga 1620
gggcgagcaa gacagcaaga ttctaagctg attcttcttg atgcttcagg tgataaagcg 1680
acaaattggc atgagcttga aagaaaaatg cgagaggagt acggaaagga aatgcgagaa 1740
ttgcaacaca tctacgaaat tgagacagct gatgaacagt cggaagatga tagggtcttg 1800
cgaatagaaa gcactggggc tcaattagac cttgacagtg ctttaccaca tctctatcat 1860
ttctgttcag tcttaacaac aaaagatttt gttgacctca ggccagactt cgtctactcc 1920
tccgaactgg gatcggaata tgttcgagca aaggtcatcc tgcctggatc ggtttctaaa 1980
cccctgcgag tccatgaaag ccgcggatcg tggttgagcg agaggtcggc tgcaaaagat 2040
gcagcgtttg aggcgtattc cgcattatac aggggggct tagtgaatga taacctactg 2100
cccctgatgg tgcacgacaa agtcatcgat gagttgactt caaagcccgt ggatactcgc 2160

```
gcgtctcttc tggaggtgaa ggaaagatta aatccatgga ttgacattgc tagagcatgg   2220
aaagaggcag aacaccatgc tggaattgtt cgcacatcgg taatgatctt caatgggatg   2280
aagctggaac tctgtcttcc aattgatcca ccggcaatac cccattaaa gctttattgg    2340
gatgctgaca ccgagttctt tgttgacttt acaaacgata tcgagatcgg caccagcgag   2400
aatatgttgg cacaggcgtt gaacgatacc aatctactat tatcagatcg tggtcgtaaa   2460
gttcacatcc agtcacgtcg aacagttgtg caatttatct tgcttcaaga ttcgggctcg   2520
ctcagttcag attgttttcc ggttgacccc aacggtaata ttaaaagtac aggttttatc   2580
agagaagtcg gtaaactaga atcgccctac atctttgaaa aatggttgcc caatgcacca   2640
gaagacgtcc catatctagc tgtggttaaa gtaagtcgcc gtgcagactt tttgcacaag   2700
gtacagaacg aaaaaccctc gtcattcact aaacaattct cgtctgttct acctgcctcg   2760
acatgtgtac aggatgtaat gcccgcacag ttgtctcggt tcggcatgat gattccttcc   2820
atcacacacc acattgaggt gcaactcgtt gtagaccgac tatccaggac catcctcaag   2880
gatctcgaaa ttagtgacca gagtcttatt cagaccgcca tcacacatgc cagttattcg   2940
ttagactcga attatcagcg tctcgaattt ctgggcgact caattctcaa attgtgtaca   3000
tcggtacaat tggtggcaga gcatctagat tggcacgaag gatatttgtc ggctatgaag   3060
gatcgtatcg tgtccaattc acggtcatca agagcggcgg ctgaagtcgg tttggatgag   3120
tatataatga ccaagaaatt cacaggtgca aaatggcgac caatgtacgt ggatgatctg   3180
gtcgtcacag aacaaaaaac aagagaaatg tcctccaaaa ttctttccga cgttgtggaa   3240
gcactcatcg gcgcatctct ccggcccgtc gagcaaatcc tcgcatatac cttcaccaaa   3300
aaatctctcc tcgtcgaagc catgacgcac ccctcttaca ccagcggcac gcaatccctc   3360
gagcgactcg agttcctcgg cgattccatt ctcgacaaca tcatcgtcac agccatgtgg   3420
tcgcactcga cgccgctctc ccacttccac atgcatctcc tgcgctctgc gctcgtcaac   3480
gccgatttcc tcgcctttct ctgcatggaa atgagcatcg accaaaacgt caccaatctg   3540
accgaaggaa aaaaccatcg catccacgaa acccactcgc gacgccgcgt ttccctcgtc   3600
agttttctcc gtcactcaag cgttcgtctc tctatctatc aaaaagaagc gctttctcgc   3660
catgcagaat tgcgcgatca gatcctcgag gcaatataca ccggtgatac attcccctgg   3720
gctctattat cccgattgga cgcgcggaaa tttttctccg atatgattga gagtttgctg   3780
ggcgcggtat ggattgatag cggctcgatg gaagtgtgca cgcagctgat cgaaagaatg   3840
ggcgtcctga gatacatgcg acggattttg aaagatggcg tgcgcatcat gcatccgaag   3900
gaggaactgg gcatcgtggc cgattctgaa aacgtcaggt acgttttgcg gcgggagaag   3960
atgggtgggg atgctaccga ggtaaatgcg gacgcggatg aagaggtacg cacggagtac   4020
cggtgcacag tatttgtggg cggggaggaa attgtagagg tgaggggtgg agcgaggaaa   4080
gaggagattc aggcaagggc tgcggagcag gcggtgcgga ttttgaaggc gaggggtcat   4140
gagaagagga atgggggtgc gggggagggg aaaaagagaa aatcgctgga tgaatag      4197
```

<210> SEQ ID NO 4
<211> LENGTH: 1398
<212> TYPE: PRT
<213> ORGANISM: Botrytis cinerea

<400> SEQUENCE: 4

```
Met Glu Tyr Thr Ser Glu Pro Asp Thr Asp Pro Asp Thr Arg Gly Ser
1               5                   10                  15
```

-continued

Leu Ile Asp Gly Arg Asp Gly Ile Glu Gly Asp Leu Ile Ala Leu Thr
            20                  25                  30

Ser Gly Glu Arg Leu Asn Glu Thr Val Glu Asp Leu Cys Ser Asp Ser
        35                  40                  45

Ser Gly Leu Ile Val Glu Asn Glu Asp Asp Asn Ser Ala Gly Glu
    50                  55                  60

Lys Gly Glu Ile Val Ile Val Thr Pro Arg Thr Tyr Gln Leu Glu Met
65                      70                  75                  80

Leu Glu Glu Ser Leu Lys Arg Asn Val Ile Val Ala Met Asp Thr Gly
                85                  90                  95

Ser Gly Lys Thr His Val Ala Val Leu Arg Ile Leu Ala Glu Leu Glu
            100                 105                 110

Arg Met Lys Pro Gly Lys Ile Ile Trp Phe Leu Ala Pro Thr Val Ala
            115                 120                 125

Leu Cys Ala Gln His His Glu Tyr Leu Gln Leu Asn Ile Pro Ser Val
        130                 135                 140

Leu Ile Lys Met Leu Ile Gly Ala Asp Gly Val Asp Arg Trp Thr Glu
145                 150                 155                 160

Gln Arg Gln Trp Asp Thr Val Leu Lys Asp Val Lys Val Val Ser
            165                 170                 175

Ser Tyr Gln Val Leu Leu Asp Ala Leu Thr His Gly Phe Val Arg Met
        180                 185                 190

Gly Arg Leu Ser Leu Ile Ile Phe Asp Glu Ala His Asn Cys Val Asn
            195                 200                 205

Lys Ala Pro Gly Ala Lys Ile Met Lys Ser Phe Tyr His Pro Tyr Lys
        210                 215                 220

Ser Ile Phe Pro Leu Pro His Ile Leu Gly Leu Ser Ala Ser Pro Val
225                 230                 235                 240

Met Arg Ser Ser Pro Gln Ser Leu Ser Asp Ile Glu Glu Thr Leu Asp
            245                 250                 255

Ala Ile Cys Cys Thr Pro Lys Ile His Arg Ala Asp Leu Arg Leu Arg
            260                 265                 270

Val Lys Leu Pro Leu Leu Ser Ile Ile Tyr Tyr Thr Pro Glu Ser Asn
        275                 280                 285

Ile Ile Val Thr Lys Thr Val Ala Ser Leu Arg Lys Ile Val Gln Ser
        290                 295                 300

Leu Asn Ile Phe Glu Asp Pro Tyr Val Leu Thr Leu Lys Arg Ser Asp
305                 310                 315                 320

Ser Glu Lys Ser Gln Arg Glu Leu Ala Lys Val Leu Lys Ser Phe Lys
            325                 330                 335

Thr Tyr Ser Gln Thr Gln Leu Lys Ser Ile Asp Lys Thr Ser Asn Glu
        340                 345                 350

Ile Ile Leu Val Glu Leu Gly Pro Trp Ala Ala Asp Tyr Tyr Ile Ser
        355                 360                 365

Thr Val Val Thr Arg Tyr Leu Lys Ala Met Ser Ala Lys Asp Thr Phe
        370                 375                 380

Ile Val Glu Asp Ser Pro Ala Ala Glu Lys Leu Tyr Ile Ala Lys Ala
385                 390                 395                 400

Leu Arg Gln Val Glu Ile Ser Pro Ser Thr Leu Ser Asp Thr Gly Lys
            405                 410                 415

Ile Ser Asn Lys Val Glu Lys Leu Leu Gly Ile Ala Gln Gln Lys
        420                 425                 430

-continued

```
Pro Pro Phe Ser Ala Ile Ile Phe Val Gln Glu Arg Ala Thr Val Ser
        435                 440                 445

Val Leu Ala His Leu Leu Ser His His Pro Leu Thr Lys Asp Arg Phe
450                 455                 460

Lys Ile Gly Thr Met Val Gly Thr Ser Leu Asn Gly Lys Arg Thr Asp
465                 470                 475                 480

Gln Ile Gly Glu Leu Val Asp Val Asn Gln Gln Lys Asp Thr Leu Ser
                485                 490                 495

Ser Phe Lys Arg Gly Lys Ile Asp Leu Ile Ala Thr Asn Val Leu
                500                 505                 510

Glu Glu Gly Ile Asp Val Pro Ala Cys Asn Leu Val Ile Cys Phe Ser
                515                 520                 525

Lys Pro Ala Asn Leu Lys Ser Phe Val Gln Arg Arg Gly Arg Ala Arg
530                 535                 540

Gln Gln Asp Ser Lys Leu Ile Leu Leu Asp Ala Ser Gly Asp Lys Ala
545                 550                 555                 560

Thr Asn Trp His Glu Leu Glu Arg Lys Met Arg Glu Glu Tyr Gly Lys
                565                 570                 575

Glu Met Arg Glu Leu Gln His Ile Tyr Glu Ile Glu Thr Ala Asp Glu
                580                 585                 590

Gln Ser Glu Asp Asp Arg Val Leu Arg Ile Glu Ser Thr Gly Ala Gln
                595                 600                 605

Leu Asp Leu Asp Ser Ala Leu Pro His Leu Tyr His Phe Cys Ser Val
                610                 615                 620

Leu Thr Thr Lys Asp Phe Val Asp Leu Arg Pro Asp Phe Val Tyr Ser
625                 630                 635                 640

Ser Glu Leu Gly Ser Glu Tyr Val Arg Ala Lys Val Ile Leu Pro Gly
                645                 650                 655

Ser Val Ser Lys Pro Leu Arg Val His Glu Ser Arg Gly Ser Trp Leu
                660                 665                 670

Ser Glu Arg Ser Ala Ala Lys Asp Ala Ala Phe Glu Ala Tyr Ser Ala
                675                 680                 685

Leu Tyr Arg Gly Gly Leu Val Asn Asp Asn Leu Leu Pro Leu Met Val
                690                 695                 700

His Asp Lys Val Ile Asp Glu Leu Thr Ser Lys Pro Val Asp Thr Arg
705                 710                 715                 720

Ala Ser Leu Leu Glu Val Lys Glu Arg Leu Asn Pro Trp Ile Asp Ile
                725                 730                 735

Ala Arg Ala Trp Lys Glu Ala Glu His His Ala Gly Ile Val Arg Thr
                740                 745                 750

Ser Val Met Ile Phe Asn Gly Met Lys Leu Glu Leu Cys Leu Pro Ile
                755                 760                 765

Asp Pro Pro Ala Ile Pro Pro Leu Lys Leu Tyr Trp Asp Ala Asp Thr
                770                 775                 780

Glu Phe Phe Val Asp Phe Thr Asn Asp Ile Glu Ile Gly Thr Ser Glu
785                 790                 795                 800

Asn Met Leu Ala Gln Ala Leu Asn Asp Thr Asn Leu Leu Ser Asp
                805                 810                 815

Arg Gly Arg Lys Val His Ile Gln Ser Arg Arg Thr Val Val Gln Phe
                820                 825                 830

Ile Leu Leu Gln Asp Ser Gly Ser Leu Ser Ser Asp Cys Phe Pro Val
                835                 840                 845

Asp Pro Asn Gly Asn Ile Lys Ser Thr Gly Phe Ile Arg Glu Val Gly
```

```
            850                 855                 860
Lys Leu Glu Ser Pro Tyr Ile Phe Glu Lys Trp Leu Pro Asn Ala Pro
865                 870                 875                 880

Glu Asp Val Pro Tyr Leu Ala Val Val Lys Val Ser Arg Arg Ala Asp
                885                 890                 895

Phe Leu His Lys Val Gln Asn Glu Lys Pro Ser Ser Phe Thr Lys Gln
                900                 905                 910

Phe Ser Ser Val Leu Pro Ala Ser Thr Cys Val Gln Asp Val Met Pro
            915                 920                 925

Ala Gln Leu Ser Arg Phe Gly Met Met Ile Pro Ser Ile Thr His His
        930                 935                 940

Ile Glu Val Gln Leu Val Val Asp Arg Leu Ser Arg Thr Ile Leu Lys
945                 950                 955                 960

Asp Leu Glu Ile Ser Asp Gln Ser Leu Ile Gln Thr Ala Ile Thr His
                965                 970                 975

Ala Ser Tyr Ser Leu Asp Ser Asn Tyr Gln Arg Leu Glu Phe Leu Gly
            980                 985                 990

Asp Ser Ile Leu Lys Leu Cys Thr Ser Val Gln Leu Val Ala Glu His
            995                 1000                1005

Leu Asp Trp His Glu Gly Tyr Leu Ser Ala Met Lys Asp Arg Ile
    1010                1015                1020

Val Ser Asn Ser Arg Ser Arg Ala Ala Ala Glu Val Gly Leu
    1025                1030                1035

Asp Glu Tyr Ile Met Thr Lys Lys Phe Thr Gly Ala Lys Trp Arg
    1040                1045                1050

Pro Met Tyr Val Asp Asp Leu Val Val Thr Glu Gln Lys Thr Arg
    1055                1060                1065

Glu Met Ser Ser Lys Ile Leu Ser Asp Val Val Glu Ala Leu Ile
    1070                1075                1080

Gly Ala Ser Leu Arg Pro Val Glu Gln Ile Leu Ala Tyr Thr Phe
    1085                1090                1095

Thr Lys Lys Ser Leu Leu Val Glu Ala Met Thr His Pro Ser Tyr
    1100                1105                1110

Thr Ser Gly Thr Gln Ser Leu Glu Arg Leu Glu Phe Leu Gly Asp
    1115                1120                1125

Ser Ile Leu Asp Asn Ile Ile Val Thr Ala Met Trp Ser His Ser
    1130                1135                1140

Thr Pro Leu Ser His Phe His Met His Leu Leu Arg Ser Ala Leu
    1145                1150                1155

Val Asn Ala Asp Phe Leu Ala Phe Leu Cys Met Glu Met Ser Ile
    1160                1165                1170

Asp Gln Asn Val Thr Asn Leu Thr Glu Gly Lys Asn His Arg Ile
    1175                1180                1185

His Glu Thr His Ser Arg Arg Val Ser Leu Val Ser Phe Leu
    1190                1195                1200

Arg His Ser Ser Val Arg Leu Ser Ile Tyr Gln Lys Glu Ala Leu
    1205                1210                1215

Ser Arg His Ala Glu Leu Arg Asp Gln Ile Leu Glu Ala Ile Tyr
    1220                1225                1230

Thr Gly Asp Thr Phe Pro Trp Ala Leu Leu Ser Arg Leu Asp Ala
    1235                1240                1245

Arg Lys Phe Phe Ser Asp Met Ile Glu Ser Leu Leu Gly Ala Val
    1250                1255                1260
```

```
Trp Ile Asp Ser Gly Ser Met Glu Val Cys Thr Gln Leu Ile Glu
    1265                1270                1275

Arg Met Gly Val Leu Arg Tyr Met Arg Ile Leu Lys Asp Gly
    1280                1285                1290

Val Arg Ile Met His Pro Lys Glu Glu Leu Gly Ile Val Ala Asp
    1295                1300                1305

Ser Glu Asn Val Arg Tyr Val Leu Arg Arg Glu Lys Met Gly Gly
    1310                1315                1320

Asp Ala Thr Glu Val Asn Ala Asp Ala Asp Glu Val Arg Thr
    1325                1330                1335

Glu Tyr Arg Cys Thr Val Phe Val Gly Gly Glu Ile Val Glu
    1340                1345                1350

Val Arg Gly Gly Ala Arg Lys Glu Glu Ile Gln Ala Arg Ala Ala
    1355                1360                1365

Glu Gln Ala Val Arg Ile Leu Lys Ala Arg Gly His Glu Lys Arg
    1370                1375                1380

Asn Gly Gly Ala Gly Glu Gly Lys Lys Arg Lys Ser Leu Asp Glu
    1385                1390                1395
```

<210> SEQ ID NO 5
<211> LENGTH: 4692
<212> TYPE: DNA
<213> ORGANISM: Verticillium dahilae

<400> SEQUENCE: 5

```
atgacgactg acgagctctc tgttggtctg gacgccaccg gcatctcaat cctcgcagat      60
ggaccggaaa acatatcgtc cagcacatca acatctacga ctggaaagga agatggatac    120
ctctgtatca acagattcac tcagaatacc gccacgaccc aggacaacca gagccgagat    180
tctgacgacg atgaggatga ctgcggcagc cacgatgaag ctgacgaaga ttcagacgaa    240
agacagtaca gcatgacccc agaaaggcct cataaaatta ccgagaagaa gcgcgcagat    300
catgctgcct ttcacgactg gcttcagagc aactccagcg agattgctca gtcaaccccT    360
cagccggctc aaaacctcaa ccacacctcc acggccctga tggtacgcga gagtgagaat    420
cgtaagatca tcgaaaatcc tcgggagtat cagattgagc tcttcgagcg ggcgaagcga    480
aagaacatca ttgccgtgtt acccactgga tcaggaaaga ccttaatcgc agcccttctt    540
ctgcgacaca ccctcgaaca agaaaccgcg gatcgacgcg cgggcaagcc caagagaatc    600
gccttttttcc tcgtggaaaa ggttgctctt gccctccaac agcacgcggt tctggagtgc    660
aatctggaat ttcccattga ccgggtatgc ggtgacatgg tacggtcgga ctggatcaag    720
gagtcatgga tgaaaagatg ggatgacaac atggtcatgg tctgcaccgc cgccatcctt    780
cagcaatgcc ttgccagatc attcatccgc atggatcaga tcaacctgct tgtcttcgat    840
gaagcacatc acgccaaggg aaatcatccg tacgcccgga tcatcaagga ctactacatt    900
acggaacctg acaagaaaag cgcccccaag atcttcggca tgactgcctc tccggtggat    960
gccctcaccg acgtcaagat tgctgccgct caactcgaag gtttgttgca tagtgagatt   1020
gcgacaatcg aggaggactc tgtatcattc aaacaaatcc agaaagaggt cgtcgaacaa   1080
gactgcaagt accctgccct cgaaccaccc ttcaccacca atcttcataa gaagatccaa   1140
gaacaggtgc gctacaacaa gaacttcgca aaggcgctga gcaattcttt agaaatgtcg   1200
agctcccttg gcagctggtg tgtcgatcgc ttctggcaga tatttctgac cgaagaaacc   1260
ctcgcgagat tggcagcgca aactgcacaa gacaacattt ttgccgatcg cgccgaaaag   1320
```

-continued

```
gagcgcgttg ccattgagga ggtccgcaac atcatcaagc aacatcagtt cctcccaatc    1380
accaaaaccc tgcaagactt gtcgtccaaa gtgctgtgcc tcctcggcca actggaattg    1440
cgcttcagtg cccctaccga tcacaagtgc atcatcttcg tggagaaacg aaacacagcc    1500
atgattctgg ctcacctcct ctccttgcct ggtattggac ctctatatct gaaaccggct    1560
gcgcttgtcg ggaacccatc tgacaacagc cctcttgcca tgtcgtacaa agagcaagtg    1620
atgacaataa caaagttcag acgtggtgaa tacaactgtc ttctcgccac ttctgtggcc    1680
gaggagggca ttgacatcgc agactgcaac attgtcattc gattcgatct tttcaactcg    1740
gtgattcagt acatacaatc caaaggccgc gctcggcact tgaactcgga gtatatttgc    1800
atggccgagc taggcaacgg caagcataca agggcgaaga tacaagcaaa ttatgacctc    1860
tccctcatcc gccaattctg cagcacactg ccagaagacc gcaagatcgt gggctgggac    1920
cccgaggcag ctcttcacca tggcgagcgc gaccataagt tccacatcgt tccatccacc    1980
ggggccaaac tcacctggac cggcagcctc gtggttctgt caaattttgc ctcttctcta    2040
caggtgaacg acgaaacact aagtccttcc tatatggtct ctctcatcgg tagcgagtac    2100
atctgcgagg tccagcttcc gagcaagtct cccattttga gcgtgtcagg cacgctccaa    2160
aagaacaaag cagaggccag gtgctccgca gcgtttgaga tgtgcatgaa gctcatcaaa    2220
ggtgggttca tcagcagtca ccttcagccg acgtttacca ggaagctccc ggccatgcga    2280
aacgcacgcc tagccatcag ctccaagaag cgtgaacggt acaatatgag ggtcaagcca    2340
gaggtatggt cacggcgtgg accggcatcc tctctgttcc tcacagtcct gaagcttcgt    2400
acacctggtg cattgaacag accatcacag ccactcgccc tcctcacacg agaggcactg    2460
ccagagcttc caggagttcc gctatttttc ggtaactgtg gtcggtccat agcggaggta    2520
gtatctgtgg cgaaacccat gcacttggat gaagtacgtc tagacagcct cagagtattc    2580
accctgcgca ttttcaaaga tgtcttcagc aaggtatacg attctcaagt cgcagacctt    2640
ccatacttcc tggcacctgc tgctcatgac cacagtcatg agttctcacc gaatgaagac    2700
ccagggtcac tgatcgactg gagccatctg ctgtcgacca agagggttga gtacttgcct    2760
tgggatgaag atcacagtcc cagcttctat caaagcaagt tgtgattga tccatacacg    2820
ggatcgcgca agctgtttct cagaggtatt cggacagatc tcaagccgac cgacttggtt    2880
ccagatggag ttcccgaacc cacattcagg ctctggaagg acgttgagca taccataaag    2940
gaatacagca tcagcctctg ggcaaagagt cgagcccgga gagctggcga atggttggac    3000
actcaacccg tggtagaagc cgagttggtc tcgctgcgcc ggaatcttct cgacgaattt    3060
gccgattcca agcatgaagg gtctagggtc tgttatgtga ttctccagcc gctacagatc    3120
tcaacactcc ctgtcgaggt cgtcgctatg gcctacaact ttcccgccat catccatcgg    3180
attgaatcga atatgatcgc ccttgacgcc tgccgtatgt tgaaccttcg agttcgtccc    3240
gacctggctc tcgaggcgat gaccaaagat tcaagcaaca gtgaagagca cgatcaggaa    3300
aagattgatt ccaggccgg catgggcaat aattatgagc gactcgagtt tctcggagac    3360
tgctttctca aaatggcaac caccatcgca cttttactc ggatccctga cagcaacgag    3420
tttgagtgtc acgtcgagcg aatgcttctt atttgcaacc agaatctgtt caatgtcgca    3480
ttaaagaaga acttgcaaga gtacattcga tcaaagcaat tcgatcgacg cagttggtac    3540
ccccagggtc tgaagcagaa ggcgggcaaa gccaaggag cacaaaactc acactcattg    3600
gccgacaagt ctattgctga tgtatgcgag gccatcattg gcgcctcata tttgtcgtac    3660
```

```
actgacgagg gcaactttga catggccgta cgcgctgtga cggccgtcgt gaggaacaaa    3720
aatcacgaca tgaaatcata cgaggactat tacaaagcat ttaagatgcc gatctggcaa    3780
gcggcggagc caagtgctgt gcagatggaa gcgtctttac agattaaaga gcagatggga    3840
tatgagttca agtctcctgc cctgctgcgg agtgccttca agcacccgtc ctaccccgt    3900 cagtttgaga gcgtgcccaa ttatcagcgc ctcgagttcc tcggtgacgc gcttctagac    3960
atggtctgcg tagactttct cttcaggaag tttcccgacg ccgatcctca atggctcact    4020
gaacacaaga tggccatggt ttcgaaccac ttcctcggaa gtctgagtgt agagttgggc    4080
ttctaccggc gtgtccttca ctttaacagc atcatggcca atcaaatcaa ggactacgtc    4140
gacgcactta ctcatgcacg ccaagaagcc gaagcggtgg cccagatctc tggcacagtc    4200
tcgcgagatt actggctcaa cgtgaagcac ccccccaaat tcctctcaga cgtggtcgag    4260
gcatacatcg gtgctatttt cgttgattca ggatacgatt atggccaggt acaggcgttc    4320
ttcgagaagc atatccggcc tttcttcgca gacatggcgc tatatgattc ctttgccagc    4380
agccaccctg tcacaacgct ggcgcgtatg atgcagcagg actttggctg ccaggactgg    4440
cggcttcttg taagtgaact gccgccgagc tgcgaagacg gcggggcagc tgcgatcact    4500
gagacggaag tgatttgtgg gttcatggtc cacggaagaa tcctgctaca tgccaagtcg    4560
tcgagtggac ggtacgccaa agtgggtgct gcaagagag cggtcgagaa gctcatgggt    4620
ctcggcaacg acaagaggt cttcggacg gacttcggct gtgactgtga ctgtgaaggt    4680
caagcaatct ag                                                       4692
```

<210> SEQ ID NO 6
<211> LENGTH: 1563
<212> TYPE: PRT
<213> ORGANISM: Verticillium dahilae

<400> SEQUENCE: 6

```
Met Thr Thr Asp Glu Leu Ser Val Gly Leu Asp Ala Thr Gly Ile Ser
1               5                   10                  15

Ile Leu Ala Asp Gly Pro Glu Asn Ile Ser Ser Ser Thr Ser Thr Ser
            20                  25                  30

Thr Thr Gly Lys Glu Asp Gly Tyr Leu Cys Ile Asn Arg Phe Thr Gln
        35                  40                  45

Asn Thr Ala Thr Thr Gln Asp Asn Gln Ser Arg Asp Ser Asp Asp Asp
    50                  55                  60

Glu Asp Asp Cys Gly Ser His Asp Glu Ala Asp Glu Asp Ser Asp Glu
65                  70                  75                  80

Arg Gln Tyr Ser Met Thr Pro Glu Arg Pro His Lys Ile Thr Glu Lys
                85                  90                  95

Lys Arg Ala Asp His Ala Ala Phe His Asp Trp Leu Gln Ser Asn Ser
            100                 105                 110

Ser Glu Ile Ala Gln Ser Thr Pro Gln Pro Ala Gln Asn Leu Asn His
        115                 120                 125

Thr Ser Thr Ala Leu Met Val Arg Glu Ser Glu Asn Arg Lys Ile Ile
    130                 135                 140

Glu Asn Pro Arg Glu Tyr Gln Ile Glu Leu Phe Glu Arg Ala Lys Arg
145                 150                 155                 160

Lys Asn Ile Ile Ala Val Leu Pro Thr Gly Ser Gly Lys Thr Leu Ile
                165                 170                 175

Ala Ala Leu Leu Leu Arg His Thr Leu Glu Gln Glu Thr Ala Asp Arg
            180                 185                 190
```

-continued

Arg Ala Gly Lys Pro Lys Arg Ile Ala Phe Phe Leu Val Glu Lys Val
        195                 200                 205

Ala Leu Ala Leu Gln Gln His Ala Val Leu Glu Cys Asn Leu Glu Phe
    210                 215                 220

Pro Ile Asp Arg Val Cys Gly Asp Met Val Arg Ser Asp Trp Ile Lys
225                 230                 235                 240

Glu Ser Trp Met Lys Arg Trp Asp Asp Asn Met Val Met Val Cys Thr
                245                 250                 255

Ala Ala Ile Leu Gln Gln Cys Leu Ala Arg Ser Phe Ile Arg Met Asp
            260                 265                 270

Gln Ile Asn Leu Leu Val Phe Asp Glu Ala His His Ala Lys Gly Asn
        275                 280                 285

His Pro Tyr Ala Arg Ile Ile Lys Asp Tyr Tyr Ile Thr Glu Pro Asp
    290                 295                 300

Lys Glu Arg Arg Pro Lys Ile Phe Gly Met Thr Ala Ser Pro Val Asp
305                 310                 315                 320

Ala Leu Thr Asp Val Lys Ile Ala Ala Gln Leu Glu Gly Leu Leu
                325                 330                 335

His Ser Glu Ile Ala Thr Ile Glu Glu Asp Ser Val Ser Phe Lys Gln
            340                 345                 350

Ile Gln Lys Glu Val Val Glu Gln Asp Cys Lys Tyr Pro Ala Leu Glu
        355                 360                 365

Pro Pro Phe Thr Thr Asn Leu His Lys Lys Ile Gln Glu Gln Val Arg
    370                 375                 380

Tyr Asn Lys Asn Phe Ala Lys Ala Leu Ser Asn Ser Leu Glu Met Ser
385                 390                 395                 400

Ser Ser Leu Gly Ser Trp Cys Val Asp Arg Phe Trp Gln Ile Phe Leu
                405                 410                 415

Thr Glu Glu Thr Leu Ala Arg Leu Ala Ala Gln Thr Ala Gln Asp Asn
            420                 425                 430

Ile Phe Ala Asp Arg Ala Glu Lys Glu Arg Val Ala Ile Glu Glu Val
        435                 440                 445

Arg Asn Ile Ile Lys Gln His Gln Phe Leu Pro Ile Thr Lys Thr Leu
    450                 455                 460

Gln Asp Leu Ser Ser Lys Val Leu Cys Leu Leu Gly Gln Leu Glu Leu
465                 470                 475                 480

Arg Phe Ser Ala Pro Thr Asp His Lys Cys Ile Ile Phe Val Glu Lys
                485                 490                 495

Arg Asn Thr Ala Met Ile Leu Ala His Leu Leu Ser Leu Pro Gly Ile
            500                 505                 510

Gly Pro Leu Tyr Leu Lys Pro Ala Ala Leu Val Gly Asn Pro Ser Asp
        515                 520                 525

Asn Ser Pro Leu Ala Met Ser Tyr Lys Glu Gln Val Met Thr Ile Thr
    530                 535                 540

Lys Phe Arg Arg Gly Glu Tyr Asn Cys Leu Leu Ala Thr Ser Val Ala
545                 550                 555                 560

Glu Glu Gly Ile Asp Ile Ala Asp Cys Asn Ile Val Ile Arg Phe Asp
                565                 570                 575

Leu Phe Asn Ser Val Ile Gln Tyr Ile Gln Ser Lys Gly Arg Ala Arg
            580                 585                 590

His Leu Asn Ser Glu Tyr Ile Cys Met Ala Glu Leu Gly Asn Gly Lys
        595                 600                 605

```
His Thr Arg Ala Lys Ile Gln Ala Asn Tyr Asp Leu Ser Leu Ile Arg
    610                 615                 620

Gln Phe Cys Ser Thr Leu Pro Glu Asp Arg Lys Ile Val Gly Trp Asp
625                 630                 635                 640

Pro Glu Ala Ala Leu His His Gly Arg Asp His Lys Phe His Ile
                    645                 650                 655

Val Pro Ser Thr Gly Ala Lys Leu Thr Trp Thr Gly Ser Leu Val Val
            660                 665                 670

Leu Ser Asn Phe Ala Ser Ser Leu Gln Val Asn Asp Glu Thr Leu Ser
        675                 680                 685

Pro Ser Tyr Met Val Ser Leu Ile Gly Ser Glu Tyr Ile Cys Glu Val
690                 695                 700

Gln Leu Pro Ser Lys Ser Pro Ile Leu Ser Val Ser Gly Thr Leu Gln
705                 710                 715                 720

Lys Asn Lys Ala Glu Ala Arg Cys Ser Ala Ala Phe Glu Met Cys Met
                    725                 730                 735

Lys Leu Ile Lys Gly Gly Phe Ile Ser Ser His Leu Gln Pro Thr Phe
            740                 745                 750

Thr Arg Lys Leu Pro Ala Met Arg Asn Ala Arg Leu Ala Ile Ser Ser
        755                 760                 765

Lys Lys Arg Glu Arg Tyr Asn Met Arg Val Lys Pro Glu Val Trp Ser
770                 775                 780

Arg Arg Gly Pro Ala Ser Ser Leu Phe Leu Thr Val Leu Lys Leu Arg
785                 790                 795                 800

Thr Pro Gly Ala Leu Asn Arg Pro Ser Gln Pro Leu Ala Leu Leu Thr
                    805                 810                 815

Arg Glu Ala Leu Pro Glu Leu Pro Gly Val Pro Leu Phe Phe Gly Asn
            820                 825                 830

Cys Gly Arg Ser Ile Ala Glu Val Val Ser Val Ala Lys Pro Met His
        835                 840                 845

Leu Asp Glu Val Arg Leu Asp Ser Leu Arg Val Phe Thr Leu Arg Ile
850                 855                 860

Phe Lys Asp Val Phe Ser Lys Val Tyr Asp Ser Gln Val Ala Asp Leu
865                 870                 875                 880

Pro Tyr Phe Leu Ala Pro Ala Ala His Asp His Ser His Glu Phe Ser
                    885                 890                 895

Pro Asn Glu Asp Pro Gly Ser Leu Ile Asp Trp Ser His Leu Leu Ser
            900                 905                 910

Thr Lys Glu Val Glu Tyr Leu Pro Trp Asp Glu Asp His Ser Pro Ser
        915                 920                 925

Phe Tyr Gln Ser Lys Phe Val Ile Asp Pro Tyr Thr Gly Ser Arg Lys
930                 935                 940

Leu Phe Leu Arg Gly Ile Arg Thr Asp Leu Lys Pro Thr Asp Leu Val
945                 950                 955                 960

Pro Asp Gly Val Pro Glu Pro Thr Phe Arg Leu Trp Lys Asp Val Glu
                    965                 970                 975

His Thr Ile Lys Glu Tyr Ser Ile Ser Leu Trp Ala Lys Ser Arg Ala
            980                 985                 990

Arg Arg Ala Gly Glu Trp Leu Asp  Thr Gln Pro Val Val  Glu Ala Glu
        995                 1000                 1005

Leu Val  Ser Leu Arg Arg Asn  Leu Leu Asp Glu Phe  Ala Asp Ser
    1010                 1015                 1020

Lys His  Glu Gly Ser Arg Val  Cys Tyr Val Ile Leu  Gln Pro Leu
```

```
            1025                1030                1035
Gln Ile Ser Thr Leu Pro Val Glu Val Val Ala Met Ala Tyr Asn
        1040                1045                1050
Phe Pro Ala Ile Ile His Arg Ile Glu Ser Asn Met Ile Ala Leu
        1055                1060                1065
Asp Ala Cys Arg Met Leu Asn Leu Arg Val Arg Pro Asp Leu Ala
        1070                1075                1080
Leu Glu Ala Met Thr Lys Asp Ser Ser Asn Ser Glu Glu His Asp
        1085                1090                1095
Gln Glu Lys Ile Asp Phe Gln Ala Gly Met Gly Asn Asn Tyr Glu
        1100                1105                1110
Arg Leu Glu Phe Leu Gly Asp Cys Phe Leu Lys Met Ala Thr Thr
        1115                1120                1125
Ile Ala Leu Phe Thr Arg Ile Pro Asp Ser Asn Glu Phe Glu Cys
        1130                1135                1140
His Val Glu Arg Met Leu Leu Ile Cys Asn Gln Asn Leu Phe Asn
        1145                1150                1155
Val Ala Leu Lys Lys Asn Leu Gln Glu Tyr Ile Arg Ser Lys Gln
        1160                1165                1170
Phe Asp Arg Arg Ser Trp Tyr Pro Gln Gly Leu Lys Gln Lys Ala
        1175                1180                1185
Gly Lys Ala Gln Gly Ala Gln Asn Ser His Ser Leu Ala Asp Lys
        1190                1195                1200
Ser Ile Ala Asp Val Cys Glu Ala Ile Ile Gly Ala Ser Tyr Leu
        1205                1210                1215
Ser Tyr Thr Asp Glu Gly Asn Phe Asp Met Ala Val Arg Ala Val
        1220                1225                1230
Thr Ala Val Val Arg Asn Lys Asn His Asp Met Lys Ser Tyr Glu
        1235                1240                1245
Asp Tyr Tyr Lys Ala Phe Lys Met Pro Ile Trp Gln Ala Ala Glu
        1250                1255                1260
Pro Ser Ala Val Gln Met Glu Ala Ser Leu Gln Ile Lys Glu Gln
        1265                1270                1275
Met Gly Tyr Glu Phe Lys Ser Pro Ala Leu Leu Arg Ser Ala Phe
        1280                1285                1290
Lys His Pro Ser Tyr Pro Arg Gln Phe Glu Ser Val Pro Asn Tyr
        1295                1300                1305
Gln Arg Leu Glu Phe Leu Gly Asp Ala Leu Leu Asp Met Val Cys
        1310                1315                1320
Val Asp Phe Leu Phe Arg Lys Phe Pro Asp Ala Asp Pro Gln Trp
        1325                1330                1335
Leu Thr Glu His Lys Met Ala Met Val Ser Asn His Phe Leu Gly
        1340                1345                1350
Ser Leu Ser Val Glu Leu Gly Phe Tyr Arg Arg Val Leu His Phe
        1355                1360                1365
Asn Ser Ile Met Ala Asn Gln Ile Lys Asp Tyr Val Asp Ala Leu
        1370                1375                1380
Thr His Ala Arg Gln Glu Ala Glu Ala Val Ala Gln Ile Ser Gly
        1385                1390                1395
Thr Val Ser Arg Asp Tyr Trp Leu Asn Val Lys His Pro Pro Lys
        1400                1405                1410
Phe Leu Ser Asp Val Val Glu Ala Tyr Ile Gly Ala Ile Phe Val
        1415                1420                1425
```

```
Asp Ser  Gly Tyr Asp Tyr Gly  Gln Val Gln Ala Phe  Phe Glu Lys
    1430                 1435                 1440

His Ile  Arg Pro Phe Phe Ala  Asp Met Ala Leu Tyr  Asp Ser Phe
    1445                 1450                 1455

Ala Ser  Ser His Pro Val Thr  Thr Leu Ala Arg Met  Met Gln Gln
    1460                 1465                 1470

Asp Phe  Gly Cys Gln Asp Trp  Arg Leu Leu Val Ser  Glu Leu Pro
    1475                 1480                 1485

Pro Ser  Cys Glu Asp Gly Gly  Ala Ala Ala Ile Thr  Glu Thr Glu
    1490                 1495                 1500

Val Ile  Cys Gly Phe Met Val  His Gly Arg Ile Leu  Leu His Ala
    1505                 1510                 1515

Lys Ser  Ser Ser Gly Arg Tyr  Ala Lys Val Gly Ala  Ala Lys Arg
    1520                 1525                 1530

Ala Val  Glu Lys Leu Met Gly  Leu Gly Asn Asp Lys  Glu Val Phe
    1535                 1540                 1545

Arg Thr  Asp Phe Gly Cys Asp  Cys Asp Cys Glu Gly  Gln Ala Ile
    1550                 1555                 1560
```

<210> SEQ ID NO 7
<211> LENGTH: 3593
<212> TYPE: DNA
<213> ORGANISM: Verticillium dahilae

<400> SEQUENCE: 7

```
atcactctac gggtaaaagc gctgagagaa tgatcatgat gaatttctat catccacgca     60
aacaatcggc actatctgtt ccccacgtcc tgggactgac cgcaagcccc ataatgcgat    120
ctaggctcga aggccttgag gcactggaac agacactgga ctcggtttgc gttacgccca    180
gattgcaccg agatgactta atgacccatg tcaaaaggcc caccgtctgt tatgtccatt    240
acgaaacgac agatgctaag gatgagccca agccggtcag catttcaagt cttcgcgaag    300
catgcagaaa tatggacatc aggcaagatc catacgttat ctgtctaaga gacaaaggca    360
ctgatcgagc acgacgtgag ctcatcaagg tccttacaag ccataaaaca gattcgcaac    420
agcaaatgaa gtctttcttc aatcaaagct tgcgagtcct gcgagatctc gggccctggg    480
cggccgagta ctacatttgg aaggttgtta cagattttct ggcaatcatt gaagcaagag    540
atcaccgcat gaatcaacgg aataccgaag aaaagcagta tctggccaac atccttcgac    600
aaatcagtat cagcgagccg ccagtcagca tgttgagtgc tcataacacg tcgaacaaag    660
taatggtgct catggaatac ttgtcatcta aagctaccga tggtactgtc gggatcatat    720
ttgtcaaaga gcgatcaact gcggcgatgc ttgcacacgt gattgagtcg catccactga    780
cacagaatag gcactcgagc gttggggttg ttgttggtgc ttccactcat ctggtaagga    840
agaaagacat gtgggatctg tctcgagcag cccacgagac agagcccctt cttcagttca    900
gatctggcca cctcaatttg ctcatcgcca cgagtgtgct tgaagagggc atcgacgttc    960
ctgcctgcaa cctcgtgatc tgttttgatg agcccgagaa tctcaaagcc tttgtccagc   1020
ggcgcggccg agcccggaag aaggattcta gcctcgtggt tcttctcccc gggacagacc   1080
acgtgcctca ggactgggaa agcatggaag cgacaatgag gacacactac gagagagaac   1140
agcgcgaaat acaaatcatg gagcagatcg aagcatccga gtctgcaaag tacgaagagt   1200
acgttgtcga gagtactaat gccagactcg acttcgagaa cgccaaagcg catctcagca   1260
acttttgtgg gcagctctct cccggggagt ttatagacaa gaggcccgaa tacatacccc   1320
```

```
gtgtggtaga caacggagta cctccatctc tgagggtcac ggtactgttg ccaagctatg   1380
ttccagctgc cgtccgccat gctgagagtc gtcgaagctg aagtcggag  catcaggcct   1440 caaaggatgc cgcttttcag gcatacgtgg ctctttacaa agcgggactg gtcaatgaac   1500
acatgcttcc actcacggta aaagatatcg tacccgcaaa cgaacctcga gtagcaacct   1560
tgcaggtcaa tggcctcttg aatgtctggc ttggtattgc ccaggcctgg atcacgagca   1620
ctgaaacctg gttaactcca gtgcacctcc gagacgcgac gggattgacg cgaggaacgt   1680
atatcatgag aatgccggta gcattgccgg cactgccttc cacgccggtg tacttcgatc   1740
gcgaaggacc atggcttctg gattttggcc cacaagaacg aaaggagaat cttgaaatgc   1800
ctgatcatac ttcagtgctg cttgcactcc actttggcca tcactggtct attgctcatg   1860
gtcagcagca ggttatcagc ttcgcttcac aagatggcga actgaatatc aggcaattaa   1920
gtgcacgggg tttcacaacc gcagatgccg accgagagga aatgctgtac ctggtacggg   1980
acgagtcagg atgcccgtat gtgtacgacc actttctaaa tggcaagccg tcacttgaac   2040
ttgttcaacg accttttccgg cgcatcgggg actctccagg ctttcaagac gcacccagta   2100
acatccccta cttggctctc agaaagtggc cgcggtacct ggccctcttg caccaacaga   2160
aggtcaacga tctactgcca caggcgacaa acaagaagcc atatgctagg gtttatccgg   2220
caccgtgggc gaaagtcgac acgattccat tagatcatgc ttactttggg gcgttgatcc   2280 cttcatttc  acacattgtc gaggttcgac tggttgcaga acagctttcc tcgagcctac   2340
ttcgtgacct caatttctca gatccctctc ttgtcctggc ggccattagc actaagggtt   2400
ccttggaagc cacaaactac gagcgccttg agcttttggg tgactctatc ctcaagcttt   2460
gcaccacggc caatgccgcc gctctgcatg gcttagtgtc gaactcgaga ttgtgtaggg   2520
ctgcactgga tgctggcctt gacaaatttg ttctaactga aaacttcact tgtcgcacgt   2580
ggcgccctat ctacgtcaac gacatgatgg aaaagggtgc tcgcgactca ggacccegta   2640 tcatgtcgac gaagacgctc gccgatattg tggaagcact catagggggcc gcatacattg   2700 acggtggcct cccaaaggca cttgggtgca tttcgatctt cctgaggag  ctcgattgga   2760 aaccgttgcc agcttgccag gagatccttt acagtttggc gtcccctgat gtgcctttgc   2820
cgccaatgct tgttccgctg gaggacctga tcggctacac gatgcatctc ctcaagactg   2880
cttcggtcaa cggcgatctt ctaggcttcc ttgcactcga gtgccatgcc gaggaagacg   2940
aggtgatcat tgatatcgat ttttctcctt ccgatacgga cttcaatcct caaaattccg   3000
ccggggtgga acagaagctc aaacagacac gccggaaaat cccccttggg aagtttatgc   3060
gccactcctc aatagaggtt gtgcagcagc agaccaaagc tgccagcgtt catgccgatc   3120
tccgaggaca gatcatgcac gctctggaac atgggtcaag ctaccctggg tctcttctcg   3180
cccgtttaca tcccgcaaag ttcttctccg acatggtcga agctgtactg ggtgccgtct   3240
gggtcgattc gggcgacatg ggcgcgtgca ttcgtgtggc ggaacgactg ggcattctgc   3300
ctgtgctctc ccgactggca aaggaggacg ttcatgtgct gcatccgaag caagagctgg   3360
gagagatcgc tggtccccgg acagtcaaat atctcctcac tttgcccgag gacgcagccg   3420
gcctgcaaag tgcaacaaga aaatatgcct gcaaggtcat ggtcggggat cgctgtgttg   3480
cagaggtgga tgacggggtc gctcgagatg aggttgagac aaaggctgca gaggttgcgg   3540
tacagacctt gaagaatgaa caggctgacg cgaaacaagt agcagaacac taa          3593

<210> SEQ ID NO 8
```

```
<211> LENGTH: 1187
<212> TYPE: PRT
<213> ORGANISM: Verticillium dahilae

<400> SEQUENCE: 8

Met Ile Met Met Asn Phe Tyr His Pro Arg Lys Gln Ser Ala Leu Ser
1               5                   10                  15

Val Pro His Val Leu Gly Leu Thr Ala Ser Pro Ile Met Arg Ser Arg
            20                  25                  30

Leu Glu Gly Leu Glu Ala Leu Glu Gln Thr Leu Asp Ser Val Cys Val
        35                  40                  45

Thr Pro Arg Leu His Arg Asp Asp Leu Met Thr His Val Lys Arg Pro
    50                  55                  60

Thr Val Cys Tyr Val His Tyr Glu Thr Thr Asp Ala Lys Asp Glu Pro
65                  70                  75                  80

Lys Pro Val Ser Ile Ser Ser Leu Arg Glu Ala Cys Arg Asn Met Asp
                85                  90                  95

Ile Arg Gln Asp Pro Tyr Val Ile Cys Leu Arg Asp Lys Gly Thr Asp
            100                 105                 110

Arg Ala Arg Arg Glu Leu Ile Lys Val Leu Thr Ser His Lys Thr Asp
        115                 120                 125

Ser Gln Gln Gln Met Lys Ser Phe Phe Asn Gln Ser Leu Arg Val Leu
    130                 135                 140

Arg Asp Leu Gly Pro Trp Ala Ala Glu Tyr Tyr Ile Trp Lys Val Val
145                 150                 155                 160

Thr Asp Phe Leu Ala Ile Ile Glu Ala Arg Asp His Arg Met Asn Gln
                165                 170                 175

Arg Asn Thr Glu Glu Lys Gln Tyr Leu Ala Asn Ile Leu Arg Gln Ile
            180                 185                 190

Ser Ile Ser Glu Pro Pro Val Ser Met Leu Ser Ala His Asn Thr Ser
        195                 200                 205

Asn Lys Val Met Val Leu Met Glu Tyr Leu Ser Ser Lys Ala Thr Asp
    210                 215                 220

Gly Thr Val Gly Ile Ile Phe Val Lys Glu Arg Ser Thr Ala Ala Met
225                 230                 235                 240

Leu Ala His Val Ile Glu Ser His Pro Leu Thr Gln Asn Arg His Ser
                245                 250                 255

Ser Val Gly Val Val Val Gly Ala Ser Thr His Leu Val Arg Lys Lys
            260                 265                 270

Asp Met Trp Asp Leu Ser Arg Ala Ala His Glu Thr Glu Pro Leu Leu
        275                 280                 285

Gln Phe Arg Ser Gly His Leu Asn Leu Leu Ile Ala Thr Ser Val Leu
    290                 295                 300

Glu Glu Gly Ile Asp Val Pro Ala Cys Asn Leu Val Ile Cys Phe Asp
305                 310                 315                 320

Glu Pro Glu Asn Leu Lys Ala Phe Val Gln Arg Arg Gly Arg Ala Arg
                325                 330                 335

Lys Lys Asp Ser Ser Leu Val Val Leu Leu Pro Gly Thr Asp His Val
            340                 345                 350

Pro Gln Asp Trp Glu Ser Met Glu Ala Thr Met Arg Thr His Tyr Glu
        355                 360                 365

Arg Glu Gln Arg Glu Ile Gln Ile Met Glu Gln Ile Glu Ala Ser Glu
    370                 375                 380

Ser Ala Lys Tyr Glu Glu Tyr Val Val Glu Ser Thr Asn Ala Arg Leu
```

```
            385                 390                 395                 400
Asp Phe Glu Asn Ala Lys Ala His Leu Ser Asn Phe Cys Gly Gln Leu
                    405                 410                 415

Ser Pro Gly Glu Phe Ile Asp Lys Arg Pro Glu Tyr Ile Pro Arg Val
                420                 425                 430

Val Asp Asn Gly Val Pro Pro Ser Leu Arg Val Thr Val Leu Leu Pro
            435                 440                 445

Ser Tyr Val Pro Ala Ala Val Arg His Ala Glu Ser Arg Arg Ser Trp
        450                 455                 460

Lys Ser Glu His Gln Ala Ser Lys Asp Ala Ala Phe Gln Ala Tyr Val
465                 470                 475                 480

Ala Leu Tyr Lys Ala Gly Leu Val Asn Glu His Met Leu Pro Leu Thr
                485                 490                 495

Val Lys Asp Ile Val Pro Ala Asn Glu Pro Arg Val Ala Thr Leu Gln
                500                 505                 510

Val Asn Gly Leu Leu Asn Val Trp Leu Gly Ile Ala Gln Ala Trp Ile
            515                 520                 525

Thr Ser Thr Glu Thr Trp Leu Thr Pro Val His Leu Arg Asp Ala Thr
        530                 535                 540

Gly Leu Thr Arg Gly Thr Tyr Ile Met Arg Met Pro Val Ala Leu Pro
545                 550                 555                 560

Ala Leu Pro Ser Thr Pro Val Tyr Phe Asp Arg Glu Gly Pro Trp Leu
                565                 570                 575

Leu Asp Phe Gly Pro Gln Glu Arg Lys Glu Asn Leu Glu Met Pro Asp
            580                 585                 590

His Thr Ser Val Leu Leu Ala Leu His Phe Gly His His Trp Ser Ile
        595                 600                 605

Ala His Gly Gln Gln Gln Val Ile Ser Phe Ala Ser Gln Asp Gly Glu
            610                 615                 620

Leu Asn Ile Arg Gln Leu Ser Ala Arg Gly Phe Thr Thr Ala Asp Ala
625                 630                 635                 640

Asp Arg Glu Glu Met Leu Tyr Leu Val Arg Asp Glu Ser Gly Cys Pro
                645                 650                 655

Tyr Val Tyr Asp His Phe Leu Asn Gly Lys Pro Ser Leu Glu Leu Val
                660                 665                 670

Gln Arg Pro Phe Arg Arg Ile Gly Asp Ser Pro Gly Phe Gln Asp Ala
            675                 680                 685

Pro Ser Asn Ile Pro Tyr Leu Ala Leu Arg Lys Trp Pro Arg Tyr Leu
        690                 695                 700

Ala Leu Leu His Gln Gln Lys Val Asn Asp Leu Leu Pro Gln Ala Thr
705                 710                 715                 720

Asn Lys Lys Pro Tyr Ala Arg Val Tyr Pro Ala Pro Trp Ala Lys Val
                725                 730                 735

Asp Thr Ile Pro Leu Asp His Ala Tyr Phe Gly Ala Leu Ile Pro Phe
                740                 745                 750

Ile Ser His Ile Val Glu Val Arg Leu Val Ala Glu Gln Leu Ser Ser
            755                 760                 765

Ser Leu Leu Arg Asp Leu Asn Phe Ser Asp Pro Ser Leu Val Leu Ala
        770                 775                 780

Ala Ile Ser Thr Lys Gly Ser Leu Glu Ala Thr Asn Tyr Glu Arg Leu
785                 790                 795                 800

Glu Leu Leu Gly Asp Ser Ile Leu Lys Leu Cys Thr Thr Ala Asn Ala
                805                 810                 815
```

Ala Ala Leu His Gly Leu Val Ser Asn Ser Arg Leu Cys Arg Ala Ala
            820                 825                 830

Leu Asp Ala Gly Leu Asp Lys Phe Val Leu Thr Glu Asn Phe Thr Cys
        835                 840                 845

Arg Thr Trp Arg Pro Ile Tyr Val Asn Asp Met Met Glu Lys Gly Ala
850                 855                 860

Arg Asp Ser Gly Pro Arg Ile Met Ser Thr Lys Thr Leu Ala Asp Ile
865                 870                 875                 880

Val Glu Ala Leu Ile Gly Ala Ala Tyr Ile Asp Gly Gly Leu Pro Lys
            885                 890                 895

Ala Leu Gly Cys Ile Ser Ile Phe Leu Arg Glu Leu Asp Trp Lys Pro
        900                 905                 910

Leu Pro Ala Cys Gln Glu Ile Leu Tyr Ser Leu Ala Ser Pro Asp Val
        915                 920                 925

Pro Leu Pro Pro Met Leu Val Pro Leu Glu Asp Leu Ile Gly Tyr Thr
        930                 935                 940

Met His Leu Leu Lys Thr Ala Ser Val Asn Gly Asp Leu Leu Gly Phe
945                 950                 955                 960

Leu Ala Leu Glu Cys His Ala Glu Glu Asp Glu Val Ile Ile Asp Ile
            965                 970                 975

Asp Phe Ser Pro Ser Asp Thr Asp Phe Asn Pro Gln Asn Ser Ala Gly
        980                 985                 990

Val Glu Gln Lys Leu Lys Gln Thr Arg Arg Lys Ile Pro Leu Trp Lys
            995                 1000                1005

Phe Met Arg His Ser Ser Ile Glu Val Val Gln Gln Gln Thr Lys
        1010                1015                1020

Ala Ala Ser Val His Ala Asp Leu Arg Gly Gln Ile Met His Ala
        1025                1030                1035

Leu Glu His Gly Ser Ser Tyr Pro Trp Ser Leu Leu Ala Arg Leu
        1040                1045                1050

His Pro Ala Lys Phe Phe Ser Asp Met Val Glu Ala Val Leu Gly
        1055                1060                1065

Ala Val Trp Val Asp Ser Gly Asp Met Gly Ala Cys Ile Arg Val
        1070                1075                1080

Ala Glu Arg Leu Gly Ile Leu Pro Val Leu Ser Arg Leu Ala Lys
        1085                1090                1095

Glu Asp Val His Val Leu His Pro Lys Gln Glu Leu Gly Glu Ile
        1100                1105                1110

Ala Gly Pro Arg Thr Val Lys Tyr Leu Leu Thr Leu Pro Glu Asp
        1115                1120                1125

Ala Ala Gly Leu Gln Ser Ala Thr Arg Lys Tyr Ala Cys Lys Val
        1130                1135                1140

Met Val Gly Asp Arg Cys Val Ala Glu Val Asp Gly Val Ala
        1145                1150                1155

Arg Asp Glu Val Glu Thr Lys Ala Ala Glu Val Ala Val Gln Thr
        1160                1165                1170

Leu Lys Asn Glu Gln Ala Asp Ala Lys Gln Val Ala Glu His
        1175                1180                1185

<210> SEQ ID NO 9
<211> LENGTH: 260
<212> TYPE: DNA
<213> ORGANISM: Botrytis cinerea

<400> SEQUENCE: 9
tgcggaagaa cttgaaggtt tgctacacag tcaaatatgt actgcagaag atcccagctt 60
gctgcagtac tcaatcaaag gtaaacctga gactcttgcc tactatgatc ccttgggccc 120
gaaattcaat actcctcttt atcttcaaat gctcccgctt ctaaaagaca atcctatctt 180
tcggaagcca tttgtatttg ggacagaagc cagtagaact ctaggatctt ggtgtgttga 240
ccagatctgg actttctgtc 260

<210> SEQ ID NO 10
<211> LENGTH: 296
<212> TYPE: DNA
<213> ORGANISM: Botrytis cinerea

<400> SEQUENCE: 10
tctttaagtg atatcgagga gactttggat gccatttgct gcacgccaaa aatacatcga 60
gcagatcttc gccttcgagt aaagctacca cttctatcta ttatctacta taccccagag 120
tcaaatatca tcgtgacgaa aactgtggcg agcctgagaa agattgtgca aagtctcaac 180
attttcgaag acccctacgt tttgacacta aaaaggagtg atagcgaaaa aagtcaacgt 240
gagctggcga aagtactcaa gagttttaag acatatagtc aaacccaatt aaagtc 296

<210> SEQ ID NO 11
<211> LENGTH: 293
<212> TYPE: DNA
<213> ORGANISM: Verticillium dahilae

<400> SEQUENCE: 11
ggcaagccca agagaatcgc ctttttcctc gtggaaaagg ttgctcttgc cctccaacag 60
cacgcggttc tggagtgcaa tctggaattt cccattgacc gggtatgcgg tgacatggta 120
cggtcggact ggatcaagga gtcatggatg aaaagatggg atgacaacat ggtcatggtc 180
tgcaccgccg ccatccttca gcaatgcctt gccagatcat tcatccgcat ggatcagatc 240
aacctgcttg tcttcgatga agcacatcac gccaagggaa atcatccgta cgc 293

<210> SEQ ID NO 12
<211> LENGTH: 319
<212> TYPE: DNA
<213> ORGANISM: Verticillium dahilae

<400> SEQUENCE: 12
acagacacgc cggaaaatcc ccctttggaa gtttatgcgc cactcctcaa tagaggttgt 60
gcagcagcag accaaagctg ccagcgttca tgccgatctc cgaggacaga tcatgcacgc 120
tctggaacat gggtcaagct accccctggtc tcttctcgcc cgtttacatc ccgcaaagtt 180
cttctccgac atggtcgaag ctgtactggg tgccgtctgg gtcgattcgg gcgacatggg 240
cgcgtgcatt cgtgtggcgg aacgactggg cattctgcct gtgctctccc gactggcaaa 300
ggaggacgtt catgtgctg 319

<210> SEQ ID NO 13
<211> LENGTH: 1021
<212> TYPE: DNA
<213> ORGANISM: Botrytis cinerea

<400> SEQUENCE: 13
ctcctggatc aggcagatga attagggaac tgatttcgac cttccagagt tctctttgcg 60
tgatgggtca cttgggtttg gttgtcggta tgctgtgggt tcggaggagt tgtcctttct 120

```
ggtttctttg ttggatagtc ctttttgggt agcttggtgt gatgcatgcg ttctgggtgt    180
gggtctcgtg aggtcttttt gtatcaagta tttttaagct tttttcttgt tctcttcttt    240
ttctgtattg gtaatgcttc ttctttatga tattctccca tcgctgcttt cgcattttct    300
aggttgtagg gtgcttccca cgtgtcttcc gccggttggt agcccttcca tcgcaccagg    360
tattgcacac ctctgcctct ttttctatgt gctaaaatcc tttccacctc atgctctatg    420
tgatcgtcaa tttcttctgg cggcggcggg tcggcggtac cctgtcgttc gtgccatggt    480
tcgagtaaag agacgtggaa tacattgtgg atcttgtagg tgggcggtaa tctaagttcg    540
tatgcttgcc cgctggtttt tatacccgtc acgacaaagg ggcctataaa tcgatcggag    600 aatttttct taggtcgcag ttgtttaatg ttctttgtgc ttagcatcac cttgtccccg    660
atgctatatc gctgtggtga ccccttcgta gtgttcttgt ttttctgatt ggttgccgat    720
ttccagaatt ctttcagctt ttctctttct ttctctaaag cgtcgatgcg ctcgcgtgct    780
gccggcgccc ttccctctaa atcggcgtcc tcgccgatat aatggaatgt gggttggaac    840
ccatacatag cctggaatgg gcttgtattg gttgtactgt gccatgtcgc gttatatgtg    900
aattcagcaa ggggcaatag cgatgcccag tcgtcttgcc tatagttggt gtagcaactt    960
atatagtgaa tcaaattttg gttttgtcgt tcggtttgac cgtcggtctg cgggtggaac   1020
g                                                                   1021
```

```
<210> SEQ ID NO 14
<211> LENGTH: 3927
<212> TYPE: DNA
<213> ORGANISM: Botrytis cinerea

<400> SEQUENCE: 14
atggcatcca gagctaccgc cacaggtcaa tctgccggag acaccaacga catcgagatg     60
accgacgccc caaaggagat cactatcaac gaaaccctta agatcgcctt accagacaag    120
taccaaggta gtcgacaaga gctcgatact ttcctcttac aacttgagat ctactttcga    180
ttcaatgagg acaagttcac taccaaggaa tccaagagta tatgggccgc atcatacctt    240
cgaggtgaag caaccaaatg gatccaacca tatttgcgcg actatttcga gcatgacgat    300
aaggatcgta tgcaacccac ccgaacaatc ttcaatagtt ttgaaggatt taagacagag    360
attcgtagaa tcttcggaaa ttccaacgag ttagaggtag cggaagataa gatcttcaac    420
ctcaagcaga caggatcagc attgaaatat gctacggaat ttcgaagata tgctggaaca    480
accaagtggg acgaaatcgc tatcatgagt cactaccgca agggactcaa accagaagtc    540
agactggaat tagaaagatc tgccgagagt acagatctga acgatctaat tcaggactcc    600
atcgaatcag atgatcgtct ctacagatat cgacaaagcc agagatcata caaaccccaa    660
ggaaatcaga agcaagggcg ttaccgcaaa aatgagggta gaccacgtta caatccacag    720
agatacggag accccatgga actagacgcc acgcactaca caaacgggaa cgatgactcg    780
gaaaagagac gaagacgaga aaacaactta tgctttgaat gtggaaaagc agggcaccga    840
gcagcagact gccgaagcaa gaagacagga ggaaaaaggg gcaacttcaa acctaagttc    900
ggcaaaggcc aacttaacgc tacctttaca atcccagaaa atccaactaa atccgaaaat    960
actgagactt tcaccgttga ggaattccag caattactaa aggaattacc acgaaatcaa   1020
gagggcatga atgcaataga cttatgggag caagagtatt acagaacccc aacaccctct   1080
gtgacagaag aaagtcatca ggacgaggca gaagcagacc acgccacgat gagctggaca   1140
```

| | |
|---|---|
| gcttgctatg atgaattctg cggaatccat cgatcagata aagaagcaac cggatggtcc | 1200 |
| cctaagaaga gaaagacgaa gaaccatcag aataatgtaa catgcgagga tttaactccc | 1260 |
| aatataactt cgcaagaagt tcgcaaagtt acccagcagt taaatgctac gggacaggca | 1320 |
| ggacagatat actgcaaggt tcagataaat ggacacatac aatcagccat gatagattca | 1380 |
| ggggctacag gaaattttat tgcaccggaa gctgagacaa tcccaatacg aatgggcata | 1440 |
| acccaacata cagaggttat acagcttgac gttgtgccat ggggccaaca acagatcatc | 1500 |
| ttaggaatgc catggttaaa ggcacataat ccgaaaatag attgggcaca aggaattgtg | 1560 |
| acatttgatc agtgcaaaag cggtcacagg gacacgctag aggcgttcgc gagacgtaac | 1620 |
| acgcgccaag gagagttgaa cgcgaacaac accggcgacg taggacaccc agtccagggt | 1680 |
| cctccattaa gagcgaaggc cagtacacct cctctacaaa tgcagaagcc aacgacacgg | 1740 |
| cacgaaatcg caatcgaggc aaaagaaaag cctacgatac cagaacagta caagaattat | 1800 |
| gaacatgttt tcaaagaacc agggatccat gaggctttac cggaacacaa gccatgggat | 1860 |
| catgagataa tattggagga aggcaagatg cctgtgcaca ccccaattta ttcaatgtca | 1920 |
| gccgatgagt taaagaggct cagagagtac atcgacgaca atttagccaa gggatggatc | 1980 |
| agggaatccg cgtcccaagt ggccagtcca actatgtgga aggatcgata tccacttcca | 2040 |
| ttagctacgg aattaagaga tcgattaggc ggagctacga tatttaccaa gatggaccta | 2100 |
| cgtaatggtt accacttgat cagaatgaag gaaggcgaag aatggaaaac cgcttcaaaa | 2160 |
| caagatacgg gctatacgac tactttcatg aggcttatga acaatgtgtt gtcacaatat | 2220 |
| ttggatactt gctgtatatg ctacttggac gacatcctag tatattcaaa caacaaggtt | 2280 |
| caacacatta aggacgttag caacatcctc gaaagcctat ccaaggcaga cttgctgtgc | 2340 |
| aaaccaagca aatgcgaatt ccatgtcaca gagacagaat tcttgggatt caccgtatca | 2400 |
| agccaagggc tcaagatgag caaaggcaag gttaaggcag tgctcgaatg gaagcagccg | 2460 |
| accacaatca aggaagtaca atcctttcta gggttcgtca acttctacag aagattcatc | 2520 |
| aagggttatt cagggattac tacacccttg accacgttaa ccagaaaaga tcaaggaagc | 2580 |
| ttcgaatgga ctgccaaagc acaggagtca ttcgatacgc tcaaacaagc agtggcagaa | 2640 |
| gagccaatac tgttgacttt tgacccagag aaagaaatca tagtggagac ggactcctcg | 2700 |
| gatttcgcta taggagcagt tctgagccaa ccgggccaga atggaaaata ccagccaatc | 2760 |
| gcattctact cccgaaaact atcaccagcc gaattgaatt acgagatata tgacaaagaa | 2820 |
| ttactggcga tagtcgatgc atttagagaa tggcgagtgt atttggaagg atcgaaatac | 2880 |
| acggtacagg tgtatacaga tcataagaac ttggtttact tcaccacaac gaagcagtta | 2940 |
| aacagacgac aggtcagatg gtcggagacc atggccaact acaatttcag aatttcatat | 3000 |
| gtcaaaggat cagaaaacgc tagagccgac gctcttagcc gaaaaccaga atatcaagaa | 3060 |
| aacaaaacgt acgagtcata cgctatattc aagaaagacg gcgaatcact ggtttacaat | 3120 |
| gcaccacagc ttgcagcaac acacctgttg aagacaacc acctcaggaa acagatccaa | 3180 |
| tcacactacg acaaggatgc tactgccaca cgcatacgca agacaataga accaggattc | 3240 |
| actatagaaa atgataccat atactttcat ggaaaagtat acattccgag tcaaatgacc | 3300 |
| aaggaatttg tgacggaaca cacgggttg ccggcacatg gacaccaagg aattgcaagg | 3360 |
| acatttgcaa gaatacggga aatcagttac ttcccacgaa tgagaacgat agttgaagaa | 3420 |
| gttgttggaa attgtgacac ctgcatacga aacaagtcat cacgacatgc tccgtatggt | 3480 |
| cagctccaga ccccagacat gccttctcag ccatggaagt ccatcacatg ggactttgtg | 3540 |

| | | | | |
|---|---|---|---|---|
| gtcaaactac | cactctcaaa | agatcctact | acaggaattg | agtacgacgc | gatactcaat | 3600 |
| atagtagaca | ggctaacgaa | atttgcatat | atgataccat | tcaaggaaac | atgggatgct | 3660 |
| gagcaactag | catatgtgtt | cctaaggatc | atagtaagca | tacacggagt | accagatgag | 3720 |
| ataatctcgg | atcgagacaa | gctctttacc | tcgaaattct | ggactacctt | attagcactt | 3780 |
| atgggtatca | agagaaagct | atcgacatct | ttccacccac | aaacagatgg | tcaaacagag | 3840 |
| aggaccaatc | agacaatgga | agcatatctt | agatgctatc | gtataaaatc | ccgataccac | 3900 |
| aagaagttaa | tgccgaatca | gcgatag | | | | 3927 |

<210> SEQ ID NO 15
<211> LENGTH: 4857
<212> TYPE: DNA
<213> ORGANISM: Botrytis cinerea

<400> SEQUENCE: 15

| | | | | | | |
|---|---|---|---|---|---|---|
| atggcatcca | gagatatcgc | cacaggtcaa | tctgccggag | acaccaacga | catcgagatg | 60 |
| accgatgccc | caaagagat | cactatcaac | gaaacactta | agatcgcctt | accagacaag | 120 |
| taccaaggta | gtcgacaaga | actcgatact | ttcctcttac | aacttgagat | ctacttccga | 180 |
| ttcaatgagg | acaagttcac | taccaaggaa | tccaagagta | tatgggccgc | atcatacctt | 240 |
| cgaggtgaag | caaccaaatg | gatccaacca | tatttgcgcg | actatttcga | gcatgacgat | 300 |
| aaggatcgca | tgcaacccac | ccgaacaatc | ttcaatagtt | ttgaaggatt | taagacagag | 360 |
| attcgtagaa | tcttcggaaa | ttccaacgag | ttagaggtag | cggaagataa | gatcttcaac | 420 |
| ctcaagcaga | caggatcagc | attgaaatat | gctacggaat | ttcgaagata | tgctggaaca | 480 |
| accaagtggg | acgaaatcgc | tatcatgagt | cactaccgta | agggactcaa | accagaagtc | 540 |
| agactggaat | tagaaagatc | tgccgagagt | acagatctga | acgatctaat | tcaggactcc | 600 |
| atcgaatcag | atgatcgtct | ctacagatat | cgacaaagcc | agagatcata | caaaccccaa | 660 |
| ggaaatcaga | agcaagggcg | ttaccgcaag | aatgagggta | gaccacgtta | caacccacag | 720 |
| agatacggag | accccatgga | actagacgct | acgcactaca | caaacgggaa | cgatgactca | 780 |
| gaaaagagac | gaagacgaga | aaacaactta | tgctttgaat | gtggaaaagc | agggcaccga | 840 |
| gcagcagaat | gccgaagcaa | gaagacagga | ggaaaaaggg | gcaacttcaa | acctaagttc | 900 |
| ggcaagggcc | aacttaatgc | cacctttgca | atctcagaaa | actcaactaa | acccgaaaat | 960 |
| actgagactt | tcaccgttga | ggaattccag | caattattag | aggaattacc | acgaaaccaa | 1020 |
| gagggcatga | atgcaataga | cttatgggaa | caagagtatt | acagaactcc | aacaccctct | 1080 |
| gtgacagaag | aaagtcacca | ggacgaggca | gaagcggacc | acgccacgat | aagctggaca | 1140 |
| gcttgctatg | acgaattctg | cggaatccat | cgatcagata | agaagcaac | cggatggttc | 1200 |
| cctaagaaga | gaaagacgaa | gaaccatcag | aataatgtaa | catgcgagga | tttaactccc | 1260 |
| aatataactt | cgcaagaagt | tcgcaaagtt | cccagcagt | aaatgctac | gggacaggca | 1320 |
| ggacagatat | actgcaaggt | tcagataaat | ggacacatac | aatcagccat | gatagattca | 1380 |
| ggggctacag | gaaattttat | tgcaccagaa | gcggcaaagt | acttggaaat | accacttcag | 1440 |
| aggaaacaat | accctatcg | attgcagtta | gttgacggac | agctagcagg | gtctgacgga | 1500 |
| aagatttcgc | aggagacaat | cccagtacga | atgagcataa | cccaacatac | agaggttata | 1560 |
| cagcttgatg | ttgtgccatt | gggccaacaa | cagatcatct | taggaatgcc | atggttaaag | 1620 |
| gcacataatc | cgaaaataga | ttgggcacaa | ggagttgtga | catttgatca | gtgcaaaagc | 1680 |

```
ggtcacaggg acacgataga ggcgtccgcg agacgtaaca cgcgccaagg agagttgaac      1740
gcgaacaaca ccggcgacgt aggacaccca gtccagggtc ctccattaag agcgaaggcc      1800
agtacacctc ctctacaaat gcagaagcca acgacacggc acgaaatcgc aatcgaggca      1860
aaagaaaggc ctacgatacc agaacagtac aagaaatatg aacatgtttt caaagaacca      1920
gggatccatg aggctttacc ggaacacaag ccatgggatc atgagataat attggaggaa      1980
ggcaagatgc ctgtgcacac cccaatttat tcaatgtcag ccgatgagtt aaagaggctc      2040
agagagtaca tcgacgacaa tttagccaag ggatggatca gggaatccgc gtcccaagtg      2100
gccagtccaa ctatgtgggt acccaagaag gatggacccg atagactagt tgtagactat      2160
agaaagctta acgcactcac taagaaggat cgatatccac ttccattagc tacggaatta      2220
agagatcgat taggcggagc tacgatattc accaagatgg acctacgtaa tggttaccac      2280
ttgatcagaa tgaaggaagg cgaagaatgg aaaaccgctt tcaaaacaag atacgggcta      2340
tacgagtacc aagttatgcc attcgggcta accaacgcac cagctacttt catgaggctt      2400
atgaacaatg tgttgtcaca atatttggat acttgctgta tatgctactt ggacgacatc      2460
ctagtatatt caaacaacaa ggttcaacac attaaggacg ttagcaacat cctcgaaagc      2520
ctatccaagg cagacttgct gtgcaaacca agcaaatgcg aattccatgt cacagagaca      2580
gaattcttgg gattcaccgt atcaagccaa gggctcaaga tgagcaaaga caaggttaag      2640
gcagtgctcg aatggaagca gccgaccaca atcaaggaag tacaatcctt tctagggttc      2700
gtcaacttct acagaagatt tatcaagggt tattcaggga ttactacacc cttgaccacg      2760
ttaaccagaa aagatcaagg aagcttcgaa tggactgcca agcacagga gtcattcgat      2820 acgctcaaac aagcagtggc agaagaacca atactgttga cttttgaccc agagaaagaa      2880
atcatagtgg agacggactc ctcggatttc gctataggag cagttctgag ccaaccgggc      2940
cagaatggaa aataccagcc aatcgcattc tactcccgaa aactatcacc agccgaattg      3000
aattacgaga tatatgacaa agaattactg gcgatagtcg atgcatttag agaatggcga      3060
gtgtatttgg aaggatcgaa atacacggta caggtgtata cagatcataa gaacttggtt      3120
tacttcacca caacgaagca gttaaacaga cgacaggtca gatggtcgga gaccatggcc      3180
aactacaatt tcagaatttc atatgtcaaa ggatcagaaa acgctagagc cgacgctctt      3240
agccgaaaac cagaatatca agaaaacaaa acgtacgagt catacgctat attcaagaaa      3300
gacggcgaat cactggttta caatgcacca cagcttgcag caacacacct gttggaagac      3360
aaccacctca ggaaacagat ccaatcacac tacgacaagg atgctactgc cacacgcata      3420
cgcaagacaa tagaaccagg attcactata gaaaatgata ccatatactt tcatggaaaa      3480
gtatacattc cgagtcaaat gaccaaggaa tttgtgacgg aacaacacgg gttgccggca      3540
catggacacc aaggaattgc aaggacattt gcaagaatac gggaaatcag ttacttccca      3600
cgaatgagaa cgtagttgaa agaagttgtt ggaaattgtg acacctgcat acgaaacaag      3660
tcatcacgac atgctccgta tggtcagctc cagaccccag acatgccttc tcagccatgg      3720
aagtccatca catgggactt tgtggtcaaa ctaccactct caaaggatcc tactacagga      3780
attgagtacg acgcgatact caatatagta gacaggctaa cgaaatttgc atatatgata      3840
ccattcaagg aaacatggga tgctgagcaa ctagcatatg tgttcctaag gatcatagta      3900
agcatacacg gagtaccaga tgagataatc tcggatcgag acaagctctt tacctcaaaa      3960
ttctggacta cctattattgc acttatgggt atcaagagaa agctatcgac atctttccac      4020
ccacaaacag atggtcaaac agagaggacc aatcagacaa tggaagcata tcttagatgc      4080
```

```
tatgtaaatt atcgacaaga caattgggta gagctattac ccatggcaca gttcgcatac   4140
aatacatcag aaacggaaac cacgaaaatc acaccagcac gagctaattt tgggtttaat   4200
ccacaagcgt ataaaatccc gataccacaa gaagttaatg ccgaatcagc gatagtacaa   4260
atcgaacagc tgaaagatct ccaagagcaa ctggctcttg atctaagatt catatcttcc   4320
agaacagcag cgtactacaa tacgaaacgt agtatggaac ctacgcttaa agagggggat   4380
aaagtttatt tgctacgacg aaacatcgaa accaagagac caagcaataa actcgaccac   4440
aggaaactag gaccattcaa gattgataag gtaataggaa cggttaatta tcgattgaaa   4500
ttaccagaca caatgaatat ccacccagta ttccacatat ccttgctcga accagcacca   4560
ccaggagcgc caaatgcgcc atttacagaa attgaaccag tcaacccaaa cgccatatac   4620
gatgtcgaaa caatactaga ctgcaaatac gtcagaaaca aggtcaagta tttgatcaaa   4680
tggttagact acccacattc agaaaacaca tgggaactca aggaagatct cagctgccct   4740
gagaagctac gggcattcca cctgaagtac ccacacctgc caataaagcc tcaagatccg   4800
cttcggacaa ctcaggcaaa gaaggatcga agaaatcgaa ggaagaagaa tcaatag      4857
```

<210> SEQ ID NO 16
<211> LENGTH: 3909
<212> TYPE: DNA
<213> ORGANISM: Botrytis cinerea

<400> SEQUENCE: 16

```
atggcatcca gagctaccgc cacaggtcag tctaccggag ataccaacga catcgagatg     60
accgatgccc caaaggagat cactatcaac gaaacactta agatcgcctt accagacaag    120
taccaaggta gtcgacaaga gctcgatact ttcctcttac aacttgagat ctacttccga    180
ttcaatgagg acaagttcac taccaaggaa tccaagagca tatgggctgc atcatacctc    240
cgaggtgaag caaccaaatg gattcaacca tatttgcgcg actatttcga gcatgacgat    300
aaggatcgca tgcaacccac ccgaacaatc ttcaatagtt ttgaaggatt taagacagag    360
attcgtagaa tcttcggaaa ttccaacgag ttagaggtag cggaagataa gatcttcaac    420
ctcaagcaga caggatcagc attgaaatat gctacggaat ttcgaagata tgctggaaca    480
accaagtggg acgaaatcgc tatcatgagt cactatcgta agggactcaa accagaagtc    540
agactggaat tagaaagatc tgccgagagt acagatctga acgatctaat tcaggactcc    600
atcgaatcag atgatcgtct ctacagatat cgacaaagcc agagatcata caaaccccaa    660
ggaaatcaga agcaagggcg ttaccgcaaa aatgagggta gaccacgtta caatccacag    720
agatacggag accccatgga actagacgcc acgcactaca caaacgggaa cgatgactcg    780
gaaaagagac gaagacgaga aaacaactta tgctttgaat gtggaaaagc agggcaccga    840
gcagcagact gccgaagcaa gaagacagga ggaaaaaggg gcaacttcaa acctaagttc    900
ggcaaaggcc aacttaacgc tacctttaca atcccagaaa atccaactaa atccgaaaat    960
actgagactt tcaccgttga ggaattccag caattactaa aggaattacc acgaaatcaa   1020
gagggcatga atgcaataga cttatgggag caagagtatt acagaacccc aacaccctct   1080
gtgacagaag aaagtcatca ggacgaggca gaagcagacc acgccacgat gagctggaca   1140
gcttgctatg atgaattctg cggaatccat cgatcagata aagaagcaac cggatggttc   1200
cctaagaaga gaaagacgaa gaaccatcag aataatgtaa catgcgagga tttaactccc   1260
aatataactt cgcaagaagt tcgcaaagtt acccagcagt taaatgctac gggacaggca   1320
```

```
ggacagatat actgcaaggt tcagataaat ggacacatac aatcagccat gatagattca    1380
ggggctacag gaattttat tgcaccggaa gctgtaaagt acttgggaat accacttcaa    1440
acgaaacaac acccctatcg attgcaggac acgctagagg cgtccgcgag acgtaacacg    1500
cgccaaggag agttgaacgc gaacaacacc ggcgacgtag acacccagt ccagggtcct    1560
ccattaagag cgaaggccag tacacctcct ctacaaatgc agaagccaac gacacggcac    1620
gaaatcgcaa tcgaggcaaa agaaaggcct acgataccag aacagtacaa gaaatatgaa    1680
catgttttca aagaaccagg gatccatgag gctttaccag aacacaagcc atgggatcat    1740
gagataatat tggaggaagg caagatgcct gtgcacaccc caatttattc aatgtcagcc    1800
gatgagttaa aaaggctcag agaatacatc gacgacaatt tagccaaggg atggatcagg    1860
gaatccgcgt cccaagtggc cagtccaact atgtgggtac caagaagga tggacccgat    1920
agactagttg tagactatag aaagcttaac gcactcacta agaaggatcg atatccactt    1980
ccattagcta cggaattaag agatcgatta ggcggagcta cgatatttac caagatggac    2040
ctacgtaatg gttaccactt gatcagaatg aaggaaggcg aagaatggaa gaccgctttc    2100
aaaacaagat acgggctata cgagtaccaa gttatgccgt tcgggctaac caacgcacca    2160
gctactttca tgaggcttat gaacaatgtg ttgtcacaat acttggatac ttgctgtata    2220
tgctacttgg acgacatcct agtatattca acaacaagg ttcaacacat taaggacgtt    2280
agcaacatcc tcgaaagcct atccaaggca gacttgctgt gcaaaccaag caaatgcgaa    2340
ttccatgtca cagagacaga cttcttggga ttcaccgtat caagccaagg gctcaagatg    2400
agcaaagaca aggttaaggc agtgctcgaa tggaaacagc caaccacaat caaggaggta    2460
caatcctttc tagggttcgt caacttctac agaagattta tcaagggtta ttcagggatt    2520
actacaccct tgaccacgtt aaccagaaaa gatcaaggaa gcttcgaatg gactgccaaa    2580
gcacaggagt cattcgatac gctcaaacaa gcagtggcag aagagccaat actattgact    2640
tttgacccag agaagaaat catagtggag acggactcct cggatttcgc tataggagca    2700
gttctgagcc aaccgggcca gaatggaaaa taccagccaa tcgcattcta ttcccgaaaa    2760
ctatcaccag ctgagttgaa ttacgagata tatgacaaag aattgctggc gatagtcgat    2820
gcatttagag aatggcgagt atatttggaa ggatcgaaat acacagtaca ggtgtataca    2880
gatcataaga acttggttta cttcaccaca acgaagcagt taaacagacg acaggtcaga    2940
tggtcggaga ccatggccaa ctacaatttc agaatttcat atgtcaaagg atcagaaaac    3000
gctagagccg acgctcttag ccgaaaacca gaatatcaag aaaacaaaac gtacgagtca    3060
tacgctatat tcaagaaaga cggcgaatca ctggtttaca atgcaccaca gcttgcagca    3120
acacacctgt tggaagacaa ctaccttagg aaacagatcc aatcacacta cgacaaggat    3180
gctactgcca cacgcatacg taagacaata gaaccaggat tcactataga aaatgatacc    3240
atatactttc atggaaaagt atacattccg agtcaaatga ccaaggaatt tgtgacggaa    3300
caacacggat tgccggcaca tggacaccaa ggaattgcaa ggacatttgc aagaatacgg    3360
gaaatcagtt acttcccacg aatgagaacg atagttgaag aagttgttgg aaattgtgac    3420
acctgcatac gaaacaagtc atcacgacat gctccgtatg gtcagctcca gaccccagac    3480
atgccttctc agccatggaa gtccatcaca tgggactttg tggtcaaact accactctcc    3540
aaggatccta ctacaggaat tgagtacgac gcgatactca atatagtaga caggctaacg    3600
aaatttgcat atatgatacc attcaaggaa acatgggatc tgagcaact agcatatgtg    3660
ttccttagga tcatagtaag catacacgga gtaccagatg agataatctc ggatcgagac    3720
```

```
aagctctttta cctcgaaatt ctggactacc ttattagcac ttatgggtat caagagaaag   3780
ctatcgacat ctttccaccc acaaacagat ggtcaaacag agaggaccaa tcagacaatg   3840
gaagcatatc ttagatgcta tcgtataaaa tcccgatacc acaagaagtt aatgccgaat   3900
cagcgatag                                                             3909

<210> SEQ ID NO 17
<211> LENGTH: 4857
<212> TYPE: DNA
<213> ORGANISM: Botrytis cinerea

<400> SEQUENCE: 17
atggcatcca gagctaccgc cacaggtcag cctaccggag ataccaacga catcgagatg     60
accgatgccc caaggagat cactatcaac gaaaccctta agatcgcctt accagacaag    120
taccaaggta gtcgacaaga gctcgatact ttcctcttac aacttgagat ctactttcga   180
ttcaatgagg acaagttcac taccaaggaa tccaagagta tatgggccgc atcatacctt   240
cgaggtgaag caaccaaatg gatccaacca tatttgcgcg actatttcga gcatgacgat   300
aaggatcgca tgcaacccac ccgaacaatc ttcaatagct ttgaaggatt taagacagag   360
attcgtagaa tcttcggaaa ttccaacgag ctagaggtag cggaagataa gatcttcaac   420
ctcaagcaga caggatcagc attgaaatat gctacgaat ttcgaagata cgctggaaca   480
accaagtggg acgaaatcgc tatcatgagt cactaccgca agggactcaa accagaagtc   540
agactggaat tagaaagatc tgccgagagt acagatctga acgatctaat tcaggactcc   600
atcgaatcag atgatcgtct ctacagatat cgacaaagcc agagatcata caaaccccaa   660
ggaaatcaga gcaagggcg ttaccgcaag aatgagggta gaccacgtta caatccacaa    720
agatacggag accccatgga actagacgct acgcactaca caaacgggaa cgatgactca   780
gaaaagagac gaagacgaga aaacaactta tgctttgaat gtggaaaagc agggcaccga   840
gcagcagact gccgaagcaa aagacagga ggaaaaaggg gcaacttcaa acctaagttc    900
ggcaaaggcc aacttaacgc tacctttaca atcccagaaa acccaactaa atccgaaaat   960
actgagactt tcaccgttga ggaattccag caattactaa aggaattacc acgaaataaa  1020
gagggcatga atgcaataga cttatgggaa caagagtatt acagaacccc aacaccctct  1080
gtgacagaag aaagtcacca ggacgaggca gaagcggacc acgccacgat gagctggaca  1140
gcttgctatg atgaattctg cggaatccat cgatcagata agaagcaac cggatggttc   1200 cccaagaaaa ggaagacgaa gaaccatcag aataatgtaa catgcacgga tttaacttca  1260
aatataactt cgcgaaaagt tcgcaaagtt acccagcagt tgaatgctac gggacaagca  1320
ggacagatat actgcaaggt tcagataaat ggacacatac aatcagccat gatagattca  1380
ggggctacag gaaattttat tgcaccagaa gctgcaaagt acttggaaat accacttcag  1440
acgaaacaat accctatcg attgcagtta gttgacggac agctagcagg gtctgacgga   1500
aagatttcgc aggagacaat cccagtacga atgggcataa cccaacatac agaggttata  1560
cagcttgacg ttgtgccatt gggccaacaa cagatcatct taggaatgcc atggttgaag  1620
gcacataatc gaaaataga ttgggcacaa ggaattgtga catttgatca gtgcaaaagc   1680
ggtcacaggg acacgctaga ggcgtccgcg agacgtaaca cgcgccaagg agagttgaac  1740
gcgaacaaca ccgcgacgt aggacaccca gtccagggtc ctccattaag agcgaaggcc   1800 agtacaccctc ctctacaaat gcagaagcca acgacacggc acgaaatcgc aatcgaggca 1860
```

-continued

```
aaagaaaggc ctacgatacc agaacagtac aagaaatatg aacatgtttt caaagaaccca   1920
gggatccatg aggctttacc ggaacacaag ccatgggatc atgagataat attggaggaa    1980
ggcaagatgc ctgtgcacac cccaatttat tcaatgtcag ccgatgagtt aaaaaggctc    2040
agagaataca tcgacgacaa tttagccaag ggatggatca gggaatccgc gtcccaagtg    2100
gccagtccaa ctatgtgggt acccaagaag gatggacccg atagactagt tgtagactat    2160
agaaagctta acgcactcac taagaaggat cgatatccac ttccattagc tacgaattaa    2220
agagatcgat taggcggagc tacgatattc accaagatgg acctacgtaa tggttaccac    2280
ttgatcagaa tgaaggaagg cgaagaatgg aaaaccgctt tcaaaacaag atacgggcta    2340
tacgagtacc aagttatgcc gttcgggcta accaacgcac cagctacttt catgaggctt    2400
atgaacaatg tgttgtcaca atatttggat acttgctgta tatgctactt ggacgacatc    2460
ctagtatatt caaacaacaa ggttcaacac attaaggacg ttagcagcat cctcgaaagt    2520
ctatccaaag cagacttgct gtgcaaacca agcaaatgcg aattccatgt cacagaaaca    2580
gaattcttgg gattcaccgt atcaagccaa gggctcaaga tgagcaaaga caaggttaag    2640
gcagtgctcg aatggaagca gccgaccaca atcaaggaag tacaatccct tctaggattt    2700
gtcaacttct atagaagatt tatcaagggt tattcaggga ttactacacc cttgaccacg    2760
ttaaccagaa aagatcaagg aagcttcgaa tggactgcca aagcacagga gtcattcgat    2820
acactcaaac aagcagtggc agaagaacca atactgttga cttttgaccc agagaaagaa    2880
atcatagtgg aaacggattc ctcagatttc gctataggag cagttctgag ccaaccgggc    2940
cagaatggaa aataccagcc aatcgcattc tactcccgaa actatcacc agccgagttg     3000
aattacgaga tatatgacaa agaattactg gcgatagtcg atgcatttag agaatggcga    3060
gtatatttgg aaggatcgaa atacacagta caggtgtata cagatcataa gaacttggtt    3120
tacttcacca caacgaagca gttaaacaga cgacaggtca gatggtcgga gaccatggcc    3180
aactacaatt tcagaatttc atatgtcaaa ggatcagaaa acgctagagc cgacgctctt    3240
agccgaaaac cagaatatca agaaaacaaa acgtacgagt catacgctat attcaagaaa    3300
gacggcgaat cactggtcta caatgcacca cagcttgcag caacacacct gttggaagac    3360
aaccacctca gaaaacagat tcaatcacac tacgacaagg atgctactgc cacacgcata    3420
cgcaagacaa tagaaccagg attcactata gaaaatgata ccatatactt tcatggaaaa    3480
gtatacattc cgagtcaaat gaccaaggaa tttgtgacgg aacaacatgg gttgccggca    3540
catggacacc aaggaattgc aaggacattt gcaagaatac gggaaatcag ttacttccca    3600
cgaatgagaa cgatagttga agaagttgtt ggaaattgtg acacctgcat acgaaacaag    3660
tcatcacgac atgctccgta tggtcagctc cagaccccag acatgccttc tcagccatgg    3720
aagtccatca catgggactt tgtggtcaaa ctaccactct caaaggatcc tactacagga    3780
attgagtacg acgcgatact caatatagta gacaggctaa cgaaatttgc atatatgata    3840
ccattcaagg aaacatggga tgctgaacaa ctagcatatg tgttcctaag gatcatagta    3900
agcatacacg gagtaccaga tgagataatc tcggatcgag acaagctctt tacctcaaaa    3960
ttctggacta cccttattag cacttatggg atcaagagaa agctatcgac atctttccac    4020
ccacaaacag atggtcaaac agagaggacc aatcagacaa tggaagcata tcttagatgc    4080
tatgtaaatt atcgcaagga caattgggta gaactattac ctatggcaca attcgcatat    4140
aatacatcgg aaacgaaaac cacgaaaatc acaccagcac gagctaattt tgggtttaat    4200
ccacaagcgt ataaaatccc gataccacaa gaagttaatg ccgaatcagc aatagtacaa    4260
```

```
gtcgaacagc tgaaaaatct ccaagagcaa ctggctcttg atctaagatt catatcttcc   4320
agaacagcag cgtactacaa tacgaaacgt agtatggaac ctacgcttaa agagggggat   4380
aaagtttatt tgctacgacg aaacatcgaa accaagagac caagcaataa actcgaccac   4440
aggaaactag gaccattcaa gattgataag gtaataggaa cggttaatta tcgattgaaa   4500
ttaccagaca caatgaatat ccacccagta ttccacatat ccttgctcga accagcacca   4560
ccaggagcgc caaatgcgcc atttacagaa attgaaccag tcaacccaaa cgccatatac   4620
gatgtcgaaa caatactaga ctgcaaatac gtcagaaaca aggtcaagta tttgatcaaa   4680
tggttagact acccacattc agaaaacaca tgggaattca aggaggatct cagctgccct   4740
gagaagctac gggcattcca cctgaagtac ccacacctgc cagtaaagcc tcaagatccg   4800
cttcggacaa ctcaggcaaa gaaggatcga agaagtcgaa ggaagaagaa tcaatag      4857
```

<210> SEQ ID NO 18
<211> LENGTH: 3909
<212> TYPE: DNA
<213> ORGANISM: Botrytis cinerea

<400> SEQUENCE: 18

```
atggcatcca gagctaccgc cacaggtcaa tctgccggag acaccaacga catcgagatg     60
accgacgccc caaaggagat cactatcaac gaaaccctta agatcgcctt accagacaag    120
taccaaggta gtcgacaaga gctcgatact ttcctcttac aacttgagat ctactttcga    180
ttcaatgagg acaagttcac taccaaggaa tccaagagta tatgggccgc atcatacctt    240
cgaggtgaag caaccaaatg gatccaacca tatttgcgcg actatttcga gcatgacgat    300
aaggatcgta tgcaacccac ccgaacaatc ttcaatagtt ttgaaggatt taagacagag    360
attcgtagaa tcttcggaaa ttccaacgag ttagaggtag cggaagataa gatcttcaac    420
ctcaagcaga caggatcagc attgaaatat gctacggaat ttcgaagata tgctggaaca    480
accaagtggg acgaaatcgc tatcatgagt cactaccgca agggactcaa accagaagtc    540
agactggaat tagaaagatc tgccgagagt acagatctga acgatctaat tcaggactcc    600
atcgaatcag atgatcgtct ctacagatat cgacaaagcc agagatcata caaaccccaa    660
ggaaatcaga agcaagggcg ttaccgcaaa aatgagggta gaccacgtta caatccacag    720
agatacggag accccatgga actagacgcc acgcactaca caaacgggaa cgatgactcg    780
gaaaagagac gaagacgaga aaacaactta tgctttgaat gtggaaaagc agggcaccga    840
gcagcagact gccgaagcaa gaagacagga ggaaaaaggg gcaacttcaa acctaagttc    900
ggcaaaggcc aacttaacgc tacctttaca atcccagaaa atccaactaa atccgaaaat    960
actgagactt tcaccgttga ggaattccag caattactaa aggaattacc acgaaatcaa   1020
gagggcatga atgcaataga cttatgggag caagagtatt acagaacccc aacaccctct   1080
gtgacagaag aaagtcatca ggacgaggca gaagcagacc acgccacgat gagctggaca   1140
gcttgctatg atgaattctg cggaatccat cgatcagata aagaagcaac cggatggtcc   1200
cctaagaaga gaaagacgaa gaaccatcag aataatgtaa catgcgagga tttaactccc   1260
aatataactt cgcaagaagt tcgcaaagtt acccagcagt taaatgctac gggacaggca   1320
ggacagatat actgcaaggt tcagataaat ggacacatac aatcagccat gatagattca   1380
ggggctacag gaaattttat tgcaccggaa gctgtaaagt acttgggaat accacttcaa   1440
acgaaacaac acccctatcg attgcaggac acgctagagg cgtccgcgag acgtaacacg   1500
```

```
cgccaaggag agttgaacgc gaacaacacc ggcgacgtag acacccagt ccagggtcct    1560 ccattaagag cgaaggccag tacacctcct ctacaaatgc agaagccaac gacacggcac    1620
gaaatcgcaa tcgaggcaaa agaaaggcct acgataccag aacagtacaa gaaatatgaa    1680
catgttttca agaaccagg gatccatgag gctttaccgg aacacaagcc atgggatcat    1740
gagataatat tggaggaagg caagatgcct gtgcacaccc aatttattc aatgtcagcc     1800 gatgagttaa aaaggctcag agaatacatc gacgacaatt tagccaaggg atggatcagg    1860
gaatccgcgt cccaagtggc cagtccaact atgtgggtac caagaagga tggacccgat    1920 agactagttg tagactatag aaagcttaac acactcacta agaaggatcg atatccactt    1980
ccattagcta cggaattaag agatcggtta ggcggagcta cgatatttac caagatggac    2040
ctacgtaatg gttaccactt gatcagaatg aaggaaggcg aagaatggaa gaccgctttc    2100
aaaacaagat acgggctata cgagtaccaa gttatgccgt tcgggctaac caacgcacca    2160
gctactttca tgaggcttat gaacaatgtg ttgtcacaat acttggatac ttgctgtata    2220
tgctacttgg acgacatcct agtatattca acaacaagg ttcaacacat taaggacgtt     2280
agcaacatcc tcgaaagcct atccaaggca gacttgctgt gcaaaccaag caaatgcgaa    2340
ttccatgtca cagagacaga attcttggga ttcaccgtat caagccaagg gctcaagatg    2400
agcaaagaca aggttaaggc agtgctcgaa tggaagcagc caaccacaat caaggaagta    2460
caatcctttc tagggttcgt caacttctac agaagattta tcaagggtta ttcagggatt    2520
actacaccct tgaccacgtt aaccagaaaa gatcaagaaa gcttcgaatg gactgccata    2580
gcacaggagt cattcgatac gctcaaacaa gcagtggcag aagagccaat actattgact    2640
tttgacccag agaaagaaat catagtggag acggactcct cggatttcgc tataggagca    2700
gttctgagcc aaccgggcca gaatggaaaa taccagccaa tcgcattcta ctcccgaaaa    2760
ctatcaccag ccgaattgaa ttacgagata tatgacaaag aattgctggc gatagtcgat    2820
gcatttagag aatggcgagt atatttggaa ggatcgaaat acacagtaca ggtgtataca    2880
gatcataaga acttggttta cttcaccaca acgaagcagt taaacagacg acaggtcaga    2940
tggtcggaga ccatggccaa ctacaatttc agaatttcat atgtcaaagg atcagaaaac    3000
gctagagccg acgctcttag ccgaaaacca gaatatcaag aaaacaaaac gtacgagtca    3060
tacgctatat tcaagaaaga cggcgaatca ctggtttaca atgcaccaca gcttgcagca    3120
acacacctgt tggaagacaa ctaccttagg aaacagatcc aatcacacta cgacaaggat    3180
gctactgcca cacgcatacg caagacaata gaaccaggat tcactataga aaatgatacc    3240
atatactttc atggaaaagt atacattccg agtcaaatga ccaaggaatt tgtgacggaa    3300
caacatgggt tgccggcaca tggacaccaa ggaattgcaa ggacatttgc aagaatacgg    3360
gaaatcagtt acttcccacg aatgagaacg atagttgaag aagttgttgg aaattgtgac    3420
acctgcatac gaaacaagtc atcacggcat gctccgtatg gtcagctcca gaccccagac    3480
atgccttctc agccatggaa gtccatcaca tgggactttg tggtcaaact accactctca    3540
aaggatccta ctacaggaat tgagtacgac gcgatactca atatagtaga caggctaacg    3600
aaatttgcat atatgatacc attcaaggaa acatgggatg ctgaacaact agcatatgtg    3660
ttcctaagga tcatagtaag catacacgga gtaccagatg agataatctc ggatcgagac    3720 aagctctttta cctcgaaatt ctggactacc ttattagcac ttatgggtat caagagaaag    3780
ctatcgacat ctttccaccc acaaacagat ggtcaaacag agaggaccaa tcagacaatg    3840
gaagcatatc ttagatgcta tcgtataaaa tcccgatacc acaagaagtt aatgccgaat    3900
``` cagcaatag 3909

<210> SEQ ID NO 19
<211> LENGTH: 3909
<212> TYPE: DNA
<213> ORGANISM: Botrytis cinerea

<400> SEQUENCE: 19
atggcatcca gagctaccgc cacaggtcag tctaccgaag ataccaacga catcgagatg 60
accgatgccc caaaggagat cactatcaac gaaacactta agatcgcctt accagacaag 120
taccaaggta gtcgacaaga gctcgatact ttcctcttac aacttgagat ctacttccga 180
ttcaatgaag acaagttcac taccaaggaa tccaagagca tatgggctgc atcatacctc 240
cgaggtgaag caaccaaatg gattcaacca tatttgcgcg actatttcga gcatgacgat 300
aaggatcgca tgcaacccac ccgaacaatc ttcaatagtt ttgaaggatt taagacagag 360
attcgtagaa tcttcggaaa ttccaacgag ttagaggtag cggaagataa gatcttcaac 420
ctcaagcaga caggatcagc attgaaatat gctacggaat ttcgaagata tgctggaaca 480
accaagtggg acgaaatcgc tatcatgagt cactactgta agggactcaa accagaagtc 540
agactagagt tagaaagatc tgccgagagt acagatctga acgatctaat tcaggactcc 600
atcgaatcag atgatcgtct ctatagatat cgacaaagcc aaagatcata caaaccccaa 660
ggaaaccaaa agcaagggcg ttaccgcaag aatgagggta gaccacgtta caatccacag 720
agatacggag accccatgga actagacgcc acgcactaca caaacgggaa cgatgactca 780
gaaaagagac gaagacgaga aaacaactta tgctttgaat gtggaaaagc agggcaccga 840
gcagtagact gccgaagcaa gaagacagga ggaaaaaggg gcaacttcaa acctaagttc 900
ggcaagggcc aacttaacgc cacctttgcc atctcagaaa actcaactaa aaccgaaaat 960
actgagactt tcaccgttga ggaatttcag caattactaa aggaattacc acgaaataaa 1020
gagggcatga atgcaataga cttatgggaa caagagtatt acagaacccc aacaccctct 1080
gtgacagaag aaagtcacca ggacgaggca gaagcggacc acgccacgat gagctggaca 1140
gcttgctatg atgaattctg cggaatccat cgatcagata aagaagcaac cggatggttc 1200
cccaagaaaa ggaagacgaa gaaccatcag aataatgtaa catgcgagga tttaactccc 1260
aatataactt cgcaagaagt tcgcaaagtt acccagcagt tgaatgctac gggacaggca 1320
ggacaagtgt actgcaaggt ccagataaat ggacacatac aatcagccat gatagattca 1380
ggggctacag gaaattttat tgcaccagaa gctgcaaagt acttggaaat accacttcaa 1440
acgaaacaac accccctatcg attgcaggac acgctagagg cgtccgcgag acgtaacacg 1500
cgccaagggg agttgaacgc gaacaacacc ggcgacgtag gacacccagt ccagggtcct 1560
ccattaagag cgaaggccag tacacctcct ctacaaatgc agaagccaac gacacggcac 1620
gaaatcgcaa tcgaggcaaa agaaaggcct acgataccag aacagtacaa gaaatatgaa 1680
catgttttca aagaaccagg gatccatgag gctttaccgg aacacaagcc atgggatcat 1740
gagataatat tggaggaagg caagatgcct gtgcacaccc caatttattc aatgtcagcc 1800
gatgagttaa aaaggctcag agaatacatc gacgacaatt tagccaaggg atggatcagg 1860
gaatccgcgt cccaagtggc cagtccaact atgtgggtac ccaagaagga tggacccgat 1920
agactagttg tagactatag aaagcttaac gcactcacta agaaggatcg atatccactt 1980
ccattagcta cggaattaag agatcgatta ggcggagcta cgatattcac caagatggac 2040

-continued

```
ctacgtaatg gttaccactt gatcagaatg aaggaaggcg aagaatggaa aaccgctttc    2100
aaaacaagat acgggctata cgagtaccaa gttatgccat tcgggctaac caacgcacca    2160
gctactttca tgaggcttat gaacaatgtg ttgtcacaat atttggatac ttgctgtata    2220
tgctacttgg acgacatcct agtatattca aacaacaagg ttcaacacat taaggacgtt    2280
agcaacatcc tcgaaagtct atccaaagca gacttgctgt gcaaaccaag caaatgcgaa    2340
ttccatgtca cagaaacaga attcttggga ttcaccgtat caagccaagg gctcaagatg    2400
agcaaagaca aggttaaggc agtgctcgaa tggaagcagc caaccacaat caaggaggta    2460
caatcctttc tagggttcgt caacttctac agaagattta tcaagggtta ttcagggatt    2520
actacaccct tgaccacgtt aaccagaaaa gatcaaggaa gcttcgaatg gactgccaaa    2580
gcacaggagt cattcgatac actcaaacaa gcagtggcag aagaaccaat actgttgact    2640
tttgacccag agaagaaat catagtggaa acggattcct cagatttcgc tataggagca    2700
gttctgagcc aaccgggcca gaatggaaaa taccagccaa tcgcattcta ctcccgaaaa    2760
ctatcaccag ctgagttaaa ttacgagata tatgacaaag aattactggc aatagtcgat    2820
gcatttagag aatggcgagt atatttggaa ggatcgaaat acacagtaca ggtgtataca    2880
gatcataaga acttggttta cttcaccaca acgaagcagt taaacagacg acaggtcaga    2940
tggtcggaga ccatggccaa ctacaatttc agaatttcat atgtcaaagg atcagaaaac    3000
gctagagccg acgctcttag ccgaaaacca gaatatcaag aaaacaaaac gtacgagtca    3060
tacgctatat tcaagaaaga cggcgaatca ctggtctaca atgcaccaca gcttgcagca    3120
acacacctgt tggaagacaa ccacctcagg aaacagatcc aatcacacta caacaaggat    3180
gctactgcca cacgcatacg caagacaata gaaccaggat tcactataga agatgatacc    3240
atatactttc atggaaaagt atacattccg agtcaaatga ccaaggaatt tgtgacggaa    3300
caacacggat tgccggcaca tggacaccaa ggaattgcaa ggacatttgc aagaatacgg    3360
gaaatcagtt acttcccacg aatgagaacg atagttgaag aagttgttgg aaattgtgac    3420
acctgcatac gaaacaagtc atcacgacat gctccgtatg gtcagctcca gaccccagac    3480
atgccttctc agccatggaa gtccatcaca tgggactttg tggtcaaact accactctca    3540
aaggatccta ctacaggaat tgagtacgac gcgatactca atatagtaga caggctaacg    3600
aaatttgcat atatgatacc attcaaggaa acatgggatg ctgagcaact agcatatgtg    3660
ttcctaaggg tcatagtaag catacacgga gtaccagatg agataatctc ggatcgagac    3720 aagctctta cctcgaaatt ctggactacc ttattagcac ttatgggtat caagagaaag    3780
ctatcgacat ctttccaccc acaaacagat ggtcaaacag agaggaccaa tcagacaatg    3840
gaagcatatc ttagatgcta tcgtataaaa tcccgatacc acaagaagtt aatgccgaat    3900
cagcaatag                                                           3909
```

<210> SEQ ID NO 20
<211> LENGTH: 4854
<212> TYPE: DNA
<213> ORGANISM: Botrytis cinerea

<400> SEQUENCE: 20

```
atggcatcca gagctaccgc cacaggtcaa tctgccggag acaccaacga catcgagatg      60
accgacgctc caaaggagat cactatcaac gaaacccttta agatcgcctt accagacaag    120
taccaaggta gtcgacaaga gctcgatact ttcctcttac aacttgagat ctacttccga    180
ttcaatgagg acaagttcac taccaaggaa tccaagagca tatgggccgc gtcatacctt    240
```

```
cgaggtgaag caaccaaatg gattcaacca tatttgcgcg actatttcga gcatgacgat    300
aaggatcgca tgcaacccac ccgaacaatc ttcaatagtt ttgaaggatt aagacagag     360 gttcgtagaa tcttcggaaa ttccaacgag ttagaggtag cggaagataa gatcttcaac    420
ctcaagcaga caggatcagc attgaaatat gctacgaatt tcgaagata tgctggaaca    480 accaagtggg acgaaatcgc tatcatgagt cactaccgca agggactcaa accagaagtc    540
agactagaat tagaaagatc tgccgagagt acagatctaa acgatctaat tcaggactcc    600
atcgaatcag atgatcgtct ctacagatat cgacaaagcc aaagatcata caaaccccaa    660
ggaaatcaga agcaagggcg ttaccgcaag aatgagggta gaccacgtta caatccacag    720
agatacggag accccatgga actagacgct acgcactaca caaacgggaa cgatgactca    780
gaaaagagac gaagacgaga taacaactta tgctttgaat gtggaaaagc agggcaccga    840
gcagcagact gccgaagcaa gaagacagga ggaaaaaggg gcaacttcaa acctaagttc    900
ggcaagggcc aacttaatgc caccttttgca atctcagaaa actcaactaa acccgaaaat    960
actgagactt tcaccgttga ggaattccag caattattag aggaattacc acgaaaccaa   1020
gagggcatga atgcaataga cttatgggaa caagagtatt acagaactcc aacaccctct   1080
gtgacagaag aaagtcacca ggacgaggca gaagcggacc acgccacgat aagctggaca   1140
gcttgctatg acgaattctg cggaatccat cgatcagata aagaagcaac cggatggttc   1200
cccaagaaga gaaagacgaa gaaccgacag aataatgtaa catgcaagga tttaactcca   1260
aatgtaactt cgcgaaaagt tcgcaaagtt acacagcaat gaatgctac gggacaggca    1320 ggacaaatat actgcacggt tcagataaat ggacacatac aatcagccat gatagattca   1380
ggggctacag ggaattttat tgcaccagaa gctgcaaagt acttggaaat accacttcaa   1440
acgaaacaac accctaccg attgcagtta gttgacggac agctagcagg gtctgacgga   1500
aagatttcgc aggagacaat cccagtacga atgggcataa cccaacatac agaggttata   1560
cagcttgacg ttgtgccatt gggccaacaa cagatcatct taggaatgcc atggttaaag   1620
gcacataatc cgaaaataga ttgggcacaa ggaattgtga catttgatca gtgcaaaagc   1680
ggtcacaggg acacgctaga ggcgttcgcg agacgtaaca cgcgccaagg agagttgaac   1740
gcgaacaaca ccggcgacgt aggacaccca gtccagggtc ctccattaag agcgaaggcc   1800
agtacacctc ctctacaaat gcagaagcca acgacacggc acgaaatcgc aatcgaggca   1860
aaagaaaagc ctacgatacc agaacagtac aagaattatg aacatgtttt caagaaccca   1920
gggatccatg aggctttacc ggaacacaag ccatgggatc atgagataat attggaggaa   1980
ggcaagatgc ctgtgcacac cccaatttat tcaatgtcag ccgatgagtt aaagaggctc   2040
agagagtaca tcgacgacaa tttagccaag ggatggatca gggaatccgc gtcccaagtg   2100
gccagtccaa ctatgtgggt acccaagaag gatggacccg atagactagt tgtagactat   2160
agaaagctta acgcactcac taagaaggat cgatatccac ttccattagc tacgaattaa   2220
agagatcgat taggcggagc tacgatattt accaagatgg acctacgtaa tggttaccac   2280
ttgatcagaa tgaaggaagg cgaagaatgg aaaaccgctt tcaaaacaag atacgggcta   2340
tacgagtacc aagttatgcc attcgggcta accaacgcac cagctacttt catgaggctt   2400
atgaacaatg tgttgtcaca atatttggat acttgctgta tatgctactt ggacgacatc   2460
ctagtatatt caaacaacaa ggttcaacac attaaggacg ttagcaacat cctcgaaagc   2520
ctatccaagg cagacttgct gtgcaaacca agcaaatgcg aattccatgt cacagagaca   2580
```

-continued

```
gaattcttgg gattcaccgt atcaagccaa gggctcaaga tgagcaaagg caaggttaag    2640
gcagtgctcg aatggaagca gccgaccaca atcaaggaag tacaatcctt tctagggttc    2700
gtcaacttct acagaagatt tatcaaaggt tattcaggga ttactacacc cttgaccacg    2760
ttaaccagaa aagatcaagg aagcttcgaa tggactgcca agcacagga gtcattcgat     2820
acgctcaaac aagcagtggc agaagagcca atactattga cttttgaccc agagaaagaa    2880
atcatagtgg agacggactc ctcggatttc gctataggag cagttctgag ccaacccgggt   2940
cagaatggaa aataccagcc aatcgcattc tactcccgaa aactatcacc agctgagttg    3000
aattacgaga tatatgacaa agaattactg gcgatagtcg atgcatttag agaatggcga    3060
gtatatttgg aaggatcgaa atacacagta caggtgtaca cagatcataa gaacttggtt    3120
tacttcacca caacgaagca gttaaacaga cgacaggtca gatggtcgga gaccatggcc    3180
aactacaact ttagaatttc atatgtcaaa ggatcagaaa atgctagagc cgacgctctt    3240
aaccgaaaac cagaatatca agaaaacaaa gcgtacgagt catacgctat attcaagaaa    3300
gacagcgaat cactggttta caatacacca cagcttgcaa caacacacct gttggaagac    3360
aaccacctca ggaaacagat ccaatcacac tacgacaagg atactactgc cacacgcata    3420
cgcaaaacaa tagaaccagg attcactata gaaaatgata ccatatactt tcatagaaaa    3480
gtatacattc cgagtcaaat gaccaaggaa tttgtgacgg aacaacacgg gttgccggca    3540
catggacacc aaggaattgc aaggacattt gcaagaatac gggaaatcag ttacttccca    3600
cgaatgagaa cgatagttga agaagttgtt ggaaattgtg acacctgcat acgaaacaag    3660
tcatcacgac atgctccgta tggtcagctc cagaccccag acatgccttc tcagccatgg    3720
aagtccatca catgggactt tgtggtcaaa ctaccactct caaaggatcc tactacagga    3780
attgagtacg acgcgatact caatatagta gacaggctaa cgaaatttgc atatatgata    3840
ccattcaagg aaacatggga tgctgagcaa ctagcatatg tgttcctaag gatcatagta    3900
agcatacacg gagtaccaga tgagataatc tcggatcgag acaagctctt tacctcgaaa    3960
ttctggacta ccttattagc acttatgggt atcaagagaa agctatcgac atcttttccac   4020
ccacaaacag atggtcaaac agagaggacc aatcagacaa tggaagcata tcttagatgc    4080
tatgtaaatt atcgacaaga caattgggta gagctattac ccatggcaca gttcgcatac    4140
aatacatcag aaacggaaac cacgaaaatc acaccagcac gagctaattt tgggtttaat    4200
ccacaagcgt ataaaatccc gataccacaa gaagttaatg ccgaatcagc gatagtacaa    4260
gtcgaacagt tgaaagatct ccaagagcaa ctggctcttg atctaagatt catatcttcc    4320
agaacagcag cgtactacaa tacgaaacgt agtatggaac ctacgcttaa agaggggggat   4380
aaagtttatt tgctacgacg aaacatcgaa accaagagac caagcaataa actcgaccac    4440
aggaaactag gaccattcaa gattgataag gtaataggaa cggttaatta tcaattgaaa    4500
ttaccagaca caatgaatat ccacccagta ttccacatat ccttgctcga accagcacca    4560
ccaggagcgc caaatgcgcc atttacagaa attgaaccag tcaacccaaa cgccatatac    4620
gatgtcgaaa caatactaga ctgcaaatac gtcagaaaca aggtcaagta tttgatcaaa    4680
tggttagact acccacattc agaaaacaca tgggaactca aggaagatct cagctgccct    4740
gagaaactac gggcattcca cctgaagtac ccacatctgc aacaaagcc tcaagctccg    4800
catcagacaa caaaggcaac gagggggtcga agaaaccaaa agaagaacca ctag         4854
```

<210> SEQ ID NO 21
<211> LENGTH: 1962

```
<212> TYPE: DNA
<213> ORGANISM: Botrytis cinerea

<400> SEQUENCE: 21
atgtgggtac ccaagaagga tggacccgat agactagttg tagactatag aaagcttaac    60
gcactcacta agaaggatcg atatccactt ccattagcta cggaattaag agatcgatta   120
ggcggagcta cgatattcac caagatggac ctactatatt caaacaacaa ggttcaacac   180
attaaggacg ttagcaacat cctcgaaagc ctatccaagg cagacttgct gtgcaaacca   240
agcaaatgcg aattccatgt cacagagaca gaattcttgg gattcaccgt atcaagccaa   300
gggctcaaga tgagcaaagg caaggttaag gcagtgctcg aatggaagca gccgaccaca   360
atcaaggaag tacaatcctt tctagggttc gtcaacttct acagaagatt tatcaaaggt   420
tattcaggga ttactacacc cttgaccacg ttaaccagaa aagatcaagg aagcttcgaa   480
tggactgcca agcacagga gtcattcgat acgctcaaac aagcagtggc agaagagcca   540
atactattga cttttgaccc agagaaagaa atcatagtgg agacggactc ctcggatttc   600
gctataggag cagttctgag ccaaccgggt cagaatggaa ataccagcc aatcgcattc   660
tactcccgaa aactatcacc agctgagttg aattacgaga tatatgacaa agaattactg   720
gcgatagtcg atgcatttag agaatggcga gtatatttgg aaggatcgaa atacacagta   780
caggtgtaca cagatcataa gaacttggtt tacttcacca caacgaagca gttaaacaga   840
cgacaggtca gatggtcgga gaccatggcc aactacaact ttagaatttc atatgtcaaa   900
ggatcagaaa atgctagagc cgacgctctt agccgaaaac cagaatatca agaaaacaaa   960
acgtacgagt catacgctat attcaagaaa gacggcgaat cactggttta caatgcacca  1020
cagcttgcag caacacacct gttggaagac aaccacctca ggaaacagat ccaatcacac  1080
tacgacaagg atgctactgc cacacgcata cgcaagacaa tagaaccagg attcactata  1140
gaaaatgata ccatatactt tcatggaaaa gtatacattc cgagtcaaat gaccaaggaa  1200
tttgtgacgg aacaacacgg gttgccggca catggacacc aaggaattgc aaggacattt  1260
gcaagaatac gggaaatcag ttacttccca cgaatgagaa cgatagttga agaagttgtt  1320
ggaaattgtg acacctgcat acgaaacaag tcatcacgac atgctccgta tggtcagctc  1380
cagaccccag acatgccttc tcagccatgg aagtccatca catgggactt tgtggtcaaa  1440
ctaccactct caaggatcc tactacagga attgagtacg acgcgatact caatatagta  1500
gacaggctaa cgaaatttgc atatatgata ccattcaagg aaacatggga tgctgagcaa  1560
ctagcatatg tgttcctaag gatcatagta agcatacacg gagtaccaga tgagataatc  1620
tcggatcgag acaagctctt tacctcgaaa ttctggacta ccttattagc acttatgggt  1680
atcaagagaa agctatcgac atctttccac ccacaaacag atggtcaaac agagaggacc  1740
aatcagacaa tggaagcata tcttagatgc tatgtaaatt atcgacaaga caattgggta  1800
gagctattac ccatggcaca gttcgcatac aatacatcag aaacgaaaac cacgaaaatc  1860
acaccagcac gagctaattt tgggtttaat ccacaagcgt ataaaatccc gataccacaa  1920
gaagttaatg ccgaatcagc gatatatgga acctacgctt aa                     1962
```

<210> SEQ ID NO 22
<211> LENGTH: 957
<212> TYPE: DNA
<213> ORGANISM: Botrytis cinerea

<400> SEQUENCE: 22

```
atggccaact acaattttag aatttcatat gtcaaaggat cagaaaacgc tagagccgac    60
gctcttagcc gaaaaccaga atatcaagaa acaaaacgt acgagtcata cgctatattc   120
aagaaagacg gcgaatcact ggtctacaat gcaccacagc ttgcagcaac acacctgttg   180
gaagacaacc acctcaggaa acagatccaa tcacactaca acaaggatgc tactgccaca   240
cgcatacgca agacaataga accaggattc actatagaag atgataccat atactttcat   300
ggaaaagtat acattccgag tcaaatgacc aaggaatttg tgacgaaaca catgggttg    360 ccggcacacg gacatcaagg gattgcaaga acatttgcaa gaatccggga atcagttac    420 ttcccacgaa tgagaacgat agttgaagaa gttgttggaa attgtgacac ctgcatacga   480
aacaagtcat cacgacatgc gccgtatggt cagctccaga ccccagacat gccttctcag   540
ccatggaagt ccatcacatg ggactttgtg gtcaaactac cactctcaaa ggatcctact   600
acaggaattg agtacgacgc gatactcaat atagtagaca ggctaacgaa attcgcatat   660
atgataccat tcaaggaaac atgggatgct gagcaactag catatgtgtt cctaaggatc   720
atagtaagca tacacggagt accagatgag ataatctcgg atcgagacaa gctctttacc   780
tcgaaattct ggactacctt attagcactt atgggtatca agagaaagct atcgacatct   840
ttccacccac aaacagatgg tcaaacagag aggaccaatc agacaatgga agcatatctt   900
agatgctatc gtataaaatc ccgataccac aagaagttaa tgccgaatca gcgatag      957
```

<210> SEQ ID NO 23
<211> LENGTH: 987
<212> TYPE: DNA
<213> ORGANISM: Botrytis cinerea

<400> SEQUENCE: 23

```
atccaatcac actacaacaa ggatgctact gccacacgca tacgcaagac aatagaacca    60
ggattcacta tagaagatga taccatatac tttcatggaa aagtatacat tccgagtcaa   120
atgaccaagg aatttgtgac ggaacaacat gggttgccgg cacacggaca tcaagggatt   180
gcaagaacat ttgcaagaat ccgggaaatc agttacttcc cacgaatgag aacgatagtt   240
gaagaagttg ttggaaattg tgacacctgc atacgaaaca agtcatcacg acatgcgccg   300
tatggtcagc tccagacccc agacatgcct tctcagccat ggaagtccat cacatgggac   360
tttgtggtca aactaccact ctcaaaggat cctactacag gaattgacat acacggagta   420
ccagatgaga taatctcgga tcgagacaag ctctttacct cgaaattctg gactacctta   480
ttagcactta tgggtatcaa gagaaagcta tcgacatctt tccacccaca aacagatggt   540
caaacagaga ggaccaatca gacaatggaa gcatatctta gatgctatgt aaattatcga   600
caagacaatt gggtagagct attacccatg gcacagttcg catacaatac atcggaaacg   660 gaaccacga aaatcacccc agcacgagct aattttgggt ttaatccaca agcgtataaa   720
atcccgatac acaagaagt taatgccgaa tcagcaatag tacaagtcga acagctgaaa   780
gatctccaag agcaactggc tcttgatcta agattcatat cttccagaac agcagcgtac   840
tacaatacga aacgtagtat ggaacctacg cttaagagg gggataaagt ttatttgcta   900
caacgaaaca tcgaaaccaa gagaccaagc aataaactcg accacaggaa actaggacca   960
ttcaagattg ataaggtaat aggaacg                                       987
```

<210> SEQ ID NO 24
<211> LENGTH: 3573
<212> TYPE: DNA
<213> ORGANISM: Botrytis cinerea

<400> SEQUENCE: 24

```
atggcatcca gagccaccgc cacaggtcag tctaccggag ataccaacga catcgagatg      60
accgatgccc caaaggagat cactatcaac gaaacactta agatcgcctt accagacaag     120
taccaaggta gtcgacaaga gctcgatact ttcctcttac aacttgagat ctacttccga     180
ttcaatgaag acaagttcac taccaaggaa tccaagagca tatgggctgc atcatacctc     240
cgaggtgaag caaccaaatg gattcaacca tatttgcgcg actatttcga gcatgacgat     300
aaggatcgca tgcaacccac ccgaacaatc ttcaatagtt ttgaaggatt aagacagag      360
attcgtagaa tcttcggaaa ttccaacgag ttagaggtag cggaagataa gatcttcaac     420
ctcaagcaga caggatcagc attgaaatat gctacggaat ttcgaagata tgctggaaca     480
accaagtggg acgaaatcgc tatcatgagt cactaccgta agggactcaa accagaagtc     540
agactagagt tagaaagatc tgccgagagt acagatctga cgatctaat tcaggactcc      600
atcgaatcag atgatcgtct ctatagatat cgacaaagcc aaagatcata caaaccccaa     660
ggaaaccaaa agcaagggcg ttaccgcaag aatgagggta gaccacgtta caatccacag     720
agatacggag acccatgga actagacgcc acgcactaca caaacgggaa cgatgactca      780
gaaaagagac gaagacgaga aaacaactta tgctttgaat gtggaaaagc agggcaccga     840
gcagtagact gccgaagcaa gaagacagga ggaaaaaggg gcaacttcaa acctaagttc     900
ggcaagggcc aacttaacgc caccttgcc atctcagaaa actcaactaa aaccgaaaat      960
actgagactt tcaccgttga ggaatttcag caattactaa aggaattacc acgaaataaa    1020
gagggcatga atgcaataga cttatgggaa caagagtatt acagaacccc aacaccctct    1080
gtgacagaag aaagtcacca ggacgaggca gaagcggacc acgccacgat gagctggaca    1140
gcttgctatg atgaattctg cggaatccat cgatcagata agaagcaac cggatggttc      1200
cccaagaaaa ggaagacgaa gaaccatcag aataatgtaa catgcgagga tttaactccc    1260
aatataactt cgcaagaagt tcgcaaagtt acccagcagt tgaatgctac gggacaggca    1320
ggacaagtgt actgcaaggt ccagataaat ggacacatac aatcagccat gatagattca    1380
ggggctacag gaattttat tgcaccagaa gctgcaaagt acttggaaat accacttcaa    1440
acgaaacaac atccctaccg attgcaggac acgctagagg cgtccgcgag acgtaacacg    1500
cgccaagggg agttgaacgc gaacaacacc ggcgactag gacacccagt ccagggtcct    1560
ccattaagag cgaaggccag tacacctcct ctacaaatgc agaagccaac gacacggcac    1620
gaaatcgcaa tcgaggcaaa agaaaggcct acgataccag aacagtacaa gaaatatgaa    1680
catgttttca aagaaccagg gatccatgag gctttaccgg aacacaagcc atgggatcat    1740
gagataatat tggaggaagg caagatgcct gtgcacaccc caatttattc aatgtcagcc    1800
gatgagttaa aaaggctcag agaatacatc gacgacaatt tagccaaggg atggatcagg    1860
gaatccgcgt cccaagtggc cagtccaact atgtgggtac caagaagga tggacccgat     1920
agactagttg tagactatag aaagcttaac gcactcacta agaaggatcg atatccactt    1980
ccattagcta cggaattaag agatcgatta ggcggagcta cgatattcac caagatggac    2040
ctacgtaatg gttaccactt gatcagaatg aaggaaggcg aagaatggaa accgctttc     2100
aaaacaagat acgggctata cgagtaccaa gttatgccat cgggctaac caacgcacca    2160
gctactttca tgaggcttat gaacaatgtg ttgtcacaat atttggatac ttgctatcaa    2220
ggaagcttcg aatggactgc caaagcacag gagtcattcg atacgctcaa gcaagcagtg    2280
```
gcagaagaac caatactgtt gacttttgac ccagagaaag aaatcatagt ggagacggac 2340
tcctcggatt tcgctatagg agcagttctg agccaaccgg gccagaatgg aaaataccag 2400
ccaatcgcat tctactcccg aaaactatca ccagctgagt taaattacga gatatatgac 2460
aaagaattac tggcaatagt cgatgcattt agagaatggc gagcatattt ggaaggatcg 2520
aaatacacag tacaggtata tacagatcat aagaacttgg tttacttcac cacaacgaag 2580
cagttaaaca gacgacaggt cagatggtcg gagaccatgg ccaactacaa ctttagaatt 2640
tcatatgtca aggatcaga aaacgctaga gccgacgctc ttagccgaaa accagaatat 2700
caagaaaaca aaacgtacga gtcatacgct atattcaaga aagacggcga atcactggtc 2760
tacaatgcac cacagcttgc agcaacacac ctgttggaag acaaccacct caggaaacag 2820
atccaatcac actacaacaa ggatgctact gccacacgca tacgcaagac aatagaacca 2880
ggattcacta tagaagatga taccatatac tttcatggaa aagtatacat tccgagtcaa 2940
atgaccaagg aatttgtgac ggaacaacat gggttgccgg cacacggaca tcaagggatt 3000
gcaagaacat ttgcaagaat ccgggaaatc agttacttcc cacgaatgag aacgatagtt 3060
gaagaagttg ttggaaattg tgacacctgc atacgaaaca agtcatcacg acatgcgccg 3120
tatggtcagc tccagacccc agacatgcct tctcagccat ggaagtccat cacatgggac 3180
tttgtggtca aactaccact ctcaaaggat cctactacag gaattgagta cgacgcgata 3240
ctcaatatag tagacaggct aacgaaattt gcatatatga taccattcaa ggaaacatgg 3300
gatgctgagc aactagcata tgtgttccta agggtcatag taagcataca cggagtacca 3360
gatgagataa tctcggatcg agacaagctc tttacctcga aattctggac taccttatta 3420
gcacttatgg gtatcaagag aaagctatcg acatctttcc acccacaaac agatggtcaa 3480
acagagagga ccaatcagac aatggaagca tatcttagat gctatcgtat aaaatcccga 3540
taccacaaga agttaatgcc gaatcagcaa tag 3573

<210> SEQ ID NO 25
<211> LENGTH: 3909
<212> TYPE: DNA
<213> ORGANISM: Botrytis cinerea

<400> SEQUENCE: 25
atggcatcca gagataccgc cacaggtcaa tctgccggag acaccaacga catcgagatg 60
accgatgccc caaaggagat cactatcaac gaaaccctta agatcgcctt accagacaag 120
taccaaggta gtcgacaaga gctcgatact ttcctcttac aacttgagat ctacttccga 180
ttcaatgagg acaagttcac taccaaggaa tccaagagta tatgggccgc atcatacctc 240
cgaggtgaag caaccaaatg gattcaacca tatttgcgcg actatttcga acatgacgat 300
aagaatcgca tgcaacccac ccgaacaatc ttcaatagtt ttgaaggatt taagacagag 360
attcgtagaa tcttcggaaa ttccaacgag ttagaggtag cggaagataa gatcttcaac 420
ctcaagcaga caggatcagc attgaaatat gctacggaat ttcgaagata tgctggaaca 480
accaagtggg acgaaatcgc tatcatgagt cactaccgca agggactcaa accagaagtc 540
agactggaat tagaaagatc tgccgagagt acagatctga acgatctaat tcaggactcc 600
atcgaatcag atgatcgtct ctacagatat cgacaaagcc agagatcata caaaccccaa 660
ggaaatcaga agcaagggcg ttaccgcaag aatgagggta gaccacgtta caatccacag 720
aggtacggag acccaatgga actagacgct acgcactaca caaacgggaa cgatgactca 780
gaaaagagac gaagacgaga aaacaactta tgctttgaat gtggaaaagc agggcaccga 840

```
gcagcagagt gccgaagcaa gaagacagga ggaaaaaggg gcaacttcaa acctaagttc      900
ggcaagggcc aacttaacgc cacctttgca atcccagaaa acccaactaa atccgaaaat      960
actgagactt tcaccattga agaattccag caattactag aggaattacc acgaaatcaa     1020
gagggcatga atgcaataga cttatgggaa caagagtatt acagaacccc aacaccctct     1080
gtaacagaag aaagtcacca ggacgaggca gaagcagacc acgccacaat gagctggaca     1140
gcctgctatg atgaattctg cggaattcat cgatcagata agaagcaac  cggatggttc     1200 cccaagaaaa ggaagacgaa gaaccatcag aataatgtaa catgcgagga tttaactccc     1260
aatacaactt cgcaagaagt tcgcaaagtt acccagcagt tgaatgctac gggacaggca     1320
ggacagatat actgcaaagt tcagataaat ggacacatac aatcagccat gatagattca     1380
ggggctacag gaaattttat tgcaccagaa gctgcaaagt acttggaaat accacttcag     1440
acgaaacaac acccctaccg attgcaggac acgctagagg cgtccgcgag acgtaacacg     1500
cgccaaggag agttgaacgc gaacgacacc ggcgacgtag acacccagt  ccagggtcct     1560 ccattaagag cgaaggccag tacacctcct ctacaaatgc agaagccaac gacacggcac     1620
gaaatcgcaa tcgaggcaaa agaaaagcct acgataccag aacagtacaa gaattatgaa     1680
catgttttca agaaccagg  gatccatgag gctttaccgg aacacaagcc atgggatcat     1740
gagataatat tggaggaagg caagatgcct gtgcacaccc caatttattc aatgtcagcc     1800
gatgagttaa aaaggctcag agaatacatc gacgacaatt tagccaaggg atggatcagg     1860
gaatccgcgt cccaagtggc cagtccaact atgtgggtac caagaagga  tggacccgat     1920 agactagttg tagactatag aaagcttaac gcactcacta agaaggatcg atatccactt     1980
ccattagcta cggaattaag agatcgatta ggcggagcta cgatatttac caagatggac     2040
ctacgtaatg gttaccactt gatcagaatg aaggaaggcg aagaatggaa aaccgctttc     2100
aaaacaagat acgggctata cgagtaccaa gttatgccat tcgggctaac caacgcacca     2160
gctactttca tgaggcttat gaacaatgtg ttgtcacaat atttggatac ttgctgtata     2220
tgctacttgg acgacatcct agtatattca aacaacaagg ttcaacacat taaggacgtt     2280
agcaacatcc tcgaaagcct atccaaggca gacttgctgt gcaaaccaag caaatgcgaa     2340
ttccatgtca cagagacaga attcttggga ttcaccgtat caagccaagg gctcaagatg     2400
agcaaaggca aggttaaggc agtgctcgaa tggaagcagc cgaccacaat caaggaagta     2460
caatcctttc tagggttcgt caacttctac agaagattta tcaaaggtta ttcagggatt     2520
actacaccct tgaccacgtt aaccagaaaa gatcaaggaa gcttcgaatg gactgccaaa     2580
gcacaggagt cattcgatac gctcaaacaa gcagtggcag aagagccaat actattgact     2640
tttgacccag agaagaaat  catagtggag acggactcct cggatttcgc tataggagca     2700
gttctgagcc aaccgggtca gaatggaaaa taccagccaa tcgcattcta ctcccgaaaa     2760
ctatcaccag ccgaattaaa ttatgaaata tacgacaaag aattactggc aatagtcgat     2820
gcatttagag aatggcgagt atatttggaa ggatcgaaat acacagtaca ggtgtacaca     2880
gatcataaga acttggttta cttcaccaca acgaagcagt taaacagacg acaggtcaga     2940
tggtcggaga ccatggccaa ctacaatttt agaatttcat atgtcaaagg atcagaaaac     3000
gctagagccg acgctcttag ccgaaaacca gaatatcaag aaaacaaaac gtacgagtca     3060
tacgctatat tcaagaaaga cggcgaatca ctggtttaca atgcaccaca gcttgcagca     3120
acacacctgt tggaagacaa ccacctcagg aaacagatcc aatcacacta cgacaaggat     3180
```

| | |
|---|---|
| gctactgcca cacgcatacg caagacaata gaaccaggat tcactataga aaatgatacc | 3240 |
| atatactttc atggaaaagt atacattccg agtcaaatga ccaaggaatt tgtgacggaa | 3300 |
| caacatgggt tgccggcaca tggacatcaa ggaattgcaa ggacatttgc aagaatacgg | 3360 |
| ggaatcagtt acttcccacg aatgagaacg atagttgaag aagttgttgg aaattgtgac | 3420 |
| acctgcatac gaaacaagtc atcacgacat gctccgtatg gtcagctcca gaccccagac | 3480 |
| atgccttctc agccatggaa gtccatcaca tgggactttg tgatcaaact accactctca | 3540 |
| aaggatccta ctacaggaat tgagtacgac gcgatactca atatagtaga caggctaacg | 3600 |
| aaatttgcat atatgatacc attcaaggaa acatgggatg ctgagcaact agcatatgtg | 3660 |
| ttcctaaggg tcatagtaag catacacgga gtaccagatg agataatctc ggatcgagac | 3720 |
| aagctcttta cctcgaaatt ctggactacc ttattagcac ttatgggtat caagagaaag | 3780 |
| ctatcgacat ctttccaccc acaaacagat ggtcaaacag agaggaccaa tcagacaatg | 3840 |
| gaagcatatc ttagatgcta tcgtataaaa tcccgatacc acaagaagtt aatgccgaat | 3900 |
| cagcgatag | 3909 |

<210> SEQ ID NO 26
<211> LENGTH: 288
<212> TYPE: DNA
<213> ORGANISM: Botrytis cinerea

<400> SEQUENCE: 26

| | |
|---|---|
| atgaccaagg aatttgtgac ggaacaacat gggttgccgg cacacggaca tcaagggatt | 60 |
| gcaagaacat ttgcaagaat ccgggaaatc agttacttcc cacgaatgag acgatagtt | 120 |
| gaagaagttg ttggaaattg tacacacctg catacgaaac aagtcatcac gacatgcgcc | 180 |
| gtatggtcag ctccagaccc cagacatgcc ttctcagcca tggaagtcca tcacatggga | 240 |
| ctttgtggtc aaactaccac tctcaaagga tcctactaca ggaattga | 288 |

<210> SEQ ID NO 27
<211> LENGTH: 11301
<212> TYPE: DNA
<213> ORGANISM: Botrytis cinerea

<400> SEQUENCE: 27

| | |
|---|---|
| caaaggggc attacgcttc caactgccga aaccctgttg tatgtcaaca ctgtaaagga | 60 |
| agtcacggat ccagagagtg cccaggaact atgtcacagc cttcccgaca gggaaacgct | 120 |
| tagacccagc tgttattctg agcgtccac tgacgctggg tccccaaata gaaggacgta | 180 |
| ctacctttac cattatagca atgttccaac caaaagataa gccgatagcg cttcgatgcc | 240 |
| ttatcgactc aggagcacaa gccaacatca tccaacaatc caagtgtatc gaatgggact | 300 |
| ggctgcctat taagaaagga acagctttag tatctgcgaa cggtaccacg atgccgtcgt | 360 |
| atggtaacca tcagttcccc gtcgaagtaa aagatcaaaa gggagagaag agaaccttca | 420 |
| cccacgagtt tactgctgct gtactagact tacccaaaat cgatgctata tttggattac | 480 |
| cctggctaca agcggtaaac ccagatatcg actggaaatc gacgtctctt cactatcgcc | 540 |
| cctctcttag cgacctcgaa atgatttctg caagcgaact ctatagcgaa gtgaaaaagg | 600 |
| gcgtccatgt atatgttata ctaccagaga tccagcccca ttaccgtaga acaacgggt | 660 |
| accgccgggt actcacgctc tccacactaa atatccccga agaataccaa gaataccaac | 720 |
| aagccttttc cgaggaagaa agcagtactc taccagaaca ccactcgatg gagcatcgca | 780 |
| ttgatctcga agccgattcg aaacctcctt gggggccaat ctattcttta tctgaagagg | 840 |

```
aatcaatagt attaagggaa tacttagtag aatatcaaaa aaagggatgg ataaggaggt    900
ccattagttc ggcaggagcg ccaatcatgt ttgttcccaa gaaggggga ggctatcggc     960
tttgtgtcga ctaccggggt ctaaatagga taaccaaaaa ggatcgaacc ccgctacccc   1020
taatcagcga gtccttagac cgacttcgac aaggtgtcgt cttcactaaa ttggacctgc   1080
gagatgccta ccaccgtatt cgtatcaggg aaggcgacga atggaagacg gcgttccgca   1140
cgcggtacgg gcaattcgaa tacttagtta tgccattcgg cctgaccaat gctccagcaa   1200
cgttccaaac atacatcaat caagcactgt caggcttgac agacaccata tgcgtagtgt   1260
acctagatga tatcctgatt tactctgagg atagagaaag ccacacgcgg gatgtccgca   1320
gggtcctcga acgccttata gaatacaagc tgttcgcaaa actgaaaaaa tgtgtctttt   1380
acacccatga ggttgaattc ctaggattcg tcgtctcggg agcgggagtg acgatggaat   1440
ccagccgcat tcaaactatt atagaatggc caacacctac aaaccttagg gagctacagg   1500
tgttcctggg cttcgcgaac ttctatcgac ggtttatcag gacctattcg acggtagccc   1560
acgggatgac cgcccttatg aagggaacaa agaaaggtaa aatggtaggg gagtttatat   1620
ggacaaagga ggcccaagat gcatttgagg cactaaagaa agcattcacc acggcaccga   1680
tactcaagca cttcgaacca tcgctccgca tcatggtcga aaccgactcg tcggtgtttg   1740
ctctaggatg catcctatcg caactattcg aaggagggac tgcagaagca ccgatacgac   1800
ggtggcaccc cgtcgcgttc tattcgagaa agctgaaccc tgcagaacaa cgatacttca   1860
ctcacgatca ggaattatta gcaatataca ctgcattcat gcaatggcgc cattacttga   1920
taggtagtcg gcacacaatc gtggtgaaat cggaccataa cagcttacaa cattttatgg   1980
tgaaaaagac cctcaatggc agacaagcta gatgggcgga agtactagca gcctacgact   2040
tcgaaatagt gtacagggca gggaaactga atccagccga cgggccatcg cgccgccccg   2100
actacgctac cgacacggag ggtatcaatg atatgctacc cacactccag aataaattaa   2160
aaagtaccgc agttatcgcg agtttatttt acgaatccac cgtgaaaacg gaaccctgc    2220
gtattgctat tagtcgcttg caaagggaag ggtatagctt gccattacgt ggacagttag   2280
tttcactggt aaaaactggt tgcaaacagt cgataccacg tcggattgcc agtgttttcg   2340
catccgacga aacggcattc gaacctatat cggagtcgat gggaaaagct ttattgcggc   2400
ttcagaaaga agacgatttt ataaagaata aagagtacct aagacaaaga ttacgttccg   2460
ccggagacgc ctcaccacgg caggtgggcg ccgacgagct ccttagacac aaggggagcg   2520
cgtacgtacc gccagacagc gctctcagag cagaaatctt agaaacgcat cacgatgacc   2580
ctattggagg tcattggggt gtcgctaaaa cattggaaat actgaagtct aaatattatt   2640
ggccttcaat gagaaaagac gtcaaacaac atgtcaaaac atgtgcggta tgccagcgaa   2700
ccgctatcaa aagacataag ccacacggcg agttacagac cctccctatt ccaaaaggac   2760
cctggaaaga gataactatg gattttatta cagatttacc tccttcgaaa cacggaaaac   2820
acgtatacga ttctattcta gtagtagtcg acaggttcac gaagctagcc cgatatatcg   2880
ccgtcaacaa gacgatatcg tctcctgaat tagctgacac tatggtcagc acagtattta   2940
aagactttgg tgtgccagag ggcatagtct ccgataggg accgcaattc gtcagtaaat   3000
tttggagtag cctaatgttt tacttgcgaa tccgtcgtaa gctgtcgacg gcgttccacc   3060
cgcagaccga cggtcaaacc gaacgacaaa accaaaattt gattcactat ataagttgct   3120
acaccaacta taggcaagac gactgggcat cgctattgcc ccttgctgaa ttcacatata   3180
```

```
acgcgacatg gcacagtaca accaatacaa gcccattcca ggctatgtat gggttccaac    3240
ccacattcca ttatatcggc gaggacgccg atttagaggg aagggcgccg gcagcacgcg    3300
agcgcatcga cgctttagag aaagaaagag aaaagctgaa agaattctgg aaatcggcaa    3360
ccaatcagaa aaacaagaac actacgaagg ggtcaccaca gcgatatagc atcggggaca    3420
aggtgatgct aagcacaaag aacattaaac aactgcgacc taagaaaaaa ttctccgatc    3480
gatttatagg cccctttgtc gtgacgggta taaaaaccag cgggcaagca tacgaactta    3540
gattaccgcc cacctacaag atccacaatg tattccacgt ctctttactc gaaccatggc    3600
acgaacgaca gggtaccgcc gacccgccgc cgccagaaga aattgacgat cacatagagc    3660
atgaggtgga aaggatttta gcacatagaa aaagaggcag aggtgtgcaa tacctggtgc    3720
gatggaaggg ctaccaaccg gcggaagaca cgtgggaagc accctacaac ctagaaaatg    3780
cgaaagcagc gatgggagaa tatcataaag aagaagcatt accaatacag aaaaagaaga    3840
gaacaagaaa aaagcttaaa aatacttgat acaaaaagac ctcacgagac ccacacccag    3900
aacgcatgca tcacaccaag ctacccaaaa aggactatcc aacaaagaaa ccagaaagga    3960
caactcctcc gaacccacag cataccgaca accaaaccca agtgacccat cacgcaaaga    4020
gaactctgga aggtcgaaat cagttcccta attcatctgc ctgatccagg aggtcagctg    4080
caatatctcg atcgccaaga aggacagaac ctacatcgct ggcatatccc ccgggactcg    4140
cgagcccgat ctgatcaacc tcacccccc cactgatctc atcttgatca ccgactcctt    4200
cctcctcgtt ctcgcgaatc tcgctgacag ggcgagctcc tgtcggaaaa ccagcggcaa    4260
cccgttgcct cttggagacc cgctccacat cagaattctc agagcgaagc ctttggggcg    4320
aatctgcttg actatcagac tcaccaatat agacttgttg aacagtgctg ggagccctct    4380
ttcgggattt aagagagcct acgggatgag agcggggtgt cggtgtgttg cgagaggcaa    4440
gctgcgacga cttagaagcg gaaagggaa tggcggatct agtcgcgagc ttatcggacc    4500
gagaacgacg aggcgtagca ggaggagcgt tcttctctacc caagcttcca aacaataaag    4560
ccggtacact ctcatccaag gggtgacgcg gggcaccggt ggtctgatga ggttgatccg    4620
acacatcatc ctcttcagga gcagactctt cggattcatt gggatccacg attacactcc    4680
tcttcaactt cgcagaacct ttccggaggc cttgctgagc cgtcgtgaag acagcggggc    4740
ccgtccggct cgatgaagca gaagcatgac ggcgacctag ggaaccagct accatattca    4800
ggccctggtt accacctggg ggccccggag gagcttgaac accctgcagt gcgtcggcga    4860
cagcgcgcac agcgcgaggg tgtataaccg gagccatgaa ctccccttct tcgtccgagt    4920
ttaaggcggc gattaatggt gcagtaggag ctgcggcggc gacgtccaag gcaggcaggt    4980
tattctaaga accatcaaat cagctatcaa cagcaccaag gggcaagagc agggcaaccg    5040
acaacgaatc gatacgaatc cacaatgcgc tccataagat cgccaattct actcaatttg    5100
gacaccagaa gaagagtcaa ttcctctgcg gactgcggtt tgtgagtccc ccttgtttta    5160
acctcttttc gaaggaaagc ctccactgcc ttgacgtatc gattacaccg gcgaatcacc    5220
acctcggagg cgtcctcatc ctcttggcta ttatccggag taaggcacca aaaggcatga    5280
gtctgatata agaggttcac gtcgggaaca aagcgaggag gtatcgggag gcagactttc    5340
ttttgtttgc gacaataact acatttagca gcaggacctt tatcaaaatg gcaaaattcg    5400
tcgttagaag agacggcaat tcgcttagaa catcgaaggc aagtagggat aactaacgcg    5460
gaaggggccc ctgcgaccg atcagcgata gcagccggag cgatgggttg cagtgcagcc    5520
atcttcgtat gagtaaataa gggggaataa tctgattgtg ggagatatat cagaggcaag    5580
```

```
aagaccccc  ttatagaact  atcggtgatc  tgccggtaag  gcggtgaggc  gcgtaagaat   5640
gccgccgttt  gcttgtttat  tgtttgtaat  gcctaaacaa  gattggaatt  gcttttggaa   5700
tgcggcgcag  ggtcgggcat  gcagcgacgc  gacgacgcga  cccacattcc  gagtaaacaa   5760 tacgaagga   agcaaacact  tctcgggacg  cgaagtgtaa  agagaggggc  tctgttacgg   5820
gacaaaacgt  gaccggctca  attaggcacg  tgacagtgga  cctctcgggt  ctactgcgtg   5880
ccgaatgggg  cccgcacacg  tataaattgt  ataatttgca  tagttataga  aaagcaatga   5940
aaagtcttgg  tgccacaata  tactagttga  ttcatttgtt  acggaggtac  ccgcaccgca   6000
acatggatta  taagataaac  ctaaggcctt  ggtgttggaa  cctacgaaaa  cagcactgta   6060
gggacagttg  aattaaaggg  taactaaaga  tagcagtaac  cgaatcaata  agcaatgatt   6120
aaaagatagg  tacctatctt  tgttggcac   ctaccctaca  gtaggcacag  gagggatagc   6180
ggttataggt  tatctagtaa  gcacaggtta  gataagcagt  agtatcatgt  aggtcacggg   6240
gcaagtgtca  cgtgatggat  agacaggata  ggcaggctat  ccaggctatc  cgtggataga   6300
caggatagac  agtctaccca  agctatccag  acgagaacga  aggtctatat  aagggaatgg   6360
gtttcattac  aatgtagagc  ttcgtgctca  agaacaatca  ttagtttcat  tactatagtt   6420
acgagaattg  caaccagtta  caaccttatt  gaattcctac  ttgaagtcta  gtctaaacca   6480
cctcgagaga  tctctagaca  cttccacgtg  accctagagg  cagctcccgt  aacactttga   6540 gcacccttc   tgcttcaagt  accgattcga  taaccaaccg  ctaatatggc  atccagagct   6600
accgccacag  gtcagtctac  cgaagatacc  aacgacatcg  agatgaccga  tgccccaaag   6660
gagatcacta  tcaacgaaac  acttaagatc  gccttaccag  acaagtacca  aggtagtcga   6720
caagagctcg  atactttcct  cttacaactt  gagatctact  tccgattcaa  tgaagacaag   6780
ttcactacca  aggaatccaa  gagcatatgg  gctgcatcat  acctccgagg  tgaagcaacc   6840
aaatggattc  aaccatattt  gcgcgactat  ttcgagcatg  acgataagga  tcgcatgcaa   6900
cccacccgaa  caatcttcaa  tagttttgaa  ggatttaaga  cagagattcg  tagaatcttc   6960
ggaaattcca  acgagttaga  ggtagcggaa  gataagatct  tcaacctcaa  gcagacagga   7020
tcagcattga  aatatgctac  ggaatttcga  agatatgctg  gaacaaccaa  gtgggacgaa   7080
atcgctatca  tgagtcacta  ctgtaaggga  ctcaaaccag  aagtcagact  agagttagaa   7140
agatctgccg  agagtacaga  tctgaacgat  ctaattcagg  actccatcga  atcagatgat   7200
cgtctctata  gatatcgaca  aagccaaaga  tcatacaaac  cccaaggaaa  ccaaaagcaa   7260
gggcgttacc  gcaagaatga  gggtagacca  cgttacaatc  cacagagata  cggagacccc   7320
atggaactag  acgccacgca  ctacacaaac  gggaacgatg  actcagaaaa  gagacgaaga   7380
cgagaaaaca  acttatgctt  tgaatgtgga  aaagcagggc  accgagcagt  agactgccga   7440
agcaagaaga  caggaggaaa  aagggcaac   ttcaaaccta  agttcggcaa  gggccaactt   7500
aacgccacct  ttgccatctc  agaaaactca  actaaaaccg  aaaatactga  gactttcacc   7560
gttgaggaat  ttcagcaatt  actaaggaa   ttaccacgaa  ataagagggg  catgaatgca   7620
atagacttat  gggaacaaga  gtattacaga  accccaacac  cctctgtgac  agaagaaagt   7680
caccaggacg  aggcagaagc  ggaccacgcc  acgatgagct  ggacagcttg  ctatgatgaa   7740
ttctgcggaa  tccatcgatc  agataaagaa  gcaaccggat  ggttccccaa  gaaaaggaag   7800
acgaagaacc  atcagaataa  tgtaacatgc  gaggatttaa  ctcccaatat  aacttcgcaa   7860
gaagttcgca  aagttaccca  gcagttgaat  gctacgggac  aggcaggaca  agtgtactgc   7920
```

```
aaggtccaga taaatggaca catacaatca gccatgatag attcaggggc tacaggaaat    7980
tttattgcac cagaagctgc aaagtacttg gaaataccac ttcaaacgaa caacaccccc    8040
tatcgattgc agttagttga tggacagcta gcagggtctg acggaaagat ttcgcaggag    8100
acaatcccag tacgaatggg cataacccaa catacagagg ttatacagct tgacgttgtg    8160
ccattgggcc aacaacagat catcttagga atgccatggt tgaaggcaca taatccgaaa    8220
atagattggg cacaaggaat tgtgacattt gatcagtgca aaagcggtca cagggacacg    8280
ctagaggcgt ccgcgagacg taacacgcgc aaggggagt tgaacgcgaa caacaccggc     8340
gacgtaggac acccagtcca gggtcctcca ttaagagcga aggccagtac acctcctcta    8400
caaatgcaga agccaacgac acggcacgaa atcgcaatcg aggcaaaaga aaggcctacg    8460
ataccagaac agtacaagaa atatgaacat gttttcaaag aaccagggat ccatgaggct    8520
ttaccggaac acaagccatg ggatcatgag ataatattgg aggaaggcaa gatgcctgtg    8580
cacaccccaa tttattcaat gtcagccgat gagttaaaaa ggctcagaga atacatcgac    8640
gacaatttag ccaagggatg gatcagggaa tccgcgtccc aagtggccag tccaactatg    8700
tgggtaccca agaaggatgg acccgataga ctagttgtag actatagaaa gcttaacgca    8760
ctcactaaga aggatcgata tccacttcca ttagctacgg aattaagaga tcgattaggc    8820
ggagctacga tattcaccaa gatggaccta cgtaatggtt accacttgat cagaatgaag    8880
gaaggcgaag aatggaaaac cgcttttcaaa acaagatacg ggctatacga gtaccaagtt    8940
atgccattcg ggctaaccaa cgcaccagct actttcatga ggcttatgaa caatgtgttg    9000
tcacaatatt tggatacttg ctgtatatgc tacttggacg acatcctagt atattcaaac    9060
aacaaggttc aacacattaa ggacgttagc aacatcctcg aaagtctatc caaagcagac    9120
ttgctgtgca aaccaagcaa atgcgaattc catgtcacag aaacagaatt cttgggattc    9180
accgtatcaa gccaagggct caagatgagc aaagacaagg ttaaggcagt gctcgaatgg    9240
aagcagccaa ccacaatcaa ggaggtacaa tcctttctag ggttcgtcaa cttctacaga    9300
agatttatca agggttattc agggattact acacccttga ccacgttaac cagaaaagat    9360
caaggaagct tcgaatggac tgccaaagca caggagtcat tcgatacact caaacaagca    9420
gtggcagaag aaccaatact gttgactttt gacccagaga agaaatcat agtggaaacg     9480
gattcctcag atttcgctat aggagcagtt ctgagccaac cgggccagaa tggaaaatac    9540
cagccaatcg cattctactc ccgaaaacta tcaccagctg agttaaatta cgagatatat    9600
gacaaagaat tactggcaat agtcgatgca tttagaatt ggcgagtata tttggaagga    9660
tcgaaataca cagtacaggt gtatacagat cataagaact tggtttactt caccacaacg    9720
aagcagttaa acagacgaca ggtcagatgg tcggagacca tggccaacta caatttcaga    9780
atttcatatg tcaaaggatc agaaaacgct agagccgacg ctcttagccg aaaaccagaa    9840
tatcaagaaa acaaaacgta cgagtcatac gctatattca agaaagacgg cgaatcactg    9900
gtctacaatg caccacagct tgcagcaaca cacctgttgg aagacaacca cctcaggaaa    9960
cagatccaat cacactacaa caaggatgct actgccacac gcatacgcaa gacaatagaa    10020
ccaggattca ctatagaaga tgataccata tactttcatg gaaagtata cattccgagt     10080
caaatgacca aggaatttgt gacggaacaa cacggattgc cggcacatgg acaccaagga    10140
attgcaagga catttgcaag aatacgggaa atcagttact tcccacgaat gagaacgata    10200
gttgaagaag ttgttggaaa ttgtgacacc tgcatacgaa acaagtcatc acgacatgct    10260
ccgtatggtc agctccagac cccagacatg cctcctcagc catggaagtc catcacatgg    10320
```

```
gactttgtgg tcaaactacc actctcaaag gatcctacta caggaattga gtacgacgcg  10380
atactcaata tagtagacag gctaacgaaa tttgcatata tgataccatt caaggaaaca  10440
tgggatgctg agcaactagc atatgtgttc ctaagggtca tagtaagcat acacggagta  10500
ccagatgaga taatctcgga tcgagacaag ctctttacct cgaaattctg gactacctta  10560
ttagcactta tgggtatcaa gagaaagcta tcgacatctt tccacccaca aacagatggt  10620
caaacagaga ggaccaatca gacaatggaa gcatatctta gatgctatgt aaattatcga  10680
caagacaatt gggtagagct attacccatg gcacagttcg catacaatac atcggaaacg  10740
gaaaccacga aaatcacccc agcacgagct aattttgggt ttaatccaca agcgtataaa  10800
atcccgatac cacaagaagt taatgccgaa tcagcaatag tacaagtcga acagctgaaa  10860
gatctccaag agcaactggc tcttgatcta agattcatat cttccagaac agcagcgtac  10920
tacaatacga aacgtagtat ggaacctacg cttaaagagg gggataaagt ttatttgcta  10980
caacgaaaca tcgaaaccaa gagaccaagc aataaactcg accacaggaa aataggacca  11040
ttcaagattg ataaggtaat aggaacggtt aattatcgat tgaaattacc agacacaatg  11100
aatatccacc cagtattcca catatccttg ctcgaaccag caccaccagg agcgccaaat  11160
gcgccattta cagaaatcga accagtcaac ccaaacgcca tatacgacgt tgaaacaata  11220
ctagattgta aatatgtcag gggcaaaatc aagtatttga tcaaatggtt agactaccca  11280
cattcggaaa acacatggga a                                            11301

<210> SEQ ID NO 28
<211> LENGTH: 936
<212> TYPE: DNA
<213> ORGANISM: Botrytis cinerea

<400> SEQUENCE: 28

```
gaagaggttg ttggcaatat tttgaagaaa gctgaggctg atttgaatgg agattaaaag     60
gggaatgaag ctgcggggcc accgatagca caaaaactac tgaagatttg aagcacgtta    120
aaattacact caggaataaa cggatggcaa gcttttcgat cgcccaaaca cggatctacg    180
actacgagtt acgcacgaca tgatttagcc ttttgtgtgc aatgatgatt agatagcatt    240
gcatttctcg aaattgacgg cacgactttt acgggcagat aatatcaaag attcctagtg    300
agcaagcggt gatgatacga tgtcattcca aaagtttttt cctcgcgaat tttatttcat    360
ttcgaaggca tctttgctta gcagcatatt cacctttgat gtcctctgta ggggatggag    420
tctctaatct cgcggtcaca atgagacgtg atgcgctgcg aagtggtgac aatttccctt    480
tacttagaat agatcatgca cacatgcatg atgcatagct agctagtttt ttattcaatg    540
atagtttaat gacaaacacg tatctagata tcctcattca tgtatctgtg ggaggttgac    600
ttaagttatg gctgacttga tagtttcatt atatatgtat atgtgatatc taagtaaaga    660
ttaaagtgaa atcgaaatgc aacgccgaaa ttctattaat tccatgaaat gatgtgatat    720
ggcatgacat gatatccaaa ctccgatttg aaatgctcca gcttcgcttt ctaaaattgg    780
taaaagggac attatttcgt ctggttgtgg gttttcattt ctgtgctcct actaggtgtg    840
aatgatagag tatgctgtgg tgtggtgtga tctcggaatt tggaaatttg agggctgtat    900
atcacctcat ttcgtgtgtc cgaatttcta cagact                              936
```

<210> SEQ ID NO 29
<211> LENGTH: 670
<212> TYPE: DNA

<213> ORGANISM: Botrytis cinerea

<400> SEQUENCE: 29
agagcatttg taggggaagg aggaaaaatt gaggaggagg ataagatgaa ttttgataaa 60
tttatttcct aacatcaggt cacaatctat gaattacatt tgatagtatt acgtatgccg 120
gtctgtacac aacacaacca tatagtaagg tatcaatcaa atgcgatgga tagtcatttc 180
aatttcttag tgaataatta caacgaacca gtaaaatagc aataactctg aaaagcttcc 240
ggactgccaa aaggtctcca ggacgagatt attacgaaga acccaagaat tcgcctagga 300
accaagataa acaaatcatc gacgtgttgc acttccatct atgcgacaat tatgccaagc 360
gagccgccag ttcttggggg tggagcgcta ggaatagggg gccggattgc catatcctta 420
tctagatcta gatggtatcg atatgataaa tcaatgcaat ggagagttaa aaagttatat 480
gccatatgat tgataattat tgacaatgca ggctatcgcg ggacaatggt aaatggttgt 540
aaaatatgga gtctatttcc ttagctagcg ataagatggg tggtttaaac acatcccgcc 600
ttctctttat cattctcctt ctcgtattca tatatcataa ttgcaaagta aggttgtatt 660
ttggactgtg 670

<210> SEQ ID NO 30
<211> LENGTH: 345
<212> TYPE: DNA
<213> ORGANISM: Verticillium dahilae

<400> SEQUENCE: 30
aagctgtcaa ttgatgcgga gggtgagtga acgtctcgtc ggcggggccc cttgaggcga 60
gcgcccgttg gggggtgttg tggcactagg ttctctaggc cggcggtgac tttcattact 120
atattagaag caaatacggc gccttcatca caataataaa tatcgatctc gagtcgattc 180
cagacccgtt ataaacctat gtctgtgcaa ccagttgggt gctaatttct tgcattatca 240
tcatggatgt tgtctatttg agtctcaggt ccagctggtg cttataggtc atctccagta 300
tgcgactacc tctctccctc tttgccattc ctaactgatt ctaac 345

<210> SEQ ID NO 31
<211> LENGTH: 1000
<212> TYPE: DNA
<213> ORGANISM: Verticillium dahilae

<400> SEQUENCE: 31
cttcatcttc caaccgccat tacctccccc atacgcgtcc tgccaaagaa tcataactgg 60
ctaaaacata agacgggact ggtcatccgc tgaaccattc cgagctatgt gtcctgattg 120
acccatctcg gcttattcgc tctcaaatac gactgcaatc gcgtgtggct tggaaaccgt 180
ggaataccat cctcatattg tcagcacctg tagcgataca gcacaatgct tgacgattcg 240
gaatcatttt ccgcttcttt gcggagcagc ggatgtccaa ttgacgatga cttgactcca 300
gaaccaacgt ccgaatcacg cgactcaacc tccctaccgt atggccttca ggacgacatc 360 ggccccccttg ctgccacccc gagccagtcg agtaacgtca caatcaatgc acgggcatac 420
cagttggaga tgctggcgga aagtaggaag aggaatatca ttctagctgt gcgaaccttc 480
cctcttgcgc cagtcaacct cgattgacac ctccatagat ggacacaggc agtggcaaga 540
cccaagtgta cgttccctgc aagccgaacc tgattattga tactgatttt cccagtgccg 600
tcctccgaat tcgagcagag ctagaagaag ggcttcaga caaggtttga caaactccac 660
ttggtagctt cgcaatcact tacagggttt tagcttgtat ggttcgtggc tcacaatgtt 720

```
gagctttgcg ctcagcagca ttctgtactg cagtctcaga ttcctgcagt tcagaccaag    780
ctgcttcttg gcagcgataa tgttgattca tggtccaacc aagagacttg gaacgctgtg    840
cttctcaacg tcaaaattgt ggtgtcaacc cctcaagttc tctgcgatgc cttgagccac    900
ggctttgtcc agatgggttc attatccttg cttgtctttg atgaaggtat tcaatcagcg    960
cagtttatca agtgttcttg ccctaacaac ggtgtagcgc                         1000
```

<210> SEQ ID NO 32
<211> LENGTH: 25
<212> TYPE: DNA
<213> ORGANISM: Verticillium dahilae

<400> SEQUENCE: 32

```
taaggatcgg aggttcgaat cagtt                                           25
```

<210> SEQ ID NO 33
<211> LENGTH: 26
<212> TYPE: DNA
<213> ORGANISM: Verticillium dahilae

<400> SEQUENCE: 33

```
gcgaggtgag aggacgacca gccaag                                          26
```

<210> SEQ ID NO 34
<211> LENGTH: 26
<212> TYPE: DNA
<213> ORGANISM: Verticillium dahilae

<400> SEQUENCE: 34

```
catctgagag gacgtcccgc catggc                                          26
```

<210> SEQ ID NO 35
<211> LENGTH: 26
<212> TYPE: DNA
<213> ORGANISM: Verticillium dahilae

<400> SEQUENCE: 35

```
gtccgggaaa tgaccagctt gagcag                                          26
```

<210> SEQ ID NO 36
<211> LENGTH: 28
<212> TYPE: DNA
<213> ORGANISM: Verticillium dahilae

<400> SEQUENCE: 36

```
atgtcgatgg tcggatgtat ccttttct                                        28
```

<210> SEQ ID NO 37
<211> LENGTH: 18
<212> TYPE: DNA
<213> ORGANISM: Verticillium dahilae

<400> SEQUENCE: 37

```
gattggaacc tcagatcc                                                   18
```

<210> SEQ ID NO 38
<211> LENGTH: 18
<212> TYPE: DNA
<213> ORGANISM: Verticillium dahilae

<400> SEQUENCE: 38

```
gcttggaacc tctgatcc                                                   18

<210> SEQ ID NO 39
<211> LENGTH: 18
<212> TYPE: DNA
<213> ORGANISM: Verticillium dahilae

<400> SEQUENCE: 39
gactctaacc ttcgatct                                                   18

<210> SEQ ID NO 40
<211> LENGTH: 19
<212> TYPE: DNA
<213> ORGANISM: Verticillium dahilae

<400> SEQUENCE: 40
tggttggaat ctctggtcc                                                  19

<210> SEQ ID NO 41
<211> LENGTH: 19
<212> TYPE: DNA
<213> ORGANISM: Verticillium dahilae

<400> SEQUENCE: 41
tggttggaat ctctggtcc                                                  19

<210> SEQ ID NO 42
<211> LENGTH: 18
<212> TYPE: DNA
<213> ORGANISM: Verticillium dahilae

<400> SEQUENCE: 42
ctggtcctcc tctcacca                                                   18

<210> SEQ ID NO 43
<211> LENGTH: 18
<212> TYPE: DNA
<213> ORGANISM: Verticillium dahilae

<400> SEQUENCE: 43
ggtggaactt cttctcag                                                   18

<210> SEQ ID NO 44
<211> LENGTH: 19
<212> TYPE: DNA
<213> ORGANISM: Verticillium dahilae

<400> SEQUENCE: 44
ttcaacctgg tgatttctc                                                  19

<210> SEQ ID NO 45
<211> LENGTH: 19
<212> TYPE: DNA
<213> ORGANISM: Verticillium dahilae

<400> SEQUENCE: 45
ttcaacctgg tgatttctc                                                  19

<210> SEQ ID NO 46
<211> LENGTH: 19
<212> TYPE: DNA
<213> ORGANISM: Verticillium dahilae

<400> SEQUENCE: 46
```

-continued ttcaacctgg tgatttctc                                                19

<210> SEQ ID NO 47
<211> LENGTH: 19
<212> TYPE: DNA
<213> ORGANISM: Verticillium dahilae

<400> SEQUENCE: 47
gtcagactgg tcatttcca                                                19

<210> SEQ ID NO 48
<211> LENGTH: 22
<212> TYPE: DNA
<213> ORGANISM: Verticillium dahilae

<400> SEQUENCE: 48
aaaaagatgc atccgatctt cg                                            22

<210> SEQ ID NO 49
<211> LENGTH: 22
<212> TYPE: DNA
<213> ORGANISM: Verticillium dahilae

<400> SEQUENCE: 49
taaaagatat attcgaccat cc                                            22

<210> SEQ ID NO 50
<211> LENGTH: 56
<212> TYPE: DNA
<213> ORGANISM: Botrytis cinerea

<400> SEQUENCE: 50
ggggacaagt ttgtacaaaa aagcaggctt gcggaagaac ttgaaggttt gctaca       56

<210> SEQ ID NO 51
<211> LENGTH: 25
<212> TYPE: DNA
<213> ORGANISM: Botrytis cinerea

<400> SEQUENCE: 51
gtccagatct ggtcaacaca ccaag                                         25

<210> SEQ ID NO 52
<211> LENGTH: 45
<212> TYPE: DNA
<213> ORGANISM: Botrytis cinerea

<400> SEQUENCE: 52
cttggtgtgt tgaccagatc tggacggatg ccatttgctg cacgc                   45

<210> SEQ ID NO 53
<211> LENGTH: 55
<212> TYPE: DNA
<213> ORGANISM: Botrytis cinerea

<400> SEQUENCE: 53
ggggaccact ttgtacaaga aagctgggta ctcttgagta ctttcgccag ctcac        55

<210> SEQ ID NO 54
<211> LENGTH: 18
<212> TYPE: DNA
<213> ORGANISM: Verticillium dahilae

<400> SEQUENCE: 54
ggatcggagg ttcgaatc                                                18

<210> SEQ ID NO 55
<211> LENGTH: 18
<212> TYPE: DNA
<213> ORGANISM: Verticillium dahilae

<400> SEQUENCE: 55
ggatcggagg ttcgaatc                                                18

<210> SEQ ID NO 56
<211> LENGTH: 18
<212> TYPE: DNA
<213> ORGANISM: Verticillium dahilae

<400> SEQUENCE: 56
ggatcggagg ttcgaatc                                                18

<210> SEQ ID NO 57
<211> LENGTH: 19
<212> TYPE: DNA
<213> ORGANISM: Verticillium dahilae

<400> SEQUENCE: 57
ggatcggagg ttcgaatca                                               19

<210> SEQ ID NO 58
<211> LENGTH: 19
<212> TYPE: DNA
<213> ORGANISM: Verticillium dahilae

<400> SEQUENCE: 58
ggatcggagg ttcgaatca                                               19

<210> SEQ ID NO 59
<211> LENGTH: 18
<212> TYPE: DNA
<213> ORGANISM: Verticillium dahilae

<400> SEQUENCE: 59
aggtgagagg acgaccag                                                18

<210> SEQ ID NO 60
<211> LENGTH: 18
<212> TYPE: DNA
<213> ORGANISM: Verticillium dahilae

<400> SEQUENCE: 60
ctgagaggac gtcccgcc                                                18

<210> SEQ ID NO 61
<211> LENGTH: 19
<212> TYPE: DNA
<213> ORGANISM: Verticillium dahilae

<400> SEQUENCE: 61
gggaaatgac cagcttgag                                               19

<210> SEQ ID NO 62
<211> LENGTH: 19
<212> TYPE: DNA
<213> ORGANISM: Verticillium dahilae

```
<400> SEQUENCE: 62
gggaaatgac cagcttgag                                                    19

<210> SEQ ID NO 63
<211> LENGTH: 19
<212> TYPE: DNA
<213> ORGANISM: Verticillium dahilae

<400> SEQUENCE: 63
gggaaatgac cagcttgag                                                    19

<210> SEQ ID NO 64
<211> LENGTH: 19
<212> TYPE: DNA
<213> ORGANISM: Verticillium dahilae

<400> SEQUENCE: 64
gggaaatgac cagcttgag                                                    19

<210> SEQ ID NO 65
<211> LENGTH: 22
<212> TYPE: DNA
<213> ORGANISM: Verticillium dahilae

<400> SEQUENCE: 65
cgatggtcgg atgtatcctt tt                                                22

<210> SEQ ID NO 66
<211> LENGTH: 22
<212> TYPE: DNA
<213> ORGANISM: Verticillium dahilae

<400> SEQUENCE: 66
cgatggtcgg atgtatcctt tt                                                22
```

CONTROLLING FUNGAL PATHOGENS BY DISABLING THEIR SMALL RNA PATHWAYS USING RNAI-BASED STRATEGY

CROSS-REFERENCE TO RELATED APPLICATIONS

The present application is a U.S. National Phase application under 35 U.S.C. § 371 of International Application No. PCT/US2016/029560, filed Apr. 27, 2016, which claims priority to U.S. Provisional Application No. 62/153,440, filed Apr. 27, 2015, and which is a Continuation-In-Part of U.S. patent application Ser. No. 14/809,063, filed Jul. 24, 2015, which claims priority to U.S. Provisional Application No. 62/028,776, filed Jul. 24, 2014, and to U.S. Provisional Application No. 62/153,440, filed Apr. 27, 2015, the entire content of each of which is incorporated by reference herein for all purposes.

STATEMENT AS TO RIGHTS TO INVENTIONS MADE UNDER FEDERALLY SPONSORED RESEARCH AND DEVELOPMENT

This invention was made with Government support under Grant No. MCB-0642843, 10S-1257576 awarded by the National Science Foundation, a NIH grant (R01 GM093008). The government has certain rights in this invention.

REFERENCE TO SEQUENCE LISTING

This application includes a Sequence Listing as a text file named "Sequence Listing 081906-1066084-218520US.txt" created Sep. 20, 2018, and containing 160,374 bytes. The material contained in this text file is incorporated by reference in its entirety for all purposes.

BACKGROUND OF THE INVENTION

In plants, pathogen attacks invoke multiple layers of host immune responses. Many pathogens of plants and animals deliver effectors into host cells to suppress host immunity, and many plants have evolved resistance proteins to recognize effectors and trigger robust resistance.

*Botrytis cinerea* is a fungal pathogen that infects flowers and almost all vegetable and fruit crops and annually causes $10-100 billion losses worldwide. With its broad host range, *B. cinerea* is a useful model for studying the pathogenicity of aggressive fungal pathogens.

BRIEF SUMMARY OF THE INVENTION

In one aspect, the present application provides for plants (or a plant cell, seed, flower, leaf, fruit, or other plant part from such plants or processed food or food ingredient from such plants) having increased resistance to a pathogen (e.g., a fungal or oomycete pathogen). In another aspect, methods of making a pathogen-resistant plant are provided. In some embodiments, the method comprises:
contacting the plant or the part of the plant with a double-stranded RNA, a small RNA (sRNA), or a small RNA duplex that targets a fungal or oomycete dicer-like (DCL) gene or long terminal repeat (LTR) region, wherein the plant is a species of the genera Asparagus, *Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Rosa, Secale, Senecio, Sinapis, Solanum, Sorghum, Trigonella, Triticum, Vitis, Vigna,* or *Zea,* and wherein the plant or the part of the plant has increased resistance to a fungal or oomycete pathogen compared to a control plant or control plant part that has not been contacted with the double-stranded RNA, sRNA, or small RNA duplex.

In some embodiments, the method comprises:
contacting a fruit, vegetable, or flower with a double-stranded RNA or a small RNA duplex that targets a fungal or oomycete dicer-like (DCL) gene or long terminal repeat (LTR) region, wherein the fruit, vegetable, or flower has increased resistance to a fungal or oomycete pathogen compared to a control fruit, vegetable, or flower that has not been contacted with the double-stranded RNA, sRNA, or small RNA duplex.

In some embodiments, the pathogen is a fungal pathogen. In some embodiments, the pathogen is *Botrytis* or *Verticillium*.

In some embodiments, the double-stranded RNA, sRNA, or small RNA duplex targets a fungal or oomycete DCL gene. In some embodiments, the double-stranded RNA, sRNA, or small RNA duplex targets any of SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:28, SEQ ID NO:29, SEQ ID NO:30, or SEQ ID NO:31 or a fragment thereof (e.g., at least 20, 30, 40, 50, 60, 70, 80, 90, 100, 150, 200, 250, 300, 350, 400, 450, 500 or more contiguous nucleotides thereof). In some embodiments, the double-stranded RNA, sRNA, or small RNA duplex comprises an inverted repeat of a sequence that is identical or substantially identical (e.g., at least 60%, 65%, 70%, 75%, 80%, 85%, 90%, 91%, 92%, 93%, 94%, 95%, 96%, 97%, 98%, or 99% identical) to any of SEQ ID NO:1, SEQ ID NO:3, SEQ ID NO:5, SEQ ID NO:7, SEQ ID NO:9, SEQ ID NO:10, SEQ ID NO:11, or SEQ ID NO:12, or a fragment thereof, or a complement thereof. In some embodiments, the double-stranded RNA, sRNA, or small RNA duplex comprises a spacer in between the inverted repeat sequences.

In some embodiments, the double-stranded RNA is siRNA. In some embodiments, the double-stranded RNA, sRNA, or small RNA duplex is sprayed or brushed onto the plant or the part of the plant (e.g., a leaf, fruit, vegetable, or flower).

In some embodiments, the method further comprises contacting the plant or the part of the plant with a second double-stranded RNA or a second small RNA duplex or a second sRNA that targets a second fungal pathogen DCL gene. In some embodiments, the method comprises contacting the plant or the part of the plant with one or more double-stranded RNAs or small RNA duplexes or sRNAs that target a DCL gene from a first species of fungal pathogen (e.g., for targeting DCL genes in *Botrytis*, e.g., a double-stranded RNA, sRNA, or small RNA duplex that targets DCL1 in *B. cinerea* and a double-stranded RNA, sRNA, or small RNA duplex that targets DCL2 in *B. cinerea*) and further comprises contacting the plant or the part of the plant with one or more double-stranded RNAs or small RNA duplexes or sRNAs that target a DCL gene from a second species of fungal pathogen (e.g., for targeting DCL genes in *Verticillium*, e.g., a double-stranded RNA, sRNA, or small RNA duplex that targets DCL1 in *V. dahilae* and a double-stranded RNA, sRNA, or small RNA duplex that targets DCL2 in *V. dahilae*).

In another aspect, methods of increasing pathogen resistance to multiple pathogens (e.g., fungal or oomycete pathogens) are provided. In some embodiments, the method comprises:

contacting the plant or the part of the plant with (1) a first double-stranded RNA, sRNA, or small RNA duplex that targets a dicer-like (DCL) gene or a long terminal repeat (LTR) region from a first species of fungal or oomycete pathogen, and (2) a second double-stranded RNA, sRNA, or small RNA duplex that targets a DCL gene or a LTR region from a second species of fungal or oomycete pathogen, wherein the plant or the part of the plant has increased resistance to the first species of pathogen and the second species of pathogen compared to a control plant or control plant part that has not been contacted with the first and second double-stranded RNAs, sRNAs, or small RNA duplexes.

In some embodiments, the method comprises contacting the plant with two or more double-stranded RNAs, sRNAs, or small RNA duplexes for targeting two or more DCL genes or LTR regions from the first species of pathogen (e.g., for targeting DCL genes in *Botrytis*, e.g., DCL1 and DCL2 in *B. cinerea*) and two or more double-stranded RNAs, sRNAs, or small RNA duplexes for targeting two or more DCL genes or LTR regions from the second species of pathogen (e.g., for targeting DCL genes in *Verticillium*, e.g., DCL1 and DCL2 in *V. dahilae*).

In another aspect, a method of making a plant having increased pathogen resistance to multiple pathogens comprises:

introducing into the plant (1) a first heterologous expression cassette comprising a first promoter operably linked to a first polynucleotide that inhibits expression of a dicer-like (DCL) gene or a long terminal repeat (LTR) region from a first species of fungal or oomycete pathogen and (2) a second heterologous expression cassette comprising a second promoter operably linked to a second polynucleotide that inhibits expression of a DCL gene or a LTR region from a second species of fungal or oomycete pathogen; and selecting a plant comprising the first expression cassette and the second expression cassette.

In some embodiments, the method comprises introducing into the plant two or more heterologous expression cassettes for targeting two or more DCL genes or LTR regions from the first species of pathogen (e.g., for targeting DCL genes in *Botrytis*, e.g., DCL1 and DCL2 in *B. cinerea*) and two or more heterologous expression cassettes for targeting two or more DCL genes or LTR regions from the second species of pathogen (e.g., for targeting DCL genes in *Verticillium*, e.g., DCL1 and DCL2 in *V. dahilae*). In some embodiments, the polynucleotide comprises an antisense nucleic acid or inhibitory RNA (RNAi) that targets the DCL gene or LTR region or a fragment thereof.

In yet another aspect, methods of cultivating a plurality of pathogen-resistant plants are provided.

BRIEF DESCRIPTION OF THE DRAWINGS

FIG. 4A-C. DCL-dependent small RNAs are important for fungal virulence. *B. cinerea* dcl1 dcl2 double mutant is much less virulent on fruits, vegetables and flowers as compared to a wild-type *Botrytis* strain. Tomato fruits and leaves (A), onions and lettuces (B), and rose flowers (C) were infected by *B. cinerea* wild type strain B05 (WT) or dcl1 dcl2 double mutant strain. Photographs were taken after 3 days for tomato leaves and 4 days for tomato fruits, onion, lettuce and rose.

FIG. 6. LTR-derived Bc-sRNA effectors are dependent on DCL1 and DCL2.

FIG. 23A-E. *Arabidopsis* plants simultaneously expressing sRNAs that target DCL genes of *B. cinerea* and *V. dahilae* show enhanced disease resistance to both pathogens. (A) Northern blot analysis indicated the expression levels of Bc-DCL1/2-sRNAs and Vd-DCL1/2-sRNAs in the *Arabidopsis* transgenic plants expressing Bc+Vd-DCLs-sRNAs. (B) Quantitative RT-PCR showed that Bc-DCL1 and Bc-DCL2 were silenced in *B. cinerea*-infected *Arabidopsis* plants expressing Bc+Vd-DCL-sRNAs compared with WT plants. (C) *Arabidopsis* plants expressing Bc+Vd-DCLs-sRNAs inhibit the virulence *B. cinerea*. Lesion sizes were measured 3 dpi using ImageJ, and error bars indicate the SD of 10 leaves. *B. cinerea* biomass was measured 3 dpi by quantitative PCR. (D) The expression level of Vd-DCL1 and Vd-DCL2 were suppressed in *V. dahilae*-infected *Arabidopsis* plants expressing Bc+Vd-DCLs-sRNAs. (E) *Arabidopsis* plants expressing Bc+Vd-DCL-sRNAs were less susceptible to *V. dahilae* compared to WT plants. Biomass of *V. dahilae* was measured at 3 weeks post inoculation. Asterisks represented statistically significant differences (P<0.01; Student's t test). Similar results were obtained from three replicates for (B)-(E).

DEFINITIONS

Figure 1:
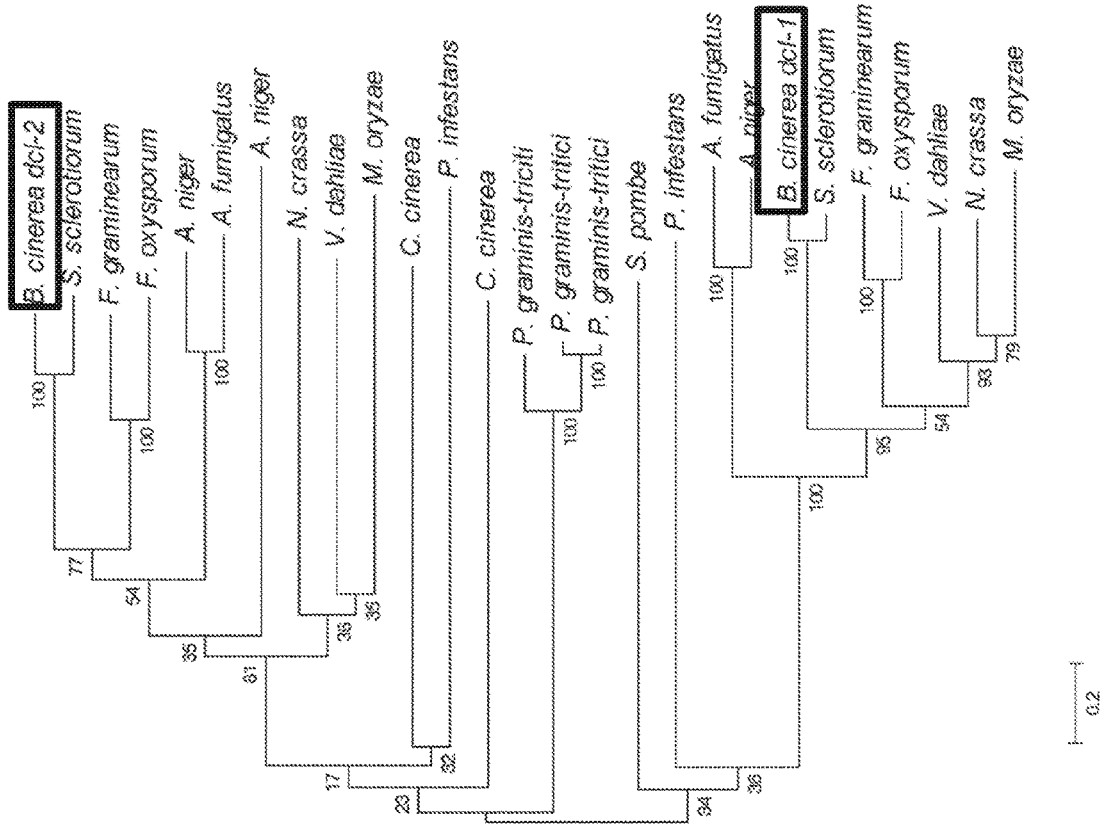
FIG. 1. The *B. cinerea* genome has two dicer-like (DCL) genes. The phylogenetic tree of DCL proteins from different pathogenic fungal species, the DCL proteins from an oomycete pathogen *Phytophthora infestans* are also included. *Schizosaccharomyces pombe* and *Neurospora crassa* were used as references.

The term "pathogen-resistant" or "pathogen resistance" refers to an increase in the ability of a plant to prevent or resist pathogen infection or pathogen-induced symptoms. Pathogen resistance can be increased resistance relative to a particular pathogen species or genus (e.g., *Botrytis*), increased resistance to multiple pathogens, or increased resistance to all pathogens (e.g., systemic acquired resistance). In some embodiments, resistance of a plant to a pathogen is "increased" when one or more symptoms of pathogen infection are reduced relative to a control (e.g., a plant in which a polynucleotide that inhibits expression of a fungal pathogen DCL gene is not expressed).

"Pathogens" include, but are not limited to, viruses, bacteria, nematodes, fungi or insects (see, e.g., Agrios, *Plant Pathology* (Academic Press, San Diego, Calif. (1988)). In some embodiments, the pathogen is a fungal pathogen. In some embodiments, the pathogen is *Botrytis*.

The term "nucleic acid" or "polynucleotide" refers to a single or double-stranded polymer of deoxyribonucleotide or ribonucleotide bases read from the 5' to the 3' end. Nucleic acids may also include modified nucleotides that permit correct read through by a polymerase and do not significantly alter expression of a polypeptide encoded by that nucleic acid.

The phrase "nucleic acid encoding" or "polynucleotide encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

Two nucleic acid sequences or polypeptides are said to be "identical" if the sequence of nucleotides or amino acid residues, respectively, in the two sequences is the same when aligned for maximum correspondence as described below. "Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. When percentage of sequence identity is used in reference to proteins or peptides, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The term "substantial identity" or "substantially identical," as used in the context of polynucleotide or polypeptide sequences, refers to a sequence that has at least 60% sequence identity to a reference sequence. Alternatively, percent identity can be any integer from 60% to 100%. Exemplary embodiments include at least: 60%, 65%, 70%, 75%, 80%, 85%, 90%, 91%, 92%, 93%, 94%, 95%, 96%, 97%, 98%, or 99%, as compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (USA.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

The term "complementary to" is used herein to mean that a polynucleotide sequence is complementary to all or a portion of a reference polynucleotide sequence. In some embodiments, a polynucleotide sequence is complementary to at least 15, at least 20, at least 25, at least 30, at least 40, at least 50, at least 75, at least 100, at least 125, at least 150, at least 175, at least 200, or more contiguous nucleotides of a reference polynucleotide sequence. In some embodiments, a polynucleotide sequence is "substantially complementary" to a reference polynucleotide sequence if at least 70%, at least 75%, at least 80%, at least 85%, at least 90%, or at least 95% of the polynucleotide sequence is complementary to the reference polynucleotide sequence.

A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition. One of skill will recognize that the inserted polynucleotide sequence need not be identical, but may be only substantially similar to a sequence of the gene from which it was derived.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "plant promoter" is a promoter capable of initiating transcription in plant cells. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions or developmental conditions.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid, and hemizygous.

DETAILED DESCRIPTION OF THE INVENTION

I. Introduction

It has been found that aggressive eukaryotic fungal pathogens, such as *Botrytis* and *Verticillium*, have evolved a novel virulence mechanism by employing small RNAs as effector molecules to suppress host immune responses to achieve successful infection. It has also been found that the majority of the small RNA effectors are generated from transposon regions, mainly the retrotransposon long terminal repeats (LTRs). As reported in genome studies of other fungal and oomycete pathogens, many fungal protein effector genes are also enriched in the transposon regions, including LTRs. These LTR-derived small RNAs, including most small RNA effectors, are generated by fungal Dicer-like proteins (DCLs).

As shown herein, DCL genes are essential for the pathogenicity of eukaryotic pathogens, such as the fungal pathogens *Botrytis* and *Verticillium*, with small RNA effectors. Thus, DCL genes are excellent targets for controlling those eukaryotic pathogens that use small RNAs as effectors. For example, *Botrytis* is a significant pathogen not only in the field, but also at post-harvesting stages, and can infect many different fruit, vegetable, and flowering plants.

Thus, one aspect of the present invention relates to controlling the diseases caused by aggressive fungal and oomycete pathogens by silencing their DCL genes and LTRs (e.g., using a host-induced gene silencing (HIGS) mechanism). In some embodiments, silencing is achieved by generating transgenic plants that express antisense (e.g., RNAi) constructs that target fungal or oomycete DCLs. In some embodiments, silencing is achieved by contacting (e.g., spraying) plants with small RNA duplexes or double stranded RNAs that target pathogen DCLs. *Botrytis* and *Verticillium* DCLs are exemplary genes that can be targeted.

II. Fungal Pathogen DCL Genes and LTR Regions

In one aspect, methods of inhibiting or silencing expression of fungal pathogen dicer-like (DCL) genes or long terminal repeat (LTR) regions are provided. In some embodiments, the method comprises expressing in a plant an expression cassette comprising a promoter operably linked to a polynucleotide that inhibits expression of a fungal pathogen DCL gene or an expression cassette comprising a promoter operably linked to a polynucleotide that inhibits expression of a fungal pathogen LTR region. In some embodiments, the method comprises contacting the plant with a construct comprising a promoter operably linked to a polynucleotide that inhibits expression of a fungal pathogen DCL gene or a construct comprising a promoter operably linked to a polynucleotide that inhibits expression of a fungal pathogen LTR region. In some embodiments, the polynucleotide comprises an antisense nucleic acid that is complementary to the DCL gene or a fragment thereof. In some embodiments, the polynucleotide comprises a small RNA duplex or a double-stranded RNA that targets the DCL gene or a fragment thereof. In some embodiments, the polynucleotide sequence comprises an inverted repeat of a sequence targeting the DCL gene, optionally with a spacer present between the inverted repeat sequences. In some embodiments, the polynucleotide comprises an antisense nucleic acid that is complementary to the LTR region or a fragment thereof. In some embodiments, the polynucleotide comprises a small RNA duplex or a double-stranded RNA that targets the LTR region or a fragment thereof. In some embodiments, the polynucleotide sequence comprises an inverted repeat of a sequence targeting the LTR region, optionally with a spacer present between the inverted repeat sequences. In some embodiments, the promoter is an inducible promoter. In some embodiments, the promoter is a constitutively active promoter.

In another aspect, plants having inhibited or silenced expression of pathogen DCL genes or LTR region are provided. In some embodiments, the plant is contacted with a polynucleotide that inhibits expression of a pathogen DCL gene or a pathogen LTR region, wherein the plant has increased pathogen resistance relative to a control plant that is not contacted with the polynucleotide. In some embodiments, the plant comprises a heterologous expression cassette, the expression cassette comprising a polynucleotide that inhibits expression of a pathogen DCL or LTR region, wherein the plant has increased pathogen resistance relative to a control plant lacking the expression cassette. In some embodiments, the polynucleotide comprises an antisense nucleic acid that is complementary to the DCL gene or LTR region or a fragment thereof. In some embodiments, the polynucleotide comprises a double stranded nucleic acid that targets the DCL gene or LTR region or a fragment thereof.

In yet another aspect, expression cassettes comprising a promoter operably linked to a polynucleotide that inhibits expression of a pathogen DCL gene, or isolated nucleic acids comprising said expression cassettes, are provided. In some embodiments, the expression cassette comprises a promoter operably linked to a polynucleotide comprising an antisense nucleic acid that is complementary to the DCL gene or a fragment thereof. In some embodiments, the expression cassette comprises a promoter operably linked to a polynucleotide comprising a double stranded nucleic acid that targets the DCL gene or a fragment thereof. In some embodiments, a plant in which the expression cassette is introduced has increased resistance to the pathogen compared to a control plant lacking the expression cassette.

Pathogen DCL Genes and Polynucleotides Targeting Pathogen DCL Genes

In some embodiments, the pathogen DCL gene or DCL promoter to be targeted or silenced is from a viral, bacterial, fungal, nematode, oomycete, or insect pathogen. In some embodiments, the DCL gene is from a fungal pathogen. Examples of plant fungal pathogens include, but are not limited to, *Botyritis, Verticillium, Magnaporthe, Sclerotinia,*

*Puccinia, Fusarium, Mycosphaerella, Blumeria, Colletotrichum, Ustilago*, and *Melampsora*. See, e.g., Dean et al., *Mol Plant Pathol* 13:804 (2012). In some embodiments, the pathogen is *Botyritis*. In some embodiments, the pathogen is *Botyritis cinera*. In some embodiments, the pathogen is *Verticillium*. In some embodiments, the pathogen is *V. dahilae*.

In some embodiments, one or more pathogen DCL genes is targeted, silenced, or inhibited in order to increase resistance to the pathogen in a plant by expressing in the plant, or contacting to the plant, a polynucleotide that inhibits expression of the pathogen DCL gene or that is complementary to the DCL gene or a fragment thereof. In some embodiments, the polynucleotide comprises an antisense nucleic acid that is complementary to the DCL gene or a fragment thereof. In some embodiments, the polynucleotide comprises a double stranded nucleic acid that targets the DCL gene, or its promoter, or a fragment thereof. In some embodiments, the polynucleotide comprises a double-stranded nucleic acid having a sequence that is identical or substantially similar (at least 60%, 65%, 70%, 75%, 80%, 85%, 90%, 91%, 92%, 93%, 94%, 95%, 96%, 97%, 98%, or 99% identical) to the DCL gene or a fragment thereof. In some embodiments, a "fragment" of a DCL gene or promoter comprises a sequence of at least 15, 16, 17, 18, 19, 20, 21, 22, 23, 24, 25, 26, 27, 28, 29, 30, 20, 30, 40, 50, 60, 70, 80, 90, 100, 150, 200, 250, 300, 350, 400, 450, 500 or more contiguous nucleotides of the DCL gene or promoter (e.g., comprises at least (e.g., at least 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, 500 or more contiguous nucleotides of any of SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:28, SEQ ID NO:29, SEQ ID NO:30, or SEQ ID NO:31). In some embodiments, the double stranded nucleic acid is a small RNA duplex or a double stranded RNA.

In some embodiments, the polynucleotide inhibits expression of a fungal pathogen DCL gene that encodes a *Botrytis* or *Verticillium* DCL protein. In some embodiments, the polynucleotide inhibits expression of a fungal DCL gene that encodes a *Botrytis* DCL protein that is identical or substantially identical (e.g., at least 60%, 65%, 70%, 75%, 80%, 85%, 90%, 91%, 92%, 93%, 94%, 95%, 96%, 97%, 98%, or 99% identical) to SEQ ID NO:2 or SEQ ID NO:4, or a fragment thereof. In some embodiments, the polynucleotide inhibits expression of a fungal DCL gene that encodes a *Verticillium* DCL protein that is identical or substantially identical (e.g., at least 60%, 65%, 70%, 75%, 80%, 85%, 90%, 91%, 92%, 93%, 94%, 95%, 96%, 97%, 98%, or 99% identical) to SEQ ID NO:6 or SEQ ID NO:8, or a fragment thereof.

In some embodiments, the polynucleotide comprises a sequence that is identical or substantially identical (e.g., at least 60%, 65%, 70%, 75%, 80%, 85%, 90%, 91%, 92%, 93%, 94%, 95%, 96%, 97%, 98%, or 99% identical) to SEQ ID NO:1 or SEQ ID NO:3 or a fragment thereof, or a complement thereof. In some embodiments, the polynucleotide comprises a sequence that is identical or substantially identical (e.g., at least 60%, 65%, 70%, 75%, 80%, 85%, 90%, 91%, 92%, 93%, 94%, 95%, 96%, 97%, 98%, or 99% identical) to SEQ ID NO:5 or SEQ ID NO:7 or a fragment thereof, or a complement thereof. In some embodiments, the polynucleotide comprises a sequence that is identical or substantially identical (e.g., at least 60%, 65%, 70%, 75%, 80%, 85%, 90%, 91%, 92%, 93%, 94%, 95%, 96%, 97%, 98%, or 99% identical) to SEQ ID NO:9, SEQ ID NO:10, SEQ ID NO:11, or SEQ ID NO:12, or a fragment thereof, or a complement thereof.

In some embodiments, the polynucleotide comprises an inverted repeat of a sequence that is identical or substantially identical (e.g., at least 60%, 65%, 70%, 75%, 80%, 85%, 90%, 91%, 92%, 93%, 94%, 95%, 96%, 97%, 98%, or 99% identical) to any of SEQ ID NO:1, SEQ ID NO:3, SEQ ID NO:5, SEQ ID NO:7, SEQ ID NO:9, SEQ ID NO:10, SEQ ID NO:11, or SEQ ID NO:12, or a fragment thereof, or a complement thereof. In some embodiments, the polynucleotide comprises a spacer in between the inverted repeat sequences.

In some embodiments, the polynucleotide targets a promoter region of a fungal pathogen DCL gene. For example, in some embodiments, the polynucleotide targets a promoter region within the sequence of any of SEQ ID NO:28, SEQ ID NO:29, SEQ ID NO:30, or SEQ ID NO:31.

In some embodiments, two or more fungal pathogen DCL genes or promoters are targeted (e.g., two, three, four or more DCL genes or promoters from the same fungal pathogen or from two or more fungal pathogens). In some embodiments, two or more *Botrytis* DCL genes or promoters are targeted. For example, in some embodiments, two or more of SEQ ID NO:1, SEQ ID NO:3, SEQ ID NO:28, and SEQ ID NO:29, or a fragment of any thereof, are targeted for inhibition of expression. In some embodiments, two or more *Verticillium* DCL genes or promoters are targeted. For example, in some embodiments, two or more of SEQ ID NO:5, SEQ ID NO:7, SEQ ID NO:30, or SEQ ID NO:31, or a fragment of any thereof, are targeted for inhibition of expression.

Pathogen LTR Regions and Polynucleotides Targeting Pathogen LTR Regions

The LTR regions that generate most small RNA effectors can be targeted for silencing. In some embodiments, such as for *B. cinerea*, sRNA effectors are derived from LTR retrotransposon regions. Additionally, the promoter regions of LTRs can also be targeted for silencing. Targeting of LTR promoter regions can trigger transcriptional gene silencing, which would avoid random silencing of host genes by LTR small RNAs.

In some embodiments, the polynucleotide targets or inhibits expression of a pathogen LTR region or of a promoter region of a pathogen LTR, wherein the pathogen is a fungal pathogen. In some embodiments, the pathogen is *Botyritis*. In some embodiments, the pathogen is *Botyritis cinera*. In some embodiments, the pathogen is *Verticillium*. In some embodiments, the pathogen is *V. dahilae*.

In some embodiments, the polynucleotide targets a sequence of any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 or a fragment thereof, or a complement thereof. In some embodiments, a "fragment" of a LTR region or LTR promoter comprises a sequence of at least 15, 20, 30, 40, 50, 60, 70, 80, 90, 100, 150, 200, 250, 300, 350, 400, 450, 500 or more contiguous nucleotides of the LTR region or LTR promoter (e.g., comprises at least 15, 20, 30, 40, 50, 60, 70, 80, 90, 100, 150, 200, 250, 300, 350, 400, 450, 500 or more contiguous nucleotides of any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27).

In some embodiments, the polynucleotide comprises an antisense nucleic acid that is complementary to any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27 or a fragment thereof. In some embodiments, the polynucleotide comprises a double-stranded nucleic acid having a sequence that is identical or substantially similar (at least 60%, 65%, 70%, 75%, 80%, 85%, 90%, 91%, 92%, 93%, 94%, 95%, 96%, 97%, 98%, or 99% identical) to any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 or a fragment thereof. In some embodiments, the polynucleotide comprises an inverted repeat of a fragment of any of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27, and further comprises a spacer region separating the inverted repeat nucleotide sequences.

In some embodiments, the polynucleotide targets a promoter region of a fungal LTR. For example, in some embodiments, the polynucleotide targets a promoter region within the sequence of SEQ ID NO:27.

Host-Induced Gene Silencing

In some embodiments, the methods of inhibiting or silencing expression of fungal pathogen DCL genes or LTR regions utilizes a host-induced gene silencing (HIGS) mechanism for producing in a host plant inhibitory RNA that subsequently moves into the pathogen to inhibit expression of a pathogen gene or region. In some embodiments, HIGS is used to produce in a plant inhibitory RNAs (e.g., sRNAs) that target one or more pathogen DCLs or LTRs. In some embodiments, wherein a pathogen has more than one DCL, HIGS is used to produce inhibitory RNAs (e.g., sRNAs) that target each of the DCLs of the pathogen (e.g., for Botrytis, targeting DCL1 and DCL2). In some embodiments, HIGS is used to produce inhibitory RNAs (e.g., sRNAs) against DCLs or LTRs of multiple pathogens.

The use of HIGS for silencing expression of pathogen genes in plants is described, e.g., in Nowara et al. (*Plant Cell* (2010) 22:3130-3141); Nunes et al. (*Mol Plant Pathol* (2012) 13:519-529); and Govindarajulu et al. (*Plant Biotechnology Journal* (2014) 1-9). Pathogen sRNAs are described, for example, in US 2015/0203865, incorporated by reference herein.

Antisense Technology

In some embodiments, antisense technology is used to silence or inactive the pathogen DCL gene or LTR. The antisense nucleic acid sequence transformed into plants will be substantially identical to at least a fragment of the gene to be silenced. In some embodiments, the antisense nucleic acid sequence that is transformed into plants is identical or substantially identical to the pathogen DCL sequence or LTR sequence to be blocked. In some embodiments, the antisense polynucleotide sequence is complementary to the pathogen DCL sequence or LTR sequence to be blocked. However, the sequence does not have to be perfectly identical to inhibit expression. Thus, in some embodiments, an antisense polynucleotide sequence that is substantially complementary (e.g., at least 70%, at least 75%, at least 80%, at least 85%, at least 90%, or at least 95% complementary) to the pathogen DCL sequence or LTR sequence to be blocked can be used (e.g., in an expression cassette under the control of a heterologous promoter, which is then transformed into plants such that the antisense nucleic acid is produced).

In some embodiments, an antisense or sense nucleic acid molecule comprising or complementary to only a fragment of the pathogen DCL gene sequence or LTR sequence can be useful for producing a plant in which pathogen gene expression is silenced. For example, a sequence of about 15, 20, 30, 40, 50, 100, 150, 200, 250, 300, 350, 400, 450, or 500 nucleotides can be used.

Catalytic RNA molecules or ribozymes can also be used to inhibit expression of a pathogen DCL gene or LTR. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *solanum nodiflorum* mottle virus and subterranean clover mottle virus. The design and use of target RNA-specific ribozymes is described in Haseloff et al. *Nature*, 334:585-591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the sequence intended to be repressed. This minimal identity will typically be greater than about 65% to the target gene sequence (e.g., DCL or LTR sequence), but a higher identity can exert a more effective repression of expression of the endogenous sequences. In some embodiments, sequences with substantially greater identity are used, e.g., at least about 80%, at least about 95%, or 100% identity are used. As with antisense regulation, the effect can be designed and tested so as to not significantly affect expression of other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. In some embodiments, a sequence of the size ranges noted above for antisense regulation is used, e.g., at least about 15, 20, 30, 40, 50, 60, 70, 80, 90, 100, 150, 200, 250, 300, 350, 400, 450, 500 or more nucleotides.

Gene expression may also be suppressed by means of RNA interference (RNAi) (and indeed co-suppression can be considered a type of RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although complete details of the mechanism of RNAi are still unknown, it is considered that the introduced double-stranded RNA is initially cleaved into small fragments, which then serve as indexes of the target gene in some manner, thereby degrading the target gene. RNAi is also known to be effective in plants (see, e.g., Chuang, C. F. & Meyerowitz, E. M., Proc. *Natl. Acad. Sci. USA* 97: 4985 (2000); Waterhouse et al., *Proc. Natl. Acad. Sci. USA* 95:13959-13964 (1998); Tabara et al. *Science* 282:430-431 (1998); Matthew, *Comp Funct. Genom.* 5: 240-244 (2004); Lu, et al., *Nucleic Acids Research* 32(21):e171 (2004)). For example, to achieve suppression of pathogen DCL expression using RNAi, a gene fragment (e.g., from a DCL gene) in an inverted repeat orientation with a spacer could be expressed in plants to generate double-stranded RNA having the sequence of an mRNA encoding the DCL protein, or a substantially similar sequence thereof (including those engineered not to translate the protein) or fragment thereof, is introduced into a plant or other organism of interest. The resulting plants/organisms can then be screened for a phenotype associated with the target protein and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g. U.S., Patent Publication No. 2004/0029283 for an example of a non-identical siRNA sequence used to suppress gene expression. The constructs encoding an RNA molecule with a stem-loop structure that is unrelated to the target gene and that is positioned distally to a sequence specific for the gene of interest may also be used to inhibit target gene expression. See, e.g. U.S., Patent Publication No. 2003/0221211. Gene silencing in plants by the expression of small RNA duplexes is also described, e.g., in Lu et al., *Nucleic Acids Res.* 32(21):e171 (2004).

The RNAi polynucleotides can encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 10, 15, 20, 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases.

Expression vectors that continually express siRNA in transiently- and stably-transfected cells have been engineered to express small hairpin RNAs, which get processed in vivo into siRNAs molecules capable of carrying out gene-specific silencing (Brummelkamp et al., *Science* 296: 550-553 (2002), and Paddison, et al., *Genes & Dev.* 16:948-958 (2002)). Post-transcriptional gene silencing by double-stranded RNA is discussed in further detail by Hammond et al., *Nature Rev Gen* 2: 110-119 (2001), Fire et al., *Nature* 391: 806-811 (1998) and Timmons and Fire, *Nature* 395: 854 (1998).

Yet another way to suppress expression of a gene in a plant is by recombinant expression of a microRNA that suppresses the target gene. Artificial microRNAs are single-stranded RNAs (e.g., between 18-25 mers, generally 21 mers), that are not normally found in plants and that are processed from endogenous miRNA precursors. Their sequences are designed according to the determinants of plant miRNA target selection, such that the artificial microRNA specifically silences its intended target gene(s) and are generally described in Schwab et al, *The Plant Cell* 18:1121-1133 (2006) as well as the internet-based methods of designing such microRNAs as described therein. See also, US Patent Publication No. 2008/0313773.

Another way to suppress expression of a gene in a plant is by application of a dsRNA to a surface of a plant or part of a plant (e.g., onto a leaf, flower, fruit, or vegetable), for example by spraying the dsRNA onto the surface or brushing the dsRNA onto the surface. Methods of applying dsRNA onto external plant parts are described, for example, in WO 2013/02560 and in Gan et al., *Plant Cell Reports* 29:1261-1268 (2010), incorporated by reference herein.

In some embodiments, antisense sequences such as dsRNA or sRNA can be synthesized in planta and extracted from the plant for subsequent use on a target plant. As a non-limiting example, constructs for producing one or more dsRNA or sRNA sequences of interest can be transiently introduced into a plant (e.g., *N. benthamiana*), for example by infiltration with *Agrobacterium*. The dsRNA or sRNA sequences are produced by the plant and then RNA is extracted from one or more tissues of the plant in order to extract the dsRNA or sRNA sequences of interest. An exemplary method of expressing and extracting antisense sequences from *N. benthamiana* is described in the Examples section below.

III. Methods of Making Plants Having Increased Pathogen Resistance

In another aspect, methods of making plants having increased pathogen resistance are provided. In some embodiments, the method comprises:
  introducing into a plant a heterologous expression cassette comprising a promoter operably linked to a polynucleotide that inhibits fungal expression of a pathogen DCL gene; and
  selecting a plant comprising the expression cassette.

In some embodiments, the method further comprises introducing into the plant a second heterologous expression cassette comprising a second promoter operably linked to a second polynucleotide that inhibits fungal expression of a second pathogen DCL gene; and selecting a plant comprising the second expression cassette.

In some embodiments, the polynucleotide that inhibits fungal expression of the pathogen DCL gene is described herein (e.g., in Section II above, e.g., an antisense polynucleotide such as a hairpin RNA or microRNA precursor). For example, in some embodiments, the polynucleotide inhibits the expression of one, two, three, four or more *Botrytis* or *Verticillium* DCL genes. In some embodiments, the polynucleotide inhibits the expression of one, two, three, four or more of SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:28, SEQ ID NO:29, SEQ ID NO:30, or SEQ ID NO:31.

In some embodiments, a plant into which the expression cassette(s) has been introduced has increased pathogen resistance relative to a control plant lacking the expression cassette(s). In some embodiments, a plant into which the expression cassette has been introduced has enhanced resistance to a fungal pathogen (e.g., *Botyritis* or *Verticillium*) relative to a control plant lacking the expression cassette.

In some embodiments, the promoter is heterologous to the polynucleotide. In some embodiments, the polynucleotide encoding the sRNA-resistant target is operably linked to an inducible promoter. In some embodiments, the promoter is pathogen inducible (e.g., a *Botrytis* inducible promoter). In some embodiments, the promoter is stress inducible (e.g., an abiotic stress inducible promoter).

In some embodiments, the method comprises:
contacting a plurality of plants with a construct comprising a promoter operably linked to a polynucleotide that inhibits fungal expression of a pathogen DCL gene or pathogen LTR region, wherein the plant has increased resistance to a pathogen compared to a control plant that has not been contacted with the construct.

In some embodiments, the method further comprises selecting a plant having increased pathogen resistance.

In some embodiments, the method comprises:
contacting a plant or a part of a plant with a double-stranded RNA, a small RNA duplex, or a small RNA (sRNA) that targets a pathogen DCL gene or pathogen LTR region, wherein the plant or part of the plant has increased resistance to the pathogen compared to a control plant that has not been contacted with the double-stranded RNA or small RNA duplex.

In some embodiments, the double-stranded RNA or small RNA duplex (e.g., siRNA) or sRNA targets *Botrytis* DCLs or *Verticillium* DCLs. In some embodiments, the double-stranded RNA or small RNA duplex or sRNA targets any of SEQ ID NO:1, SEQ ID NO:3, SEQ ID NO:5, or SEQ ID NO:7 or a fragment thereof. In some embodiments, the double-stranded RNA is an siRNA. In some embodiments, the siRNA comprises a sequence that is identical to any of SEQ ID NO:1, SEQ ID NO:3, SEQ ID NO:5, SEQ ID NO:7, SEQ ID NO:9, SEQ ID NO:10, SEQ ID NO:11, or SEQ ID NO:12, or a fragment thereof (e.g., a fragment of at least 15, 16, 17, 18, 19, 20, 21, 22, 23, 24, 25, 26, 27, 28, 29, 30, or more contiguous nucleotides) or a complement thereof.

In some embodiments, the method comprises contacting the plant or the part of the plant with two, three, four, five, or more double-stranded RNAs or small RNA duplexes (e.g., siRNAs) or sRNAs for targeting two, three, four, five, or more pathogen DCL genes or pathogen LTR regions from one, two, three or more different pathogens. As a non-limiting example, in some embodiments, the plant is contacted with a double-stranded RNA or small RNA duplex (e.g., siRNA) or sRNA that targets *Botrytis* DCL1 and a double-stranded RNA or small RNA duplex (e.g., siRNA) or sRNA that targets *Botrytis* DCL2. As another non-limiting example, in some embodiments, the plant is contacted with a double-stranded RNA or small RNA duplex (e.g., siRNA) or sRNA that targets *Verticillium* DCL1 and a double-stranded RNA or small RNA duplex (e.g., siRNA) or sRNA that targets *Verticillium* DCL2. As yet another non-limiting example, in some embodiments, the plant is contacted with a double-stranded RNA or small RNA duplex (e.g., siRNA) or sRNA that targets one or more DCLs of *Botrytis* (e.g., *Botrytis* DCL1 and/or *Botrytis* DCL2) and with a double-stranded RNA or small RNA duplex (e.g., siRNA) or sRNA that targets one or more DCLs of *Verticillium* (e.g., *Verticillium* DCL1 and *Verticillium* DCL2).

In some embodiments, the double-stranded RNA or small RNA duplex (e.g., siRNA) or sRNA is sprayed or brushed onto the plant or part of the plant (e.g., onto a leaf, a fruit, vegetable, or flower). In some embodiments, the double-stranded RNA or small RNA duplex (e.g., siRNA) or sRNA is contacted to (e.g., sprayed or brushed onto) a part of a plant that has been removed from the plant. As a non-limiting example, the double-stranded RNA or small RNA duplex (e.g., siRNA) or sRNA can be contacted to (e.g., sprayed or brushed onto) a fruit, vegetable, or flower that has already been cut from a plant. In some embodiments, the double-stranded RNA or small RNA duplex (e.g., siRNA) or sRNA is contacted to (e.g., sprayed or brushed onto) a part of a plant (e.g., a fruit, vegetable, or flower) while the part is still attached to the plant.

IV. Polynucleotides and Recombinant Expression Vectors

The isolation of polynucleotides of the invention may be accomplished by a number of techniques. For instance, oligonucleotide probes based on the sequences disclosed here can be used to identify the desired polynucleotide in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. Alternatively, cDNA libraries from plants or plant parts (e.g., flowers) may be constructed.

The cDNA or genomic library can then be screened using a probe based upon a sequence disclosed here. Probes may be used to hybridize with genomic DNA or cDNA sequences to isolate homologous genes in the same or different plant species. Alternatively, antibodies raised against a polypeptide can be used to screen an mRNA expression library.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic DNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: A Guide to Methods and Applications. (Innis, M, Gelfand, D., Sninsky, J. and White, T., eds.), Academic Press, San Diego (1990).

Polynucleotides can also be synthesized by well-known techniques as described in the technical literature. See, e.g., Carruthers et al., Cold Spring Harbor Symp. *Quant. Biol.* 47:411-418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Once a polynucleotide sequence that inhibits expression of a fungal dicer-like (DCL) gene or LTR region, or that is complementary to a fungal pathogen DCL gene or LTR region or a fragment thereof, is obtained, it can be used to prepare an expression cassette for expression in a plant. In some embodiments, expression of the polynucleotide is directed by a heterologous promoter.

Any of a number of means well known in the art can be used to drive expression of the polynucleotide sequence of interest in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, expression can be conditioned to only occur under certain conditions (e.g., using an inducible promoter).

For example, a plant promoter fragment may be employed to direct expression of the polynucleotide sequence of interest in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the polynucleotide sequence of interest in a specific tissue (tissue-specific promoters) or may be otherwise under more precise environmental control (inducible promoters). Examples of tissue-specific promoters under developmental control include promoters that initiate transcription only in certain tissues, such as leaves or guard cells (including but not limited to those described in WO/2005/085449; U.S. Pat. No. 6,653,535; Li et al., *Sci China C Life Sci.* 2005 April; 48(2):181-6; Husebye, et al., *Plant Physiol, April* 2002, Vol. 128, pp. 1180-1188; and Plesch, et al., *Gene*, Volume 249, Number 1, 16 May 2000, pp. 83-89(7)). Examples of environmental conditions that may affect transcription by inducible promoters include the presence of a pathogen, anaerobic conditions, elevated temperature, or the presence of light.

In some embodiments, the promoter is a constitutive promoter. In some embodiments, the promoter is an inducible promoter. In some embodiments, the promoter is stress inducible (e.g., inducible by abiotic stress). In some embodiments, the promoter is pathogen inducible. In some embodiments, the promoter is induced upon infection by *Botyrtis*. Non-limiting examples of pathogen inducible promoters include *Botyritis*-Induced Kinase 1 (BIK1) and the plant defensing gene PDF1.2. See, e.g., Penninckx et al., *Plant Cell* 10:2103-2113 (1998); see also Veronese et al., *Plant Cell* 18:257-273 (2006).

In some embodiments, a polyadenylation region at the 3'-end of the coding region can be included. The polyadenylation region can be derived from a NH3 gene, from a variety of other plant genes, or from T-DNA.

The vector comprising the sequences will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

V. Production of Transgenic Plants

As detailed herein, embodiments of the present invention provide for transgenic plants comprising recombinant expression cassettes for expressing a polynucleotide sequence as described herein (e.g., a polynucleotide that inhibits expression of a fungal pathogen dicer-like (DCL) gene or a polynucleotide that inhibits expression of a fungal pathogen LTR region, such as a polynucleotide that expresses a hairpin RNA or microRNA precursor). In some embodiments, a transgenic plant is generated that contains a complete or partial sequence of a polynucleotide that is derived from a species other than the species of the transgenic plant. It should be recognized that transgenic plants encompass the plant or plant cell in which the expression cassette is introduced as well as progeny of such plants or plant cells that contain the expression cassette, including the progeny that have the expression cassette stably integrated in a chromosome.

In some embodiments, the transgenic plants comprising recombinant expression cassettes for expressing a polynucleotide sequence as described herein have increased or enhanced pathogen resistance compared to a plant lacking the recombinant expression cassette, wherein the transgenic plants comprising recombinant expression cassettes for expressing the polynucleotide sequence have about the same growth as a plant lacking the recombinant expression cassette. Methods for determining increased pathogen resistance are described, e.g., in Section VI below.

A recombinant expression vector as described herein may be introduced into the genome of the desired plant host by a variety of conventional techniques. For example, the DNA construct may be introduced directly into the genomic DNA of the plant cell using techniques such as electroporation and microinjection of plant cell protoplasts, or the DNA construct can be introduced directly to plant tissue using ballistic methods, such as DNA particle bombardment. Alternatively, the DNA construct may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. While transient expression of the polynucleotide sequence of interest is encompassed by the invention, generally expression of construction of the invention will be from insertion of expression cassettes into the plant genome, e.g., such that at least some plant offspring also contain the integrated expression cassette.

Microinjection techniques are also useful for this purpose. These techniques are well known in the art and thoroughly described in the literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example, Horsch et al. *Science* 233:496-498 (1984), and Fraley et al. *Proc. Natl. Acad. Sci. USA* 80:4803 (1983).

Transformed plant cells derived by any of the above transformation techniques can be cultured to regenerate a whole plant that possesses the transformed genotype and thus the desired phenotype such as enhanced pathogen resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

VI. Selecting for Plants with Increased Pathogen Resistance

The expression cassettes and antisense constructs (e.g., double-stranded RNA or small RNA duplexes, e.g., siRNAs) of the invention can be used to confer increased or enhanced pathogen resistance on essentially any plant or part of a plant. Thus, the invention has use over a broad range of plants, including but not limited to species from the genera *Allium, Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Rosa, Secale, Senecio, Sinapis, Solanum, Sorghum, Trigonella, Triticum, Vitis, Vigna*, and *Zea*. In some embodiments, the plant is a vining plant, e.g., a species from the genus *Vitis*. In some embodiments, the plant is an ornamental plant, e.g., a species from the genus Rosa. In some embodiments, the plant is a vegetable- or fruit-producing plant, e.g., a tomato plant or a strawberry plant. In some embodiments, the plant is a monocot. In some embodiments, the plant is a dicot.

Plants (or parts of plants) with increased pathogen resistance can be selected in many ways. One of ordinary skill in the art will recognize that the following methods are but a few of the possibilities. One method of selecting plants or parts of plants (e.g., fruits, vegetables, leaves, and flowers) with increased pathogen resistance is to determine resistance of a plant to a specific plant pathogen. Possible pathogens include, but are not limited to, viruses, bacteria, nematodes, fungi or insects (see, e.g., Agrios, *Plant Pathology* (Academic Press, San Diego, Calif.) (1988)). One of skill in the art will recognize that resistance responses of plants vary depending on many factors, including what pathogen, compound, or plant is used. Generally, increased resistance is measured by the reduction or elimination of disease symptoms (e.g., reduction in the number or size of lesions or reduction in the amount of fungal biomass on the plant or a part of the plant) when compared to a control plant. In some embodiments, resistance is increased when the number or sizes of lesions or amount of fungal biomass on the plant or on a part of the plant is decreased by at least about 10%, 20%, 30%, 40%, 50%, 60%, 70%, 80%, 90% or more relative to a control (e.g., relative to a plant in which a heterologous polynucleotide targeting a fungal pathogen DCL or LTR has not been expressed).

In some cases, increased resistance can also be measured by the production of the hypersensitive response (HR) of the plant (see, e.g., Staskawicz et al. (1995) *Science* 268(5211): 661-7). Plants with increased pathogen resistance can produce an enhanced hypersensitive response relative to control plants.

Increased pathogen resistance can also be determined by measuring the increased expression of a gene operably linked a defense related promoter. Measurement of such expression can be measured by quantifying the accumulation of RNA or subsequent protein product (e.g., using Northern or Western blot techniques, respectively (see, e.g., Sambrook et al. and Ausubel et al.).

VII. Examples

Example 1: Targeting DCL Genes to Attenuate Fungal Virulence

Eukaryotic small RNAs (sRNAs) are short regulatory noncoding RNAs that induce silencing of target genes at transcriptional and posttranscriptional levels. The endoribonuclease Dicer or Dicer-like proteins (DCLs) process double-stranded RNAs (dsRNAs) or RNAs with hairpin structures, giving rise to mostly 20-30-nt long sRNAs, which are loaded into Argonaute (AGO) proteins to induce gene silencing of their complementary targets by guiding mRNA cleaving or degradation, translational inhibition, DNA methylation, and histone modification. The role of sRNAs in plant-pathogen interactions, including the role of noncoding sRNAs from bacterial and eukaryotic plant pathogens in pathogenicity, is described in Weiberg et al., *Annu. Rev. Phytopathol.* 2014, 52:22.1-22.22, incorporated by reference herein.

sRNA effectors, like those found in *B. cinerea*, are transcribed from transposable elements (TEs) and suppress host immune-related genes. Host plant resistance genes are often clustered in genomic loci enriched with TEs. Similarly, protein effector genes are often found in clusters and interspersed with TEs. See, e.g., Weiberg at FIG. 2.

Because most of the *Botrytis* small RNA effectors are generated from LTR regions, there are multiple copies for each LTR, which makes Bc-sRNA knockouts impractical if not impossible. Therefore, to solve this problem, *Botrytis* DCL knockout mutants were generated.

Figure 2:
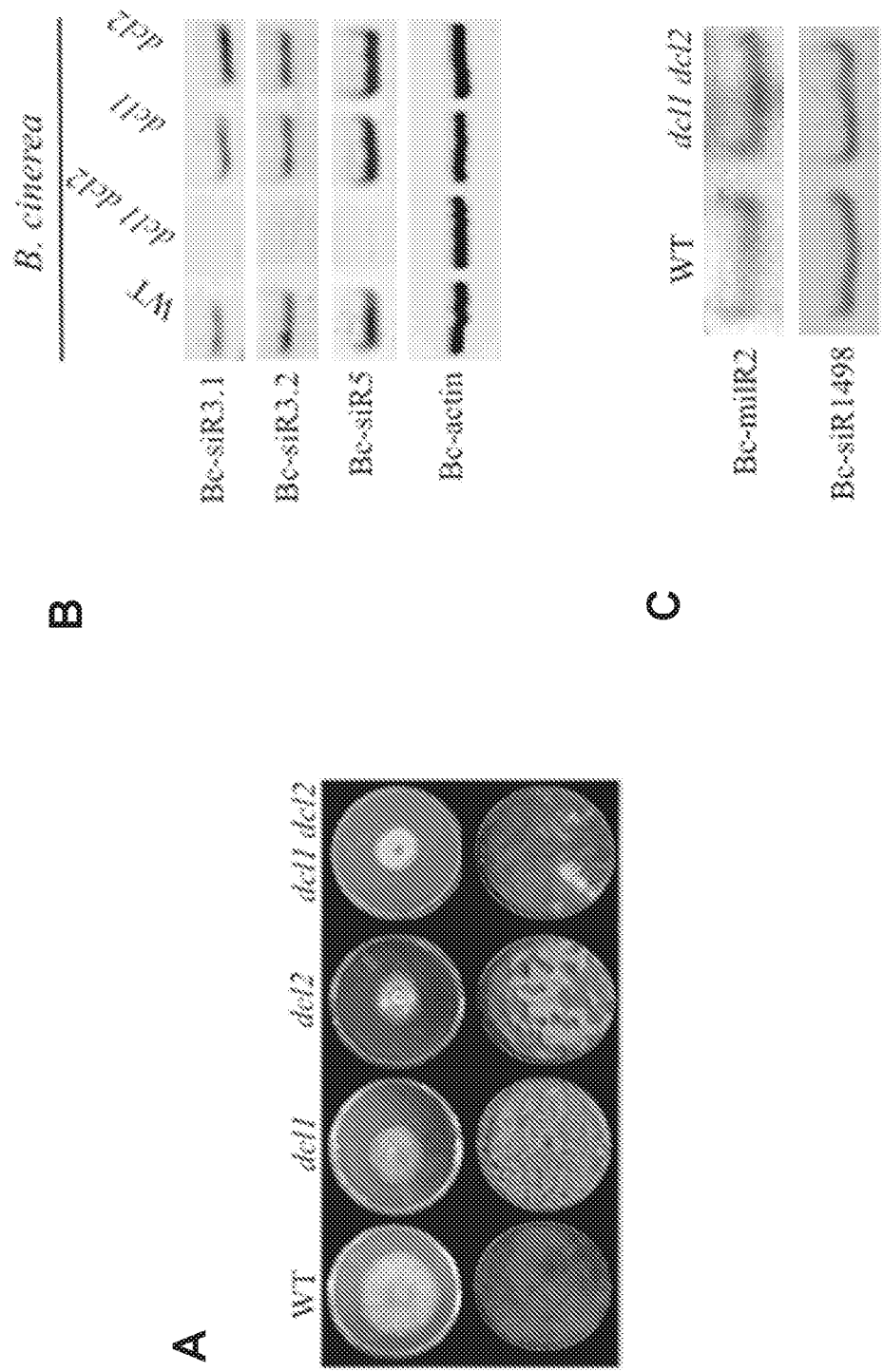
FIG. 2A-C. *B. cinerea* (Bc)-sRNAs are dependent on both *B. cinerea* DCL proteins. All of the *B. cinerea* dcl1, dcl2, and dcl1 dcl2 mutant strains showed growth retardation and delayed development of conidiospores (A), but only the double mutant strain could not produce Bc-sRNA effectors (B). DCL-independent sRNAs were used as a control (C).

As shown in FIG. 1, the *B. cinerea* genome has two DCLs (dcl-1 and dcl-2). Single- and double-mutant (dcl1, dcl2, and dcl1 dcl2 mutant) strains were generated. As shown in FIG. 2, all of the *B. cinerea* dcl1, dcl2, and dcl1 dcl2 mutant strains showed growth retardation and delayed development of conidiospores (FIG. 2A), but only the double mutant strain (dcl1 dcl2) could not produce Bc-sRNA effectors (FIG. 2B).

Figure 3:
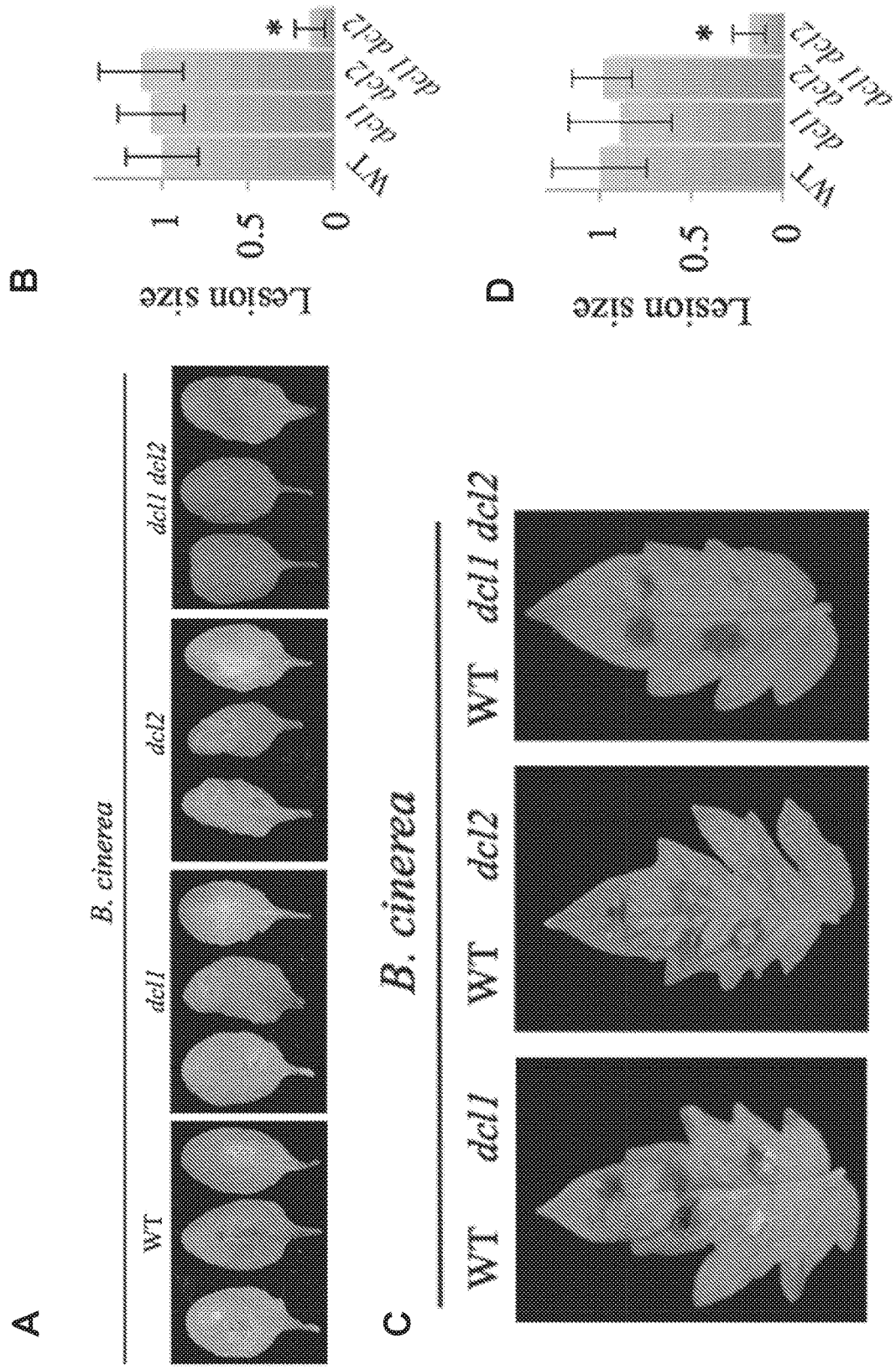
FIG. 3A-D. *B. cinerea* DCLs are essential for its pathogenicity. *B. cinerea* dcl1 dcl2 double mutant, but not dcl1 or dcl2 single mutants, produced much weaker disease symptoms than did the wild type in both *Arabidopsis* (A-B) and *S. lycopersicum* (C-D).
Figure 5A:
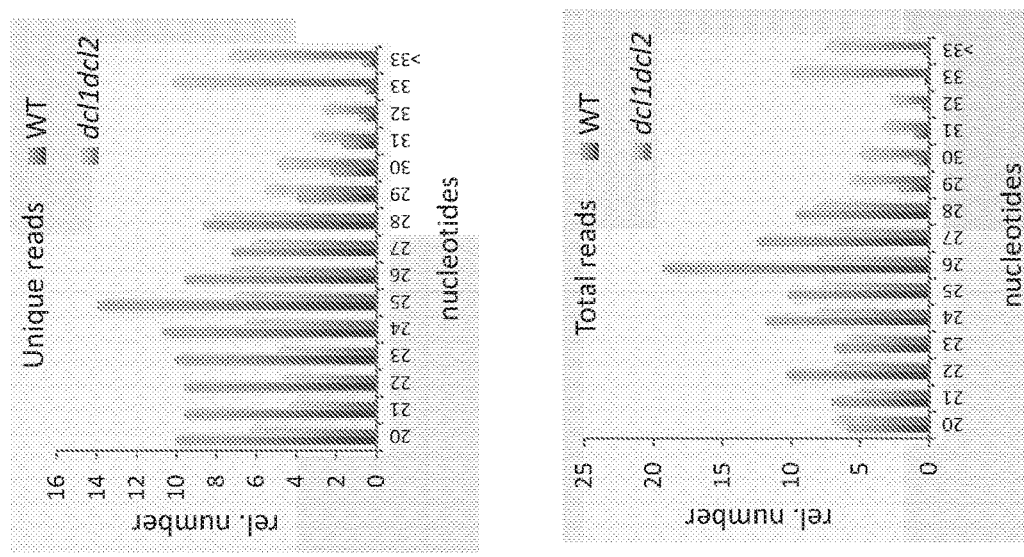
FIG. 5A-B. *Botrytis* DCLs are responsible for generating long terminal repeat (LTR)-derived sRNAs. Genome-wide comparative sRNA analysis on dcl1 dcl2 and wild-type revealed that *Botrytis* DCLs are responsible for generating LTR-derived sRNAs, many of which are sRNA effectors.
Figure 5B:
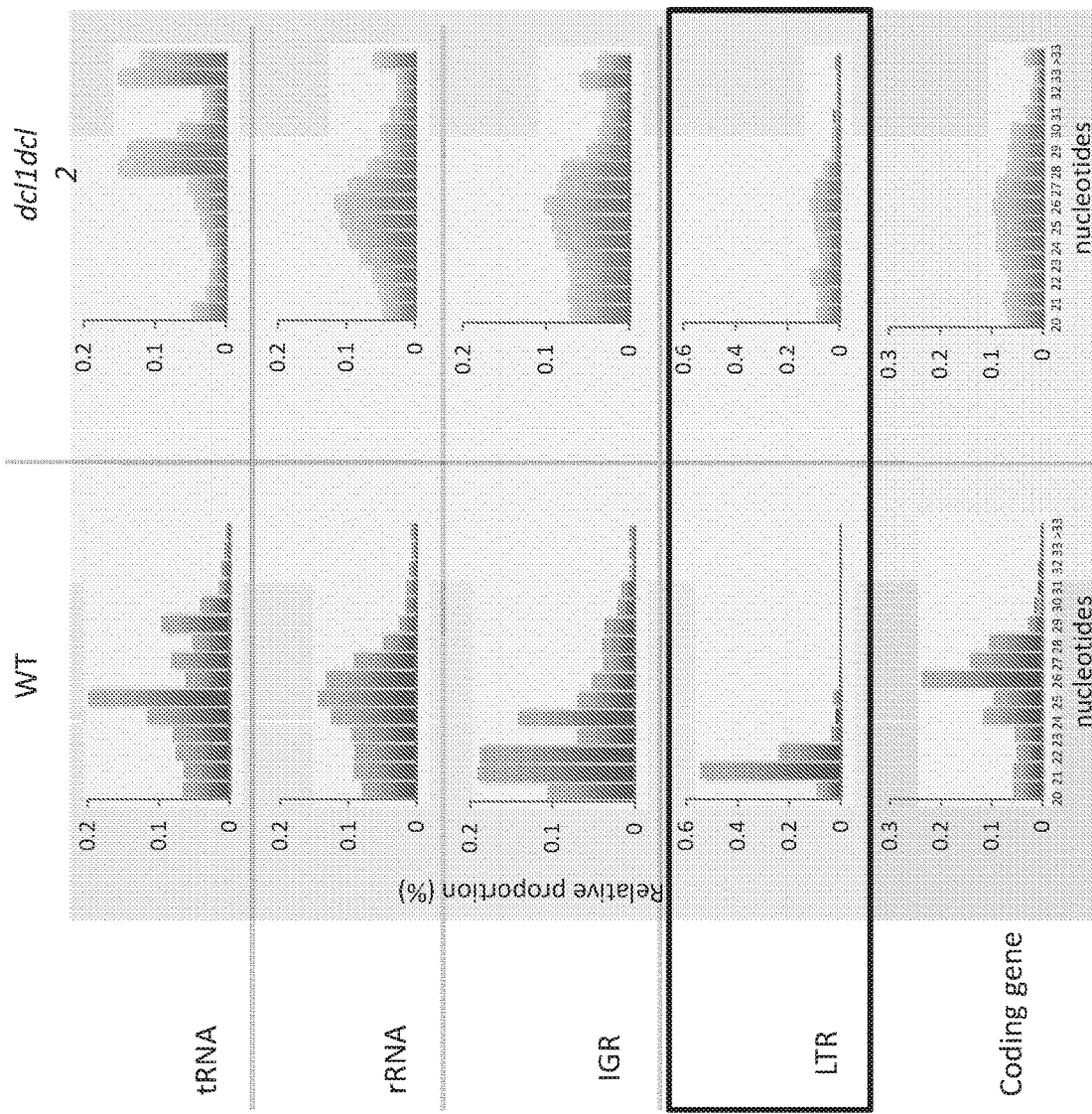
Figure 7:
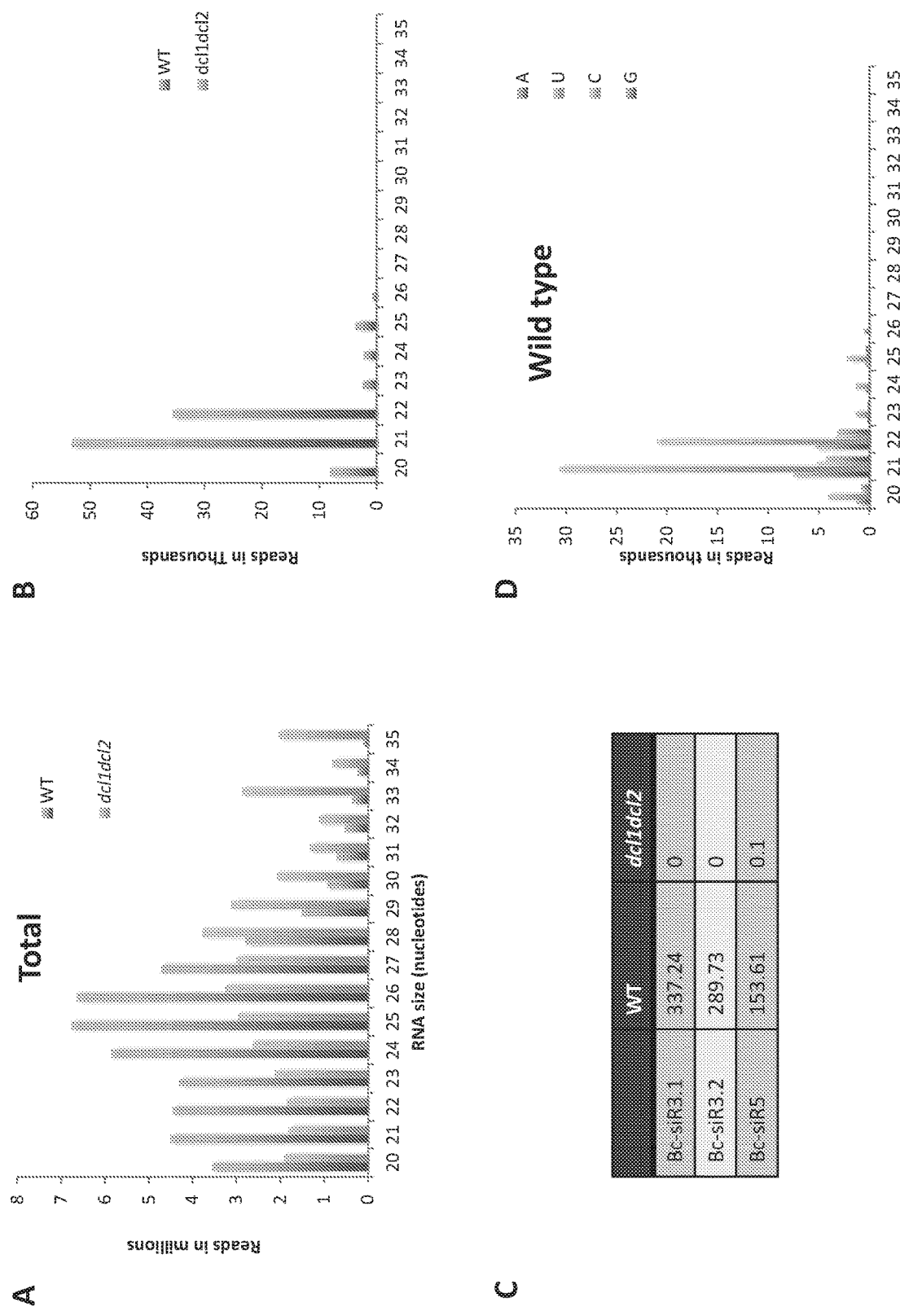
FIG. 7A-D. Retrotransposon-derived Bc-sRNAs are mostly BcDCL-dependent. Two libraries were constructed from wild type *B. cinerea* and the dcl1 dcl2 double mutant and sequenced using Illumina deep sequencing. (A) The read numbers of all Bc-sRNA reads from the two libraries according to sRNA size. (B) The read numbers of retrotransposon-derived Bc-sRNA from the two libraries according to sRNA size. (C) The normalized read numbers of Bc-siR3.1, Bc-siR3.2, and Bc-siRS from the two libraries. (D) The read numbers of retrotransposon-derived Bc-sRNAs according to 5' nucleotide (A, U, C, or G) and sRNA size. The X-axis in A, B, and D indicates RNA size in nucleotides.
Figure 8:
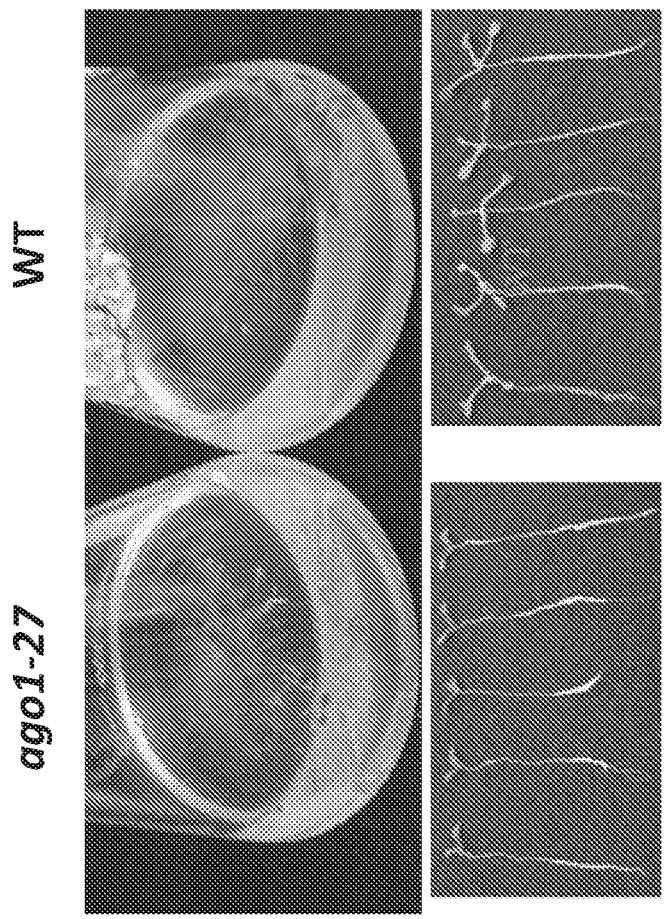
FIG. 8. Some *Verticillium* small RNAs were highly enriched in AGO1 pull-down fraction after infection. Root culture was performed to obtain material for immunoprecipitation of AGO1-associated small RNA in wild-type (WT) and ago1-27 mutant *Arabidopsis* following infection. sRNAs that are associated with *Arabidopsis* AGO1 were pulled down and subjected to deep sequencing.

*B. cinerea* DCLs are essential for the pathogenicity of *B. cinerea*. As shown in FIG. 3, dcl1 dcl 2 double mutants, but not dcl1 or dcl2 single mutants, produced much weaker disease symptoms than did the wild type in both *Arabidopsis* and *S. lycopersicum*, and largely attenuated the virulence of *B. cinerea*. Similarly, FIG. 4 shows that *B. cinerea* dcl1 dcl 2 double mutants are much less virulent on fruit, vegetables, and flowers.

A genome-wide comparative sRNA analysis on a dcl1 dcl2 mutant strain and wild-type revealed that *Botrytis* DCLs are responsible for generating LTR-derived sRNAs, many of which are sRNA effectors. See, FIG. 5A-B, FIG. 6, and FIG. 7A-D.

Figure 10:
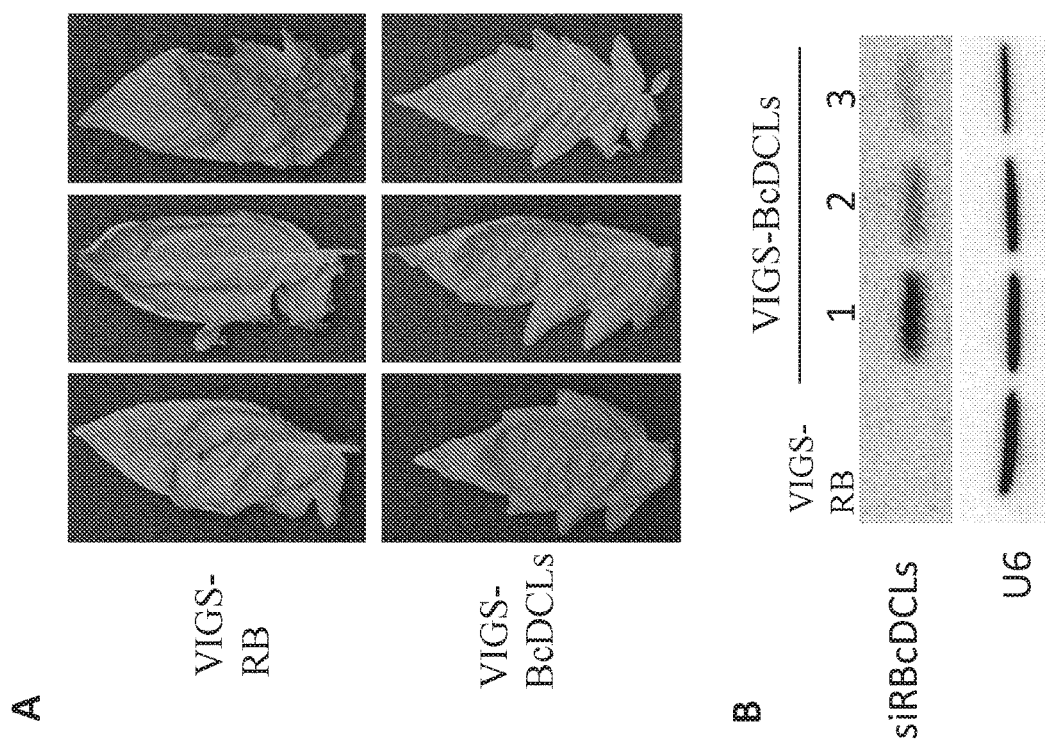
FIG. 10A-B. Knocking down BcDCLs by virus induced gene silencing (VIGS) in tomato enhances plant resistance to *B. cinerea*. (A) The fifth, sixth, and seventh leaves of tomato VIGS-RB and VIGS-BcDCLs plants were detached and infected with *B. cinerea* using spray inoculation. Photographs were taken 3 dpi. Three biological repeats indicated similar results. (B) The levels of siRBcDCLs from the corresponding infected leaves were measured by Northern blot. U6 was used as loading control.
Figure 11:
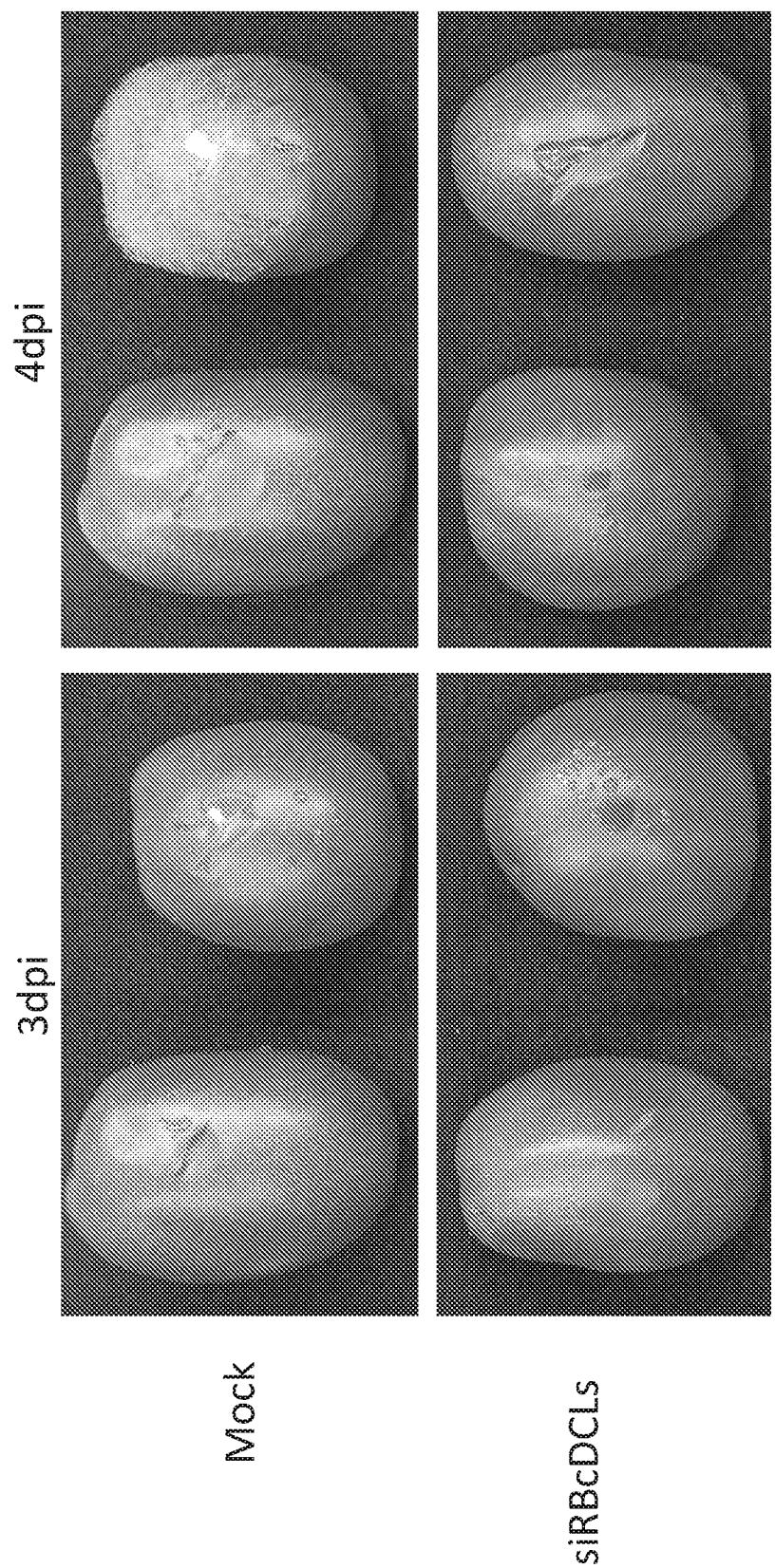
FIG. 11. Tomato was more resistant against *B. cinerea* when sprayed with RNA containing siRBcDCLs. Mock RNA: Total RNA extracted from tobacco infiltrated by mock. siRBcDCLs RNA: Small RNA extracted from tobacco infiltrated by Agrobacteria carrying siRBcDCLs producing vector (pHellsgate8-B052DCLs).
Figure 12:
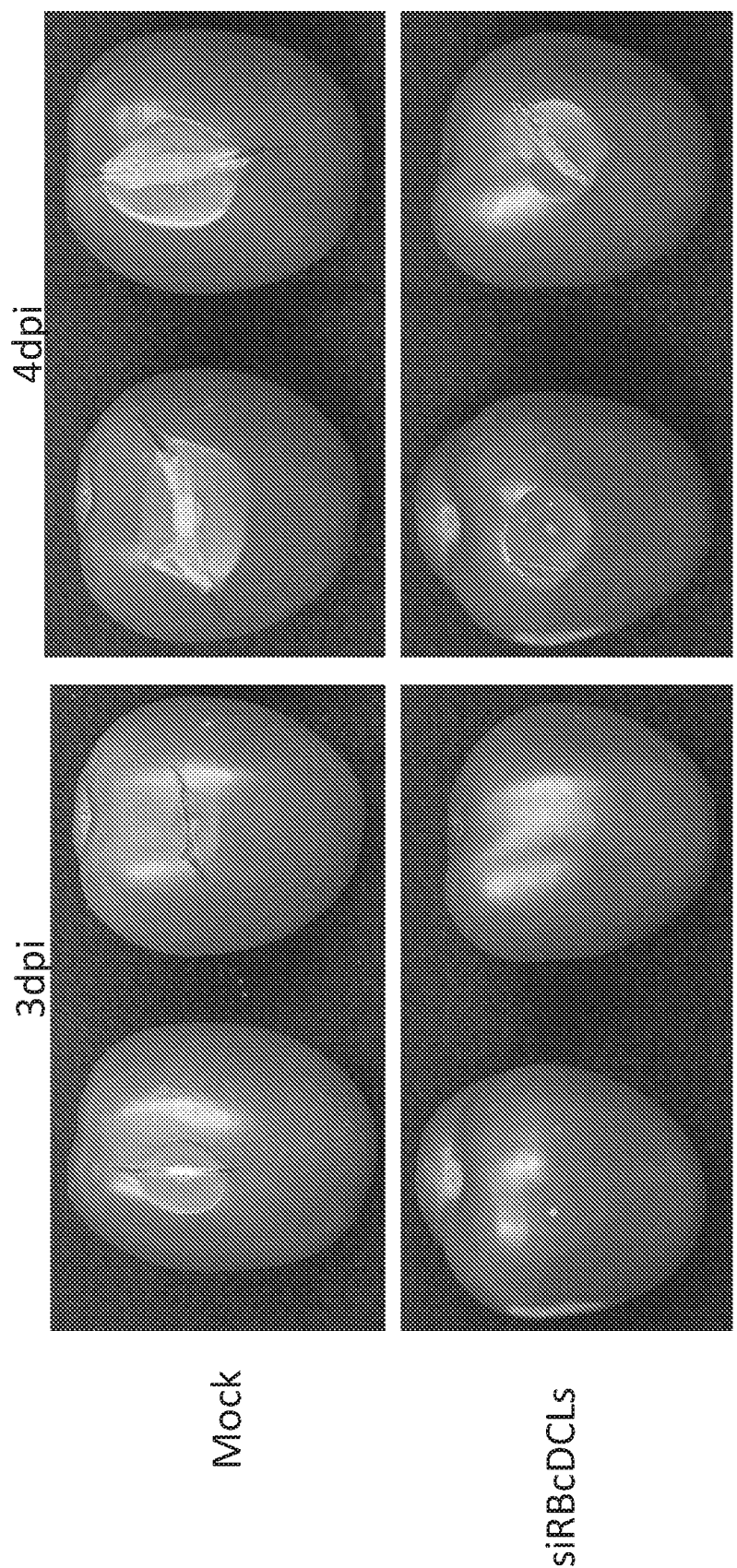
FIG. 12. *B. cinerea* was less virulent to tomatoes when mixed with *N. benthamiana* total RNA containing siRBcDCLs. Mock RNA: Total RNA extracted from tobacco infiltrated by mock. siRBcDCLs RNA: Small RNA extracted from tobacco infiltrated by Agrobacteria carrying siRBcDCLs producing vector (pHellsgate8-B052DCLs).
Figure 13:
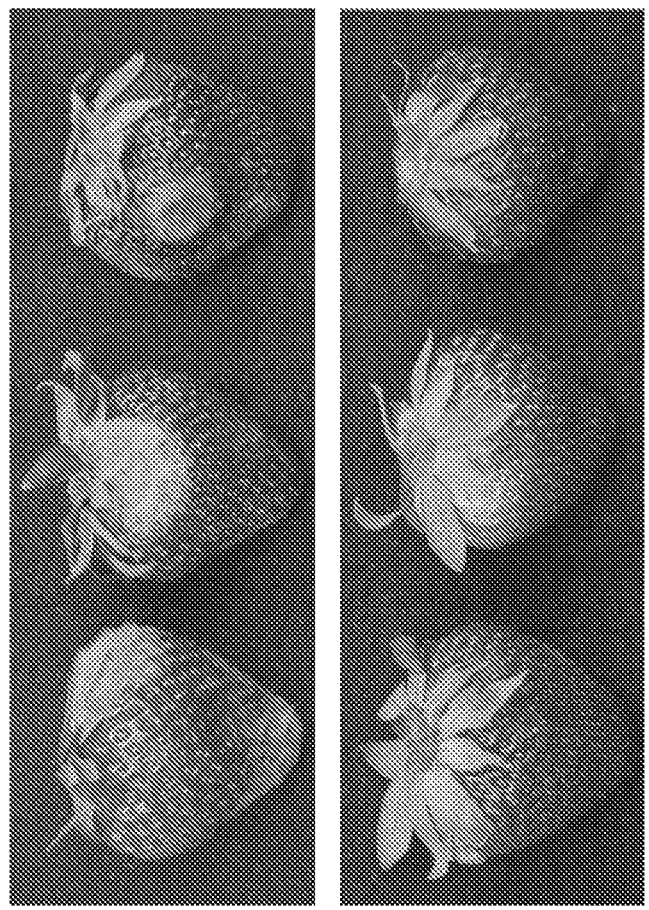
FIG. 13. *B. cinerea* was less virulent to strawberries when mixed with RNA containing siRBcDCLs. Mock RNA: Total RNA extracted from tobacco infiltrated by mock. siRBcDCLs RNA: Small RNA extracted from tobacco infiltrated by Agrobacteria carrying siRBcDCLs producing vector (pHellsgate8-B052DCLs).
Figure 14:
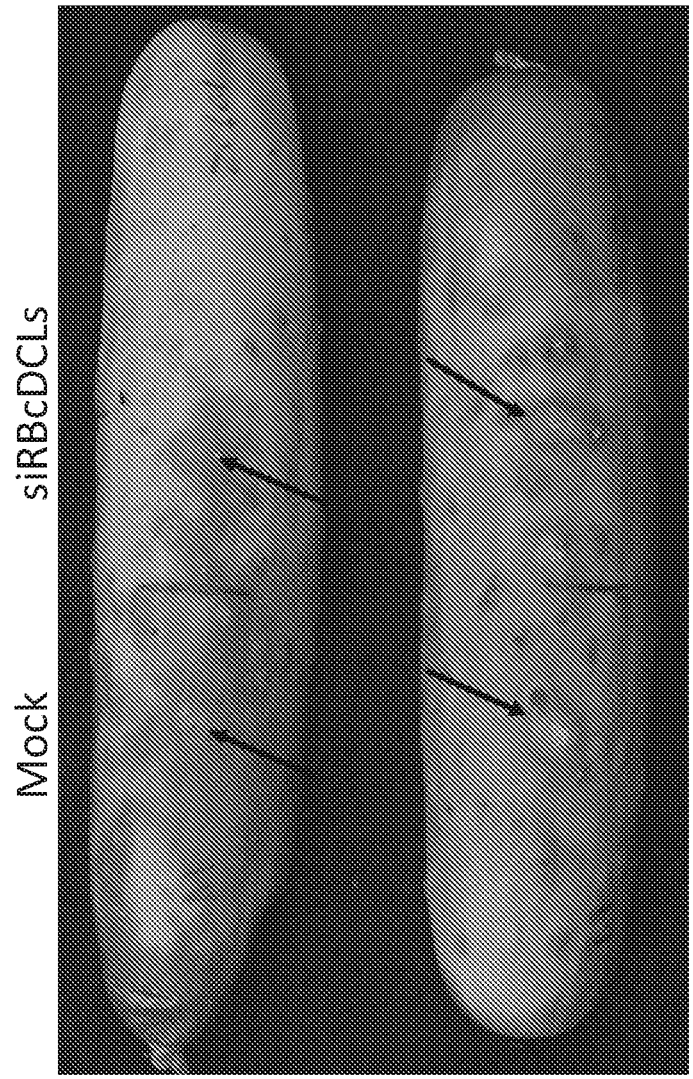
FIG. 14. *B. cinerea* was less virulent to cucumbers when mixed with RNA containing siRBcDCLs. Mock RNA: Total RNA extracted from tobacco infiltrated by mock. siRBcDCLs RNA: Small RNA extracted from tobacco infiltrated by Agrobacteria carrying siRBcDCLs producing vector (pHellsgate8-B052DCLs).
Figure 15:
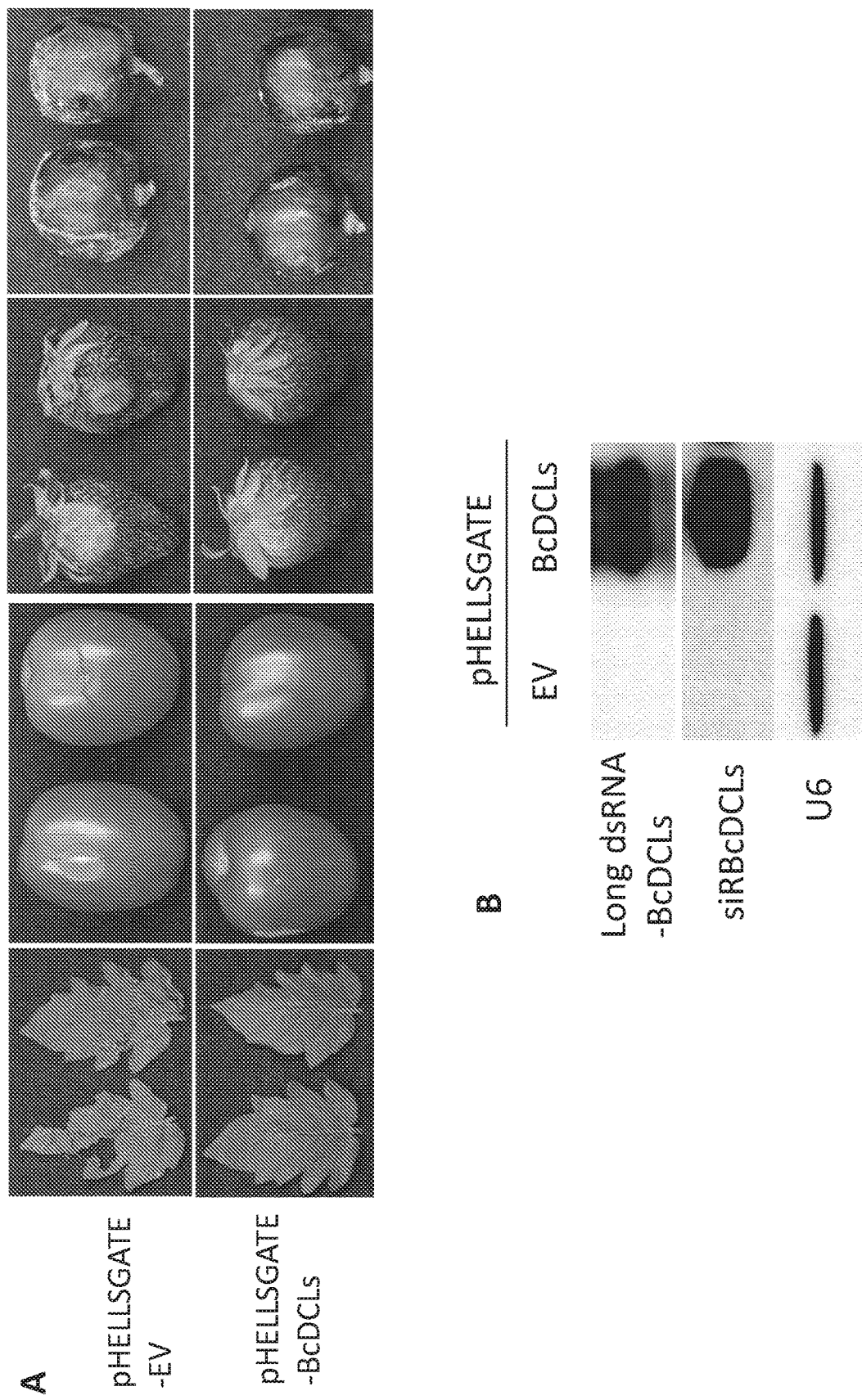
FIG. 15A-B. Spraying fruits with RNAs extracted from *N. Benthamiana* expressing Bc-DCL-targeting sRNAs exhibited reduced gray mold disease symptoms caused by *B. cinerea*. (A) T statistically significant differences (P<0.01; Student's t test). These experiments were repeated three times and yielded similar results.
Figure 16:
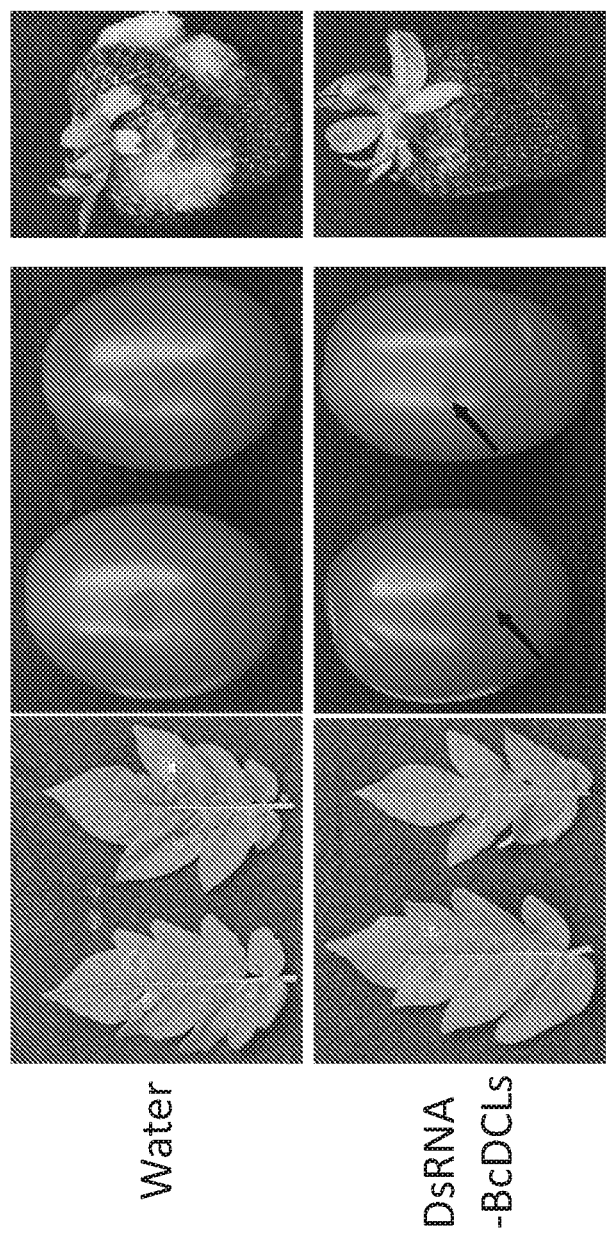
Figure 17:
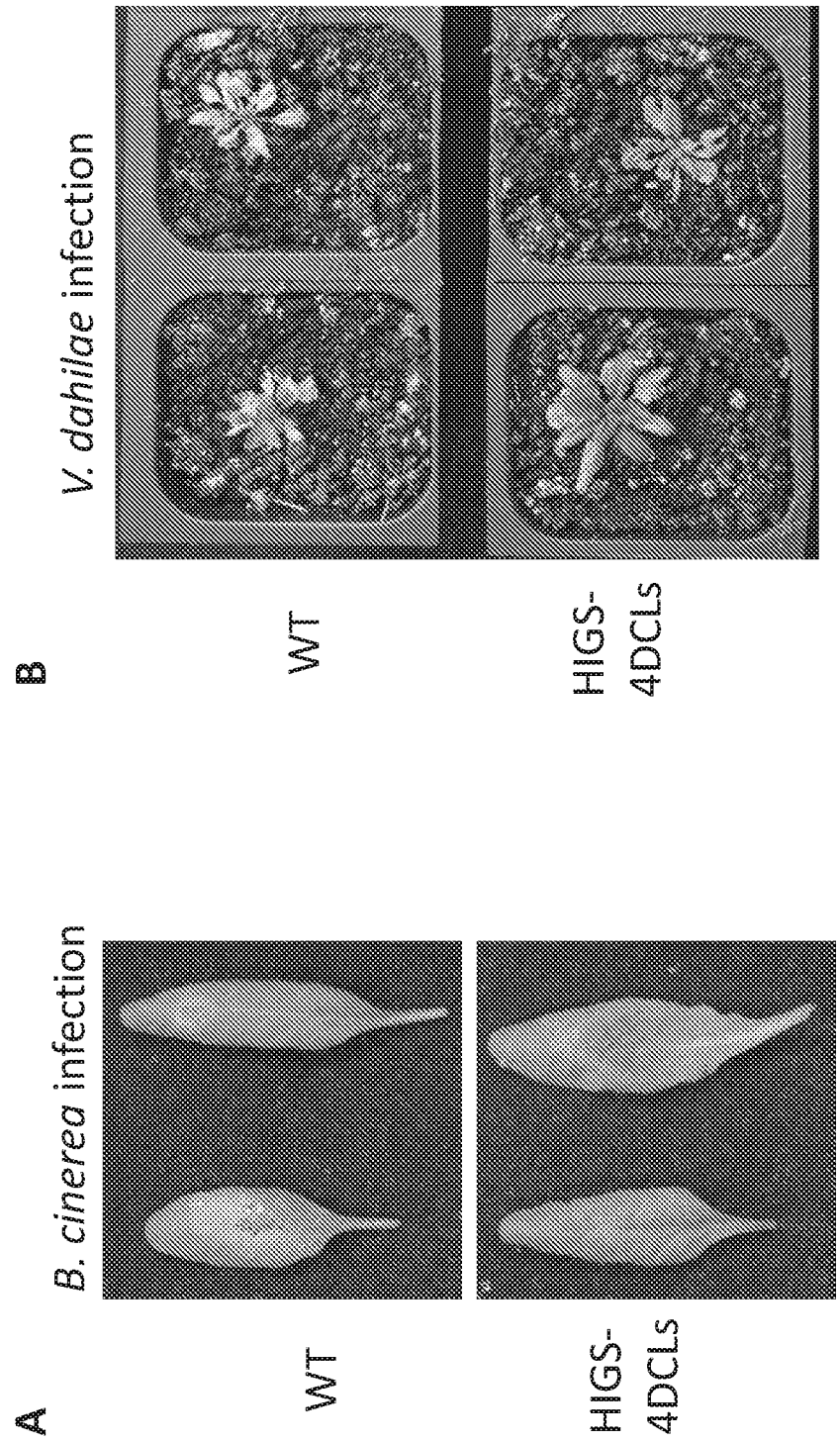

*B. cinerea* delivers small RNAs into host cells (e.g., plant cells) to suppress host immune systems. See, e.g., Weiberg at FIG. 2. Another fungal plant pathogen, *Verticillium dahliae*, also depends on AGO1 function for its pathogenicity. See, e.g., Ellendorf et al., *J. Exp Bot* 2009; 60:591-602. This suggests that *Verticillium* is likely to have a similar RNAi virulence mechanism as *B. cinerea*. Because *Verticil-* shown in FIG. 10, virus induced gene silencing (VIGS) against *B. cinerea* dcl1 dcl2 (spray inoculation) increased plant tolerance against *B. cinerea*.

TABLE 1

Infection-enriched *Verticillium* small RNAs have potential host targets

| Verticillium Small RNA Sequences | Reads in Infected | Reads in control | Enriched fold | Score | Targeting sequences (SEQ ID NO:) | Target Genes |
|---|---|---|---|---|---|---|
| TAAGGATCGGAGGT TCGAATCAGTT SEQ ID NO: 32 | 724.7 | 0.0 | U/A | 3 | 3'-CTAAGCTTGGAGGCTAGG-5' (54)<br>\|\|\|\|x\|\|\|\|\|\|\|x\|\|\|\|\|<br>5'-GATTGGAACCTCAGATCC-3' (37) | Cysteine/Histidine-rich C1 domain family protein |
|  |  |  |  | 3 | 3'-CTAAGCTTGGAGGCTAGG-5' (55)<br>\|x\|\|x\|\|\|\|\|\|\|:\|\|\|\|\|<br>5'-GCTTGGAACCTCTGATCC-3' (38) | Cysteine/Histidine-rich C1 domain family protein |
|  |  |  |  | 3.5 | 3'-CTAAGCTTGGAGGCTAGG-5' (56)<br>\|\|x\|\|x\|\|\|\|\|:\|\|\|\|\|:<br>5'-GACTCTAACCTTCGATCT-3' (39) | WRKY DNA-binding protein 2 |
|  |  |  |  | 4.5 | 3'-ACTAAGCTTGGAGGCTAGG-5' (57)<br>\|\|:\|\|x\|\|\|:\|\|\|:\|:\|\|\|<br>5'-TGGTTGGAATCTCTGGTCC-3' (40) | Disease resistance protein (TIR-NBS-LRR class) |
|  |  |  |  | 4.5 | 3'-ACTAAGCTTGGAGGCTAGG-5' (58)<br>\|\|:\|\|x\|\|\|:\|\|\|:\|:\|\|\|<br>5'-TGGTTGGAATCTCTGGTCC-3' (41) | Disease resistance protein (TIR-NBS-LRR class) family |
| GCGAGGTGAGAGGA CGACCAGCCAAG SEQ ID NO: 33 | 10116.0 | 5.2 | 1938 | 3 | 3'-GACCAGCAGGAGAGTGGA-5' (59)<br>\|\|\|\|\|\|x\|\|\|\|\|\|\|\|\|\|x<br>5'-CTGGTCCTCCTCTCACCA-3' (42) | mitogen-activated protein kinase kinase kinase 5 |
| CATCTGAGAGGACG TCCCGCCATGGC SEQ ID NO: 34 | 5785.1 | 4.6 | 1266 | 4.5 | 3'-CCGCCCTGCAGGAGAGTC-5' (60)<br>\|\|:\|\|x\|\|x\|\|:\|\|\|\|\|\|<br>5'-GGTGGAACTTCTTCTCAG-3' (43) | Leucine-rich repeat protein kinase family protein |
| GTCCGGGAAATGAC CAGCTTGAGCAG SEQ ID NO: 35 | 2717.7 | 4.6 | 595 | 4.5 | 3'-GAGTTCGACCAGTAAAGGG-5' (61)<br>:\|\|\|\|x\|\|\|\|\|x\|\|\|\|:\|<br>5'-TTCAACCTGGTGATTTCTC-3' (44) | Cystein/Histidine-rich C1 domain family protein |
|  |  |  |  | 4.5 | 3'-GAGTTCGACCAGTAAAGGG-5' (62)<br>:\|\|\|\|x\|\|\|\|\|x\|\|\|\|:\|<br>5'-TTCAACCTGGTGATTTCTC-3' (45) | Cystein/Histidine-rich C1 domain family protein |
|  |  |  |  | 4.5 | 3'-GAGTTCGACCAGTAAAGGG-5' (63)<br>:\|\|\|\|x\|\|\|\|\|x\|\|\|\|:\|<br>5'-TTCAACCTGGTGATTTCTC-3' (46) | Cystein/Histidine-rich C1 domain family protein |
|  |  |  |  | 4.25 | 3'-GAGTTCGACCAGTAAAGGG-5' (64)<br>x\|\|\|:x\|\|\|\|\|\|\|\|\|\|\|\|x<br>5'-GTCAGACTGGTCATTTCCA-3' (47) | AGD2-like defense response protein 1 |
| ATGTCGATGGTCGG ATGTATCCTTTTCT SEQ ID NO: 36 | 3164.0 | 46.3 | 68 | 4.5 | 3'-TTTTCCTATGTAGGCTGGTAGC-5' (65)<br>\|\|\|\|x\|\|\|:\|\|\|\|\|\|\|\|:\|x\|\|\|<br>5'-AAAAAGATGCATCCGATCTTCG-3' (48) | Ankyrin repeat family protein |
|  |  |  |  | 4.5 | 3'-TTTTCCTATGTAGGCTGGTAGC-5' (66)<br>x\|\|\|x\|\|\|\|:\|\|:\|\|\|\|\|\|\|\|x<br>5'-TAAAAGATATATTCGACCATCC-3' (49) | Cystein/Histidine-rich C1 domain family protein |

*lium* infects the plants through roots, we used root culture to get more material for immunoprecipitation of *Arabidopsis* AGO1-associated small RNA. sRNAs that are associated with *Arabidopsis* AGO1 were pulled down and subjected to deep sequencing. We found that some of the *Verticillium* small RNAs were highly enriched after infection. We found that 41 Vd-sRNAs had *A. thaliana* (At) targets (using 100 rpm and 10 fold enrichment as a cutoff). Table 1 below shows examples of infection-enriched *Verticillium* small RNAs that have potential host targets.

Figure 9:
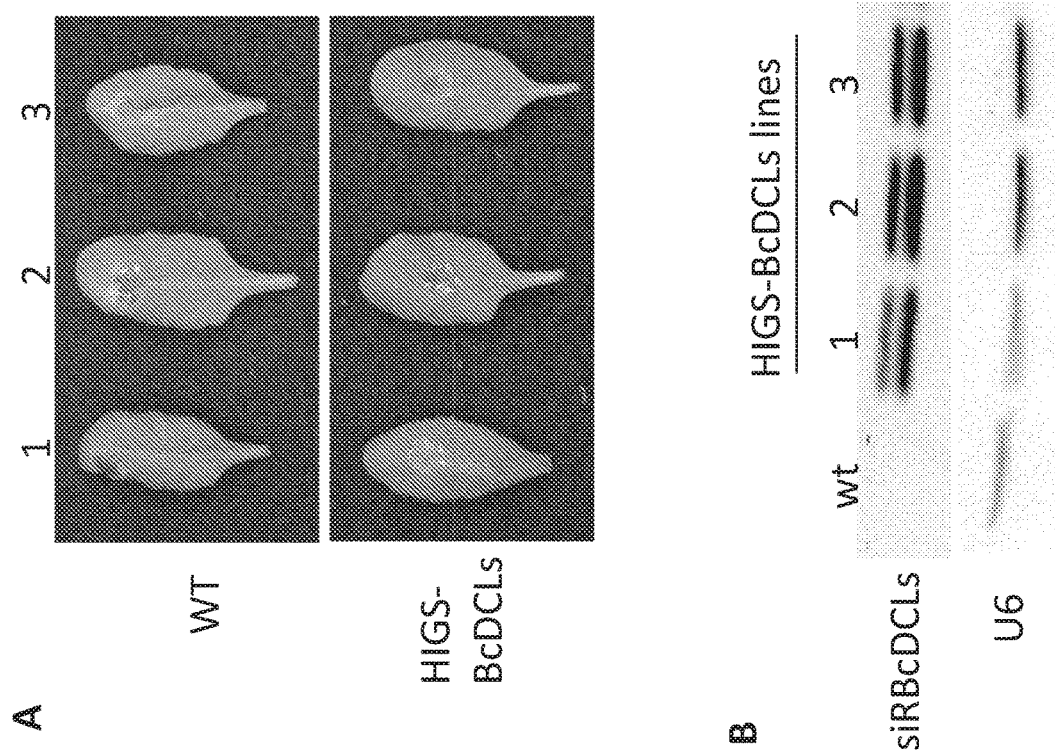
FIG. 9A-B. Knocking down BcDCLs by host induced gene silencing (HIGS) in transgenic *Arabidopsis* enhances plant resistance to *B. cinerea*. (A) Three selected *B. cinerea* dcl1dcl2 (HIGS-BcDCL) lines as well as wild type plants were infected with *B. cinerea*. Photographs were taken 4 days post infection (dpi). Three biological repeats indicated similar results. (B) The expression level of siRBcDCLs from wild type and three selected transgenic lines transformed with HIGS-BcDCLs as measured by Northern blot. U6 was used as loading control.

These results suggest that RNAi constructs, which target fungal Dicer-like protein genes to attenuate fungal virulence, can be expressed in host plants (including, but not limited to, tomato, grape and other commercially important crops). Alternatively, the RNAi constructs can be contacted to the plant, such as by being sprayed on a surface of the plant (e.g., onto the surface of a leaf) for promoting fungal resistance. As shown in FIG. 9, host induced gene silencing (HIGS) against *B. cinerea* dcl1 dcl2 (drop inoculation) increased plant tolerance against *B. cinerea*. Additionally, as Example 2: Increasing Fungal Resistance or Tolerance in Fruits and Vegetables by In Vitro Silencing of Fungal Pathogen DCLs Enhanced fungal resistance was observed when fruits, leaves, and vegetables were treated with sRNAs targeting fungal pathogen DCL genes. The following protocol was used for treating fruits, leaves, or vegetables with RNAs extracted from *N. Benthamiana* expressing Bc-DCL-targeting sRNAs.

Protocol

1. Plasmid construction. *B. cinerea* DCL1 (BcDCL1) RNAi fragment was amplified by using *B. cinerea* cDNAs as template, forward primer BcDCL1RNAi-F: 5'-GGGGACAAGTTTGTA-CAAAAAAGCAGGCTTGCGGAAGAACTT-GAAGGTTTGCTA CA-3' (SEQ ID NO:50) and reverse primer BcDCL1RNAi-R: 5'-GTCCAGATCTGGT-CAACACACCAAG-3' (SEQ ID NO:51), 2.52 bp. BcDCL2 RNAi fragment was amplified by the forward primer BcDCL2RNAi-F: 5'-CTTGGTGTGTTGACCA-GATCTGGACGGATGCCATTTGCTGCACGC-3' (SEQ ID NO:52) and reverse primer BcDCL2RNAi-R: 5'-GGGGACCACTTTGTA-CAAGAAAGCTGGGTACTCTTGAGTACTTTCGC CAGCTCAC-3' (SEQ ID NO:53), 238 bp. These two RNAi fragments were integrated together by overlapping PCR as BcDCL-RNAi, which was cloned into pDONR207 by BP reactions (Life Technologies), and finally to destination vector pHELLSGATE 8.0 by LR reactions (Life Technologies) as pHELLSGATE-BcDCL-RNAi. This vector as well as a negative control pHELLSGATE 8.0 empty vector were transformed into A. tumefaciens GV3101 strain.

2. Generate DCL-targeting sRNAs in N. benthamiana. The A. tumefaciens GV3101 strain carrying pHELLSGATE-BcDCL-RNAi (RNAi strain) and pHELLSGATE 8.0 empty vector (EV strain) were cultured in liquid LB with antibiotics (100 μg/μl Spectinomycin, 50 μg/μl Gentamycin and 50 μg/μl Rifampicin) overnight at 28° C. shaker. Both EV and RNAi A. tumefaciens cultures were centrifuged at 4000 rpm for 15 min at room temperature, and resuspended bacterial pellets with 5 mL infiltration buffer (10 mM $MgCl_2$, 10 mM MES, and 0.2 mM Acetosyringone). The OD600 of both EV and RNAi strain solutions were adjusted to 1.0, and kept on room temperature for 4 hours. Both solutions were diluted to OD600=0.5 by infiltration buffer right before infiltration. Then, the EV and RNAi strain solutions were used to infiltrate the 4 weeks old leaves of *N. benthamiana*. and allowed 2 days infection to over express DCL-targeting sRNAs in RNAi strain treated tissues.

3. Extract the sRNAs from *N. benthamiana*. The infiltrated *N. benthamiana* leaf tissues were harvested separately based on the strains (EV or RNAi) that infiltrated, and freeze them immediately in liquid nitrogen. 10 g of each tissue were ground into fine powder in the liquid nitrogen with mortars and pestles, and total RNAs were extracted by using TRIzol Reagent (Life Technologies). Resolved the RNA pellets in 500 μl DEPC treated $H_2O$, and the concentration of both EV and RNAi total RNAs was examined by nanodrop. The final concentration of these two RNAs samples were both adjusted. to 50 ng/μl for further use. The sRNAs targeting Bc-DCLs were only present in the RNAi set, but not in the EV set, which was used as a negative control.

4. Treat the vegetables or fruits with the RNA extracts. Two sets of vegetables or fruits under similar conditions, (e.g., similar freshness, maturity, size, shape, etc.) were gently washed and put in a plastic box with a wetted filter paper on the bottom to keep moisture. The first set was evenly treated with RNA extracts from EV strain infiltrated tissues, the other set was evenly treated with RNA extracts from RNAi strain infiltrated tissues. RNA extracts were applied by spray or by drop inoculation.

5. *B. cinerea* infection. *B. cinerea* infection was carried out after the spray of RNA extracts. The spores from 10 days old *B. cinerea* grown on Malt Extract Agar medium were eluted in sterile $H_2O$, and the fungal mycelia were filtered from the spores by nylon cloth. *B. cinerea* spore concentration was calculated by hemocytometer and diluted in B5 medium (10 mM Sucrose, 10 mM $KH_2PO_4$, Tween-20 0.025%). 15 μl of *Botrytis* spore solution ($2\times10^{-5}$) was sprayed on the surface of the sprayed fruits or vegetable, and allowed 2-4 days *B. cinerea* inoculation. Different vegetables or fruits took different time to obtain obvious disease symptoms.

Alternatively, a "mix" method was used for administering a 1:1 mixture of total RNAs as described above and *Botrytis* spore solution ($4\times10^{-5}$). 15 ul of the mixed solution was directly dropped on the surface of 2 sets of fruits or vegetables under similar conditions.

Results

As shown in FIG. 11, tomato was more resistant against *B. cinerea* when sprayed with RNA containing siRBcDCLs. Additionally, FIGS. 12-14 show that *B. cinerea* was less virulent when mixed with *N. benthamiana* total RNA containing siRBcDCLs and applied to tomato (FIG. 12), strawberry (FIG. 13), or cucumber (FIG. 14).

In another experiment, pretreating tomato leaves and fruits, strawberry fruits, and grape fruits with the total RNA from N. Benthamiana infiltrated with pHELLSGATE-BcDCLs and pHELLSGATE-EV by spray for 24 hours, followed by *B. cinerea* drop inoculation on the sprayed area of the fruits, reduced gray mold disease symptoms caused by *B. cinerea*. See, FIG. 15A-B.

In yet another experiment, Spraying tomato leaves and fruits with in vitro transcribed dsRNA against BcDCLs reduced gray mold disease caused by *B. cinerea* on tomato and strawberry. Tomato leaves and fruits and strawberry fruits were pre-treated with water or in vitro transcribed long dsRNA against BcDCLs for 24 hours, followed by *B. cinerea* drop inoculation right on the pretreated area of the leaves or fruits. See, FIG. 16.

Example 3: Increasing Plant Tolerance to Multiple Pathogens

Host induced gene silencing (HIGS) was used to silence the dicer-like protein (DCL) genes of two fungal pathogens in plants. An RNAi approach for targeting two DCLs from *Botrytis* and two DCLs from *Verticillium* was used in *Arabidopsis*, resulting in the generation of "HIGS-4DCLs" lines. The HIGS-4DCLs lines, as well as wild type *Arabidopsis* plants, were infected with *B. cinerea* by drop inoculation on the leaves and were infected with *V. dahilae* by root inoculation. Three weeks after infection, the HIGS-4DCLs lines exhibited increased tolerance to both pathogens relative to the wild-type plants. See, FIG. 17. Thus, the gene targeting approaches described herein can be utilized for targeting multiple pathogens at the same time.

Example 4: Dicer-Targeting Small RNA-Mediated Plant Protection Against *Botrytis cinerea* and Other Pathogens that Utilize Small RNA Effectors Eukaryotic pathogens, such as fungi and oomycetes, cause billions of dollars crop losses worldwide annually. *B. cinerea* poses a serious threat to over 200 plant species, including nearly all vegetables and fruits as well as many flowers, in their pre- and post-harvest stages by causing grey mold disease. Williamson et al., *Mol Plant Pathol* 8, 561-580 (2007); van Kan, *Trends in Plant Science* 11:247-253 (2006)). Current disease control is mainly achieved by fungicide application, which is costly and environmentally hazardous. HIGS has worked effectively against a variety of fungal and oomycete pathogens, such as *Blumeria graminis* (Nowara et al., *Plant Cell* 22, 3130-3141 (2010); Pliego et al., *Molecular Plant-Microbe Interactions* 26, 633-642 (2013); Whigham et al., *Molecular Plant-Microbe Interactions* 28, 968-983 (2015)), *Puccinia tritici* (Panwar et al, *Plant Molecular Biology* 81, 595-608 (2013)), *Fusarium* spp. (Koch et al., *PNAS* 110, 19324-19329 (2013); Ghag et al., *Plant Biotechnology Journal* 12:541-553 (2014); Cheng et al., *Plant Biotechnology Journal*, doi:10.1111/pbi.12352 (2015)), *Phytophthora infestans* (Jahan et al., *Journal of Experimental Botany* 66:2785-2794 (2015); Sanju et al.,

*Functional & Integrative Genomics* 15:697-706 (2015), and *Phytophthora capsici* (Vega-Arreguin et al., *Molecular Plant-Microbe Interactions* 27, 770-780 (2014). However, successful HIGS largely depends on plant transformation technology that is not available for many crops, and furthermore, the safety of genetically modified organisms (GMOs) is still a major concern to the public.

Results

Figure 18:
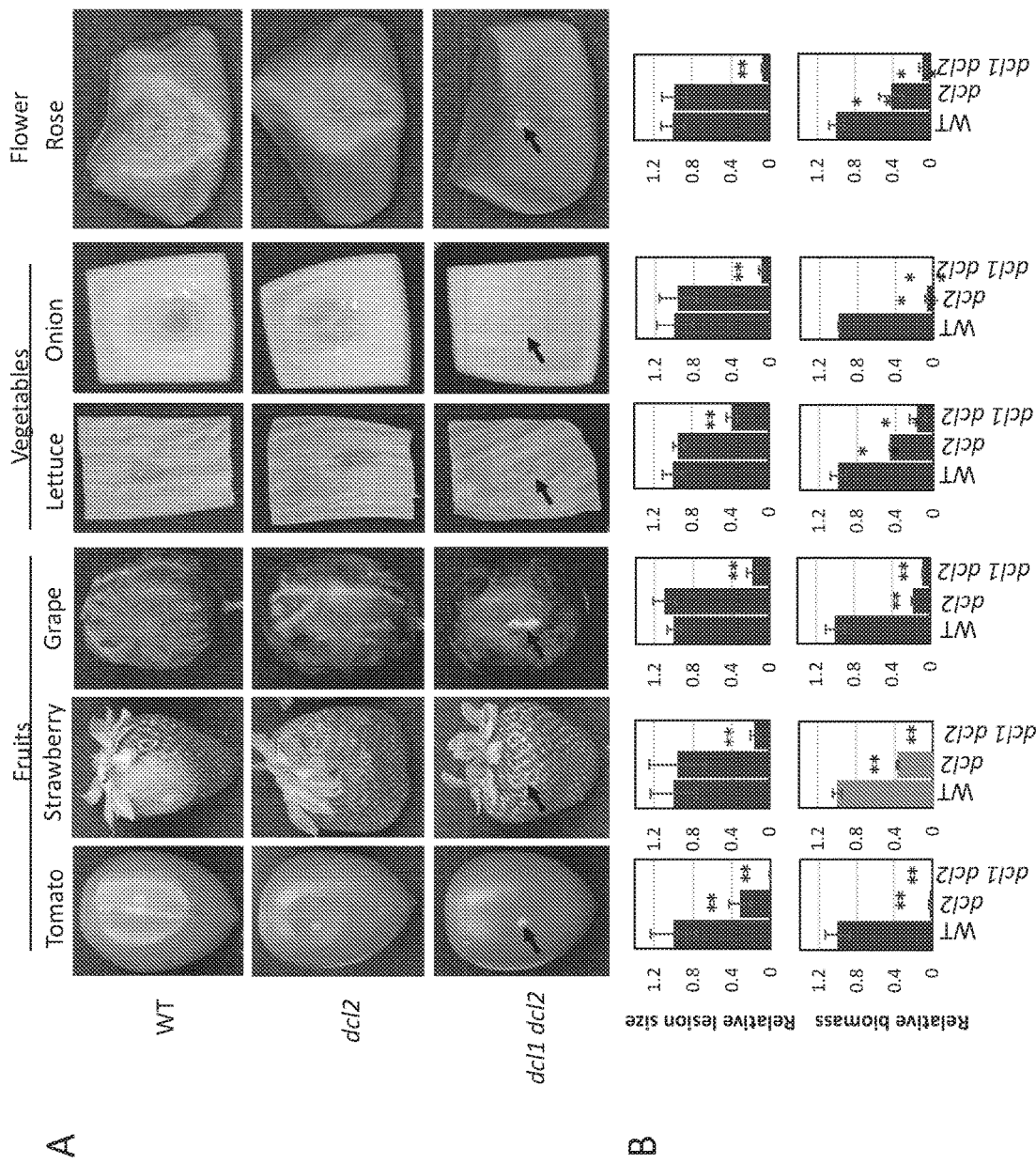

As discussed above in Example 1, only the dcl1 dcl2 double mutant of *B. cinerea*, but not the dcl1 or dcl2 single mutants, failed to produce Bc-sRNA effectors, suggesting that these Bc-sRNA effectors are dependent on both Bc-DCL1 and Bc-DCL2. To fully evaluate the contribution of Bc-DCL-dependent Bc-sRNA effectors to *B. cinerea* pathogenicity on a wide range of economically important crops, various fruits (tomato—*Solanum lycopersicum* 'Roma', strawberry—*Fragaria* x *ananassa*, and grape—*Vitis labrusca* 'Concord'), vegetables (iceberg lettuce—*Lactuca sativa* and onion—*Allium cepa* L.), and flower petals (rose—*Rosa hybrida* L.) were inoculated with the dcl1 dcl2 double mutant. The dcl2 single mutant, and wild-type (WT) strains were used as controls. The dcl1 dcl2 double mutant showed much weaker pathogenicity and produced significantly smaller lesions than the WT strain on all the samples (FIG. 18A-B, P<0.01), whereas the dcl2 single mutant generated smaller lesions than the WT strain on tomato, but it created comparable lesions to the WT strain on strawberry, grape, lettuce, onion, and rose petal (FIG. 18A-B). These results indicate that sRNA effectors play a critical role in *B. cinerea* pathogenicity, because even though dcl2 strain showed clear reduction of fungal growth, it could still produce Bc-sRNA effectors and cause obvious disease symptoms.

To assess the DCL1 and DCL2-dependent Bc-sRNA population globally, we profiled total sRNAs isolated from the dcl1 dcl2 double mutant as well as the WT strain. In the WT strain, Bc-sRNAs ranged from 20 to 35 nucleotides (nt) in length (data not shown), with an enrichment of 24-27-nt species. The abundance of 20-27-nt sRNA species was clearly reduced but not completely eliminated in the dcl1 dcl2 double mutant (data not shown), pointing to the existence of DCL-independent sRNA biogenesis pathways in *B. cinerea*, as reported in *Neurospora crassa* (Lee et al., *Molecular Cell* 38:803-814 (2010); Jin al., *Molecular Cell* 38:775-777 (2010)). Most strikingly, the sRNAs derived from retrotransposons (ranging from 20-26-nt and peaking at 21-22-nt) were almost completely eliminated in the dcl1 dcl2 double mutant (data not shown), which indicates that Bc-DCL1/2 are mostly responsible for generating sRNAs from retrotransposons. The sRNAs from intergenic non-coding (IGN) regions (mainly the 21-, 22- and 24-nt sRNAs) and antisense to open reading frames (ORFs-antisense, mainly the 21-22-nt sRNAs) were also largely reduced in dcl1 dcl2, although the sRNAs from the sense transcripts of ORFs (ORFs-sense) were not changed significantly. As reported previously (Weiberg et al.) and as discussed in Example 1, the majority of predicted sRNA effectors are from retrotransposon long terminal repeats (LTRs); thus, Bc-DCL1/2 are largely responsible for generating sRNA effectors and contribute significantly to *B. cinerea* pathogenicity. This makes Bc-DCL1/2 ideal targets to test whether sRNA-mediated silencing would be an efficient strategy for controlling gray mold disease.

To test whether host-generated sRNAs can move from plant cells to *B. cinerea* and whether silencing Bc-DCL1/2 would efficiently suppress disease symptoms of *B. cinerea* on plants, we generated transgenic *Arabidopsis* plants expressing sRNAs that target both Bc-DCLs. A DNA fragment containing 252 base-pair (bp) and 238 bp segments from the non-conserved regions of Bc-DCL1 and Bc-DCL2, respectively, was cloned into the pHELLSGATE vector system (Helliwell et al., *Methods in Enzymology* 392:24-35 (2005)). Two DNA segments were used, one each from Bc-DCL1 and Bc-DCL2, because there is no DNA region outside the conserved domains with sufficient homology between the two DCLs to silence both DCLs. DNA regions in the conserved functional domains were avoided to eliminate any off-target effects on DCL genes from other species. These selected Bc-DCL DNA regions have only 3.5% to 4.8% sequence identity to *Arabidopsis* DCLs, and indeed, no host DCL genes were silenced (data not shown). The hairpin RNA products transcribed from the pHELLSGATE construct in the transgenic plants were processed into sRNAs by plant DCLs to target Bc-DCL1 and Bc-DCL2 (FIG. 19A). These plants exhibited much smaller lesions and less fungal growth after *B. cinerea* infection when compared with the WT plants (FIG. 19B-C). Relative expression of Bc-DCL1 and Bc-DCL2 was clearly suppressed in *B. cinerea* collected from the transgenic plants compared to those from WT plants (FIG. 19D). These results suggest that Bc-DCL1/2-targeting sRNAs (Bc-DCL1/2-sRNAs) produced in plant cells moved into the fungal cells and efficiently silenced Bc-DCL1 and Bc-DCL2, which led to suppression of fungal virulence and growth, and inhibition of disease.

To determine whether this Bc-DCL1/2-targeting RNAi strategy could also efficiently control gray mold disease in tomato plants, we introduced the same Bc-DCL1/2 fragment into the tobacco rattle virus (TRV) silencing system (Liu et al., *Plant Journal* 31:777-786 (2002), which triggered the expression of Bc-DCL1/2-sRNAs in tomato. Three weeks after agro-infiltration, the tomato plants were infected with *B. cinerea* using spray inoculation. The tomato leaves expressing Bc-DCL1/2-sRNAs displayed very mild to almost no disease symptoms at 3 dpi (FIG. 19E-G), whereas the control leaves, which expressed sRNAs targeting a potato late blight resistance gene RB that is not present in tomato (Song et al., PNAS 100:9128-9133 (2003), showed very severe water soaked disease lesions (FIG. 19F-G). The growth of *B. cinerea* was also significantly reduced on the leaves expressing Bc-DCL1/2-sRNAs compared with the control, and the expression of Bc-DCL1 and Bc-DCL2 was largely reduced in *B. cinerea* grown on these leaves as well (FIG. 19H). These data further support that sRNAs can move from plant cells to fungal cells, and they can efficiently silence fungal DCL genes and suppress pathogen virulence.

Figure 20:
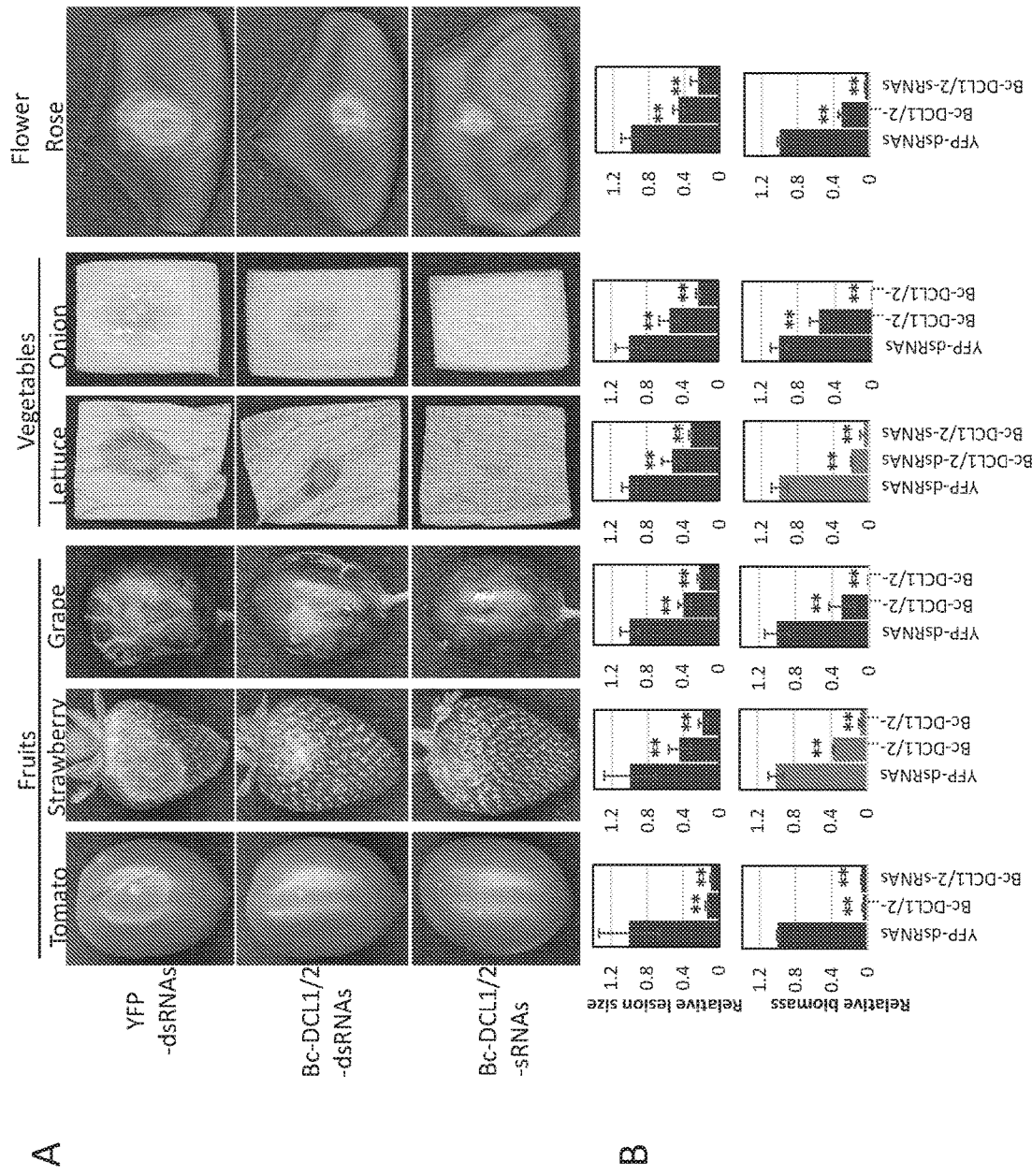

*B. cinerea* also infects many other plant species, in addition to *Arabidopsis* and tomato. Gray mold disease is a very serious problem in post-harvest management, as it destroys millions of fruits, vegetables, and flowers during the packing, transportation, and storage processes each year. Unfortunately, stable transformation and virus-induced gene silencing technologies have not been developed in many host species. Uptake of RNAs from environments, a phenomenon named environmental RNAi, was observed in *C. elegans* and other insects. See, e.g., Winston et al., *PNAS* 104:10565-10570 (2007); Ivashuta et al., *RNA* 21:840-850 (2015). Spraying dsRNAs targeting the actin gene of potato beetle *Leptinotarsa decemlineata* on potato leaves could inhibit the larva growth (San Miguel et al., *Pest Management Science, doi:*10.1002/ps.4056 (2015)). Therefore, we attempted to externally apply synthetic Bc-DCL1/2-sRNAs or their double-stranded RNA precursors (Bc-DCL1/2-dsRNAs) on the surface of fruits, vegetables, and flowers, to test whether *B. cinerea* is capable of taking up dsRNAs and/or sRNAs from the environment and inducing silencing of its own genes. The same Bc-DCL1/2 fragment was transcribed in vitro from both ends and gave rise to Bc-DCL1/2-dsRNAs. The Bc-DCL1/2-dsRNAs were subjected to RNAse III treatment to generate Bc-DCL1/2-sRNAs in vitro. The Bc-DCL1/2-sRNAs and the precursor dsRNAs (20 ng/µl) were externally applied on fruits (tomato, strawberry, and grape), vegetables (lettuce and onion), and flower petals (rose), and followed with *B. cinerea* infection. All the plants treated with Bc-DCL1/2-sRNAs and -dsRNAs developed much weaker disease symptoms (FIG. 20A-B) and supported significantly less growth of *B. cinerea* (FIG. 20B) compared to the YFP-dsRNAs-treated controls, suggesting that externally applied Bc-DCL1/2-sRNAs and -dsRNAs can inhibit pathogen virulence, probably via the suppression of both fungal growth and Bc-sRNA effector biogenesis. Bc-DCL1/2-sRNAs had slightly stronger effects than Bc-DCL1/2-dsRNAs.

Figure 21:
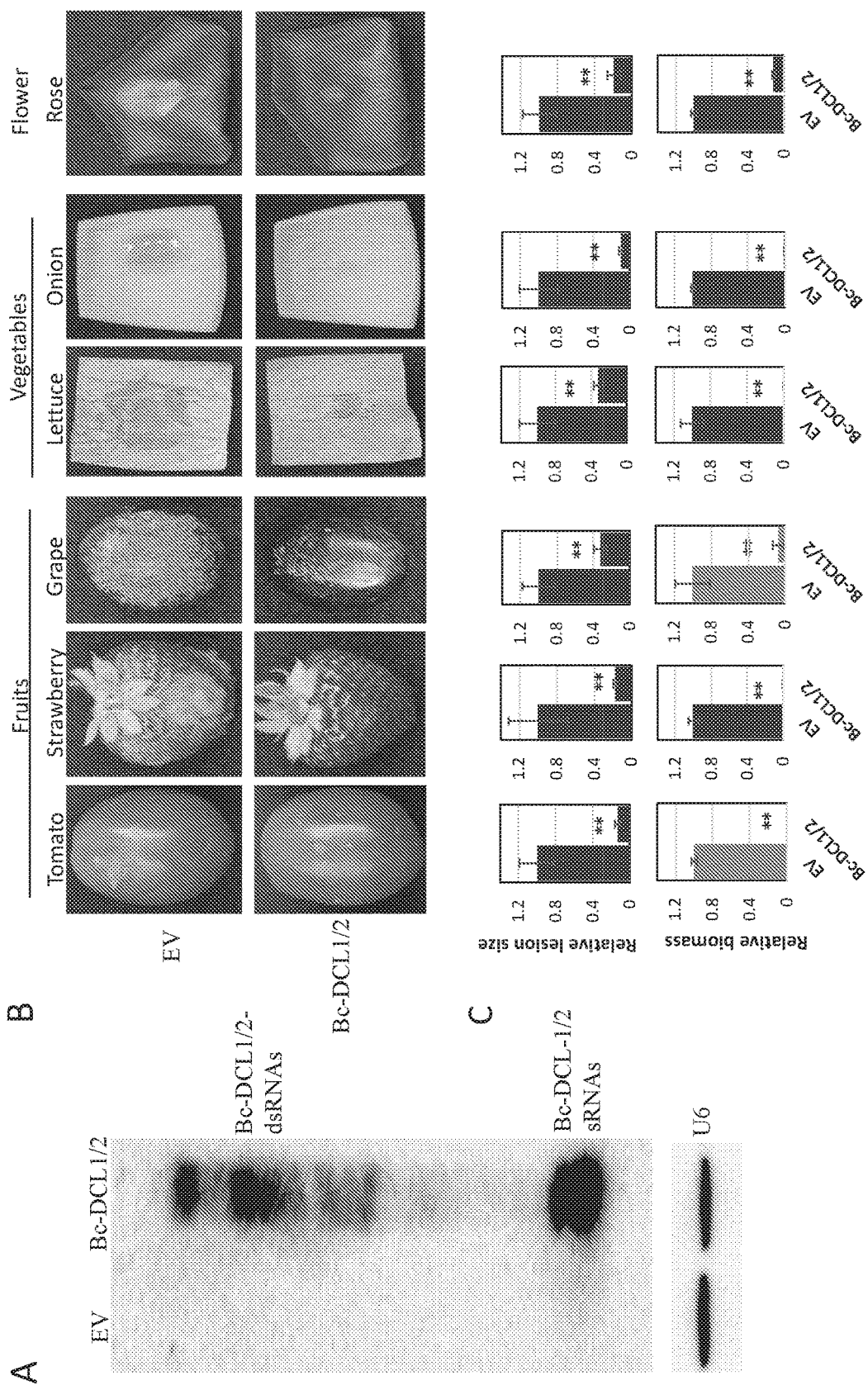

Although external treatment of Bc-DCL1/2-sRNAs and the precursor Bc-DCL1/2-dsRNAs can inhibit fungal disease, in vitro RNA synthesis is too costly. In order to obtain a large amount of Bc-DCL1/2-sRNAs and -dsRNAs at a much lower cost, we transiently expressed pHELLSGATE-Bc-DCL1/2 vector in *N. benthamiana*, which yielded a large amount of Bc-DCL1/2-sRNAs and -dsRNA precursors two to three days after Agrobacterial inoculation (FIG. 21A). The pHELLSGATE empty vector (EV) was used as a control. The purified total RNAs were applied onto the surface of fruits, vegetables, and rose petals and followed with *B. cinerea* infection. All the plants treated with the RNA extracts containing Bc-DCL1/2-sRNAs and -dsRNAs developed less severe disease symptoms and showed decreased fungal growth than those treated with RNAs extracted from EV plants (FIG. 21B-C). This result demonstrates that the Bc-DCL1/2-sRNAs and -dsRNAs, but not *N. benthamiana* total RNA, can protect plants from *B. cinerea* infection.

Figure 22:
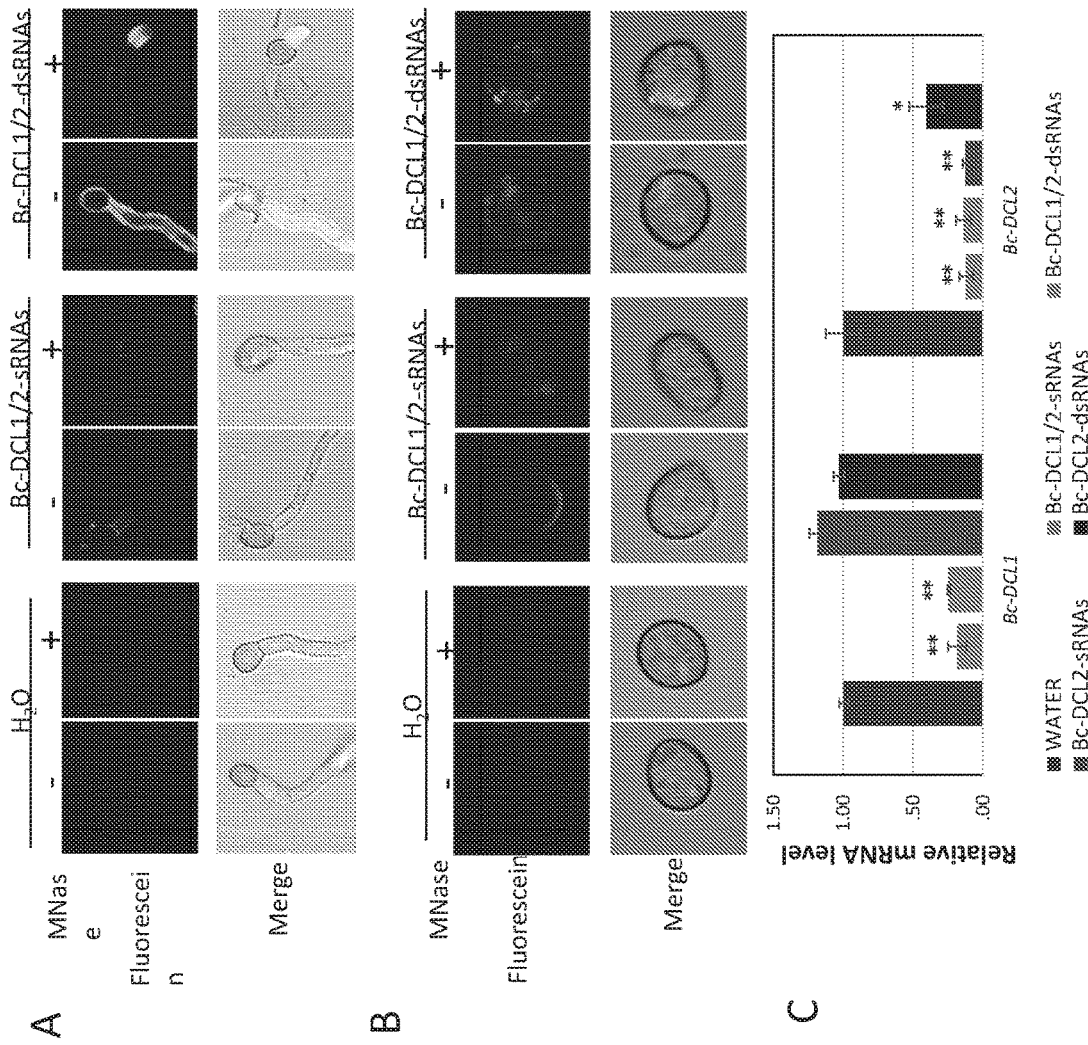
FIG. 22A-C. *B. cinerea* cells take up Bc-DCL1/2-sRNAs and -dsRNAs, which silenced Bc-DCL1 and Bc-DCL2. (A) Fluorescent Bc-DCL1/2-sRNAs and -dsRNAs were examined in the *B. cinerea* cells after 12 hours of co-culturing with *B. cinerea* spores on solid ME medium. Fluorescence-labeled DCL1/2-sRNAs and -dsRNAs were detected in the *B. cinerea* cells. They were still present in the *B. cinerea* cells after MNase treatment. (B) Fluorescent Bc-DCL1/2-sRNAs and -dsRNAs were observed in *B. cinerea* protoplasts after 16 hours of co-culturing with *B. cinerea* spores in liquid YEPD medium. MNase treatment of the protoplast did not eliminate the fluorescence. (C)Bc-DCL1 and Bc-DCL2 were examined at 40 hours after *B. cinerea* spores were co-cultured with Bc-DCL1/2-sRNAs and -dsRNAs in the liquid YEPD medium. Bc-DCL2-targeting sRNAs and dsRNAs only downregulated Bc-DCL2 but not Bc-DCL1.

The effect of externally applied Bc-DCL1/2-sRNAs and -dsRNAs molecules on *B. cinerea* virulence and growth could be a result of the direct uptake of dsRNAs and sRNAs from the ambient environment by *B. cinerea* or an indirect process that involves plant uptake and processing prior to transport into *B. cinerea* cells. In order to test whether sRNA and dsRNA can directly enter *B. cinerea* cells or require an intermediate step involving plant hosts, we removed the plants out of the picture, and directly applied the Bc-DCL1/2-sRNAs and -dsRNAs on *B. cinerea* spores and germinated them on solid malt extract (ME) medium. To visualize the RNAs, we labeled the RNAs with fluorescein-12-UTP by in vitro transcription. Microscopic inspection of germinating conidiospores after 12 hours revealed fluorescent RNA signals accumulating in fungal cells (FIG. 22A). To eliminate the possibility that the observed fluorescent RNAs are adhering to the exterior cell wall, we treated the fungal hyphae with Micrococcal nuclease (MNase), and the fluorescence signal still remained, indicating the RNA indeed was taken up into *B. cinerea* cells. To further confirm this conclusion, the fluorescent RNAs were added into liquid culture of germinating *B. cinerea* spores, and the grown *B. cinerea* were subjected to protoplast preparation. The fluorescence signal was clearly detected in the *B. cinerea* protoplasts even after MNase treatment (FIG. 22B). Bc-DCL1/2 were silenced by both Bc-DCL1/2-sRNAs and -dsRNAs, and only Bc-DCL2, but not Bc-DCL1, was silenced by Bc-DCL2-sRNAs and -dsRNAs (FIG. 22C). The growth of *B. cinerea* was reduced by treatment with Bc-DCL1/2-sRNAs compared to water treatment, and it was reduced to a lesser extent by treatment with Bc-DCL1/2-dsRNAs, Bc-DCL2-sRNAs, and -dsRNAs (data not shown). These data support that the Bc-DCL1/2-sRNAs and -dsRNAs were indeed translocated into the fungal cells, and they efficiently silenced fungal DCL genes. This RNA uptake mechanism makes it possible to develop a new generation of environmentally friendly RNA-based "fungicides."

Such an RNAi-based disease control method could be powerful if it is effective against multiple pathogens. For example, we could design DCL-targeting dsRNAs or sRNAs to silence DCL genes of multiple pathogens that utilize sRNA effectors. The soil borne fungal pathogen *Verticillium dahliae* is another economically important fungal pathogen, which causes *verticillium* wilt on a wide range of plant species, including herbaceous annuals, perennials, and woody species (Fradin et al., *Mol Plant Pathol.* 7:71-86 (2006); Klosterman et al., *Annual Review of Phytopathology* 47:39-62 (2009). To date, there is no effective control method other than toxic fungicide application. As discussed above in Example 1, *V. dahliae* also utilizes host AGO1 for its sRNA effector functions; thus, targeting Vd-DCL genes could also be a potential strategy for controlling *verticillium* wilt disease.

To test whether the RNAi-based method can simultaneously control *V. dahliae* and *B. cinerea*, we generated *Arabidopsis* transgenic plants that express hairpin RNAs targeting DCL genes of both fungi. *V. dahliae* also has two DCL genes. Again, we were not able to find a DNA region outside the conserved domains that has sufficient homology between Vd-DCL1 and Vd-DCL2 (Vd-DCL1/2), or between the DCLs of *V. dahliae* and *B. cinerea* to silence two or multiple DCLs. Thus, we had to select two DNA segments, each from Vd-DCL1 (156 bp) and Vd-DCL2 (156 bp), which had 2.2% to 3.1% identity to the four At-DCLs (data not shown), and fused them to a 164 bp fragment of Bc-DCL1 and 151 bp fragment of Bc-DCL2, both derived from the Bc-DCL1/2 RNAi DNA fragment. This ligated product was then cloned into the pHELLSGATE vector. These transgenic plants expressed high levels of both Bc-DCL1/2-sRNAs and Vd-DCL1/2-sRNAs (FIG. 23A). As expected, the expression of *Arabidopsis* DCL genes was not affected in these transgenic lines (data not shown). Pathogen infection assays revealed that these transgenic plants are indeed more resistant to both *B. cinerea* and *V. dahliae* (FIGS. 23C and 23E). Expression levels of Bc-DCL1/2 and Vd-DCL1/2 were significantly reduced in the *B. cinerea* and *V. dahliae* grown on these transgenic plants than those from the WT plants (FIGS. 23B and 23D). Thus, this RNAi-based disease management strategy that targets pathogen DCL genes is efficient in controlling multiple fungal pathogens that use sRNA effectors.

Discussion

We have provided the first example of bi-directional sRNA trafficking between a fungal pathogen and its interacting hosts. Plant host-generated Bc-DCL-targeting sRNAs can be transported into *B. cinerea* to silence Bc-DCL genes for disease control. In *C. elegans*, dsRNA uptake from the environment requires dsRNAs that are longer than 50 bp, instead of shorter dsRNAs or mature sRNAs. See, e.g., Winston et al., PNAS 104:10565-10570 (2007); McEwan et al., *Molecular Cell* 47:746-754 (2012). Some herbivorous insects are also capable of taking up dsRNAs that are longer than 50-60 bp, but not sRNAs (Ivashuta et al., RNA 21:840-850 (2015). Here, we show that *B. cinerea* can take up both sRNAs and dsRNAs directly, and both can induce silencing of *B. cinerea* genes efficiently, suggesting that the RNA uptake channels or pathways may differ in different organisms.

Eukaryotic pathogens, including fungi and oomycetes, cause serious crop losses annually. Currently, fungicide and chemical spray is still the most common disease control strategy, yet they pose serious threats to human health and environments. Over the last few years, the stable plant transformation-based HIGS system was proven to efficiently control a range of pests, nematodes, filamentous pathogens, and parasitic plants in various plant models and crop species. See, e.g., Baum et al., *Nat Biotechnol* 25:1322-1326 (2007); Huang et al., *PNAS* 103:14302-14306 (2006); Nowara et al. (*Plant Cell* 22:3130-3141 (2010). However, these successful HIGS studies relied on a plant transformation system that is not available for many crops. Some commonly selected pathogen target genes that are important for pathogen propagation and infection include parasitism genes, effector encoding genes, or fungal ergosterol biosynthesis related genes. We found that *B. cinerea* DCL genes are essential for the biogenesis of sRNA effectors as well as fungal growth and development. They are the ideal targets for controlling pathogens that use sRNA effectors. Here, we have discovered that *B. cinerea* can take up dsRNAs or sRNAs from the environment and induce environmental RNAi, making it possible to directly use such dsRNAs and sRNAs for disease management. We show that spraying BcDCL1/2-sRNAs and -dsRNAs on the surface of various fruits, vegetables, and flowers can efficiently control gray mold disease. This RNAi-based new generation of "RNA fungicides" could circumvent the technical limitation of transformation and the public’s concerns about GMOs and provide an easy-to-use and environmentally friendly disease management tool for crop products both pre- and post-harvest. Furthermore, such RNA-based strategies could be easily designed to target multiple pathogens.

Materials and Methods

Plasmid construction: The plasmids pHELLSGATE-Bc-DCL1/2 and pHELLSGATE-Bc+Vd-DCLs were constructed following the methods outlined for the Hellsgate8.0 system (Helliwell et al., *Methods in Enzymology* 392:24-35 (2005)). The Bc-DCL1/2 RNAi fragment was obtained by integrating Bc-DCL1 (252 bp) and Bc-DCL2 (238 bp) fragments via overlapping PCR. The Bc+Vd-DCLs RNAi fragment was obtained by integrating the 315 bp Bc-DCL1/2 RNAi fragment (164 bp of Bc-DCL1 and 151 bp of Bc-DCL2) and RNAi fragments of Vd-DCL1 (156 bp) and Vd-DCL2 (156 bp) via overlapping PCR. The RNAi fragments were cloned separately into pDONR207 using Gateway® BP clonase (Life Technologies, Carlsbad, Calif.), then into the destination vector pHELLSGATE8.0 using Gateway® LR clonase (Life Technologies, Carlsbad, Calif.). For the pTRV2-Bc-DCL1/2 plasmid, the pDONR207-Bc-DCL1/2 vector was cloned into pTRV2 EV to obtain pTRV2-Bc-DCL1/2 using LR clonase (Life Technologies, Carlsbad, Calif.) (Weiberg et al., *Science* 342:118-123 (2013)).

In vitro synthesis of YFP-dsRNAs, Bc-DCL1/2-dsRNAs and -sRNAs: Following the MEGAscript® RNAi Kit instructions (Life Technologies, Carlsbad, Calif.), T7 promoter sequence were introduced into both 5' and 3' ends of the YFP and Bc-DCL1/2 RNAi fragments by PCR, respectively. After purification, the DNA fragments containing T7 promoters at both ends were used for in vitro transcription. To obtain Bc-DCL1/2-sRNAs, the synthesized Bc-DCL1/2-dsRNAs were digested into sRNAs with ShortCut® RNase III (NEB Ipswich, Mass.).

In vitro RNA fluorescence labeling and confocal microscopy examination: Bc-DCL-dsRNAs were labeled with fluorescence following the Fluorescein RNA Labeling Mix kit instructions (Sigma, St. Louis, Mo.). The fluorescent Bc-DCL-sRNAs were obtained from the digestion of fluorescent Bc-DCL-dsRNAs with ShortCut® RNase III (NEB Ipswich, Mass.). For the confocal examination of fluorescent RNA-treated *B. cinerea* grown on the microscopic slides, 4 μl of a $10^5$ spores/ml solution and 4 μl of 100 ng/μl fluorescent Bc-DCL-sRNAs or -dsRNAs was mixed and dropped on the solid ME medium prepared on the microscopic slides. After 12 hours of incubation in the dark, fluorescence was examined using confocal microscope SP5. To detect fluorescent RNA trafficking into the *B. cinerea* protoplast, $10^7$*B. cinerea* spores were cultured in 10 ml YEPD, and 2 μg of fluorescent Bc-DCL-sRNAs or -dsRNAs were added. The protoplasts were isolated as described previously (Gronover et al., *Molecular Plant-Microbe Interactions* 14:1293-1302 (2001)) after 40 hours, followed by KCl buffer or 75 U Micrococcal Nuclease (Thermo Scientific, Waltham, Mass.) treatment at 37° C. for 30 min. Fluorescence was examined using confocal microscope SP5.

Preparation of N. Benthamiana total RNA with or without Bc-DCL1/2-sRNAs and -dsRNAs: Four-week old *N. benthamiana* plants were infiltrated with *A. tumefaciens* strain carrying pHellsgate-Bc-DCL1/2 or pHellsgate-EV. The leaf tissue was harvested 2 dpi and used for total RNA extraction.

External application of RNAs on the surface of plant materials: All RNAs were adjusted to a concentration of 20 ng/μl with RNase-free water before use. For in vitro synthetic YFP-dsRNA, Bc-DCL1/2-sRNAs and Bc-DCL1/2-dsRNA, 20 μl RNA (20 ng/μl) was dropped or sprayed onto the surfaces of the plant materials. For *N. benthamiana* total RNA extracts, the surfaces of plant materials were evenly sprayed with 20 ng/μl RNAs.

Fungal pathogen assay and disease quantification: The *B. cinerea* strain B05.10 and *V. dahilae* strain JR2 were cultured on Malt extract agar (2% malt extract, 1% Bacto Peptone) and potato dextrose agar (PDA), respectively. The *B. cinerea* spores were diluted in 1% Sabouraud Maltose Broth buffer to a final concentration of $10^4$ spores/ml for spray inoculation on tomato leaf and $10^5$ spores/ml for the drop or spray of other plant materials (Mengiste et al, *Plant Cell* 14:2551-2565 (2003)). 10 μl spore suspension was used in drop or sprayed area of all plant materials, except tomato fruits in which 20 μl was dropped. *V. dahilae* soil-inoculation assay was performed as described previously.

*Arabidopsis* root culture and infection: For *Arabidopsis* liquid root culture inoculation, 2-week old *Arabidopsis* were grown in root culture (0.32% MS Salt, 2% Sucrose, 0.1% MES, pH5.8 by KOH), and *V. dahilae* spores were added into the culture to the final concentration of 10' spores/nil, After 5 min inoculation, the root culture was replaced with fresh sterile solution, The fungal biomass quantification was performed as described previously (Gachon et al., *Plant Physiol Bioch* 42:367-371 (2004)).

Cloning and data analysis of *Arabidopsis* AGO1- and AGO2-associated sRNAs: *V. dahilae* infected *Arabidopsis* prepared in liquid root culture were collected at 2 and 4 dpi. At-AGO1 and At-AGO2 immunoprecipitations were performed using anti-AGO1 and anti-AGO2 peptide antibodies (Zhang et al., *Mol Cell* 42:356-366 (2011)). At-AGO1-and At-AGO2-associated RNAs were extracted and used for sRNA library construction and Illumina HiSeq 2000 deep sequencing (Weiberg et al., *Science* 342:118-123 (2013)). The read number of Vd-sRNAs in At-AGO1 and At-AGO2 IP libraries was normalized with total *V. dahilae* sRNAs after removing tRNA, rRNA, snoRNA, snRNA, etc. The Vd-sRNAs that had a higher than 100 RPM after normalization and also had host target genes in *Arabidopsis* were selected. At-AGO1 associated Vd-sRNA effectors were defined as the selected Vd-sRNAs with a 10 times greater read number in the At-AGO1 IP library compared to the At-AGO2 IP library. At-AGO2 associated Vd-sRNA effectors were defined as the selected Vd-sRNAs with a 10 times greater read number in the At-AGO2 IP library compared to the At-AGO1 IP library.

Example 5: Exemplary DCL Gene and Protein Sequences

```
SEQ ID NO: 1—Botrytis cinerea DCL1 genomic DNA sequence (selected RNAi fragment
marked by bolded text)
ATGACGAGAGACGCAGCAGCAGCAAAAAGTCTCTACCATTGGCGAAGAAAAGGCGTCA

CTCCTTCAGCCGAAGAGGATCTTCTATCGTTTGATGATATTGTTACTGCCGTTCCACCTAC

AATCTTGTCTTCGTCTGTCGCTCCATATACTTCTCGAGATAAGATACCTTCTGCATCTGGC

AACGGAGATGCTATAGCAGATGTTAGCAGTGGTTACCTCAAACAGGCTACCGTATCTTCT

CATTCTGCTCAAGTCCGATCATCTTCAAACGGCAATCAAGGTGATGCCAAAAGTTCTCCC

TCTCTTTCACCTGATAGTAAACTGGAATTCATCTTTGGGCCTCCTTTAAGGGAGCCAGAG

AAGCCATTCTTTAATAAATCTTCTTATTCGTTTCGAGATTCGAGAGGGTTGAGCAGAAAT

CGGGCTTCTTCTTCTATGGAAAATTCGAGAACTCTCGATCCAAAGATACTCAAACCAGTT

ATCATCAATAATCACCAGGGCGAATGCTTCCAAGAGGCTTCCAGAACAGGTATACCTCA

GGCTGATACTTTTGATAAATCTTCCCTTGCTAAGACTGCGGATATGGATTTGTCACCAGTT

TCTCACCATGCGGATGTGCTTGCGACGACGGTCACTGCACAGCATTCTGCAATAGCCGCC

CAGAACGCAGCTCAAAGCTCTAAGATGCCAGGTCCTGAAGCTTTTTTACTTGCCGAAAAG

GACGAGGCAGGTTCTCCCGTTGTTATATCACTGGGTTCTGCAAACCAAATTCCTTCTGGA

AACATTTCTTTGCAGCTTGATTCACCATCTCTGGAAAACCATTCTCCAAATGTGACCCCA

ATCAACAAAGTCCCTACACCATTCGCACTTTCTACAAGGACAACCGATGACGTTTTCGCA

GAACTTAGGCGGCCTTTGCATCCCCAAGCTATTCAGAGCCAGATTGATATCAAGACTTCC

TCTTGTGTTGATAGTTATAACACGAATGATGAGATTCTAGACAACAATCAAGGTTCCAAT

CAAAAAGATCTCTCATGTTGTTGAAAAGGATAAGGAAGAGGAAGAGGAAGAGGATATGA

ACCAAGCCATACCCGATATCAAACGTATCTCAGCACGAAAACAAAAGAACGCTGCCATA

TTTGACGTTTTTCTTAAGGAAGCTACCAAACTACCAAAGACAGAAAAGACTTCACATGCG

AATGATGAAGCAATTCAGTCTACTAGGTGGTTGATTGACCAAGCAGAAAAACAGCATAT

TATAGAAAGTCCCAGGGACTATCAACTTGAATTGTTTGAGAAGGCAAAGAAACAGAACA

TTATAGCTGTACTTGATACAGGATCTGGCAAGACATTCATTGCAGTTCTCTTACTTCGGTG

GATCATAGACCAAGAGCTTGAAGATAGAGCTATTGGCAAGCCTCATCGTGTTTCATTCTT

CCTGTGGAAGAAACGACTGGATACGAATATGGTCATTGTCTGCACTGCAGAAATTTTGCG

CCAATGCCTGCACCATTCGTTTGTTACAATGGCTCAAATAAATCTGCTAATTTTCGATGA

AGCCCACCATGCAAAGAAGGATCATCCTTATGCTAGGATTATTAAAGATTTTTATCGCAA

TGACACGGAAAAGGATATCGCTCTGCCTAAAATATTTGGGATGACAGCATCACCGGTAG

ATGCTAGAGATAATGTCAAGAAAGCTGCGGAAGAACTTGAAGGTTTGCTACACAGTC

AAATATGTACTGCAGAAGATCCCAGCTTGCTGCAGTACTCAATCAAAGGTAAACCT

GAGACTCTTGCCTACTATGATCCCTTGGGCCCGAAATTCAATACTCCTCTTTATCTT

CAAATGCTCCCGCTTCTAAAAGACAATCCTATCTTTCGGAAGCCATTTGTATTTGGG

ACAGAAGCCAGTAGAACTCTAGGATCTTGGTGTGTTGACCAGATCTGGACTTTCTGT

CTTCAAGAAGAAGAGTCTAAGAAACTACAAGCAAGGACGGAGCAGGCGCATCATAAGA

AGAGAGTCCCGGAGCCACTTGAAGTGCTAGAGAAACGCAAGGAACAACTTGAACAAGC
```

```
CAAATCCATTGTCGAAAATCACACTTTCGAGCCACCACACTTTGCATCAAGATTATTGGA

TGATTTCACAACAAAAGTTCACTATTCGAATAATTTATCTACTAAAGTCGTTGCTCTCTTG

AGTATTCTCAAAGATCGTTTCCAACGACCCACCAATGACAAGTGTATTGTATTTGTCAAA

GAAAGATACACCGCACGCCTTCTAGCCTCACTTCTCTCCACACC

TGAAGCTGGGACACCATTCTTGAAGGCTGCACCGCTGGTTGGTACTACGTCTGCTTCAGC

CGGGGAAATGCATATCACATTTAGATCACAAACTCTTACTATGCACAACTTTCGCAATGG

TAAAATCAACTGCCTTATCGCAACATCAGTTGCTGAAGAAGGTCTTGACATTCCTGACTG

TAACCTCGTTGTCAGATTCGATTTGTACAATACAGTCATTCAGTACATTCAATCTAGAGG

TCGTGCTAGGCATATCAATTCAAGGTACTACCATATGGTAGAGAGCCACAACGAGGAAC

AGATTCGTACAATCAAAGAGGTTTTGAAGCATGAGAAATGCTAAAGCTTTTTGCTTGTG

CTCTTCCAGAAGATCGAAAATTGACCGGAAACAACTTCAATATGGATTACTTCCTCAGAA

AAGAACGAGGCCACAGAATTTACCCTGTCCCGAATAGTGACGCAAAACTTACTTACAGA

ATGAGCTTAACGGTCCTATCTGCCTTCGTTGACTCACTTCCTCGAGCCCCAGAGTCGGTTC

TTCGAGTGGATTATGTCGTCACAACTGTCGATAAGCAGTTTATCTGTGAGGCCATTTTGC

CAGAAGAAGCACCCATACGCGGAGCAATTGGTCGGCCAGCAACAACTAAACAAGTGGCC

AAATGCTCAGCAGCCTTTGAAACTTGTGTGATTCTGCACCAGAAAGGATACATCAACGAC

TACCTACTTTCTACATTTAAAAGATCAGCACACATGATGAGAAATGCACTTTTGGCTGTG

GATGGAAAGAAGCAAGAAGCTTATGATATGCAGACTAAACCAACTTTATGGTCTTCGAA

AGGGAAACAAGGCATATTTTATATGACTGTCTTGTCTCTCAAATCTCCAGATAATCTTGA

CAGAGCATCTCAGCCATTGGGCTTACTGACAAGATCACCCTTGCCTGATTTGCCAGAATT

TGTTCTTCATTTCGGAGCAGGGCGAAACTCTCCAACCTCGTGCGTACCTCTCGCTTCCTCA

ATTACGCTCGAAAAAAACAAGCTTGACCAAGTTAATATGTTCACCCTATGTTTATTCCAA

GATGTGTTCAGTAAAGCATACAAATCAGATCCGGATAGTATGCCATACTTTCTGGTTCCT

ATCAACTGCCTGAATGCTATTGTCGACTGGAAATCACAAAACCCAATGTCAATAATCGAT

TGGGAGACAGTTGAATATGTCCAAGACTTCGAGAATAAGCAAGCTGATAAGCCATGGGA

GCACAAGCCATGGTTAGGAAAGCCTGACGATTATTTCAAAGACAAATTCATAACTGATC

CCTTTGACGGGTCTCGAAAATTGTGGTCCGTTGGAATCACAAAAGAATACAGACCATTGG

ATCCAGTCCCACCAAACACGGCGCCCAGGAAGGGAGCTAGAAAGAACAATAGTAATATC

ATGGAGTATAGTTGTAGTCTCTGGGCAAAGGCTAGAGCAAAACGAACTTTTGATGAAGA

ACAGCCTGTTATTGAAGCAACCTACATTTCACTTCGGAGAAATTTGCTTGATGAATTTGA

TGGAGGTGAGCTCGAGACTTCAAAGAAGAGTTTTATTATTTTAGAACCATTGAAGGTATC

ACCTCTTCCAACTACCGTGGGTGCAATGGCCTATCTTTTACCTGCAATTATTCATCGAGTT

GAGTCATATCTCATTGCTCTTGAAGCAACAGACTTGTTACATCTTGATATCCGTCCTGATC

TTGCGCTAGAGGCTGTTACCAAGGATTCCGACAATTCTGGAGAGCATGGTGAGGAACAG

ACAAACTTTCAACGTGGAATGGGCAATAATTATGAACGATTGGAATTTCTTGGGGACTGC

TTCTTGAAGATGGGAACGTCAATATCTCTATACGGTCTAAATCCTGATAGTGATGAATTC

CGCTACCATGTTGATCGTATGTGTCTGATTTGCAACAAAAATCTGTTCAATACGGCTTTG

AAATTAGAGCTTTACAAATACATTCGGTCGGCAGCCTTCAACCGACGAGCTTGGTATCCC

GAAGGCCCCGAATTATTAAGAGGAAAGACAGCCACGGCACCCAAATACCCACAAGCTCGG

CGATAAGTCAGTTGCAGATGTTTGTGAAGCAATGATTGGAGCTGCTTTACTAAGCCACCA
```

-continued

```
CGAAAGCAAGTCCATGGATAATGCGGTTCGCGCCGTTACTGAAGTTGTCAATAGTGACA

ACCACAATGCTGTTGTATGGTCTGATTATTACAAATTGTATGAGAAACCAAAATGGCAAA

CTGCTACAGCTACAGCTGCACAAATAG

ATATGGCAAGACAAGTTGAAATGAAACATCCATATCATTTCAAACACCCACGCCTGTTAA

GATCAGCTTTCATCCATCCGGCATACTTGTTCATCTATGAACAAATTCCTTGTTATCAACG

TCTCGAATTTTTGGGTGATTCGCTACTCGATATGGCATGTGTCAACTTCCTTTTTCACAAC

CACCCAACAAAAGATCCTCAGTGGCTCACTGAGCACAAGATGGCTATAGTATCCAATCA

GTTTCTTGGAGCTCTTTGTGTCAAATTAGGCTTCCACAAACATCTACTGACACTCGATTCT

CAAGTTCAAAAAATGATTGCAGATTACTCCTCAGATATCAATGAAGCTCTCATTCAAGCC

AAAACGGACGCAAAGAGAGTCGGCAAAGTAGAAGATGATTACGCTCGTGATTATTGGAT

TGCCGTCCGTCAACCTCCTAAATGTCTTCCCGATATTGTAGAAGCATTCATTGGTGCCATT

TTTGTCGACTCTGAGTATGACTACGGTGAAGTTGAGAAGTTCTTTGAAATGCATATCAGA

TGGTACTTTGAGGATATGGGCATCTACGATACCTATGCTAACAAGCACCCAACCACTTTC

CTTACTAATTTCTTGCAAAAGAACATGGGATGTGAGGACTGGGCACCAGTTAGTAAGGA

AGTACCTGGAGAGGATGGTAGAAAGAATGTTGTAGTTTGCGGGGTCATCATACACAATA

AGGTGGTATCAACTGCCACTGCCGAAAGTATGAGATATGCTAGGGTCGGAGCAGCGAGG

AATGCCTTGAGAAAATTGGAGGGAATGAGTGTCCGAGAATTCAGGGATGAATACGGGTG

CTCATGTGAAGGTGATGTTGTTGATGAAGAGGGCAATATTGAATTTGTTGAACGTGAAGA

CGGGATGGAGGGGATCGGTATGGGATATTGA
```

SEQ ID NO: 2—Botrytis cinerea DCL1 protein sequence
```
MTRDAAAAKSLYHWRRKGVTPSAEEDLLSFDDIVTAVPPTILSSSVAPYTSRDKIPSASGNG

DAIADVSSGYLKQATVSSHSAQVRSSSNGNQGDAKSSPSLSPDSKLEFIFGPPLREPEKPFF

NKSSYSFRDSRGLSRNRASSSMENSRTLDPKILKPVIINNHQGECFQEASRTGIPQADTFDK

SSLAKTADMDLSPVSHHADVLATTVTAQHSAIAAQNAAQSSKMPGPEAFLLAEKDEAGSPVV

ISLGSANQIPSGNISLQLDSPSLENHSPNVTPINKVPTPFALSTRTTDDVFAELRRPLHPQA

IQSQIDIKTSSCVDSYNTNDEILDNNQGSNQKDLHVVEKDKEEEEEDMNQAIPDIKRISAR

KQKNAAIFDVFLKEATKLPKTEKTSHANDEAIQSTRWLIDQAEKQHIIESPRDYQLELFEKA

KKQNIIAVLDTGSGKTFIAVLLLRWIIDQELEDRAIGKPHRVSFFLWKKRLDTNMVIVCTAE

ILRQCLHHSFVTMAQINLLIFDEAHHAKKDHPYARIIKDFYRNDTEKDIALPKIFGMTASPV

DARDNVKKAAEELEGLLHSQICTAEDPSLLQYSIKGKPETLAYYDPLGPKFNTPLYLQMLPL

LKDNPIFRKPFVFGTEASRTLGSWCVDQIWTFCLQEEESKKLQARTEQAHHKKRVPEPLEVL

EKRKEQLEQAKSIVENHTFEPPHFASRLLDDFTTKVHYSNNLSTKVVALLSILKDRFQRPTN

DKCIVFVKERYTARLLASLLSTPEAGTPFLKAAPLVGTTSASAGEMHITFRSQTLTMHNFRN

GKINCLIATSVAEEGLDIPDCNLVVRFDLYNTVIQYIQSRGRARHINSRYYHMVESHNEEQI

RTIKEVLKHEKMLKLFASALPEDRKLTGNNFNMDYFLRKERGHRIYPVPNSDAKLTYRMSLT

VLSAFVDSLPRAPESVLRVDYVVTTVDKQFICEAILPEEAPIRGAIGRPATTKQVAKCSAAF

ETCVILHQKGYINDYLLSTFKRSAHMMRNALLAVDGKKQEAYDMQTKPTLWSSKGKQGIFYM

TVLSLKSPDNLDRASQPLGLLTRSPLPDLPEFVLHFGAGRNSPTSCVPLASSITLEKNKLDQ

VNMFTLCLFQDVFSKAYKSDPDSMPYFLVPINCLNAIVDWKSQNPMSIIDWETVEYVQDFEN

KQADKPWEHKPWLGKPDDYFKDKFITDPFDGSRKLWSVGITKEYRPLDPVPPNTAPRKGARK

NNSNIMEYSCSLWAKARAKRTFDEEQPVIEATYISLRRNLLDEFDGGELETSKKSFIILEPL
```

KVSPLPTTVGAMAYLLPAIIHRVESYLIALEATDLLHLDIRPDLALEAVTKDSDNSGEHGEE

QTNFQRGMGNNYERLEFLGDCFLKMGTSISLYGLNPDSDEFRYHVDRMCLICNKNLFNTALK

LELYKYIRSAAFNRRAWYPEGPELLRGKTATAPNTHKLGDKSVADVCEAMIGAALLSHHESK

SMDNAVRAVTEVVNSDNHNAVVWSDYYKLYEKPKWQTATATAAQIDMARQVEMKHPYHFKHP

RLLRSAFIHPAYLFIYEQIPCYQRLEFLGDSLLDMACVNFLFHNHPTKDPQWLTEHKMAIVS

NQFLGALCVKLGFHKHLLTLDSQVQKMIADYSSDINEALIQAKTDAKRVGKVEDDYARDYWI

AVRQPPKCLPDIVEAFIGAIFVDSEYDYGEVEKFFEMHIRWYFEDMGIYDTYANKHPTTFLT

NFLQKNMGCEDWAPVSKEVPGEDGRKNVVVCGVIIHNKVVSTATAESMRYARVGAARNALRK

LEGMSVREFRDEYGCSCEGDVVDEEGNIEFVEREDGMEGIGMGY*

SEQ ID NO: 3—*Botrytis cinerea* DCL2 genomic DNA sequence (selected RNAi fragment marked by bolded text)
ATGGAATACACTTCGGAACCTGACACTGACCCGGATACACGCGGTAGCCTTATCGATGGT

CGAGATGGGATTGAAGGGGATCTTATTGCTTTGACGTCTGGGGAACGACTTAATGAGACT

GTAGAGGATTTATGTAGTGACTCATCAGGATTGATTGTTGAGAATGAAGATGATGATAAC

AGCGCAGGGGAGAAGGGAGAGATTGTGATAGTAACACCAAGAACATACCAACTGGAAA

TGTTGGAAGAGAGTTTGAAAAGGAATGTCATCGTTGCGATGGATACAGGAAGTGGCAAG

ACACATGTGGCCGTTCTCCGAATACTAGCGGAACTTGAGCGGATGAAGCCTTTGCAAGAT

AATATGGTTTCTTGCGCCTACCGTTGCGCTCTGTGCTCAGCATCACGAATATCTCCAGCTG

AATATTCCCTCTGTTTTGATCAAAATGCTTATTGGTGCTGATGGTGTGGATCGATGGACA

GAGCAGAGACACTTGGGATACGGTCTTGAAGGATGTCAAGGTAGTCGTATCTTCCTATCA

AGTTCTTCTAGATGCCCTTACACACGGATTCGTACGCATGGGCGTCTGTCCTTGATCATT

TTTGATGAAGCACATAATTGTGTAAATAAAGCGCCAGGGGCTAAAATTATGAAATCTTTC

TATCATCCGTATAAATCGATATTCCCACTTCCCCACATTCTGGGCCTCACGGCCAGCCCTG

TCATGAGATCCAGTCCACAATCTTTAAGTGATATCGAGGAGACTTTGGATGCCATTTG

CTGCACGCCAAAAATACATCGAGCAGATCTTCGCCTTCGAGTAAAGCTACCACTTCT

ATCTATTATCTACTATACCCCAGAGTCAAATATCATCGTGACGAAAACTGTGGCGAG

CCTGAGAAAGATTGTGCAAAGTCTCAACATTTTCGAAGACCCCTACGTTTTGACACT

AAAAAGGAGTGATAGCGAAAAAAGTCAACGTGAGCTGGCGAAAGTACTCAAGAGTT

TTAAGACATATAGTCAAACCCAATTAAAGTCAATCGACAAAACTAGCAACGAGATTAT

TCTTGTAGAGCTAGGCCCATGGGCTGCAGATTACTATATCTCAACAGTGGTGACGAGATA

CTTGAAGGCAATGTCGGCAAAGGACACTTTCATTGTTGAAGATTCACCAGCTGCCGAGA

AGCTATATATTGCCAAGGCTCTCAGACAAGTCGAAATCTCTCCTTCAACTCTCTCAGATA

CAGGCAAAATTTCTAACAAGGTTGAAAAGCTACTGGGGATAATTGCGCAACAGAAGCCT

CCCTTTTCCGCTATTATATTTGTCCAAGAAAGAGCCACGGTGTCTGTGCTAGCCCATCTAT

TATCGCATCATCCATTGACAAAGGATCGTTTTAAGATTGGAACCATGGTTGGCACATCCT

TAAATGGCAAGCGTACAGACCAAATAGGAGAGCTTGTCGATGTTAATCAACAAAAAGAC

ACTTTGTCAAGTTTCAAGCGTGGAAAAATTGATATCCTTATAGCTACAAATGTATTGGAA

GAGGGAATTGATGTTCCTGCCTGTAATCTAGTGATCTGCTTTAGTAAACCAGCAAACCTC

AAATCTTTCGTACAAAGACGAGGGCGAGCAAGACAGCAAGATTCTAAGCTGATTCTTCTT

GATGCTTCAGGTGATAAAGCGACAAATTGGCATGAGCTTGAAAGAAAAATGCGAGAGGA

GTACGGAAAGGAAATGCGAGAATTGCAACACATCTACGAAATTGAGACAGCTGATGAAC

AGTCGGAAGATGATAGGGTCTTGCGAATAGAAAGCACTGGGGCTCAATTAGACCTTGAC

-continued

```
AGTGCTTTACCACATCTCTATCATTTCTGTTCAGTCTTAACAACAAAAGATTTTGTTGACC
TCAGGCCAGACTTCGTCTACTCCTCCGAACTGGGATCGGAATATGTTCGAGCAAAGGTCA
TCCTGCCTGGATCGGTTTCTAAACCCCTGCGAGTCCATGAAAGCCGCGGATCGTGGTTGA
GCGAGAGGTCGGCTGCAAAGATGCAGCGTTTGAGGCGTATTCCGCATTATACAGGGGG
GGCTTAGTGAATGATAACCTACTGCCCCTGATGGTGCACGACAAAGTCATCGATGAGTTG
ACTTCAAAGCCCGTGGATACTCGCGCGTCTCTTCTGGAGGTGAAGGAAAGATTAAATCCA
TGGATTGACATTGCTAGAGCATGGAAAGAGGCAGAACACCATGCTGGAATTGTTCGCAC
ATCGGTAATGATCTTCAATGGGATGAAGCTGGAACTCTGTCTTCC
AATTGATCCACCGGCAATACCCCCATTAAAGCTTTATTGGGATGCTGACACCGAGTTCTT
TGTTGACTTTACAAACGATATCGAGATCGGCACCAGCGAGAATATGTTGGCACAGGCGTT
GAACGATACCAATCTACTATTATCAGATCGTGGTCGTAAAGTTCACATCCAGTCACGTCG
AACAGTTGTGCAATTTATCTTGCTTCAAGATTCGGGCTCGCTCAGTTCAGATTGTTTTCCG
GTTGACCCCAACGGTAATATTAAAAGTACAGGTTTTATCAGAGAAGTCGGTAAACTAGA
ATCGCCCTACATCTTTGAAAAATGGTTGCCCAATGCACCAGAAGACGTCCCATATCTAGC
TGTGGTTAAAGTAAGTCGCCGTGCAGACTTTTTGCACAAGGTACAGAACGAAAAACCCT
CGTCATTCACTAAACAATTCTCGTCTGTTCTACCTGCCTCGACATGTGTACAGGATGTAAT
GCCCGCACAGTTGTCTCGGTTCGGCATGATGATTCCTTCCATCACACACCACATTGAGGT
GCAACTCGTTGTAGACCGACTATCCAGGACCATCCTCAAGGATCTCGAAATTAGTGACCA
GAGTCTTATTCAGACCGCCATCACACATGCCAGTTATTCGTTAGACTCGAATTATCAGCG
TCTCGAATTTCTGGGCGACTCAATTCTCAAATTGTGTACATCGGTACAATTGGTGGCAGA
GCATCTAGATTGGCACGAAGGATATTTGTCGGCTATGAAGGATCGTATCGTGTCCAATTC
ACGGTCATCAAGAGCGGCGGCTGAAGTCGGTTTGGATGAGTATATAATGACCAAGAAAT
TCACAGGTGCAAAATGGCGACCAATGTACGTGGATGATCTGGTCGTCACAGAACAAAAA
ACAAGAGAAATGTCCTCCAAAATTCTTTCCGACGTTGTGGAAGCACTCATCGGCGCATCT
CTCCGGCCCGTCGAGCAAATCCTCGCATATACCTTCACCAAAAAATCTCTCCTCGTCGAA
GCCATGACGCACCCCTCTTACACCAGCGGCACGCAATCCCTCGAGCGACTCGAGTTCCTC
GGCGATTCCATTCTCGACAACATCATCGTCACAGCCATGTGGTCGCACTCGACGCCGCTC
TCCCACTTCCACATGCATCTCCTGCGCTCTGCGCTCGTCAACGCCGATTTCCTCGCCTTTC
TCTGCATGGAAATGAGCATCGACCAAAACGTCACCAATCTGACCGAAGGAAAAAACCAT
CGCATCCACGAAACCCACTCGCGACGCCGCGTTTCCCTCGTCAGTTTTCTCCGTCACTCA
AGCGTTCGTCTCTCTATCTATCAAAAAGAAGCGCTTTCTCGCCATGCAGAATTGCGCGAT
CAGATCCTCGAGGCAATATACACCGGTGATACATTCCCCTGGGCTCTATTATCCCGATTG
GACGCGCGGAAATTTTTCTCCGATATGATTGAGAGTTTGCTGGGCGCGGTATGGATTGAT
AGCGGCTCGATGGAAGTGTGCACGCAGCTGATCGAAAGAATGGGCGTCCTGAGATACAT
GCGACGGATTTTGAAAGATGGCGTGCGCATCATGCATCCGAAGGAGGAACTGGGCATCG
TGGCCCGATTCTGAAAACGTCAGGTACGTTTTGCGGCGGGAGAAGATGGGTGGGGATGCT
ACCGAGGTAAATGCGGACGCGGATGAAGAGGTACGCACGGAGTACCGGTGCACAGTATT
TGTGGGCGGGGAGGAAATTGTAGAGGTGAGGGGTGGAGCGAGGAAAGAGGAGATTCAG
GCAAGGGCTGCGGAGCAGGCGGTGCGGATTTTGAAGGCGAGGGGTCATGAGAAGAGGA
ATGGGGGTGCGGGGGAGGGGAAAAAGAGAAAATCGCTGGATGAATAG
```

SEQ ID NO: 4—Botrytis cinerea DCL2 protein sequence
MEYTSEPDTDPDTRGSLIDGRDGIEGDLIALTSGERLNETVEDLCSDSSGLIVENEDDDNSA

GEKGEIVIVTPRTYQLEMLEESLKRNVIVAMDTGSGKTHVAVLRILAELERMKPGKIIWFLA

PTVALCAQHHEYLQLNIPSVLIKMLIGADGVDRWTEQRQWDTVLKDVKVVVSSYQVLLDALT

HGFVRMGRLSLIIFDEAHNCVNKAPGAKIMKSFYHPYKSIFPLPHILGLSASPVMRSSPQSL

SDIEETLDAICCTPKIHRADLRLRVKLPLLSIIYYTPESNIIVTKTVASLRKIVQSLNIFED

PYVLTLKRSDSEKSQRELAKVLKSFKTYSQTQLKSIDKTSNEIILVELGPWAADYYISTVVT

RYLKAMSAKDTFIVEDSPAAEKLYIAKALRQVEISPSTLSDTGKISNKVEKLLGIIAQQKPP

FSAIIFVQERATVSVLAHLLSHHPLTKDRFKIGTMVGTSLNGKRTDQIGELVDVNQQKDTLS

SFKRGKIDILIATNVLEEGIDVPACNLVICFSKPANLKSFVQRRGRARQQDSKLILLDASGD

KATNWHELERKMREEYGKEMRELQHIYEIETADEQSEDDRVLRIESTGAQLDLDSALPHLYH

FCSVLTTKDFVDLRPDFVYSSELGSEYVRAKVILPGSVSKPLRVHESRGSWLSERSAAKDAA

FEAYSALYRGGLVNDNLLPLMVHDKVIDELTSKPVDTRASLLEVKERLNPWIDIARAWKEAE

HHAGIVRTSVMIFNGMKLELCLPIDPPAIPPLKLYWDADTEFFVDFTNDIEIGTSENMLAQA

LNDTNLLLSDRGRKVHIQSRRTVVQFILLQDSGSLSSDCFPVDPNGNIKSTGFIREVGKLES

PYIFEKWLPNAPEDVPYLAVVKVSRRADFLHKVQNEKPSSFTKQFSSVLPASTCVQDVMPAQ

LSRFGMMIPSITHHIEVQLVVDRLSRTILKDLEISDQSLIQTAITHASYSLDSNYQRLEFLG

DSILKLCTSVQLVAEHLDWHEGYLSAMKDRIVSNSRSSRAAAEVGLDEYIMTKKFTGAKWRP

MYVDDLVVTEQKTREMSSKILSDVVEALIGASLRPVEQILAYTFTKKSLLVEAMTHPSYTSG

TQSLERLEFLGDSILDNIIVTAMWSHSTPLSHFHMHLLRSALVNADFLAFLCMEMSIDQNVT

NLTEGKNHRIHETHSRRRVSLVSFLRHSSVRLSIYQKEALSRHAELRDQILEAIYTGDTFPW

ALLSRLDARKFFSDMIESLLGAVWIDSGSMEVCTQLIERMGVLRYMRRILKDGVRIMHPKEE

LGIVADSENVRYVLRREKMGGDATEVNADADEEVRTEYRCTVFVGGEEIVEVRGGARKEEIQ

ARAAEQAVRILKARGHEKRNGGAGEGKKRKSLDE*

SEQ ID NO: 5—Verticillium dahilae DCL (VAD_00471.1) genomic DNA sequence
(selected RNAi fragment marked by bolded text)
ATGACGACTGACGAGCTCTCTGTTGGTCTGGACGCCACCGGCATCTCAATCCTCGCAGAT

GGACCGGAAAACATATCGTCCAGCACATCAACATCTACGACTGGAAAGGAAGATGGATA

CCTCTGTATCAACAGATTCACTCAGAATACCGCCACGACCCAGGACAACCAGAGCCGAG

ATTCTGACGACGATGAGGATGACTGCGGCAGCCACGATGAAGCTGACGAAGATTCAGAC

GAAAGACAGTACAGCATGACCCCAGAAAGGCCTCATAAAATTACCGAGAAGAAGCGCG

CAGATCATGCTGCCTTTCACGACTGGCTTCAGAGCAACTCCAGCGAGATTGCTCAGTCAA

CCCCTCAGCCGGCTCAAAACCTCAACCACACCTCCACGGCCCTGATGGTACGCGAGAGT

GAGAATCGTAAGATCATCGAAAATCCTCGGGAGTATCAGATTGAGCTCTTCGAGCGGGC

GAAGCGAAAGAACATCATTGCCGTGTTACCCACTGGATCAGGAAAGACCTTAATCGCAG

CCCTTCTTCTGCGACACACCCTCGAACAAGAAACCGCGGATCGACGCGCGGGCAAGCCC

AAGAGAATCGCCTTTTTCCTCGTGGAAAAGGTTGCTCTTGCCCTCCAACAGCACGC

GGTTCTGGAGTGCAATCTGGAATTTCCCATTGACCGGGTATGCGGTGACATGGTAC

GGTCGGACTGGATCAAGGAGTCATGGATGAAAAGATGGGATGACAACATGGTCATG

GTCTGCACCGCCGCCATCCTTCAGCAATGCCTTGCCAGATCATTCATCCGCATGGAT

CAGATCAACCTGCTTGTCTTCGATGAAGCACATCACGCCAAGGGAAATCATCCGTA

CGCCCGGATCATCAAGGACTACTACATTACGGAACCTGACAAAGAAAGGCGCCCCAAGA

-continued

```
TCTTCGGCATGACTGCCTCTCCGGTGGATGCCCTCACCGACGTCAAGATTGCTGCCGCTC

AACTCGAAGGTTTGTTGCATAGTGAGATTGCGACAATCGAGGAGGACTCTGTATCATTCA

AACAAATCCAGAAAGAGGTCGTCGAACAAGACTGCAAGTACCCTGCCCTCGAACCACCC

TTCACCACCAATCTTCATAAGAAGATCCAAGAACAGGTGCGCTACAACAAGAACTTCGC

AAAGGCGCTGAGCAATTCTTTAGAAATGTCGAGCTCCCTTGGCAGCTGGTGTGTCGATCG

CTTCTGGCAGATATTTCTGACCGAAGAAACCCTCGCGAGATTGGCAGCGCAAACTGCAC

AAGACAACATTTTTGCCGATCGCGCCGAAAAGGAGCGCGTTGCCATTGAGGAGGTCCGC

AACATCATCAAGCAACATCAGTTCCTCCCAATCACCAAAACCCTGCAAGACTTGTCGTCC

AAAGTGCTGTGCCTCCTCGGCCAACTGGAATTGCGCTTCAGTGCCCCTACCGATCACAAG

TGCATCATCTTCGTGGAGAAACGAAACACAGCCATGATTCTGGCTCACCTCCTCTCCTTG

CCTGGTATTGGACCTCTATATCTGAAACCGGCTGCGCTTGTCGGGAACCCATCTGACAAC

AGCCCTCTTGCCATGTCGTACAAAGAGCAAGTGATGACAATAACAAAGTTCAGACGTGG

TGAATACAACTGTCTTCTCGCCACTTCTGTGGCCGAGGAGGGCATTGACATCGCAGACTG

CAACATTGTCATTCGATTCGATCTTTTCAACTCGGTGATTCAGTACATACAATCCAAAGG

CCGCGCTCGGCACTTGAACTCGGAGTATATTTGCATGGCCGAGCTAGGCAACGGCAAGC

ATACAAGGGCGAAGATACAAGCAAATTATGACCTCTCCCTCATCCGCCAATTCTGCAGCA

CACTGCCAGAAGACCGCAAGATCGTGGGCTGGGACCCCGAGGCAGCTCTTCACCATGGC

GAGCGCGACCATAAGTTCCACATCGTTCCATCCACCGGGGCCAAACTCACCTGGAC

CGGCAGCCTCGTGGTTCTGTCAAATTTTGCCTCTTCTCTACAGGTGAACGACGAAACACT

AAGTCCTTCCTATATGGTCTCTCTCATCGGTAGCGAGTACATCTGCGAGGTCCAGCTTCC

GAGCAAGTCTCCCATTTTGAGCGTGTCAGGCACGCTCCAAAAGAACAAAGCAGAGGCCA

GGTGCTCCGCAGCGTTTGAGATGTGCATGAAGCTCATCAAAGGTGGGTTCATCAGCAGTC

ACCTTCAGCCGACGTTTACCAGGAAGCTCCCGGCCATGCGAAACGCACGCCTAGCCATC

AGCTCCAAGAAGCGTGAACGGTACAATATGAGGGTCAAGCCAGAGGTATGGTCACGGCG

TGGACCGGCATCCTCTCTGTTCCTCACAGTCCTGAAGCTTCGTACACCTGGTGCATTGAA

CAGACCATCACAGCCACTCGCCCTCCTCACACGAGAGGCACTGCCAGAGCTTCCAGGAG

TTCCGCTATTTTTCGGTAACTGTGGTCGGTCCATAGCGGAGGTAGTATCTGTGGCGAAAC

CCATGCACTTGGATGAAGTACCTTCTAGACAGCCTCAGAGTATTCACCCTGCGCATTTTCA

AAGATGTCTTCAGCAAGGTATACGATTCTCAAGTCGCAGACCTTCCATACTTCCTGGCAC

CTGCTGCTCATGACCACAGTCATGAGTTCTCACCGAATGAAGACCCAGGGTCACTGATCG

ACTGGAGCCATCTGCTGTCGACCAAAGAGGTTGAGTACTTGCCTTGGGATGAAGATCAC

AGTCCCAGCTTCTATCAAAGCAAGTTTGTGATTGATCCATACACGGGATCGCGCAAGCTG

TTTCTCAGAGGTATTCGGACAGATCTCAAGCCGACCGACTTGGTTCCAGATGGAGTTCCC

GAACCCACATTCAGGCTCTGGAAGGACGTTGAGCATACCATAAAGGAATACAGCATCAG

CCTCTGGGCAAAGAGTCGAGCCCGGAGAGCTGGCGAATGGTTGGACACTCAACCCGTGG

TAGAAGCCGAGTTGGTCTCGCTGCGCCGGAATCTTCTCGACGAATTTGCCGATTCCAAGC

ATGAAGGGTCTAGGGTCTGTTATGTGATTCTCCAGCCGCTACAGATCTCAACACTCCCTG

TCGAGGTCGTCGCTATGGCCTACAACTTTCCCGCCATCATCCATCGGATTGAATCGAATA

TGATCGCCCTTGACGCCTGCCGTATGTTGAACCTTCGAGTTCGTCCCGACCTGGCTCTCGA

GGCGATGACCAAAGATTCAAGCAACAGTGAAGAGCACGATCAGGAAAAGATTGATTTCC

AGGCCGGCATGGGCAATAATTATGAGCGACTCGAGTTTCTCGGAGACTGCTTTCTCAAAA
```

```
TGGCAACCACCATCGCACTTTTTACTCGGATCCCTGACAGCAACGAGTTTGAGTGTCACG

TCGAGCGAATGCTTCTTATTTGCAACCAGAATCTCTTTCAATGTCGCATTAAAGAAGAACT

TGCAAGAGTACATTCGATCAAAGCAATTCGATCGACGCAGTTGGTACCCCCAGGGTCTG

AAGCAGAAGGCGGGCAAAGCCCAAGGAGCACAAAACTCACACTTATTGGCCGACAAGT

CTATTGCTGATGTATGCGAGGCCATCATTGGCGCCTCATATTTGTCGTACACTGACGAGG

GCAACTTTGACATGGCCGTACGCGCTGTGACGGCCGTCGTGAGGAACAAAAATCACGAC

ATGAAATCATACGAGGACTATTACAAAGCATTTAAGATGCCGATCTGGCAAGCGGCGGA

GCCAAGTGCTGTGCAGATGGAAGCGTCTTTACAGATTAAAGAGCAGATGGGATATGAGT

TCAAGTCTCCTGCCCTGCTGCGGAGTGCCTTCAAGCACCCGTCCTACCCCCGTCAGTTTG

AGAGCGTGCCCAATTATCAGCGCCTCGAGTTCCTCGGTGACGCGCTTCTAGACATGGTCT

GCGTAGACTTTCTCTTCAGGAAGTTTCCCGACG

CCGATCCTCAATGGCTCACTGAACACAAGATGGCCATGGTTTCGAACCACTTCCTCGGAA

GTCTGAGTGTAGAGTTGGGCTTCTACCGGCGTGTCCTTCACTTTAACAGCATCATGGCCA

ATCAAATCAAGGACTACGTCGACGCACTTACTCATGCACGCCAAGAAGCCGAAGCGGTG

GCCCAGATCTCTGGCACAGTCTCGCGAGATTACTGGCTCAACGTGAAGCACCCCCCCAAA

TTCCTCTCAGACGTGGTCGAGGCATACATCGGTGCTATTTTCGTTGATTCAGGATACGATT

ATGGCCAGGTACAGGCGTTCTTCGAGAAGCATATCCGGCCTTTCTTCGCAGACATGGCGC

TATATGATTCCTTTGCCAGCAGCCACCCTGTCACAACGCTGGCGCGTATGATGCAGCAGG

ACTTTGGCTGCCAGGACTGGCGGCTTCTTGTAAGTGAACTGCCGCCGAGCTGCGAAGACG

GCGGGGCAGCTGCGATCACTGAGACGGAAGTGATTTGTGGGTTCATGGTCCACGGAAGA

ATCCTGCTACATGCCAAGTCGTCGAGTGGACGGTACGCCAAAGTGGGTGCTGCAAAGAG

AGCGGTCGAGAAGCTCATGGGTCTCGGCAACGACAAAGAGGTCTTTCGGACGGACTTCG

GCTGTGACTGTGACTGTGAAGGTCAAGCAATCTAG
```

SEQ ID NO: 6—*Verticillium dahilae* DCL (VAD_00471.1) protein sequence
MTTDELSVGLDATGISILADGPENISSSTSTSTTGKEDGYLCINRFTQNTATTQDNQSRDSD

DDEDDCGSHDEADEDSDERQYSMTPERPHKITEKKRADHAAFHDWLQSNSSEIAQSTPQPAQ

NLNHTSTALMVRESENRKIIENPREYQIELFERAKRKNIIAVLPTGSGKTLIAALLRHTLE

QETADRRAGKPKRIAFFLVEKVALALQQHAVLECNLEFPIDRVCGDMVRSDWIKESWMKRWD

DNMVMVCTAAILQQCLARSFIRMDQINLLVFDEAHHAKGNHPYARIIKDYYITEPDKERRPK

IFGMTASPVDALTDVKIAAAQLEGLLHSEIATIEEDSVSFKQIQKEVVEQDCKYPALEPPFT

TNLHKKIQEQVRYNKNFAKALSNSLEMSSSLGSWCVDRFWQIFLTEETLARLAAQTAQDNIF

ADRAEKERVAIEEVRNIIKQHQFLPITKTLQDLSSKVLCLLGQLELRFSAPTDHKCIIFVEK

RNTAMILAHLLSLPGIGPLYLKPAALVGNPSDNSPLAMSYKEQVMTITKFRRGEYNCLLATS

VAEEGIDIADCNIVIRFDLFNSVIQYIQSKGRARHLNSEYICMAELGNGKHTRAKIQANYDL

SLIRQFCSTLPEDRKIVGWDPEAALHHGERDHKFHIVPSTGAKLTWTGSLVVLSNFASSLQV

NDETLSPSYMVSLIGSEYICEVQLPSKSPILSVSGTLQKNKAEARCSAAFEMCMKLIKGGFI

SSHLQPTFTRKLPAMRNARLAISSKKRERYNMRVKPEVWSRRGPASSLFLTVLKLRTPGALN

RPSQPLALLTREALPELPGVPLFFGNCGRSIAEVVSVAKPMHLDEVRLDSLRVFTLRIFKDV

FSKVYDSQVADLPYFLAPAAHDHSHEFSPNEDPGSLIDWSHLLSTKEVEYLPWDEDHSPSFY

QSKFVIDPYTGSRKLFLRGIRTDLKPTDLVPDGVPEPTFRLWKDVEHTIKEYSISLWAKSRA

RRAGEWLDTQPVVEAELVSLRRNLLDEFADSKHEGSRVCYVILQPLQISTLPVEVVAMAYNF

PAIIHRIESNMIALDACRMLNLRVRPDLALEAMTKDSSNSEEHDQEKIDFQAGMGNNYERLE

FLGDCFLKMATTIALFTRIPDSNEFECHVERMLLICNQNLFNVALKKNLQEYIRSKQFDRRS

WYPQGLKQKAGKAQGAQNSHSLADKSIADVCEAIIGASYLSYTDEGNFDMAVRAVTAVVRNK

NHDMKSYEDYYKAFKMPIWQAAEPSAVQMEASLQIKEQMGYEFKSPALLRSAFKHPSYPRQF

ESVPNYQRLEFLGDALLDMVCVDFLFRKFPDADPQWLTEHKMAMVSNHFLGSLSVELGFYRR

VLHFNSIMANQIKDYVDALTHARQEAEAVAQISGTVSRDYWLNVKHPPKFLSDVVEAYIGAI

FVDSGYDYGQVQAFFEKHIRPFFADMALYDSFASSHPVTTLARMMQQDFGCQDWRLLVSELP

PSCEDGGAAAITETEVICGFMVHGRILLHAKSSSGRYAKVGAAKRAVEKLMGLGNDKEVFRT

DFGCDCDCEGQAI*

SEQ ID NO: 7—*Verticillium dahilae* DCL (VAD_06945.1) genomic DNA sequence
(selected RNAi fragment marked by bolded text)
ATCACTCTACGGGTAAAAGCGCTGAGAGAATGATCATGATGAATTTCTATCATCCACGCA

AACAATCGGCACTATCTGTTCCCCACGTCCTGGGACTGACCGCAAGCCCCATAATGCGAT

CTAGGCTCGAAGGCCTTGAGGCACTGGAACAGACACTGGACTCGGTTTGCGTTACGCCC

AGATTGCACCGAGATGACTTAATGACCCATGTCAAAAGGCCCACCGTCTGTTATGTCCAT

TACGAAACGACAGATGCTAAGGATGAGCCCAAGCCGCTTCAGCATTTCAACTTCTTCGCGA

AGCATGCAGAAATATGGACATCAGGCAAGATCCATACCTTTATCTGTCTAAGAGACAAAG

GCACTGATCGAGCACGACGTGAGCTCATCAAGGTCCTTACAAGCCATAAAACAGATTCG

CAACAGCAAATGAAGTCTTTCTTCAATCAAAGCTTGCGAGTCCTGCGAGATCTCGGGCCC

TGGGCGGCCGAGTACTACATTTGGAAGGTTGTTACAGATTTTCTGGCAATCATTGAAGCA

AGAGATCACCGCATGAATCAACGGAATACCGAAGAAAAGCAGTATCTGGCCAACATCCT

TCGACAAATCAGTATCAGCGAGCCGCCAGTCAGCATGTTGAGTGCTCATAACACGTCGA

ACAAAGTAATGGTGCTCATGGAATACTTGTCATCTAAAGCTACCGATGGTACTGTCGGGA

TCATATTTGTCAAAGAGCGATCAACTGCGGCGATGCTTGCACACGTGATTGAGTCGCATC

CACTGACACAGAATAGGCACTCGAGCGTTGGGGTTGTTGTTGGTGCTTCCACTCATCTGG

TAAGGAAGAAAGACATGTGGGATCTGTCTCGAGCAGCCCACGAGACAGAGCCCCTTCTT

CAGTTCAGATCTGGCCACCTCAATTTGCTCATCGCCACGAGTGTGCTTGAAGAGGGCATC

GACGTTCCTGCCTGCAACCTCGTGATCTGTTTTGATGAGCCCGAGAATCTCAAAGCCTTT

GTCCAGCGGCGCGGCCGAGCCCGGAAGAAGGATTCTAGCCTCGTGGTTCTTCTCCCCGGG

ACAGACCACGTGCCTCAGGACTGGAAAGCATGGAAGCGACAATGAGGACACACTACG

AGAGAGAACAGCGCGAAATACAAATCATGGAGCAGATCGAAGCATCCGAGTCTGCAAA

GTACGAAGAGTACGTTGTCGAGAGTACTAATGCCAGACTCGACTTCGAGAACGCCAAAG

CGCATCTCAGCAACTTTTGTGGGCAGCTCTCTCCCGGGGAGTTTATAGACAAGAGGCCCG

AATACATACCCCGTGTGGTAGACAACGGAGTACCTCCATCTCTGAGGGTCACGGTACTGT

TGCCAAGCTATGTTCCAGCTGCCGTCCGCCATGCTGAGAGTCGTCGAAGCTGGAAGTCGG

AGCATCAGGCCTCAAAGGATGCCGCTTTTCAGGCATACGTGGCTCTTTACAAAGCGGGAC

TGGTCAATGAACACATGCTTCCACTCACGGTAAAAGATATCGTACCCGCAAACGAACCTC

GAGTAGCAACCTTGCAGGTCAATGGCCTCTTGAATGTCTGGCTTGGTATTGCCCAGGCCT

GGATCACGAGCACTGAAACCTGGTTAACTCCAGTGCACCTCCGAGACGCGACGGGATTG

ACGCGAGGAACGTATATCATGAGAATGCCGGTAGCATTGCCGGCACTGCCTTCCACGCC

GGTGTACTTCGATCGCGAAGGACCATGGCTTCTGGATTTTGGCCCACAAGAACGAAAGG

```
AGAATCTTGAAATGCCTGATCATACTTCAGTGCTGCTTGCACTCCACTTTGGCCATCACTG

GTCTATTGCTCATGGTCAGCAGCAGGTTATCAGCTTCGCTTCACAAGATGGCGA

ACTGAATATCAGGCAATTAAGTGCACGGGGTTTCACAACCGCAGATGCCGACCGAGAGG

AAATGCTGTACCTGGTACGGGACGAGTCAGGATGCCCGTATGTGTACGACCACTTTCTAA

ATGGCAAGCCGTCACTTGAACTTGTTCAACGACCTTTCCGGCGCATCGGGGACTCTCCAG

GCTTTCAAGACGCACCCAGTAACATCCCCTACTTGGCTCTCAGAAAGTGGCCGCGGTACC

TGGCCCTCTTGCACCAACAGAAGGTCAACGATCTACTGCCACAGGCGACAAACAAGAAG

CCATATGCTAGGGTTTATCCGGCACCGTGGGCGAAAGTCGACACGATTCCATTAGATCAT

GCTTACTTTGGGGCGTTGATCCCTTTCATTTCACACATTGTCGAGGTTCGACTGGTTGCAG

AACAGCTTTCCTCGAGCCTACTTCGTGACCTCAATTTCTCAGATCCCTCTCTTGTCCTGGC

GGCCATTAGCACTAAGGGTTCCTTGGAAGCCACAAACTACGAGCGCCTTGAGCTTTTGGG

TGACTCTATCCTCAAGCTTTGCACCACGGCCAATGCCGCCGCTCTGCATGGCTTAGTGTC

GAACTCGAGATTGTGTAGGGCTGCACTGGATGCTGGCCTTGACAAATTTGTTCTAACTGA

AAACTTCACTTGTCGCACGTGGCGCCCTATCTACGTCAACGACATGATGGAAAAGGGTGC

TCGCGACTCAGGACCCCGTATCATGTCGACGAAGACGCTCGCCGATATTGTGGAAGCACT

CATAGGGGCCGCATACATTGACGGTGGCCTCCCAAAGGCACTTGGGTGCATTTCGATCTT

CCTGAGGGAGCTCGATTGGAAACCGTTGCCAGCTTGCCAGGAGATCCTTTACAGTTTGGC

GTCCCCTGATGTGCCTTTGCCGCCAATGCTTGTTCCGCTGGAGGACCTGATCGGCTACAC

GATGCATCTCCTCAAGACTGCTTCGGTCAACGGCGATCTTCTAGGCTTCTTTGCACTCGA

GTGCCATGCCGAGGAAGACGAGGTGATCATTGATATCGATTTTTCTCCTTCCGATACGGA

CTTCAATCCTCAAAATTCCGCCGGGGTGGAACAGAAGCTCAAACAGACACGCCGGAAA

ATCCCCCTTTCCAAGTTTATGCGCCACTCCTCAATAGAGGTTGTGCACCAGCAGAC

CAAAGCTGCCACCCTTCATCCCGATCTCCCACCACAGATCATGCACCCTCTGCAAC

ATGGGTCAAGCTACCCCTGGTCTCTTCTCGCCCGTTTACATCCCGCAAAGTTCTTCT

CCCACATCCTCGAACCTGTACTCCGTGCCGTCTCCCTCGATTCCCGCCACATCGCC

GCGTGCATTCGTGTCGCCCAACGACTGCCCATTCTCCCTCTGCTCTCCCGACTGGC

AAAGGAGGACGTTCATGTCCTGCATCCGAAGCAAGAGCTGGGAGAGATCGCTGGTCCC

CGGACAGTCAAATATCTCCTCACTTTGCCCGAGGACGCAGCCGGCCTGCAAAGTGCAAC

AAGAAAATATGCCTGCAAGGTCATGGTCGGGGATCGCTGTGTTGCAGAGGTGGATGACG

GGGTCGCTCGAGATGAGGTTGAGACAAAGGCTGCAGAGGTTGCGGTACAGACCTTGAAG

AATGAACAGGCTGACGCGAAACAAGTAGCAGAACACTAA
```

SEQ ID NO: 8—*Verticillium dahilae* DCL (VAD_06945.1) protein sequence
MIMMNFYHPRKQSALSVPHVLGLTASPIMRSRLEGLEALEQTLDSVCVTPRLHRDDLMTHVK

RPTVCYVHYETTDAKDEPKPVSISSLREACRNMDIRQDPYVICLRDKGTDRARRELIKVLTS

HKTDSQQQMKSFFNQSLRVLRDLGPWAAEYYIWKVVTDFLAIIEARDHRMNQRNTEEKQYLA

NILRQISISEPPVSMLSAHNTSNKVMVLMEYLSSKATDGTVGIIFVKERSTAAMLAHVIESH

PLTQNRHSSVGVVVGASTHLVRKKDMWDLSRAAHETEPLLQFRSGHLNLLIATSVLEEGIDV

PACNLVICFDEPENLKAFVQRRGRARKKDSSLVVLLPGTDHVPQDWESMEATMRTHYEREQR

EIQIMEQIEASESAKYEEYVVESTNARLDFENAKAHLSNFCGQLSPGEFIDKRPEYIPRVVD

NGVPPSLRVTVLLPSYVPAAVRHAESRRSWKSEHQASKDAAFQAYVALYKAGLVNEHMLPLT

VKDIVPANEPRVATLQVNGLLNVWLGIAQAWITSTETWLTPVHLRDATGLTRGTYIMRMPVA

-continued

```
LPALPSTPVYFDREGPWLLDFGPQERKENLEMPDHTSVLLALHFGHHWSIAHGQQQVISFAS

QDGELNIRQLSARGFTTADADREEMLYLVRDESGCPYVYDHFLNGKPSLELVQRPFRRIGDS

PGFQDAPSNIPYLALRKWPRYLALLHQQKVNDLLPQATNKKPYARVYPAPWAKVDTIPLDHA

YFGALIPFISHIVEVRLVAEQLSSSLLRDLNFSDPSLVLAAISTKGSLEATNYERLELLGDS

ILKLCTTANAAALHGLVSNSRLCRAALDAGLDKFVLTENFTCRTWRPIYVNDMMEKGARDSG

PRIMSTKTLADIVEALIGAAYIDGGLPKALGCISIFLRELDWKPLPACQEILYSLASPDVPL

PPMLVPLEDLIGYTMHLLKTASVNGDLLGFLALECHAEEDEVIIDIDFSPSDTDFNPQNSAG

VEQKLKQTRRKIPLWKFMRHSSIEVVQQQTKAASVHADLRGQIMHALEHGSSYPWSLLARLH

PAKFFSDMVEAVLGAVWVDSGDMGACIRVAERLGILPVLSRLAKEDVHVLHPKQELGEIAGP

RTVKYLLTLPEDAAGLQSATRKYACKVMVGDRCVAEVDDGVARDEVETKAAEVAVQTLKNEQ

ADAKQVAEH*

SEQ ID NO: 9—RNAi fragment from B. cinerea DCL1 cDNA
TGCGGAAGAAGCTTGAAGGTTTGCTACACAGTCAAATATGTACTGCAGAAGATCCCAGCTT

GCTGCACTTACTCAATCAAAGGTAAACCTGAGACTCTTGCCTACTATGATCCCTTGGGCCC

GAAATTCAATACTCCTCTTTATCTTCAAATGCTCCCGCTTCTAAAAGACAATCCTATCTTT

CGGAAGCCATTTGTATTTGGGACAGAAGCCAGTAGAACTCTAGGATCTTGGTGTGTTGAC

CAGATCTGGACTTTCTGTC

SEQ ID NO: 10—RNAi fragment from B. cinerea DCL2 cDNA
TCTTTAAGTGATATCGAGGAGACTTTGGATGCCATTTGCTGCACGCCAAAAATACATCGA

GCAGATCTTCGCCTTCGAGTAAAGCTACCACTTCTATCTATTATCTACTATACCCCAGAGT

CAAATATCATCGTGACGAAAACTGTGGCGAGCCTGAGAAAGATTGTGCAAAGTCTCAAC

ATTTTCGAAGACCCCTACGTTTTGACACTAAAAAGGAGTGATAGCGAAAAAAGTCAACG

TGAGCTGGCGAAAGTACTCAAGAGTTTTAAGACATATAGTCAAACCCAATTAAAGTC

SEQ ID NO: 11—RNAi fragment from V. dahliae DCL(VDAG_00471) cDNA
GGCAAGCCCAAGAGAATCGCCTTTTTCCTCGTGGAAAAGGTTGCTCTTGCCCTCCAACAG

CACGCGGTTCTGGAGTGCAATCTGGAATTTCCCATTGACCGGGTATGCGGTGACATGCTTA

CGGTCGGACTGGATCAAGGAGTCATGGATGAAAAGATGGGATGACAACATGGTCATGGT

CTGCACCGCCGCCATCCTTCAGCAATGCCTTGCCAGATCATTCATCCGCATGGATCAGAT

CAACCTGCTTGTCTTCGATGAAGCACATCACGCCAAGGGAAATCATCCGTACGC

SEQ ID NO: 12—RNAi fragment from V. dahliae DCL (VDAG 06945.1) cDNA
ACAGACACGCCGGAAAATCCCCCTTTGGAAGTTTATGCGCCACTCCTCAATAGAGGTTGT

GCAGCAGCAGACCAAAGCTGCCAGCGTTCATGCCGATCTCCGAGGACAGATCATGCACG

CTCTGGAACATGGGTCAAGCTACCCCTGGTCTCTTCTCGCCCGTTTACATCCCGCAAAGTT

CTTCTCCGACATGGTCGAAGCTGTACTGGGTGCCGTCTGGGTCGATTCGGGCGACATGGG

CGCGTGCATTCGTGTGGCGGAACGACTGGGCATTCTGCCTGTGCTCTCCCGACTGGCAAA

GGAGGACGTTCATGTGCTG

SEQ ID NO: 13—LTR for siR3
>B. cinerea (B05.10) Botrytis cinerea supercontig 1.56 [DNA]
218751-219771-
CTCCTGGATCAGGCAGATGAATTAGGGAACTGATTTCGACCTTCCAGAGTTCTCTTTGCG

TGATGGGTCACTTGGGTTTGGTTGTCGGTATGCTGTGGGTTCGGAGGAGTTGTCCTTTCT

GGTTTCTTTGTTGGATAGTCCTTTTTGGGTAGCTTGGTGTGATGCATGCGTTCTGGGTGT

GGGTCTCGTGAGGTCTTTTTGTATCAAGTATTTTAAGCTTTTTTCTTGTTCTCTTCTTT

TTCTGTATTGGTAATGCTTCTTCTTTATGATATTCTCCCATCGCTGCTTTCGCATTTTCT
```

-continued

```
AGGTTGTAGGGTGCTTCCCACGTGTCTTCCGCCGGTTGGTAGCCCTTCCATCGCACCAGG

TATTGCACACCTCTGCCTCTTTTTCTATGTGCTAAAATCCTTTCCACCTCATGCTCTATG

TGATCGTCAATTTCTTCTGGCGGCGGCGGGTCGGCGGTACCCTGTCGTTCGTGCCATGGT

TCGAGTAAAGAGACGTGGAATACATTGTGGATCTTGTAGGTGGGCGGTAATCTAAGTT

CG

TATGCTTGCCCGCTGGTTTTTATACCCGTCACGACAAAGGGGCCTATAAATCCATCGGAG

AATTTTTTCTTAGGTCGCAGTTGTTTAATGTTCTTTGTGCTTAGCATCACCTTGTCCCCG

ATGCTATATCCCTGTGGTGACCCCTTCGTAGTGTTCTTGTTTTTCTGATTGGTTGCCGAT

TTCCAGAATTCTTTCAGCTTTTCTCTTTCTTTCTCTAAAGCGTCGATGCGCTCGCGTGCT

GCCGGCGCCCTTCCCTCTAAATCGGCGTCCTCGCCGATATAATGGAATGTGGGTTGGAAC

CCATACATAGCCTGGAATGGCCTTGTATTGGTTGTACTGTGCCATGTCGCGTTATATGTG

AATTCACCAAGGGGCAATAGCGATGCCCACTCGTCTTGCCTATAGTTGGTGTAGCAACTT

ATATAGTGAATCAAATTTTGGTTTTGTCGTTCGGTTTGACCGTCGGTCTGCGGCTGGAAC

G

SEQ ID NO: 14—LTR for siR5
> BC1G_08572.1 retrotransposable element Tf2 1 protein type 1
(Transcript: BC1T_08572)
ATGGCATCCAGAGCTACCGCCACAGGTCAATCTGCCGGAGACACCAACGACATCGAGAT

GACCGACGCCCCAAAGGAGATCACTATCAACGAAACCCTTAAGATCGCCTTACCAGACA

AGTACCAAGGTAGTCGACAAGAGCTCGATACTTTCCTCTTACAACTTGAGATCTACTTTC

GATTCAATGAGGACAAGTTCACTACCAAGGAATCCAAGAGTATATGGGCCGCATCATAC

CTTCGAGGTGAAGCAACCAAATGGATCCAACCATATTTGCGCGACTATTTCGAGCATGAC

GATAAGGATCGTATGCAACCCACCCGAACAATCTTCAATAGTTTTGAAGGATTTAAGACA

GAGATTCGTAGAATCTTCGGAAATTCCAACGAGTTAGAGGTAGCGGAAGATAAGATCTT

CAACCTCAAGCAGACAGGATCAGCATTGAAATATGCTACGGAATTTCGAAGATATGCTG

GAACAACCAAGTGGGACGAAATCGCTATCATGAGTCACTACCGCAAGGGACTCAAACCA

GAAGTCAGACTGGAATTAGAAAGATCTGCCGAGAGTACAGATCTGAACGATCTAATTCA

GGACTCCATCGAATCAGATGATCGTCTCTACAGATATCGACAAAGCCAGAGATCATACA

AACCCCAAGGAAATCAGAACCAAGGGCGTTACCGCAAAAATGAGGGTAGACCACGTTA

CAATCCACAGAGATACGGAGACCCCATGGAACTAGACGCCACGCACTACACAAACGGGA

ACGATGACTCGGAAAAGAGACGAAGACCAGAAAAACAACTTATGCTTTGAATGTGGAAA

ACCAGGGCACCGAGCAGCAGACTGCCGAAGCAAGAAGACAGGAGGAAAAAGGGGCAA

CTTCAAACCTAAGTTCGGCAAAGGCCAACTTAACGCTACCTTTACAATCCCAGAAAATCC

AACTAAATCCGAAAATACTGAGACTTTCACCGTTGAGGAATTCCACCAATTACTAAAGG

AATTACCACGAAATCAAGAGGGCATGAATGCAATAGACTTATGGGAGCAAGAGTATTAC

AGAACCCCAACACCCTCTGTGACAGAAGAAAGTCATCAGGACGAGGCAGAAGCAGACC

ACGCCACGATGAGCTGGACACCTTGCTATGATGAATTCTGCGGAATCCATCGATCAGATA

AAGAAGCAACCGGATGGTCCCCTAAGAAGAGAAAGACGAAGAACCATCAGAATAATGT

AACATGCGAGGATTTAACTCCCAATATAACTTCGCAAGAAGTTCGCAAACTTACCCAGC

AGTTAAATGCTACGGGACAGGCAGGACAGATATACTGCAAGGTTCAGATAAATGGACAC

ATACAATCAGCCATGATAGATTCAGGCGCTACAGGAAATTTTATTGCACCGGAAGCTGA

GACAATCCCAATACGAATGGGCATAACCCAACATACAGAGGTTATACAGCTTGACGTTG
```

```
TGCCATTGGGCCAACAACAGATCATCTTAGGAATGCCATGGTTAAAGGCACATAATCCG

AAAATAGATTGGGCACAAGGAATTGTGACATTTGATCAGTGCAAAAGCGGTCACAGGGA

CACGCTAGAGGCGTTCGCGAGACGTAACACGCGCCAAGGAGAGTTGAACGCGAACAAC

ACCGGCGACGTAGGACACCCAGTCCAGGGTCCTCCATTAAGAGCGAAGGCCAGTACACC

TCCTCTACAAATGCAGAAGCCAACGACACGGCACGAAATCGCAATCGAGGCAAAAGAA

AAGCCTACCATACCAGAACAGTACAAGAATTATGAACATGTTTTCAAAGAACCAGGGAT

CCATGAGGCTTTACCGGAACACAAGCCATGGGATCATGAGATAATATTGGAGGAAGGCA

AGATGCCTGTGCACACCCCAATTTATTCAATGTCAGCCGATGAGTTAAAGAGGCTCAGAG

AGTACATCGACGACAATTTAGCCAAGGGATGGATCAGGGAATCCGCGTCCCAACTGGCC

AGTCCAACTATGTGGAAGGATCGATATCCACTTCCATTAGCTACGGAATTAAGAGATCGA

TTAGGCGGAGCTACGATATTTACCAAGATGGACCTACGTAATGGTTACCACTTGATCAGA

ATGAAGGAAGGCGAAGAATGGAAAACCGCTTCAAAACAAGATACGGGCTATACGACTA

CTTTCATGAGGCTTATGAACAATGTGTTGTCACAATATTTGGATACTTGCTGTATATGCTA

CTTGGACGACATCCTAGTATATTCAAACAACAAGGTTCAACACATTAAGGACGTTAG

CAACATCCTCGAAAGCCTATCCAAGGCAGACTTGCTGTGCAAACCAAGCAAATGCGAAT

TCCATGTCACAGAGACAGAATTCTTGGGATTCACCGTATCAAGCCAAGGGCTCAAGATG

AGCAAAGGCAAGGTTAAGGCAGTGCTCGAATGGAAGCAGCCGACCACAATCAAGGAAG

TACAATCCTTTCTAGGGTTCGTCAACTTCTACAGAAGATTCATCAAGGGTTATTCAGGGA

TTACTACACCCTTGACCACGTTAACCAGAAAAGATCAAGGAAGCTTCGAATGGACTGCC

AAAGCACAGGAGTCATTCGATACGCTCAAACAAGCAGTGGCAGAAGAGCCAATACTGTT

GACTTTTGACCCAGAGAAAGAAATCATAGTGGAGACGGACTCCTCGGATTTCGCTATAG

GAGCAGTTCTGAGCCAACCGGGCCAGAATGGAAAATACCAGCCAATCGCATTCTACTCC

CGAAAACTATCACCAGCCGAATTGAATTACGAGATATATGACAAAGAATTACTGGCGAT

AGTCGATGCATTTAGAGAATGGCGAGTGTATTTGGAAGGATCGAAATACACGGTACAGG

TGTATACAGATCATAAGAACTTGGTTTACTTCACCACAACGAAGCAGTTAAACAGACGA

CAGGTCAGATGGTCGGAGACCATGGCCAACTACAATTTCAGAATTTCATATGTCAAAGG

ATCAGAAAACGCTAGAGCCGACGCTCTTAGCCGAAAACCAGAATATCAAGAAAACAAA

ACGTACGAGTCATACGCTATATTCAAGAAAGACGGCGAATCACTGGTTTACAATGCACC

ACAGCTTGCAGCAACACACCTGTTGGAAGACAACCACCTCAGGAAACAGATCCAATCAC

ACTACGACAAGGATGCTACTGCCACACGCATACGCAAGACAATAGAACCAGGATTCACT

ATAGAAAATGATACCATATACTTTCATGGAAAGTATACATTCCGAGTCAAATGACCA

AGGAATTTGTGACGGAACAACACGGGTTGCCGGCACATGGACACCAAGGAATTGCAAGG

ACATTTGCAAGAATACGGGAAATCAGTTACTTCCCACGAATGAGAACGATAGTTGAAGA

AGTTGTTGGAAATTGTGACACCTGCATACGAAACAAGTCATCACGACATGCTCCGTATGG

TCAGCTCCAGACCCCAGACATGCCTTCTCAGCCATGGAAGTCCATCACATGGGACTTTGT

GGTCAAACTACCACTCTCAAAAGATCCTACTACAGGAATTGAGTACGACGCGATACTCA

ATATAGTAGACAGGCTAACGAAATTTGCATATATGATACCATTCAAGGAAACATGGGAT

GCTGAGCAACTAGCATATGTGTTCCTAAGGATCATAGTAAGCATACACGGAGTACCAGA

TGAGATAATCTCGGATCGAGACAAGCTCTTTACCTCGAAATTCTGGACTACCTTATTAGC

ACTTATGGGTATCAAGAGAAAGCTATCGACATCTTTCCACCCACAAACAGATGGTCAAA
```

SEQ ID NO: 15—LTR for siR5
> BC1G_15284.1-enzymatic polyprotein
ATGGCATCCAGAGATATCGCCACAGGTCAATCTGCCGGAGACACCAACGACATCGAGAT

GACCGATGCCCCAAAAGAGATCACTATCAACGAAACACTTAAGATCGCCTTACCAGACA

AGTACCAAGGTAGTCGACAAGAACTCGATACTTTCCTCTTACAACTTGAGATCTACTTCC

GATTCAATGAGGACAAGTTCACTACCAAGGAATCCAAGAGTATATGGGCCGCATCATAC

CTTCGAGGTGAAGCAACCAAATGGATCCAACCATATTTGCGCGACTATTTCGAGCATGAC

GATAAGGATCGCATGCAACCCACCCGAACAATCTTCAATAGTTTTGAAGGATTTAAGAC

AGAGATTCGTAGAATCTTCGGAAATTCCAACGAGTTAGAGGTAGCGGAAGATAAGATCT

TCAACCTCAAGCAGACAGGATCAGCATTGAAATATGCTACGGAATTTCGAAGATATGCT

GGAACAACCAAGTGGGACGAAATCGCTATCATGAGTCACTACCGTAAGGGACTCAAACC

AGAAGTCAGACTGGAATTAGAAAGATCTGCCGAGAGTACAGATCTGAACGATCTAATTC

AGGACTCCATCGAATCAGATGATCGTCTCTACAGATATCGACAAAGCCAGAGATCATAC

AAACCCCAAGGAAATCAGAAGCAAGGGCGTTACCGCAAGAATGAGGGTAGACCACGTT

ACAACCCACAGAGATACGGAGACCCCATGGAACTAGACGCTACGCACTACACAAACGGG

AACGATGACTCAGAAAAGAGACGAAGACGAGAAAACAACTTATGCTTTGAATCTTGGAA

AAGCAGGGCACCGAGCAGCAGAATGCCGAAGCAAGAAGACAGGAGGAAAAAGGGGCA

ACTTCAAACCTAAGTTCGGCAAGGGCCAACTTAATGCCACCTTTGCAATCTCAGAAAACT

CAACTAAACCCGAAAATACTGAGACTTTCACCGTTGAGGAATTCCAGCAATTATTAGAG

GAATTACCACGAAACCAAGAGGGCATGAATGCAATAGACTTATGGGAACAAGAGTATTA

CAGAACTCCAACACCCTCTGTGACAGAAGAAAGTCACCAGGACGAGGCAGAAGCGGAC

CACGCCACGATAAGCTGGACAGCTTGCTATGACGAATTCTGCGGAATCCATCGATCAGAT

AAAGAAGCAACCGGATGGTTCCCTAAGAAGAGAAAGACGAAGAACCATCAGAATAATG

TAACATGCGAGGATTTAACTCCCAATATAACTTCGCAAGAAGTTCGCAAAGTTACCCAGC

AGTTAAATGCTACGGGACAGGCAGGACAGATATACTGCAAGGTTCAGATAAATGGACAC

ATACAATCAGCCATGATAGATTCAGGGGCTACAGGAAATTTTATTGCACCAGAAGCGGC

AAAGTACTTGGAAATACCACTTCAGAGGAAACAATACCCCTATCGATTGCAGTTAGTTGA

CGGACAGCTAGCAGGGTCTGACGGAAAGATTTCGCAGGAGACAATCCCAGTACGAATGA

GCATAACCCAACATACAGAGGTTATACAGCTTGATGTTGTGCCATTGGGCCAACAACAG

ATCATCTTAGGAATGCCATGGTTAAAGGCACATAATCCGAAAATAGATTGGGCACAAGG

AGTTGTGACATTTGATCAGTGCAAAAGCGGTCACAGGGACACGATAGAGGCGTCCGCGA

GACGTAACACGCGCCAAGGAGAGTTGAACGCGAACAACACCGGCGACGTAGGACACCC

AGTCCAGGGTCCTCCATTAAGAGCGAAGGCCAGTACACCTCCTCTACAAATGCAGAAGC

CAACGACACGGCACGAAATCGCAATCGAGGCAAAAGAAAGGCCTACGATACCAGAACA

GTACAAGAAATATGAACATGTTTTCAAAGAACCAGGGATCCATGAGGCTTTACCGGAAC

ACAAGCCATGGGATCATGAGATAATATTGGAGGAAGGCAAGATGCCTGTGCACACCCCA

ATTTATTCAATGTCAGCCGATGAGTTAAAGAGGCTCAGAGAGTACATCGACGACAATTTA

GCCAAGGGATGGATCAGGGAATCCGCGTCCCAAGTGGCCAGTCCAACTATGTGGGTACC

CAAGAAGGATGGACCCGATAGACTAGTTGTAGACTATAGAAAGCTTAACGCACTCACTA

-continued

```
AGAAGGATCGATATCCACTTCCATTAGCTACGGAATTAAGAGATCGATTAGGCGGAGCT

ACGATATTCACCAAGATGGACCTACGTAATGGTTACCACTTGATCAGAATGAAGGAAGG

CGAAGAATGGAAAACCGCTTTCAAAACAAGATACGGGCTATACGAGTACCAAGTTATGC

CATTCGGGCTAACCAACGCACCAGCTACTTTCATGAGGCTTATGAACAATGTCTTGTCAC

AATATTTGGATACTTGCTGTATATGCTACTTGGACGACATCCTAGTATATTCAAACAACA

AGGTTCAACACATTAAGGACTGTAGCAACATCCTCGAAAGCCTATCCAAGGCAGACTTG

CTGTGCAAACCAAGCAAATGCGAATTCCATGTCACAGAGACAGAATTCTTGGGATTCAC

CGTATCAAGCCAAGGGCTCAAGATGAGCAAAGACAAGGTTAAGGCAGTGCTCGAATGGA

AGCAGCCGACCACAATCAAGGAAGTACAATCCTTTCTAGGGTTCGTCAACTTCTACAGAA

GATTTATCAAGGGTTATTCAGGGATTACTACACCCTTGACCACGTTAACCAGAAAAGATC

AAGGAAGCTTCGAATGGACTGCCAAAGCACAGGAGTCATTCGATACGCTCAAACAAGCA

GTGGCAGAAGAACCAATACTGTTGACTTTTGACCCAGAGAAAGAAATCATAGTGGAGAC

GGACTCCTCGGATTTCGCTATAGGAGCAGTTCTGAGCCAACCGGGCCAGAATGGAAAAT

ACCAGCCAATCGCATTCTACTCCCGAAAACTATCACCAGCCGAATTGAATTACGAGATAT

ATGACAAAGAATTACTGGCGATAGTCGATGCATTTAGAGAATGGCGAGTGTATTTGGAA

GGATCGAAATACACGGTACAGGTGTATACAGATCATAAGAACTTGGTTTACTTCACCACA

ACGAAGCAGTTAAACAGACGACAGGTCAGATGGTCGGAGACCATGGCCAACTACAATTT

CAGAATTTCATATGTCAAAGGATCAGAAAACGCTAGAGCCGACGCTCTTAGCCGAAAAC

CAGAATATCAAGAAAACAAAACGTACGAGTCATACGCTATATTCAAGAAAGACGGCGAA

TCACTGGTTTACAATGCACCACAGCTTGCAGCAACACACCTGTTGGAAGACAACCACCTC

AGGAAACAGATCCAATCACACTACGACAAGGATGCTACTGCCACACGCATACGCAAGAC

AATAGAACCAGGATTCACTATAGAAAATGATACCATATACTTTCATGGAAAAGTATACA

TTCCGAGTCAAATGACCAAGGAATTTGTGACGGAACAACACGGGTTGCCGGCACATGG

ACACCAAGGAATTGCAAGGACATTTGCAAGAATACGGGAAATCAGTTACTTCCCACGAA

TGAGAACGATAGTTGAAGAAGTTGTTGGAAATTGTGACACCTGCATACGAAACAAGTCA

TCACGACATGCTCCGTATGGTCAGCTCCAGACCCCAGACATGCCTTCTCAGCCATGGAAG

TCCATCACATGGGACTTTGTGGTCAAACTACCACTCTCAAAGGATCCTACTACAGGAATT

GAGTACGACGCGATACTCAATATAGTAGACAGGCTAACGAAATTTGCATATATGATACC

ATTCAAGGAAACATGGGATGCTGAGCAACTAGCATATGTGTTCCTAAGGATCATAGTAA

GCATACACGGAGTACCAGATGAGATAATCTCGGATCGAGACAAGCTCTTTACCTCAAAA

TTCTGGACTACCTTATTAGCACTTATGGGTATCAAGAGAAAGCTATCGACATCTTTCCAC

CCACAAACAGATGGTCAAACAGAGAGGACCAATCAGACAATGGAAGCATATCTTAGATG

CTATGTAAATTATCGACAAGACAATTGGGTAGAGCTATTACCCATGGCACAGTTCGCATA

CAATACATCAGAAACGGAAACCACGAAAATCACACCAGCACGAGCTAATTTTGGGTTTA

ATCCACAAGCGTATAAAATCCCGATACCACAAGAAGTTAATGCCGAATCAGCGATAGTA

CAAATCGAACAGCTGAAAGATCTCCAAGAGCAACTGGCTCTTGATCTAAGATTCATATCT

TCCAGAACAGCAGCGTACTACAATACGAAACGTAGTATGGAACCTACGCTTAAAGAGGG

GGATAAAGTTTATTTGCTACGACGAAACATCGAAACCAAGAGACCAAGCAATAAACTCG

ACCACAGGAAACTAGGACCATTCAAGATTGATAAGGTAATAGGAACGGTTAATTATCGA

TTGAAATTACCAGACACAATGAATATCCACCCAGTATTCCACATATCCTTGCTCGAACCA

GCACCACCAGGAGCGCCAAATGCGCCATTTACAGAAATTGAACCAG
```

```
TCAACCCAAACGCCATATACGATGTCGAAACAATACTAGACTGCAAATACGTCAGAAAC

AAGGTCAAGTATTTGATCAAATGGTTAGACTACCCACATTCAGAAAACACATGGGAACT

CAAGGAAGATCTCAGCTGCCCTGAGAAGCTACGGGCATTCCACCTGAAGTACCCACACC

TGCCAATAAAGCCTCAAGATCCGCTTCGGACAACTCAGGCAAAGAAGGATCGAAGAAAT

CGAAGGAAGAAGAATCAATAG
```

SEQ ID NO: 16-LTR for siR5
>BC1G_04408.1 retrotransposable element Tf2 1 protein type 1

```
ATGGCATCCAGAGCTACCGCCACAGGTCAGTCTACCGGAGATACCAACGACATCGAGAT

GACCGATGCCCCAAAGGAGATCACTATCAACGAAACACTTAAGATCGCCTTACCAGACA

AGTACCAAGGTAGTCGACAAGAGCTCGATACTTTCCTCTTACAACTTGAGATCTACTTCC

GATTCAATGAGGACAAGTTCACTACCAAGGAATCCAAGAGCATATGGGCTGCATCATAC

CTCCGAGGTGAAGCAACCAAATGGATTCAACCATATTTGCGCGACTATTTCGACCATGAC

GATAAGGATCGCATGCAACCCACCCGAACAATCTTCAATAGTTTTGAAGGATTTAAGAC

AGAGATTCGTAGAATCTTCGGAAATTCCAACGAGTTAGAGGTAGCGGAAGATAAGATCT

TCAACCTCAAGCAGACAGGATCAGCATTGAAATATGCTACGGAATTTCGAAGATATGCT

GGAACAACCAAGTGGGACGAAATCGCTATCATGAGTCACTATCGTAAGGGACTCAAACC

AGAAGTCAGACTGGAATTAGAAAGATCTGCCGAGAGTACAGATCTGAACGATCTAATTC

AGGACTCCATCGAATCAGATGATCGTCTCTACAGATATCGACAAAGCCAGAGATCATAC

AAACCCCAAGGAAATCAGAAGCAAGGGCGTTACCGCAAAAATGAGGGTAGACCACGTT

ACAATCCACAGAGATACGGAGACCCCATGGAACTAGACGCCACGCACTACACAAACGGG

AACGATGACTCGGAAAAGAGACGAAGACGAGAAAACAACTTATGCTTTGAATGTGGAA

AAGCAGGGCACCGAGCAGCAGACTGCCGAAGCAAGAAGACAGGAGGAAAAAGGGGCA

ACTTCAAACCTAAGTTCGGCAAAGGCCAACTTAACGCTACCTTTACAATCCCAGAAAATC

CAACTAAATCCGAAAATACTGAGACTTTCACCGTTGAGGAATTCCAGCAATTACTAAAG

GAATTACCACGAAATCAAGAGGGCATGAATGCAATAGACTTATGGGAGCAAGAGTATTA

CAGAACCCCAACACCCTCTGTGACAGAAGAAAGTCATCAGGACGAGGCAGAAGCAGAC

CACGCCACGATGAGCTGGACAGCTTGCTATGATGAATTCTGCGGAATCCATCGATCAGAT

AAAGAAGCAACCGGATGGTTCCCTAAGAAGAGAAAGACGAAGAACCATCAGAATAATG

TAACATGCGAGGATTTAACTCCCAATATAACTTCGCAAGAAGTTCGCAAAGTTACCCAGC

AGTTAAATGCTACGGGACAGGCAGGACAGATATACTGCAAGGTTCAGATAAATGGACAC

ATACAATCAGCCATGATAGATTCAGGGGCTACAGGAAATTTTATTGCACCGGAAGCTGT

AAAGTACTTGGGAATACCACTTCAAACGAAACAACACCCCTATCGATTGCAGGACACGC

TAGAGGCGTCCGCGAGACGTAACACGCGCCAAGGAGAGTTGAACGCGAACAACACCGG

CGACGTAGGACACCCAGTCCAGGGTCCTCCATTAAGAGCGAAGGCCAGTACACCTCCTC

TACAAATGCAGAAGCCAACGACACGGCACGAAATCGCAATCGAGGCAAAAGAAAGGCC

TACGATACCAGAACAGTACAAGAAATATGAACATGTTTTCAAAGAACCAGGGATCCATG

AGGCTTTACCAGAACACAAGCCATGGGATCATGAGATAATATTGGAGGAAGGCAAGATG

CCTGTGCACACCCCAATTTATTCAATGTCAGCCGATGACTTAAAAAGGCTCAGAGAATAC

ATCGACGACAATTTAGCCAAGGGATGGATCAGGGAATCCGCGTCCCAAGTGGCCAGTCC

AACTATGTGGGTACCCAAGAAGGATGGACCCGATAGACTAGTTGTAGACTATAGAAAGC

TTAACGCACTCACTAAGAAGGATCGATATCCACTTCCATTAGCTACGGAATTAAGAGATC
```

-continued

```
GATTAGGCGGAGCTACGATATTTACCAAGATGGACCTACGTAATGGTTACCACTTGATCA

GAATGAAGGAAGGCGAAGAATGGAAGACCGCTTTCAAAACAAGATACGGGCTATACGA

GTACCAAGTTATGCCGTTCGGGCTAACCAACGCACCAGCTACTTTCATGAGGCTTATGAA

CAATGTGTTGTCACAATACTTGGATACTTGCTGTATATGCTACTTGGACGACATCCTAGT

ATATTCAAACAACAAGGTTCAACACATTAAGGACGTTAGCAACATCCTCGAAAGCCT

ATCCAAGGCAGACTTGCTGTGCAAACCAAGCAAATGCGAATTCCATGTCACAGAGACAG

ACTTCTTGGGATTCACCGTATCAAGCCAAGGGCTCAAGATGAGCAAAGACAAGGTTAAG

GCAGTGCTCGAATGGAAACAGCCAACCACAATCAAGGAGGTACAATCCTTTCTAGGGTT

CGTCAACTTCTACAGAAGATTTATCAAGGGTTATTCACGGATTACTACACCCTTGACCAC

GTTAACCAGAAAAGATCAAGGAAGCTTCGAATGGACTGCCAAAGCACAGGAGTCATTCG

ATACGCTCAAACAAGCAGTGGCAGAAGAGCCAATACTATTGACTTTTGACCCAGAGAAA

GAAATCATAGTGGAGACGGACTCCTCGGATTTCGCTATAGGAGCAGTTCTGAGCCAACC

GGGCCAGAATGGAAAATACCAGCCAATCGCATTCTATTCCCGAAAACTATCACCAGCTG

AGTTGAATTACGAGATATATGACAAAGAATTGCTGGCGATAGTCGATGCATTTAGAGAA

TGGCGAGTATATTTGGAAGGATCGAAATACACAGTACAGGTGTATACAGATCATAAGAA

CTTGGTTTACTTCACCACAACGAAGCAGTTAAACAGACGACAGGTCAGATGGTCGGAGA

CCATGGCCAACTACAATTTCAGAATTTCATATGTCAAAGGATCAGAAAACGCTAGAGCC

GACGCTCTTAGCCGAAAACCAGAATATCAAGAAAACAAAACGTACGAGTCATACGCTAT

ATTCAAGAAAGACGGCGAATCACTGGTTTACAATGCACCACAGCTTGCAGCAACACACC

TGTTGGAAGACAACTACCTTAGGAAACAGATCCAATCACACTACGACAAGGATGCTACT

GCCACACGCATACGTAAGACAATAGAACCAGGATTCACTATAGAAAATGATACCATATA

CTTTCATGGAAAAGTATACATTCCGAGTCAAATGACCAAGGAATTTGTGACGGAACAA

CACGGATTGCCGGCACATGGACACCAAGGAATTGCAAGGACATTTGCAAGAATACGGGA

AATCAGTTACTTCCCACGAATGAGAACGATAGTTGAAGAAGTTGTTGGAAATTGTGACA

CCTGCATACGAAACAAGTCATCACGACATGCTCCGTATGGTCAGCTCCAGACCCCAGAC

ATGCCTTCTCAGCCATGGAAGTCCATCACATGGGACTTTGTGGTCAAACTACCACTCTCC

AAGGATCCTACTACAGGAATTGAGTACGACGCGATACTCAATATAGTAGACAGGCTAAC

GAAATTTGCATATATGATACCATTCAAGGAAACATGGGATGCTGAGCAACTAGCATATG

TGTTCCTTAGGATCATAGTAAGCATACACGGAGTACCAGATGAGATAATCTCGGATCGA

GACAAGCTCTTTACCTCGAAATTCTGGACTACCTTATTAGCACTTATGGGTATCAAGAGA

AAGCTATCGACATCTTTCCACCCACAAACAGATGGTCAAACAGAGAGGACCAATCAGAC

AATGGAAGCATATCTTAGATGCTATCGTATAAAATCCCGATACCACAAGAAGTTAATGCC

GAATCAGCGATAG

SEQ ID NO: 17-LTR for siR5
>BC1G_12842.1 retrotransposable element Tf2 1 protein type 1
(Transcript: BC1T_12842)
ATGGCATCCAGAGCTACCGCCACAGGTCAGCCTACCGGAGATACCAACGACATCGAGAT

GACCGATGCCCCAAAGGAGATCACTATCAACGAAACCCTTAAGATCGCCTTACCAGACA

AGTACCAAGGTAGTCGACAAGAGCTCGATACTTTCCTCTTACAACTTGAGATCTACTTTC

GATTCAATGAGGACAAGTTCACTACCAAGGAATCCAAGAGTATATGGGCCGCATCATAC

CTTCGAGGTGAAGCAACCAAATGGATCCAACCATATTTGCGCGACTATTTCGAGCATGAC

GATAAGGATCGCATGCAACCCACCCGAACAATCTTCAATAGCTTTGAAGGATTTAAGAC
```

-continued

```
AGAGATTCGTAGAATCTTCGGAAATTCCAACGAGCTAGAGGTAGCGGAAGATAAGATCT
TCAACCTCAAGCAGACAGGATCAGCATTGAAATATGCTACGGAATTTCGAAGATACGCT
GGAACAACCAAGTGGGACGAAATCGCTATCATGAGTCACTACCGCAAGGGACTCAAACC
AGAAGTCAGACTGGAATTAGAAAGATCTGCCGAGAGTACAGATCTGAACGATCTAATTC
AGGACTCCATCGAATCAGATGATCGTCTCTACAGATATCGACAAAGCCAGAGATCATAC
AAACCCCAAGGAAATCAGAAGCAAGGGCGTTACCGCAAGAATGAGGGTAGACCACGTT
ACAATCCACAAAGATACGGAGACCCCATGGAACTAGACGCTACGCACTACACAAACGGG
AACGATGACTCAGAAAAGAGACGAAGACGAGAAAACAACTTATGCTTTGAATGTGGAA
AAGCAGGGCACCGAGCAGCAGACTGCCGAAGCAAGAAGACAGGAGGAAAAAGGGGCA
ACTTCAAACCTAAGTTCGGCAAAGGCCAACTTAACGCTACCTTTACAATCCCAGAAAACC
CAACTAAATCCGAAAATACTGAGACTTTCACCGTTGAGGAATTCCAGCAATTACTAAAG
GAATTACCACGAAATAAAGAGGGCATGAATGCAATAGACTTATGGGAACAAGAGTATTA
CAGAACCCCAACACCCTCTGTGACAGAAGAAAGTCACCAGGACGAGGCAGAAGCGGAC
CACGCCACGATGAGCTGGACAGCTTGCTATGATGAATTCTGCGGAATCCATCGATCAGAT
AAAGAAGCAACCGGATGCTTTCCCCAAGAAAAGGAAGACGAAGAACCATCAGAATAATG
TAACATGCACGGATTTAACTTCAAATATAACTTCGCGAAAAGTTCGCAAAGTTACCCAGC
AGTTGAATGCTACGGGACAAGCAGGACAGATATACTGCAAGCGTCAGATAAATGGACAC
ATACAATCAGCCATGATAGATTCAGGGGCTACAGGAAATTTTATTGCACCAGAAGCTGC
AAAGTACTTGGAAATACCACTTCAGACGAAACAATACCCCTATCGATTGCAGTTAGTTGA
CGGACAGCTAGCAGGGTCTGACGGAAAGATTTCGCAGGAGACAATCCCAGTACGAATGG
GCATAACCCAACATACAGAGGTTATACAGCTTGACGTTGTGCCATTGGGCCAACAACAG
ATCATCTTAGGAATGCCATGGTTGAAGGCACATAATCCGAAAATAGATTGGGCACAAGG
AATTGTGACATTTGATCAGTGCAAAAGCGGTCACAGGGACACGCTAGAGGCGTCCGCGA
GACGTAACACGCGCCAAGGAGAGTTGAACGCGAACAACACCGGCGACGTAGGACACCC
AGTCCAGGGTCCTCCATTAAGAGCGAAGGCCAGTACACCTCCTCTACAAATGCAGAAGC
CAACGACACGGCACGAAATCGCAATCGAGGCAAAAGAAAGGCCTACGATACCAGAACA
GTACAAGAAATATGAACATGTTTTCAAAGAACCAGGGATCCATGAGGCTTTACCGGAAC
ACAAGCCATGGGATCATGAGATAATATTGGAGGAAGGCAAGATGCCTGTGCACACCCCA
ATTTATTCAATGTCAGCCGATGAGTTAAAAAGGCTCAGAGAATACATCGACGACAATTTA
GCCAAGGGATGGATCAGGGAATCCGCGTCCCAAGTGGCCAGTCCAACTATGTGGGTACC
CAAGAAGGATGGACCCGATAGACTAGTTGTAGACTATAGAAAGCTTAACGCACTCACTA
AGAAGGATCGATATCCACTTCCATTAGCTACGGAATTAAGAGATCGATTAGGCGGAGCT
ACGATATTCACCAAGATGGACCTACGTAATGGTTACCACTTGATCAGAATGAAGGAAGG
CGAAGAATGGAAAACCGCTTTCAAAACAAGATACGGGCTATACGAGTACCAAGTTATGC
CGTTCGGGCTAACCAACGCACCAGCTACTTTCATGAGGCTTATGAACAATGTGTTGTCAC
AATATTTGGATACTTGCTGTATATGCTACTTGGACGACATCCTAGTATATTCAAACAACA
AGGTTCAACACATTAAGGACGTTAGCAGCATCCTCGAAAGTCTATCCAAAGCAGACTTG
CTGTGCAAACCAAGCAAATGCGAATTCCATGTCACAGAAACAGAATTCTTGGGATTCAC
CGTATCAAGCCAAGGGCTCAAGATGAGCAAAGACAAGGTTAAGGCAGTGCTCGAATGGA
AGCAGCCGACCACAATCAAGGAAGTACAATCCTTTCTAGGATTTGTCAACTTCTATAGAA
GATTTATCAAGGGTTATTCAGGGATTACTACACCCTTGACCACGTTAACCAGAAAAGATC
```

AAGGAAGCTTCGAATGGACTGCCAAAGCACAGGAGTCATTCGATACACTCAAACAAGCA

GTGGCAGAAGAACCAATACTGTTGACTTTTGACCCAGAGAAAGAAATCATAGTGGAAAC

GGATTCCTCAGATTTCGCTATAGGAGCAGTTCTGAGCCAACCGGGCCAGAATGGAAAAT

ACCAGCCAATCGCATTCTACTCCCGAAAACTATCACCAGCCGAGTTGAATTACGAGATAT

ATGACAAAGAATTACTGGCGATAGTCGATGCATTTAGAGAATGGCGAGTATATTTGGAA

GGATCGAAATACACAGTACAGGTGTATACAGATCATAAGAACTTGGTTTACTTCACCACA

ACGAAGCAGTTAAACAGACGACAGGTCAGATGGTCGGAGACCATGGCCAACTACAATTT

CAGAATTTCATATGTCAAAGGATCAGAAAACGCTAGAGCCGACGCTCTTAGCCGAAAAC

CAGAATATCAAGAAAACAAAACGTACCTAGTCATACGCTATATTCAAGAAAGACGGCGAA

TCACTGGTCTACAATGCACCACAGCTTGCAGCAACACACCTGTTGGAAGACAACCACCTC

AGAAAACAGATTCAATCACACTACGACAAGGATGCTACTGCCACACGCATACGCAAGAC

AATAGAACCAGGATTCACTATAGAAAATGATACCATATACTTTCATGGAAAAGTATACA

TTCCGAGTCAAATGACCAAGGAATTTGTGACGGAACAACATGGGTTGCCGGCACATGG

ACACCAAGGAATTGCAAGGACATTTGCAAGAATACGGGAAATCAGTTACTTCCCACGAA

TGAGAACGATAGTTGAAGAAGTTGTTGGAAATTGTGACACCTGCATACGAAACAAGTCA

TCACGACATGCTCCGTATGGTCAGCTCCAGACCCCAGACATGCCTTCTCAGCCATGAAG

TCCATCACATGGGACTTTGTGGTCAAACTACCACTCTCAAAGGATCCTACTACAGGAATT

GAGTACGACGCGATACTCAATATAGTAGACAGGCTAACGAAATTTGCATATATGATACC

ATTCAAGGAAACATGGGATGCTGAACAACTAGCATATGTGTTCCTAAGGATCATAGTAA

GCATACACGGAGTACCAGATGAGATAATCTCGGATCGAGACAAGCTCTTTACCTCAAAA

TTCTGGACTACCTTATTAGCACTTATGGGTATCAAGAGAAAGCTATCGACATCTTTCCAC

CCACAAACAGATGGTCAAACAGAGAGGACCAATCAGACAATGGAAGCATATCTTAGATG

CTATGTAAATTATCGACAAGACAATTGGGTAGAACTATTACCTATGGCACAATTCGCATA

TAATACATCGGAAACGGAAACCACGAAAATCACACCAGCACGAGCTAATTTTGGGTTTA

ATCCACAAGCGTATAAAATCCCGATACCACAAGAAGTTAATGCCGAATCAGCAATAGTA

CAAGTCGAACAGCTGAAAAATCTCCAAGAGCAACTGGCTCTTUATCTAAGATTCATATCT

TCCAGAACAGCAGCGTACTACAATACGAAACGTAGTATGGAACCTACGCTTAAAGAGGG

GGATAAAGTTTATTTGCTACGACGAAACATCGAAACCAAGAGACCAAGCAATAAACTCG

ACCACAGGAAACTAGGACCATTCAAGATTGATAAGGTAATAGGAACGGTTAATTATCGA

TTGAAATTACCAGACACAATGAATATCCACCCAGTATTCCACATATCCTTGCTCGAACCA

GCACCACCAGGAGCGCCAAATGCGCCATTTACAGAAATTGAACCAG

TCAACCCAAACGCCATATACGATGTCGAAACAATACTAGACTGCAAATACGTCAGAAAC

AAGGTCAAGTATTTGATCAAATGGTTAGACTACCCACATTCAGAAAACACATGGGAATT

CAAGGAGGATCTCAGCTGCCCTGAGAAGCTACGGGCATTCCACCTGAAGTACCCACACC

TGCCAGTAAAGCCTCAAGATCCG

CTTCGGACAACTCAGGCAAAGAAGGATCGAAGAAGTCGAAGGAAGAAGAATCAATAG

SEQ ID NO: 18—LTR for siR5
>BC1G_07532-retrotransposable element Tf2 1 protein type 1
ATGGCATCCAGAGCTACCGCCACACGTCAATCTGCCGGAGACACCAACGACATCGAGAT

GACCGACGCCCCAAAGGAGATCACTATCAACGAAACCCTTAAGATCGCCTTACCAGACA

AGTACCAAGGTAGTCGACAAGAGCTCGATACTTTCCTCTTACAACTTGAGATCTACTTTC

```
GATTCAATGAGGACAAGTTCACTACCAAGGAATCCAAGAGTATATGGGCCGCATCATAC

CTTCGAGGTGAAGCAACCAAATGGATCCAACCATATTTGCGCGACTATTTCGAGCATGAC

GATAAGGATCGTATGCAACCCACCCGAACAATCTTCAATAGTTTTGAAGGATTTAAGACA

GAGATTCGTAGAATCTTCGGAAATTCCAACGAGTTAGAGGTAGCGGAAGATAAGATCTT

CAACCTCAAGCAGACAGGATCAGCATTGAAATATGCTACGGAATTTCGAAGATATGCTG

GAACAACCAAGTGGGACGAAATCGCTATCATGAGTCACTACCGCAAGGGACTCAAACCA

GAAGTCAGACTGGAATTAGAAAGATCTGCCGAGAGTACAGATCTGAACGATCTAATTCA

GGACTCCATCGAATCAGATGATCGTCTCTACAGATATCGACAAAGCCAGAGATCATACA

AACCCCAAGGAAATCAGAAGCAAGGGCGTTACCGCAAAAATGAGGGTAGACCACGTTA

CAATCCACAGAGATACGGAGACCCCATGGAACTAGACGCCACGCACTACACAAACGGGA

ACGATGACTCGGAAAAGAGACGAAGACGAGAAAACAACTTATGCTTTGAATGTGGAAA

AGCAGGGCACCGAGCAGCAGACTGCCGAAGCAAGAAGACAGGAGGAAAAAGGGGCAA

CTTCAAACCTAAGTTCGGCAAAGGCCAACTTAACGCTACCTTTACAATCCCAGAAAATCC

AACTAAATCCGAAAATACTGAGACTTTCACCGTTGAGGAATTCCAGCAA1TACTAAAGG

AATTACCACGAAATCAAGAGGGCATGAATGCAATAGACTTATGGGAGCAAGAGTATTAC

AGAACCCCAACACCCTCTGTGACAGAAGAAAGTCATCAGGACGAGGCAGAAGCAGACC

ACGCCACGATGAGCTGGACAGCTTGCTATGATGAATTCTGCGGAATCCATCGATCAGATA

AAGAAGCAACCGGATGGTCCCCTAAGAAGAGAAAGACGAAGAACCATCAGAATAATGT

AACATGCGAGGATTTAACTCCCAATACTAACTTCGCAAGAAGTTCGCAAAGTTACCCAGC

AGTTAAATGCTACGGGACAGGCAGGACAGATATACTGCAAGGTTCAGATAAATGGACAC

ATACAATCAGCCATGATAGATTCAGGGGCTACAGGAAATTTTATTGCACCGGAAGCTGT

AAAGTACTTGGGAATACCACTTCAAACGAAACAACACCCCTATCGATTGCAGGACACGC

TAGAGGCGTCCGCGAGACGTAACACGCGCCAAGGAGAGTTGAACGCGAACAACACCGG

CGACGTAGGACACCCAGTCCAGGGTCCTCCATTAAGAGCGAAGGCCAGTACACCTCCTC

TACAAATGCAGAAGCCAACGACACGGCACGAAATCGCAATCGAGGCAAAAGAAAGGCC

TACGATACCAGAACAGTACAAGAAATATGAACATGTTTTCAAAGAACCAGGGATCCATG

AGGCTTTACCGGAACACAAGCCATGGGATCATGAGATAATATTGGAGGAAGGCAAGATG

CCTGTGCACACCCCAATTTATTCAATGTCAGCCGATGAGTTAAAAAGGCTCAGAGAATAC

ATCGACGACAATTTAGCCAAGGGATGGATCAGGGAATCCGCGTCCCAAGTGGCCAGTCC

AACTATGTGGGTACCCAAGAAGGATGGACCCGATAGACTAGTTGTAGACTATAGAAAGC

TTAACACACTCACTAAGAAGGATCGATATCCACTTCCATTAGCTACGGAATTAAGAGATC

GGTTAGGCGGAGCTACGATATTTACCAAGATGGACCTACGTAATGGTTACCACTTGATCA

GAATGAAGGAAGGCGAAGAATGGAAGACCGCTTTCAAAACAAGATACGGGCTATACGA

GTACCAAGTTATGCCGTTCGGGCTAACCAACGCACCAGCTACTTTCATGAGGCTTATGAA

CAATGTGTTGTCACAATACTTGGATACTTGCTGTATATGCTACTTGGACGACATCCTAGT

ATATTCAAACAACAAGGTTVAACACATTAAGGACCTTTAGCAACATCCTCGAAAGCCTAT

CCAAGGCACTACTTGCTGTGCAAACCAAGCAAATGCGAATTCCATGTCACAGAGACAGAA

TTCTTGGGATTCACCGTATCAAGCCAAGGGCTCAAGATGAGCAAAGACAAGGTTAAGGC

AGTGCTCGAATGGAAGCAGCCAACCACAATCAAGGAAGTACAATCCTTTCTAGGGTTCG

TCAACTTCTACAGAAGATTTATCAAGGGTTATTCAGGGATTACTACACCCTTGACCACGT

TAACCAGAAAAGATCAAGAAAGCTTCGAATGGACTGCCATAGCACAGGAGTCATTCGAT
```

-continued

```
ACGCTCAAACAAGCAGTGGCAGAAGAGCCAATACTATTGACTTTTGACCCAGAGAAAGA

AATCATAGTGGAGACGGACTCCTCGGATTTCGCTATAGGAGCAGTTCTGAGCCAACCGG

GCCAGAATGGAAAATACCAGCCAATCGCATTCTACTCCCGAAAACTATCACCAGCCGAA

TTGAATTACGAGATATATGACAAAGAATTGCTGGCGATAGTCGATGCATTTAGAGAATG

GCGAGTATATTTGGAAGGATCGAAATACACAGTACAGGTGTATACAGATCATAAGAACT

TGGTTTACTTCACCACAACGAAGCAGTTAAACAGACGACAGGTCAGATGGTCGGAGACC

ATGGCCAACTACAATTTCAGAATTTCATATGTCAAAGGATCAGAAAACGCTAGAGCCGA

CGCTCTTAGCCGAAAACCAGAATATCAAGAAAACAAAACGTACGAGTCATACGCTATAT

TCAAGAAAGACGGCGAATCACTGGTTTACAATGCACCACAGCTTGCAGCAACACACCTG

TTGGAAGACAACTACCTTAGGAAACAGATCCAATCACACTACGACAAGGATGCTACTGC

CACACGCATACGCAAGACAATAGAACCAGGATTCACTATAGAAATGATACCATATACT

TTCATGGAAAAGTATACATTCCGAGTCAAATGACCAAGGAATTTGTGACGGAACAACA

TGGGTTGCCGGCACATGGACACCAAGGAATTGCAAGGACATTTGCAAGAATACGGGAAA

TCAGTTACTTCCCACGAATGAGAACGATAGTTGAAGAAGTTGTTGGAAATTGTGACACCT

GCATACGAAACAAGTCATCACGGCATGCTCCGTATGGTCAGCTCCAGACCCCAGACATG

CCTTCTCAGCCATGGAAGTCCATCACATGGGACTTTGTGGTCAAACTACCACTCTCAAAG

GATCCTACTACAGGAATTGAGTACGACGCGATACTCAATATAGTAGACAGGCTAACGAA

ATTTGCATATATGATACCATTCAAGGAAACATGGGATGCTGAACAACTAGCATATGTGTT

CCTAAGGATCATAGTAAGCATACACGGAGTACCAGATGAGATAATCTCGGATCGAGACA

AGCTCTTTACCTCGAAATTCTGGACTACCTTATTAGCACTTATGGGTATCAAGAGAAAGC

TATCGACATCTTTCCACCCACAAACAGATGGTCAAACAGAGAGGACCAATCAGACAATG

GAAGCATATCTTAGATGCTATCGTATAAAATCCCGATACCACAAGAAGTTAATGCCGAAT

CAGCAATAG
SEQ ID NO: 19—LTR for siR5
>BC1G_09712-enzymatic polyprotein
ATGGCATCCAGAGCTACCGCCACAGGTCAGTCTACCGAAGATACCAACGACATCGAGAT

GACCGATGCCCCAAAGGAGATCACTATCAACGAAACACTTAAGATCGCCTTACCAGACA

AGTACCAAGGTAGTCGACAAGAGCTCGATACTTTCCTCTTACAACTTGAGATCTACTTCC

GATTCAATGAAGACAAGTTCACTACCAAGGAATCCAAGAGCATATGGGCTGCATCATAC

CTCCGAGGTGAAGCAACCAAATGGATTCAACCATATTTGCGCGACTATTTCGAGCATGAC

GATAAGGATCGCATGCAACCCACCCGAACAATCTTCAATAGTTTTGAAGGATTTAAGAC

AGAGATTCGTAGAATCTTCGGAAATTCCAACGAGTTAGAGGTAGCGGAAGATAAGATCT

TCAACCTCAAGCAGACAGGATCAGCATTGAAATATGCTACGGAATTTCGAAGATATGCT

GGAACAACCAAGTGGGACGAAATCGCTATCATGAGTCACTACTGTAAGGGACTCAAACC

AGAAGTCAGACTAGAGTTAGAAAGATCTGCCGAGAGTACAGATCTGAACGATCTAATTC

AGGACTCCATCGAATCAGATGATCGTCTCTATAGATATCGACAAAGCCAAAGATCATAC

AAACCCCAAGGAAACCAAAAGCAAGGGCGTTACCGCAAGAATGAGGGTAGACCACGTT

ACAATCCACAGAGATACGGAGACCCCATGGAACTAGACGCCACGCACTACACAAACGGG

AACGATGACTCAGAAAAGAGACGAAGACGAGAAAACAACTTATGCTTTGAATGTGGAA

AAGCAGGGCACCGAGCAGTAGACTGCCGAAGCAAGAAGACAGGAGGAAAAAGGGGCA

ACTTCAAACCTAAGTTCGGCAAGGGCCAACTTAACGCCACCTTTGCCATCTCAGAAAACT
```

-continued

```
CAACTAAAACCGAAAATACTGAGACTTTCACCGTTGAGGAATTTCAGCAATTACTAAAG

GAATTACCACGAAATAAAGAGGGCATGAATGCAATAGACTTATGGGAACAAGAGTATTA

CAGAACCCCAACACCCTCTGTGACAGAAGAAAGTCACCAGGACGAGGCAGAAGCGGAC

CACGCCACGATGAGCTGGACAGCTTGCTATGATGAATTCTGCGGAATCCATCGATCAGAT

AAAGAAGCAACCGGATGGTTCCCCAAGAAAAGGAAGACGAAGAACCATCAGAATAATG

TAACATGCGAGGATTTAACTCCCAATATAACTTCGCAAGAAGTTCGCAAAGTTACCCAGC

AGTTGAATGCTACGGGACAGGCAGGACAAGTGTACTGCAAGGTCCAGATAAATGGACAC

ATACAATCAGCCATGATAGATTCAGGGGCTACAGGAAATTTTATTGCACCAGAAGCTGC

AAAGTACTTGGAAATACCACTTCAAACGAAACAACACCCCTATCGATTGCAGGACACGC

TAGAGGCGTCCGCGAGACGTAACACGCGCCAAGGGGAGTTGAACGCAACAACACCGG

CGACGTAGGACACCCAGTCCAGGGTCCTCCATTAAGAGCGAAGGCCAGTACACCTCCTC

TACAAATGCAGAAGCCAACGACACGGCACGAAATCGCAATCGAGGCAAAAGAAAGGCC

TACGATACCAGAACAGTACAAGAAATATGAACATGTTTTCAAAGAACCAGGGATCCATG

AGGCTTTACCGGAACACAAGCCATGGGATCATGAGATAATATTGGAGGAAGGCAAGATG

CCTGTGCACACCCCAATTTATTCAATGTCAGCCGATGAGTTAAAAAGGCTCAGAGAATAC

ATCGACGACAATTTAGCCAAGGGATGGATCAGGGAATCCGCGTCCCAAGTGGCCAGTCC

AACTATGTGGGTACCCAAGAAGGATGGACCCGATAGACTAGTTGTAGACTATAGAAAGC

TTAACGCACTCACTAAGAAGGATCGATATCCACTTCCATTAGCTACGGAATTAAGAGATC

GATTAGGCGGAGCTACGATATTCACCAAGATGGACCTACGTAATGGTTACCACTTGATCA

GAATGAAGGAAGGCGAAGAATGGAAAACCGCTTTCAAAACAAGATACGGGCTATACGA

GTACCAAGTTATGCCATTCGGGCTAACCAACGCACCAGCTACTTTCATGAGGCTTATGAA

CAATGTGTTGTCACAATATTTGGATACTTGCTGTATATGCTACTTGGACGACATCCTAGTA

TATTCAAACAACAAGGTTCAACACATTAAGGACGTTAGCAACATCCTCGAAAGTCT

ATCCAAAGCAGACTTGCTGTGCAAACCAAGCAAATGCGAATTCCATGTCACAGAAACAG

AATTCTTGGGATTCACCGTATCAAGCCAAGGGCTCAAGATGAGCAAAGACAAGGTTAAG

GCAGTGCTCGAATGGAAGCAGCCAACCACAATCAAGGAGGTACAATCCTTTCTAGGGTT

CGTCAACTTCTACAGAAGATTTATCAAGGGTTATTCAGGGATTACTACACCCTTGACCAC

GTTAACCAGAAAAGATCAAGGAAGCTTCGAATGGACTGCCAAAGCACAGGAGTCATTCG

ATACACTCAAACAAGCAGTGGCAGAAGAACCAATACTGTTGACTTTTGACCCAGAGAAA

GAAATCATAGTGGAAACGGATTCCTCAGATTTCGCTATAGGAGCAGTTCTGAGCCAACC

GGGCCAGAATGGAAAATACCAGCCAATCGCATTCTACTCCCGAAAACTATCACCAGCTG

AGTTAAATTACGAGATATATGACAAAGAATTACTGGCAATAGTCGATGCATTTAGAGAA

TGGCGAGTATATTTGGAAGGATCGAAATACACAGTACAGGTGTATACAGATCATAAGAA

CTTGGTTTACTTCACCACAACGAAGCAGTTAAACAGACGACACGTCAGATGGTCGGAGA

CCATGGCCAACTACAATTTCAGAATTTCATATGTCAAAGGATCAGAAAACGCTAGAGCC

GACGCTCTTAGCCGAAAACCAGAATATCAAGAAAACAAAACGTACGAGTCATACGCTAT

ATTCAAGAAAGACGGCGAATCACTGGTCTACAATGCACCACAGCTTGCAGCAACACACC

TGTTGGAAGACAACCACCTCAGGAAACAGATCCAATCACACTACAACAAGGATGCTACT

GCCACACGCATACGCAAGACAATAGAACCAGGATTCACTATAGAAGATGATACCATATA

CTTTCATGGAAAAGTATACATTCCGAGTCAAATGACCAAGGAATTTGTGACGGAACAA

CACGGATTGCCGGCACATGGACACCAAGGAATTGCAAGGACATTTGCAAGAATACGGGA
```

```
AATCAGTTACTTCCCACGAATGAGAACGATAGTTGAAGAAGTTGTTGGAAATTGTGACA

CCTGCATACGAAACAAGTCATCACGACATGCTCCGTATGGTCAGCTCCAGACCCCAGAC

ATGCCTTCTCAGCCATGGAAGTCCATCACATGGGACTTTGTGGTCAAACTACCACTCTCA

AAGGATCCTACTACAGGAATTGAGTACCTACGCGATACTCAATATAGTAGACAGGCTAAC

GAAATTTGCATATATGATACCATTCAAGGAAACATGGGATGCTGAGCAACTAGCATATG

TGTTCCTAAGGGTCATAGTAAGCATACACGGAGTACCAGATGAGATAATCTCGGATCGA

GACAAGCTCTTTACCTCGAAATTCTGGACTACCTTATTAGCACTTATGGGTATCAAGAGA

AAGCTATCGACATCTTTCCACCCACAAACAGATGGTCAAACAGAGGACCAATCAGAC

AATGGAAGCATATCTTAGATGCTATCGTATAAAATCCCGATACCACAAGAAGTTAATGCC

GAATCAGCAATAG

SEQ ID NO: 20—LTR for siR5
>BC1G_15972-enzymatic polyprotein
ATGGCATCCAGAGCTACCGCCACAGGTCAATCTGCCGGAGACACCAACGACATCGAGAT

GACCGACGCTCCAAAGGAGATCACTATCAACGAAACCCTTAAGATCGCCTTACCAGACA

AGTACCAAGGTAGTCGACAAGAGCTCGATACTTTCCTCTTACAACTTGAGATCTACTTCC

GATTCAATGAGGACAAGTTCACTACCAAGGAATCCAAGAGCATATGGGCCGCGTCATAC

CTTCGAGGTGAAGCAACCAAATGGATTCAACCATATTTGCGCGACTATTTCGAGCATGAC

GATAAGGATCGCATGCAACCCACCCGAACAATCTTCAATAGTTTTGAAGGATTTAAGAC

AGAGGTTCGTAGAATCTTCGGAAATTCCAACGAGTTAGAGGTAGCGGAAGATAAGATCT

TCAACCTCAAGCAGACAGGATCAGCATTGAAATATGCTACGGAATTTCGAAGATATGCT

GGAACAACCAAGTGGGACGAAATCGCTATCATGAGTCACTACCGCAAGGGACTCAAACC

AGAAGTCAGACTAGAATTAGAAAGATCTGCCGAGAGTACAGATCTAAACGATCTAATTC

AGGACTCCATCGAATCAGATGATCGTCTCTACAGATATCGACAAAGCCAAAGATCATAC

AAACCCCAAGGAAATCAGAAGCAAGGGCGTTACCGCAAGAATGAGGGTAGACCACGTT

ACAATCCACAGAGATACGGAGACCCCATGGAACTAGACGCTACGCACTACACAAACGGG

AACGATGACTCAGAAAAGAGACGAAGACGAGATAACAACTTATGCTTTGAATGTGGAAA

AGCAGGGCACCGAGCAGCAGACTGCCGAAGCAAGAAGACAGGAGGAAAAAGGGGCAA

CTTCAAACCTAAGTTCGGCAAGGGCCAACTTAATGCCACCTTTGCAATCTCAGAAAACTC

AACTAAACCCGAAAATACTGAGACTTTCACCGTTGAGGAATTCCAGCAATTATTAGAGG

AATTACCACGAAACCAAGAGGGCATGAATGCAATAGACTTATGGGAACAAGAGTATTAC

AGAACTCCAACACCUCTGTGACAGAAGAAAGTCACCAGGACGAGGCAGAAGCGGACC

ACGCCACGATAAGCTGGACAGCTTGCTATGACGAATTCTGCGGAATCCATCGATCAGAT

AAAGAAGCAACCGGATGGTTCCCCAAGAAGAGAAAGACGAAGAACCGACAGAATAATG

TAACATGCAAGGATTTAACTCCAAATGTAACTTCGCGAAAAGTTCGCAAAGTTACACAG

CAATTGAATGCTACGGGACAGGCAGGACAAATATACTGCACGGTTCAGATAAATGGACA

CATACAATCAGCCATGATAGATTCAGGGGCTACAGGGAATTTTATTGCACCAGAAGCTG

CAAAGTACTTGGAAATACCACTTCAAACGAAACAACACCCCTACCGATTGCAGTTAGTTG

ACGGACAGCTAGCAGGGTCTGACGGAAAGATTTCGCAGGAGACAATCCCAGTACGAATG

GGCATAACCCAACATACAGAGGTTATACAGCTTGACGTTGTGCCATTGGGCCAACAACA

GATCATCTTAGGAATGCCATGGTTAAAGGCACATAATCCGAAAATAGATTGGGCACAAG

GAATTGTGACATTTGATCAGTGCAAAAGCGGTCACAGGGACACGCTAGAGGCGTTCGCG
```

-continued

```
AGACGTAACACGCGCCAAGGAGAGTTGAACGCGAACAACACCGGCGACGTAGGACACC
CAGTCCAGGGTCCTCCATTAAGAGCGAAGGCCAGTACACCTCCTCTACAAATGCAGAAG
CCAACGACACGGCACGAAATCGCAATCGAGGCAAAAGAAAAGCCTACGATACCAGAAC
AGTACAAGAATTATGAACATGTTTTCAAAGAACCAGGGATCCATGAGGCTTTACCGGAA
CACAAGCCATGGGATCATGAGATAATATTGGAGGAAGGCAAGATGCCTGTGCACACCCC
AATTTATTCAATGTCAGCCGATGAGTTAAAGAGGCTCAGAGAGTACATCGACGACAATTT
AGCCAAGGGATGGATCAGGGAATCCGCGTCCCAAGTGGCCAGTCCAACTATGTGGGTAC
CCAAGAAGGATGGACCCGATAGACTAGTTGTAGACTATAGAAAGCTTAACGCACTCACT
AAGAAGGATCGATATCCACTTCCATTAGCTACGGAATTAAGAGATCGATTAGGCGGAGC
TACGATATTTACCAAGATGGACCTACGTAATGGTTACCACTTGATCAGAATGAAGGAAG
G
CGAAGAATGGAAAACCGCTTTCAAAACAAGATACGGGCTATACGAGTACCAAGTTATGC
CATTCGGGCTAACCAACGCACCAGCTACTTTCATGAGGCTTATGAACAATGTGTTGTCAC
AATATTTGGATACTTGCTGTATATGCTACTTGGACGACATCCTAGTATATTCAAACAACA
AGGTTCAACACATTAAGGACGTTAGCAACATCCTCGAAAGCCTATCCAAGGCAGACTTG
CTGTGCAAACCAAGCAAATGCGAATTCCATGTCACAGAGACAGAATTCTTGGGATTCAC
CGTATCAAGCCAAGGGCTCAAGATGAGCAAAGGCAAGGTTAAGGCAGTGCTCGAATGGA
AGCAGCCGACCACAATCAAGGAAGTACAATCCTTTCTAGGGTTCGTCAACTTCTACAGAA
GATTTATCAAAGGTTATTCAGGGATTACTACACCCTTGACCACGTTAACCAGAAAAGATC
AAGGAAGCTTCGAATGGACTGCCAAAGCACAGGAGTCATTCGATACGCTCAAACAAGCA
GTGGCAGAAGAGCCAATACTATTGACTTTTGACCCAGAGAAAGAAATCATAGTGGAGAC
GGACTCCTCGGATTTCGCTATAGGAGCAGTTCTGAGCCAACCGGGTCAGAATGGAAAAT
ACCAGCCAATCGCATTCTACTCCCGAAAACTATCACCAGCTGAGTTGAATTACGAGATAT
ATGACAAAGAATTACTGGCGATAGTCGATGCATTTAGAGAATGGCGAGTATATTTGGAA
GGATCGAAATACACAGTACAGGTGTACACAGATCATAAGAACTTGGTTTACTTCACCAC
AACGAAGCAGTTAAACAGACGACAGGTCAGATGGTCGGAGACCATGGCCAACTACAACT
TTAGAATTTCATATGTCAAAGGATCAGAAAATGCTAGAGCCGACGCTCTTAACCGAAAA
CCAGAATATCAAGAAAACAAAGCGTACGAGTCATACGCTATATTCAAGAAAGACAGCGA
ATCACTGGTTTACAATACACCACAGCTTGCAACAACACACCTGTTGGAAGACAACCACCT
CAGGAAACAGATCCAATCACACTACGACAAGGATACTACTGCCACACGCATACGCAAAA
CAATAGAACCAGGATTCACTATAGAAAATGATACCATATACTTTCATAGAAAAGTATAC
ATTCCGAGTCAAATGACCAAGGAATTTGTGACGGAACAACACGGGTTGCCGGCACATG
GACACCAAGGAATTGCAAGGACATTTGCAAGAATACGGGAAATCAGTTACTTCCCACGA
ATGAGAACGATAGTTGAAGAAGTTGTTGGAAATTGTGACACCTGCATACGAAACAAGTC
ATCACGACATGCTCCGTATGGTCAGCTCCAGACCCCAGACATGCCTTCTCAGCCATGGAA
GTCCATCACATGGGACTTTGTGGTCAAACTACCACTCTCAAAGGATCCTACTACAGGAAT
TGAGTACGACGCGATACTCAATATAGTAGACAGGCTAACGAAATTTGCATATATGATAC
CATTCAAGGAAACATGGGATGCTGAGCAACTAGCATATGTGTTCCTAAGGATCATAGTA
AGCATACACGGAGTACCAGATGAGATAATCTCGGATCGAGACAAGCTCTTTACCTCGAA
ATTCTGGACTACCTTATTAGCACTTATGGGTATCAAGAGAAAGCTATCGACATCTTTCCA
CCCACAAACAGATGGTCAAACAGAGAGGACCAATCAGACAATGGAAGCATATCTTAGAT
```

```
GCTATGTAAATTATCGACAAGACAATTGGGTAGAGCTATTACCCATGGCACAGTTCGCAT

ACAATACATCAGAAACGGAAACCACGAAAATCACACCAGCACGAGCTAATTTTGGGTTT

AATCCACAAGCGTATAAAATCCCGATACCACAAGAAGTTAATGCCGAATCAGCGATAGT

ACAAGTCGAACAGTTGAAAGATCTCCAAGAGCAACTGGCTCTTGATCTAAGATTCATATC

TTCCAGAACAGCAGCGTACTACAATACGAAACGTAGTATGGAACCTACGCTTAAAGACG

GGGATAAAGTTTATTTGCTACGACGAAACATCGAAACCAAGAGACCAAGCAATAAACTC

GACCACAGGAAACTAGGACCATTCAAGATTGATAAGGTAATAGGAACGGTTAATTATCA

ATTGAAATTACCAGACACAATGAATATCCACCCAGTATTCCACATATCCTTGCTCGAACC

AGCACCACCAGGAGCGCCAAATGCGCCATTTACAGAAATTGAACCAG

TCAACCCAAACGCCATATACGATGTCGAAACAATACTAGACTGCAAATACGTCAGAAAC

AAGGTCAAGTATTTGATCAAATGGTTAGACTACCCACATTCAGAAAACACATGGGAACT

CAAGGAAGATCTCAGCTGCCCTGAGAAACTACGGGCATTCCACCTGAAGTACCCACATC

TGCCAACAAAGCCTCAAGCTCCG

CATCAGACAACAAAGGCAACGAGGGGTCGAAGAAACCAAAAGAAGAACCACTAG

SEQ ID NO: 21-LTR for siR5
>BC1G_13999 retrotransposable element Tf2 1 protein type 1
ATGTGGGTACCCAAGAAGGATGGACCCGATAGACTAGTTGTAGACTATAGAAAGCTTAA

CGCACTCACTAAGAAGGATCGATATCCACTTCCATTAGCTACGGAATTAAGAGATCGATT

AGGCGGAGCTACGATATTCACCAAGATGGACCTACTATATTCAAACAACAAGGTTCAAC

ACATTAAGGACGTTAGCAACATCCTCGAAAGCCTATCCAAGGCAGACTTGCTGTGCAAA

CCAAGCAAATGCGAATTCCATGTCACAGAGACAGAATTCTTGGGATTCACCGTATCAAG

CCAAGGGCTCAAGATGAGCAAAGGCAAGGTTAAGGCAGTGCTCGAATGGAAGCAGCCG

ACCACAATCAAGGAAGTACAATCCTTTCTAGGGTTCGTCAACTTCTACAGAAGATTTATC

AAAGGTTATTCAGGGATTACTACACCCTTGACCACGTTAACCAGAAAAGATCAAGGAAG

CTTCGAATGGACTGCCAAAGCACAGGAGTCATTCGATACGCTCAAACAAGCAGTGGCAG

AAGAGCCAATACTATTGACTTTTGACCCAGAGAAAGAAATCATAGTGGAGACGGACTCC

TCGGATTTCGCTATAGGAGCAGTTCTGAGCCAACCGGGTCAGAATGGAAAATACCAGCC

AATCGCATTCTACTCCCGAAAACTATCACCAGCTGAGTTGAATTACGAGATATATGACAA

AGAATTACTTTGCGATAGTCGATGCATTTAGAGAATGGCGAGTATATTTGGAAGGATCGA

AATACACAGTACAGGTGTACACAGATCATAAGAACTTGGTTTACTTCACCACAACGAAG

CAGTTAAACAGACGACAGGTCAGATGGTCGGAGACCATGGCCAACTACAACTTTAGAAT

TTCATATGTCAAAGGATCAGAAAATGCTAGAGCCGACGCTCTTAGCCGAAAACCAGAAT

ATCAAGAAAACAAAACGTACGAGTCATACCTCTATATTCAAGAAAGACGGCGAATCACTG

GTTTACAATGCACCACAGCTTGCAGCAACACACCTGTTGGAAGACAACCACCTCAGGAA

ACAGATCCAATCACACTACGACAAGGATGCTACTGCCACACGCATACGCAAGACAATAG

AACCAGGATTCACTATAGAAAATGATACCATATACTTTCATGGAAAAGTATACATTCCG

AGTCAAATGACCAAGGAATTTGTGACGGAACAACACGGGTTGCCGGCACATGGACACCA

AGGAATTGCAAGGACATTTGCAAGAATACGGGAAATCAGTTACTTCCCACGAATGAGAA

CGATAGTTGAAGAAGTTGTTGGAAATTGTGACACCTGCATACGAAACAAGTCATCACGA

CATGCTCCGTATGGTCAGCTCCAGACCCCAGACATGCCTTCTCAGCCATGGAAGTCCATC

ACATGGGACTTTGTGGTCAAACTACCACTCTCAAAGGATCCTACTACAGGAATTGAGTAC
```

-continued

```
GACGCGATACTCAATATAGTAGACAGGCTAACGAAATTTGCATATATGATACCATTCAA

GGAAACATGGGATGCTGAGCAACTAGCATATGTGTTCCTAAGGATCATAGTAAGCATAC

ACGGAGTACCAGATGAGATAATCTCGGATCGAGACAAGCTCTTTACCTCGAAATTCTGG

ACTACCTTATTAGCACTTATGGGTATCAAGAGAAAGCTATCGACATCTTTCCACCCACAA

ACAGATGGTCAAACAGAGAGGACCAATCAGACAATGGAAGCATATCTTAGATGCTATGT

AAATTATCGACAAGACAATTGGGTAGAGCTATTACCCATGGCACAGTTCGCATACAATA

CATCAGAAACGGAAACCACGAAAATCACACCAGCACGAGCTAATTTTGGGTTTAATCCA

CAAGCGTATAAAATCCCGATACCACAAGAAGTTAATGCCGAATCAGCGATATATGGAAC

CTACGCTTAA

SEQ ID NO: 22—LTR for siR5
>BC1G_04888.1 retrotransposable element Tf2 1 protein type 1
(Transcript: BC1T_04888)
ATGGCCAACTACAATTTTAGAATTTCATATGTCAAAGGATCAGAAAACGCTAGAGCCGA

CGCTGTTAGCCGAAAACCAGAATATCAAGAAAACAAAACGTACGAGTCATACGCTATAT

TCAAGAAAGACGGCGAATCACTGGTCTACAATGCACCACAGCTTGCAGCAACACACCTG

TTGGAAGACAACCACCTCAGGAAACAGATCCAATCACACTACAACAAGGATGCTACTGC

CACACCTCATACGCAAGACAATAGAACCAGGATTCACTATAGAAGATGATACCATATACT

TTCATGGAAAAGTATACATTCCGAGTCAAATGACCAAGGAATTTGTGACGGAACAACA

TGGGTTGCCGGCACACGGACATCAAGGGATTGCAAGAACATTTGCAAGAATCCGGGAAA

TCAGTTACTTCCCACGAATGAGAACGATAGTTGAAGAAGTTGTTGGAAATTGTGACACCT

GCATACGAAACAAGTCATCACGACATGCGCCGTATGGTCAGCTCCAGACCCCAGACATG

CCTTCTCAGCCATGGAAGTCCATCACATGGGACTTTGTGGTCAAACTACCACTCTCAAAG

GATCCTACTACAGGAATTGAGTACGACGCGATACTCAATATAGTAGACAGGCTAACGAA

ATTCGCATATATGATACCATTCAAGGAAACATGGGATGCTGAGCAACTAGCATATGTGTT

CCTAAGGATCATAGTAAGCATACACGGAGTACCAGATGAGATAATCTCGGATCGAGACA

AGCTCTTTACCTCGAAATTCTGGACTACCTTATTAGCACTTATGGGTATCAAGAGAAAGC

TATCGACATCTTTCCACCCACAAACAGATGGTCAAACAGAGAGGACCAATCAGACAATG

GAAGCATATCTTAGATGCTATCGTATAAAATCCCGATACCACAAGAAGTTAATGCCGAAT

CAGCGATAG

SEQ ID NO: 23—LTR for siR5
>BC1G_16375.1 hypothetical protein similar to truncated Pol
(Transcript: BC1T_16375)
ATCCAATCACACTACAACAAGGATGCTACTGCCACACGCATACGCAAGACAATAGAACCA

GGATTCACTATAGAAGATGATACCATATACTTTCATGGAAAAGTATACATTCCGAGTCAAA

TGACCAAGGAATTTGTGACGGAACAACATGGGTTGCCGGCACACGGACATCAAGGGATTG

CAAGAACATTTGCAAGAATCCGGGAAATCAGTTACTTCCCACGAATGAGAACGATAGTTG

AAGAAGTTGTTGGAAATTGTGACACCTGCATACGAAACAAGTCATCACGACATGCGCCGT

ATGGTCAGCTCCAGACCCCAGACATGCCTTCTCAGCCATGGAAGTCCATCACATGGGACTT

TGTGGTCAAACTACCACTCTCAAAGGATCCTACTACAGGAATTGACATACACGGAGTACCA

GATGAGATAATCTCGGATCGAGACAAGCTCTTTACCTCGAAATTCTGGACTACCTTATTAGC

ACTTATGGGTATCAAGAGAAAGCTATCGACATCTTTCCACCCACAAACAGATGGTCAAACA

GAGAGGACCAATCAGACAATGGAAGCATATCTTAGATGCTATGTAAATTATCGACAAGACA

ATTGGGTAGAGCTATTACCCATGGCACAGTTCGCATACAATACATCGGAAACGGAAACCAC

GAAAATCACCCCAGCACGAGCTAATTTTGGGTTTAATCCACAAGCGTATAAAATCCCGATA
```

CCACAAGAAGTTAATGCCGAATCAGCAATAGTACAAGTCGAACAGCTGAAAGATCTCCAA

GAGCAACTGGCTCTTGATCTAAGATTCATATCTTCCAGAACAGCAGCGTACTACAATACGA

AACGTAGTATGGAACCTACGCTTAAAGAGGGGGATAAAGTTTATTTGCTACAACGAAACAT

CGAAACCAAGAGACCAAGCAATAAACTCGACCACAGGAAACTAGGACCATTCAAGATTG

ATAAGGTAATAGGAACG

SEQ ID NO: 24—LTR for siR5
>BC1G_06254.1 retrotransposable element Tf2 1 protein type 1
(Transcript: BC1T_06254)
ATGGCATCCAGAGCCACCGCCACAGGTCAGTCTACCGGAGATACCAACGACATCGAGATG

ACCGATGCCCCAAAGGAGATCACTATCAACGAAACACTTAAGATCGCCTTACCAGACAAG

TACCAAGGTAGTCGACAAGAGCTCGATACTTTCCTCTTACAACTTGAGATCTACTTCCGAT

TCAATGAAGACAAGTTCACTACCAAGGAATCCAAGAGCATATGGGCTGCATCATACCTCCG

AGGTGAAGCAACCAAATGGATTCAACCATATTTGCGCGACTATTTCGAGCATGACGATAAG

GATCGCATGCAACCCACCCGAACAATCTTCAATAGTTTTGAAGGATTTAAGACAGAGATTC

GTAGAATCTTCGGAAATTCCAACGAGTTAGAGGTAGCGGAAGATAAGATCTTCAACCTCA

AGCAGACAGGATCAGCATTGAAATATGCTACGGAATTTCGAAGATATGCTGGAACAACCA

AGTGGGACGAAATCGCTATCATGAGTCACTACCGTAAGGGACTCAAACCAGAAGTCAGAC

TAGAGTTAGAAAGATCTGCCGAGAGTACAGATCTGAACGATCTAATTCAGGACTCCATCGA

ATCAGATGATCGTCTCTATAGATATCGACAAAGCCAAAGATCATACAAACCCCAAGGAAAC

CAAAAGCAAGGGCGTTACCGCAAGAATGAGGGTAGACCACGTTACAATCCACAGAGATAC

GGAGACCCCATGGAACTAGACGCCACGCACTACACAAACGGGAACGATGACTCAGAAAA

GAGACGAAGACGAGAAAACAACTTATGCTTTGAATGTGGAAAAGCAGGGCACCGAGCAG

TAGACTGCCGAAGCAAGAAGACAGGAGGAAAAAGGGGCAACTTCAAACCTAAGTTCGGC

AAGGGCCAACTTAACGCCACCTTTGCCATCTCAGAAAACTCAACTAAAACCGAAAATACT

GAGACTTTCACCGTTGAGGAATTTCAGCAATTACTAAAGGAATTACCACGAAATAAAGAG

GGCATGAATGCAATAGACTTATGGGAACAAGAGTATTACAGAACCCCAACACCCTCTGTG

ACAGAAGAAAGTCACCAGGACGAGGCAGAAGCGGACCACGCCACGATGAGCTGGACAG

CTTGCTATGATGAATTCTGCGGAATCCATCGATCAGATAAAGAAGCAACCGGATGGTTCCC

CAAGAAAAGGAAGACGAAGAACCATCAGAATAATGTAACATGCGAGGATTTAACTCCCAA

TATAACTTCGCAAGAAGTTCGCAAAGTTACCCAGCAGTTGAATGCTACGGGACAGGCAGG

ACAAGTGTACTGCAAGGTCCAGATAAATGGACACATACAATCAGCCATGATAGATTCAGGG

GCTACAGGAAATTTTATTGCACCAGAAGCTGCAAAGTACTTGGAAATACCACTTCAAACG

AAACAACATCCCTACCGATTGCAGGACACGCTAGAGGCGTCCGCGAGACGTAACACGCGC

CAAGGGGAGTTGAACGCGAACAACACCGGCGACGTAGGACACCCAGTCCAGGGTCCTCC

ATTAAGAGCGAAGGCCAGTACACCTCCTCTACAAATGCAGAAGCCAACGACACGGCACG

AAATCGCAATCGAGGCAAAAGAAAGGCCTACGATACCAGAACAGTACAAGAAATATGAAC

ATGTTTTCAAAGAACCAGGGATCCATGAGGCTTTACCGGAACACAAGCCATGGGATCATG

AGATAATATTGGAGGAAGGCAAGATGCCTGTGCACACCCCAATTTATTCAATGTCAGCCGA

TGAGTTAAAAAGGCTCAGAGAATACATCGACGACAATTTAGCCAAGGGATGGATCAGGGA

ATCCGCGTCCCAAGTGGCCAGTCCAACTATGTGGGTACCCAAGAAGGATGGACCCGATAG

ACTAGTTGTAGACTATAGAAAGCTTAACGCACTCACTAAGAAGGATCGATATCCACTTCCA

TTAGCTACGGAATTAAGAGATCGATTAGGCGGAGCTACGATATTCACCAAGATGGACCTAC

```
GTAATGGTTACCACTTGATCAGAATGAAGGAAGGCGAAGAATGGAAAACCGCTTTCAAAA

CAAGATACGGGCTATACGAGTACCAAGTTATGCCATTCGGGCTAACCAACGCACCAGCTAC

TTTCATGAGGCTTATGAACAATGTGTTGTCACAATATTTGGATACTTGCTATCAAGGAAGCT

TCGAATGGACTGCCAAAGCACAGGAGTCATTCGATACGCTCAAGCAAGCAGTGGCAGAA

GAACCAATACTGTT

GACTTTTGACCCAGAGAAAGAAATCATAGTGGAGACGGACTCCTCGGATTTCGCTATAGG

AGCAGTTCTGAGCCAACCGGGCCAGAATGGAAAATACCAGCCAATCGCATTCTACTCCCG

AAAACTATCACCAGCTGAGTTAAATTACGAGATATATGACAAAGAATTACTGGCAATAGTC

GATGCATTTAGAGAATGGCGAGCATATTTGGAAGGATCGAAATACACAGTACAGGTATATA

CAGATCATAAGAACTTGGTTTACTTCACCACAACGAAGCAGTTAAACAGACGACAGGTCA

GATGGTCGGAGACCATGGCCAACTACAACTTTAGAATTTCATATGTCAAAGGATCAGAAAA

CGCTAGAGCCGACGCTCTTAGCCGAAAACCAGAATATCAAGAAAACAAAACGTACGAGTC

ATACGCTATATTCAAGAAAGACGGCGAATCACTGGTCTACAATGCACCACAGCTTGCAGCA

ACACACCTGTTGGAAGACAACCACCTCAGGAAACAGATCCAATCACACTACAACAAGGAT

GCTACTGCCACACGCATACGCAAGACAATAGAACCAGGATTCACTATAGAAGATGATACCA

TATACTTTCATGGAAAAGTATACATTCCGAGTCAAATGACCAAGGAATTTGTGACGGAAC

AACATGGGTTGCCGGCACACGGACATCAAGGGATTGCAAGAACATTTGCAAGAATCCGGG

AAATCAGTTACTTCCCACGAATGAGAACGATAGTTGAAGAAGTTGTTGGAAATTGTGACA

CCTGCATACGAAACAAGTCATCACGACATGCGCCGTATGGTCAGCTCCAGACCCCAGACA

TGCCTTCTCAGCCATGGAAGTCCATCACATGGGACTTTGTGGTCAAACTACCACTCTCAAA

GGATCCTACTACAGGAATTGAGTACGACGCGATACTCAATATAGTAGACAGGCTAACGAAA

TTTGCATATATGATACCATTCAAGGAAACATGGGATGCTGAGCAACTAGCATATGTGTTCCT

AAGGGTCATAGTAAGCATACACGGAGTACCAGATGAGATAATCTCGGATCGAGACAAGCT

CTTTACCTCGAAATTCTGGACTACCTTATTAGCACTTATGGGTATCAAGAGAAAGCTATCGA

CATCTTTCCACCCACAAACAGATGGTCAAACAGAGAGGACCAATCAGAC

AATGGAAGCATATCTTAGATGCTATCGTATAAAATCCCGATACCACAAGAAGTTAATGCCGA

ATCAGCAATAG

SEQ ID NO: 25—LTR for siR5
>BC1G_08449.1 retrotransposable element Tf2 1 protein type 1
(Transcript: BC1T_08449)
ATGGCATCCAGAGATACCGCCACAGGTCAATCTGCCGGAGACACCAACGACATCGAGATG

ACCGATGCCCCAAAGGAGATCACTATCAACGAAACCCTTAAGATCGCCTTACCAGACAAG

TACCAAGGTAGTCGACAAGAGCTCGATACTTTCCTCTTACAACTTGAGATCTACTTCCGAT

TCAATGAGGACAAGTTCACTACCAAGGAATCCAAGAGTATATGGGCCGCATCATACCTCCG

AGGTGAAGCAACCAAATGGATTCAACCATATTTGCGCGACTATTTCGAACATGACGATAAG

AATCGCATGCAACCCACCCGAACAATCTTCAATAGTTTTGAAGGATTTAAGACAGAGATTC

GTAGAATCTTCGGAAATTCCAACGAGTTAGAGGTAGCGGAAGATAAGATCTTCAACCTCA

AGCAGACAGGATCAGCATTGAAATATGCTACGGAATTTCGAAGATATGCTGGAACAACCA

AGTGGGACGAAATCGCTATCATGAGTCACTACCGCAAGGGACTCAAACCAGAAGTCAGAC

TGGAATTAGAAAGATCTGCCGAGAGTACAGATCTGAACGATCTAATTCAGGACTCCATCGA

ATCAGATGATCGTCTCTACAGATATCGACAAAGCCAGAGATCATACAAACCCCAAGGAAAT

CAGAAGCAAGGGCGTTACCGCAAGAATGAGGGTAGACCACGTTACAATCCACAGAGGTA
```

```
CGGAGACCCAATGGAACTAGACGCTACGCACTACACAAACGGGAACGATGACTCAGAAA
AGAGACGAAGACGAGAAAACAACTTATGCTTTGAATGTGGAAAAGCAGGGCACCGAGCA
GCAGAGTGCCGAAGCAAGAAGACAGGAGGAAAAAGGGGCAACTTCAAACCTAAGTTCG
GCAAGGGCCAACTTAACGCCACCTTTGCAATCCCAGAAAACCCAACTAAATCCGAAATA
CTGAGACTTTCACCATTGAAGAATTCCAGCAATTACTAGAGGAATTACCACGAAATCAAGA
GGGCATGAATGCAATAGACTTATGGGAACAAGAGTATTACAGAACCCCAACACCCTCTGTA
ACAGAAGAAAGTCACCAGGACGAGGCAGAAGCAGACCACGCCACAATGAGCTGGACAG
CCTGCTATGATGAATTCTGCGGAATTCATCGATCAGATAAAGAAGCAACCGGATGGTTCCC
CAAGAAAAGGAAGACGAAGAACCATCAGAATAATGTAACATGCGAGGATTTAACTCCCAA
TACAACTTCGCAAGAAGTTCGCAAAGTTACCCAGCAGTTGAATGCTACGGGACAGGCAGG
ACAGATATACTGCAAAGTTCAGATAAATGGACACATACAATCAGCCATGATAGATTCAGGG
GCTACAGGAAATTTTATTGCACCAGAAGCTGCAAAGTACTTGGAAATACCACTTCAGACG
AAACAACACCCCTACCGATTGCAGGACACGCTAGAGGCGTCCGCGAGACGTAACACGCG
CCAAGGAGAGTTGAACGCGAACGACACCGGCGACGTAGGACACCCAGTCCAGGGTCCTC
CATTAAGAGCGAAGGCCAGTACACCTCCTCTACAAATGCAGAAGCCAACGACACGGCACG
AAATCGCAATCGAGGCAAAAGAAAAGCCTACGATACCAGAACAGTACAAGAATTATGAAC
ATGTTTTCAAAGAACCAGGGATCCATGAGGCTTTACCGGAACACAAGCCATGGGATCATG
AGATAATATTGGAGGAAGGCAAGATGCCTGTGCACACCCCAATTTATTCAATGTCAGCCGA
TGAGTTAAAAAGGCTCAGAGAATACATCGACGACAATTTAGCCAAGGGATGGATCAGGGA
ATCCGCGTCCCAAGTGGCCAGTCCAACTATGTGGGTACCCAAGAAGGATGGACCCGATAG
ACTAGTTGTAGACTATAGAAAGCTTAACGCACTCACTAAGAAGGATCGATATCCACTTCCA
TTAGCTACGGAATTAAGAGATCGATTAGGCGGAGCTACGATATTTACCAAGATGGACCTAC
GTAATGGTTACCACTTGATCAGAATGAAGGAAGGCGAAGAATGGAAAACCGCTTTCAAAA
CAAGATACGGGCTATACGAGTACCAAGTTATGCCATTCGGGCTAACCAACGCACCAGCTAC
TTTCATGAGGCTTATGAACAATGTGTTGTCACAATATTTGGATACTTGCTGTATATGCTACTT
GGACGACATCCTAGTATATTCAAACAACAAGGTTCAACACATTAAGGACGTTAGCAACATC
CTCGAAAGCCT
ATCCAAGGCAGACTTGCTGTGCAAACCAAGCAAATGCGAATTCCATGTCACAGAGACAGA
ATTCTTGGGATTCACCGTATCAAGCCAAGGGCTCAAGATGAGCAAAGGCAAGGTTAAGGC
AGTGCTCGAATGGAAGCAGCCGACCACAATCAAGGAAGTACAATCCTTTCTAGGGTTCGT
CAACTTCTACAGAAGATTTATCAAAGGTTATTCAGGGATTACTACACCCTTGACCACGTTA
ACCAGAAAAGATCAAGGAAGCTTCGAATGGACTGCCAAAGCACAGGAGTCATTCGATAC
GCTCAAACAAGCAGTGGCAGAAGAGCCAATACTATTGACTTTTGACCCAGAGAAAGAAAT
CATAGTGGAGACGGACTCCTCGGATTTCGCTATAGGAGCAGTTCTGAGCCAACCGGGTCA
GAATGGAAAATACCAGCCAATCGCATTCTACTCCCGAAAACTATCACCAGCCGAATTAAAT
TATGAAATATACGACAAAGAATTACTGGCAATAGTCGATGCATTTAGAGAATGGCGAGTATA
TTTGGAAGGATCGAAATACACAGTACAGGTGTACACAGATCATAAGAACTTGGTTTACTTC
ACCACAACGAAGCAGTTAAACAGACGACAGGTCAGATGGTCGGAGACCATGGCCAACTA
CAATTTTAGAATTTCATATGTCAAAGGATCAGAAAACGCTAGAGCCGACGCTCTTAGCCGA
AAACCAGAATATCAAGAAAACAAAACGTACGAGTCATACGCTATATTCAAGAAAGACGGC
```

-continued

GAATCACTGGTTTACAATGCACCACAGCTTGCAGCAACACACCTGTTGGAAGACAACCAC

CTCAGGAAACAGATCCAATCACACTACGACAAGGATGCTACTGCCACACGCATACGCAAG

ACAATAGAACCAGGATTCACTAAGAAAATGATACCATATACTTTCATGGAAAAGTATACA

TTCCGAGTCAAATGACCAAGGAATTTGTGACGGAACAACATGGGTTGCCGGCACATGGA

CATCAAGGAATTGCAAGGACATTTGCAAGAATACGGGGAATCAGTTACTTCCCACGAATG

AGAACGATAGTTGAAGAAGTTGTTGGAAATTGTGACACCTGCATACGAAACAAGTCATCA

CGACATGCTCCGTATGGTCAGCTCCAGACCCCAGACATGCCTTCTCAGCCATGGAAGTCCA

TCACATGGGACTTTGTGATCAAACTACCACTCTCAAAGGATCCTACTACAGGAATTGAGTA

CGACGCGATACTCAATATAGTAGACAGGCTAACGAAATTTGCATATATGATACCATTCAAGG

AAACATGGGATGCTGAGCAACTAGCATATGTGTTCCTAAGGGTCATAGTAAGCATACACGG

AGTACCAGATGAGATAATCTCGGATCGAGACAAGCTCTTTACCTCGAAATTCTGGACTACC

TTATTAGCACTTATGGGTATCAAGAGAAAGCTATCGACATCTTTCCACCCACAAACAGATG

GTCAAACAG-AGAGGACCAATCAGACAATGGAAGCATATCTTAGATGCTATCGTATAAAATC

CCGATACCACAAGAAGTTAATGCCGAATCAGCGATAG

SEQ ID NO: 26—LTR for siR5
>BC1G_16170.1 hypothetical protein similar to integrase
(Transcript: BC1T_16170)
<u>ATG</u>ACCAAGGAATTTGTGACGGAACAACATGGGTTGCCGGCACACGGACATCAAGGGAT

TGCAAGAACATTTGCAAGAATCCGGGAAATCAGTTACTTCCCACGAATGAGAACGATAG

TTGAAGAAGTTGTTGGAAATTGTACACACCTGCATACGAAACAAGTCATCACGACATGC

GCCGTATGGTCAGCTCCAGACCCCAGACATGCCTTCTCAGCCATGGAAGTCCATCACATG

GGACTTTGTGGTCAAACTACCACTCTCAAAGGATCCTACTACAGGAATTGA

SEQ ID NO: 27—Botrytis LTR genomic DNA sequence
>B. cinerea (B05.10) Botrytis cinerea supercontig 1.56 [DNA] 215700-227000
+
CAAAGGGGGCATTACGCTTCCAACTGCCGAAACCCTGTTGTATGTCAACACTGTAAAGG

A

AGTCACGGATCCAGAGAGTGCCCAGGAACTATGTCACAGCCTTCCCGACAGGGAAACGC

T

TAGACCCAGCTGTTATTCTGAGCGTCCCACTGACGCTGGGTCCCCAAATAGAAGGACGTA

CTACCTTTACCATTATAGCA<u>ATG</u>TTCCAACCAAAAGATAAGCCGATAGCGCTTCGATGCC

TTATCGACTCAGGAGCACAAGCCAACATCATCCAACAATCCAAGTGTATCGAATGGGAC

T

GGCTGCCTATTAAGAAAGGAACAGCTTTAGTATCTGCGAACGGTACCACGATGCCGTCGT

ATGGTAACCATCAGTTCCCCGTCGAAGTAAAAGATCAAAAGGGAGAGAAGAGAACCTTC

A

CCCACGAGTTTACTGCTGCTGTACTAGACTTACCCAAAATCGATGCTATATTTGGATTAC

CCTGGCTACAAGCGGTAAACCCAGATATCGACTGGAAATCGACGTCTCTTCACTATCGCC

CCTCTCTTAGCGACCTCGAAATGATTTVTGCAAGCGAACTCTATAGCGAAGTGAAAAAGG

GCGTCCATGTATATGTTATACTACCAGAGATCCAGCCCCATTACCGTAGAGACAACGGGT

ACCGCCGGGTACTCACGCTCTCCACACTAAATATCCCCGAACAATACCAAGAATACCAA

C

AAGCCTTTTCCGAGGAAGAAAGCAGTACTCTACCAGAACACCACTCGATGGAGCATCGC

A

-continued

TTGATCTCGAAGCCGATTCGAAACCTCCTTGGGGGCCAATCTATTCTTTATCTGAAGAGG
AATCAATAGTATTAAGGGAATACTTAGTAGAATATCAAAAAAAGGGATGGATAAGGAGG
T
CCATTAGTTCGGCAGGAGCGCCAATCATGTTTGTTCCCAAGAAGGGGGGAGGCTATCGG
C
TTTGTGTCGACTACCGGGGTCTAAATAGGATAACCAAAAAGGATCGAACCCCGCTACCC
C
TAATCAGCGAGTCCTTAGACCGACTTCGACAAGGTGTCGTCTTCACTAAATTGGACCTGC
GAGATGCCTACCACCGTATTCGTATCAGGGAAGGCGACGAATGGAAGACGGCGTTCCGC
A
CGCGGTACGGGCAATTCGAATACTTAGTTATGCCATTCGGCCTGACCAATGCTCCAGCAA
CGTTCCAAACATACATCAATCAAGCACTGTCAGGCTTGACAGACACCATATGCGTAGTGT
ACCTAGATGATATCCTGATTTACTCTGAGGATAGAGAAAGCCACACGCGGGATGTCCGC
A
GGGTCCTCGAACGCCTTATAGAATACAAGCTGTTCGCAAAACTGAAAAAATGTGTCTTTT
ACACCCATGAGGTTGAATTCCTAGGATTCGTCGTCTCGGGAGCGGGAGTGACGATGGAA
T
CCAGCCGCATTCAAACTATTATAGAATGGCCAACACCTACAAACCTTAGGGAGCTACAG
G
TGTTCCTGGGCTTCGCGAACTTCTATCGACGGTTTATCAGGACCTATTCGACGGTAGCCC
ACGGGATGACCGCCCTTATGAAGGGAACAAAGAAAGGTAAAATGGTAGGGGAGTTTATA
T
GGACAAAGGAGGCCCAAGATGCATTTGAGGCACTAAAGAAAGCATTCACCACGGCACCG
A
TACTCAAGCACTTCGAACCATCGCTCCGCATCATGGTCGAAACCGACTCGTCGGTGTTTG
CTCTAGGATGCATCCTATCGCAACTATTCGAAGGAGGGACTGCAGAAGCACCGATACGA
C
GGTGGCACCCCGTCGCGTTCTATTCGAGAAAGCTGAACCCTGCAGAACAACGATACTTCA
CTCACGATCAGGAATTATTAGCAATATACACTGCATTCATGCAATGGCGCCATTACTTGA
TAGGTAGTCGGCACACAATCGTGGTGAAATCGGACCATAACAGCTTACAACATTTTATGG
TGAAAAAGACCCTCAATGGCAGACAAGCTAGATGGGCGGAAGTACTAGCAGCCTACGAC
T
TCGAAATAGTGTACAGGGCAGGGAAACTGAATCCAGCCGACGGGCCATCGCGCCGCCCC
G
ACTACGCTACCGACACGGAGGGTATCAATGATATGCTACCCACACTCCAGAATAAATTA
A
AAAGTACCGCAGTTATCGCGAGTTTATTTTACGAATCCACCGTGAAAACGGAACCCCTGC
GTATTGCTATTAGTCGCTTGCAAAGGGAAGGGTATAGCTTGCCATTACGTGGACAGTTAG
TTTCACTGGTAAAAACTGGTTGCAAACAGTCGATACCACGTCGGATTGCCAGTGTTTTCG
CATCCGACGAAACGGCATTCGAACCTATATCGGAGTCGATGGGAAAAGCTTTATTGCGG

C

TTCAGAAAGAAGACGATTTTATAAAGAATAAAGAGTACCTAAGACAAAGATTACGTTCC

G

CCGGAGACGCCTCACCACGGCAGGTGGGCGCCGACGAGCTCCTTAGACACAAGGGGAGC

G

CGTACGTACCGCCAGACAGCGCTCTCAGAGCAGAAATCTTAGAAACGCATCACGATGAC

C

CTATTGGAGGTCATTGGGGTGTCGCTAAAACATTGGAAATACTGAAGTCTAAATATTATT

GGCCTTCAATGAGAAAAGACGTCAAACAACATGTCAAAACATGTGCGGTATGCCAGCGA

A

CCGCTATCAAAAGACATAAGCCACACGGCGAGTTACAGACCCTCCCTATTCCAAAAGGA

C

CCTGGAAAGAGATAACTATGGATTTTATTACAGATTTACCTCCTTCGAAACACGGAAAAC

ACGTATACGATTCTATTCTAGTAGTAGTCGACAGGTTCACGAAGCTAGCCCGATATATCG

CCGTCAACAAGACGATATCGTCTCCTGAATTAGCTGACACTATGGTCAGCACAGTATTTA

AAGACTTTGGTGTGCCAGAGGGCATAGTCTCCGATAGGGACCGCAATTCGTCAGTAAA

T

TTTGGAGTAGCCTAATGTTTTACTTGCGAATCCGTCGTAAGCTGTCGACGGCGTTCCACC

CGCAGACCGACGGTCAAACCGAACGACAAAACCAAAATTTGATTCACTATATAAGTTGC

T

ACACCAACTATAGGCAAGACGACTGGGCATCGCTATTGCCCCTTGCTGAATTCACATATA

ACGCGACATGGCACAGTACAACCAATACAAGCCCATTCCAGGCTATGTATGGGTTCCAA

C

CCACATTCCATTATATCGGCGAGGACGCCGATTTAGAGGGAAGGGCGCCGGCAGCACGC

G

AGCGCATCGACGCTTTAGAGAAAGAAAGAGAAAAGCTGAAAGAATTCTGGAAATCGGC

AA

CCAATCAGAAAAACAAGAACACTACGAAGGGGTCACCACAGCGATATAGCATCGGGGA

CA

AGGTGATGCTAAGCACAAAGAACATTAAACAACTGCGACCTAAGAAAAAATTCTCCGAT

C

GATTTATAGGCCCCTTTGTCGTGACGGGTATAAAAACCAGCGGGCAAGCATACGAACTT

A

GATTACCGCCCACCTACAAGATCCACAATGTATTCCACGTCTCTTTACTCGAACCATGGC

ACGAACGACAGGGTACCGCCGACCCGCCGCCGCCAGAAGAAATTGACGATCACATAGAG

C

ATGAGGTGGAAAGGATTTTAGCACATAGAAAAAGAGGCAGAGGTGTGCAATACCTGGTG

C

GATGGAAGGGCTACCAACCGGCGGAAGACACGTGGGAAGCACCCTACAACCTAGAAAA

TG
CGAAAGCAGCGATGGGAGAATATCATAAAGAAGAAGCATTACCAATACAGAAAAAGAA
GA
GAACAAGAAAAAAGCTTAAAAATACTTGATACAAAAAGACCTCACGAGACCCACACCCA
G
AACGCATGCATCACACCAAGCTACCCAAAAAGGACTATCCAACAAAGAAACCAGAAAG
GA
CAACTCCTCCGAACCCACAGCATACCGACAACCAAACCCAAGTGACCCATCACGCAAAG
A
GAACTCTGGAAGGTCGAAATCAGTTCCCTAATTCATCTGCCTGATCCAGGAGGTCAGCTG
CAATATCTCGATCGCCAAGAAGGACAGAACCTACATCGCTGGCATATCCCCCGGGACTC
G
CGAGCCCGATCTGATCAACCTCACCCCCCCCACTGATCTCATCTTGATCACCGACTCCTT
CCTCCTCGTTGTCGCGAATCTCGCTGACAGGGCGAGCTCCTGTCGGAAAACCAGCGGCAA
CCCGTTGCCTCTTGGAGACCCGCTCCACATCAGAATTCTCAGAGCGAAGCCTTTGGGGCG
AATCTGCTTGACTATCAGACTCACCAATATAGACTTGTTGAACAGTGCTGGGAGCCCTCT
TTCGGGATTTAAGAGAGCCTACGGGATGAGAGCGGGGTGTCGGTGTGTTGCGAGAGGCA
A
GCTGCGACGACTTAGAAGCGGAAAGGGGAATGGCGGATCTAGTCGCGAGCTTATCGGAC
C
GAGAACGACGAGGCGTAGCAGGAGGAGCGCTTTCTACCCAAGCTTCCAAACAATAAA
G
CCGGTACACTCTCATCCAAGGGGTGACGCGGGGCACCGGTGGTCTGATGAGGTTGATCC
G
ACACATCATCCTCTTCAGGAGCAGACTCTTCGGATTCATTGGGATCCACGATTACACTCC
TCTTCAACTTCGCAGAACCTTTCCGGAGGCCTTGCTGAGCCGTCGTGAAGACAGCGGGGC
CCGTCCGGCTCGATGAAGCAGAAGCATGACGGCGACCTAGGGAACCAGCTACCATATTC
A
GGCCCTGGTTACCACCTGGGGGCCCCGGAGGAGCTTGAACACCCTGCAGTGCGTCGGCG
A
CAGCGCGCACAGCGCGAGGGTGTATAACCGGAGCCATGAACTCCCCTTCTTCGTCCGAGT
TTAAGGCGGCGATTAATGGTGCAGTAGGAGCTGCGGCGGCGACGTCCAAGGCAGGCAGG
T
TATTCTAAGAACCATCAAATCAGCTATCAACAGCACCAAGGGGCAAGAGCAGGGCAACC
G
ACAACGAATCGATACGAATCCACAATGCGCTCCATAAGATCGCCAATTCTACTCAATTTG
GACACCAGAAGAAGAGTCAATTCCTCTGCGGACTGCGGTTTGTGAGTCCCCCCTTGTTTA
ACCTCTTTTCGAAGGAAAGCCTCCACTGCCTTGACGTATCGATTACACCGGCGAATCACC
ACCTCGGAGGCGTCCTCATCCTCTTGGCTATTATCCGGAGTAAGGCACCAAAAGGCATGA
GTCTGATATAAGAGGTTCACGTCGGGAACAAAGCGAGGAGGTATCGGGAGGCAGACTTT

CTTTTGTTTGCGACAATAACTACATTTAGCAGCAGGACCTTTATCAAAATGGCAAAATTCG

TCGTTAGAAGAGACGGCAATTCGCTTAGAACATCGAAGGCAAGTAGGGATAACTAACGCG

GAAGGGGCCGCTGCGGACCGATCAGCGATAGCAGCCGGAGCGATGGGTTGCAGTGCAGCC

ATCTTCGTATGAGTAAATAAGGGGGAATAATCTGATTGTGGGAGATATATCAGAGGCAAG

AAGACCCCCCTTATAGAACTATCGGTGATCTGCCGGTAAGGCGGTGAGGCGCGTAAGAAT

GCCGCCGTTTGCTTGTTTATTGTTTGTAATGCCTAAACAAGATTGGAATTGCTTTTGGAA

TGCGGCGCAGGGTCGGGCATGCAGCGACGCGACGACGCGACCCACATTCCGAGTAAACAA

TACGGAAGGAAGCAAACACTTCTCGGGACGCGAAGTGTAAAGAGAGGGGCTCTGTTACGG

GACAAAACGTGACCGGCTCAATTAGGCACGTGACAGTGGACCTCTCGGGTCTACTGCGTG

CCGAATGGGGCCCGCACACGTATAAATTGTATAATTTGCATAGTTATAGAAAAGCAATGA

AAAGTCTTGGTGCCACAATATACTAGTTGATTCATTTGTTACGGAGGTACCCGCACCGCA

ACATGGATTATAAGATAAACCTAAGGCCTTGGTGTTGGAACCTACGAAAACAGCACTGTA

GGGACAGTTGAATTAAAGGGTAACTAAAGATAGCAGTAACCGAATCAATAAGCAATGATT

AAAAGATAGGTACCTATCTTTTGTTGGCACCTACCCTACAGTAGGCACAGGAGGGATAGC

GGTTATAGGTTATCTAGTAAGCACAGGTTAGATAAGCAGTAGTATCATGTAGGTCACGGG

GCAAGTGTCACGTGATGGATAGACAGGATAGGCAGGCTATCCAGGCTATCCGTGGATAGA

CAGGATAGACAGTCTACCCAAGCTATCCAGACGAGAACGAAGGTCTATATAAGGGAATGG

GTTTCATTACAATGTAGAGCTTCGTGCTCAAGAACAATCATTAGTTTCATTACTATAGTT

ACGAGAATTGCAACCAGTTACAACCTTATTGAATTCCTACTTGAAGTCTAGTCTAAACCA

CCTCGAGAGATCTCTAGACACTTCCACGTGACCCTAGAGGCAGCTCCCGTAACACTTTGA

GCACCCTTTCTGCTTCAAGTACCGATTCGATAACCAACCGCTAATATGGCATCCAGAGCT

ACCGCCACAGGTCAGTCTACCGAAGATACCAACGACATCGAGATGACCGATGCCCCAAAG

GAGATCACTATCAACGAAACACTTAAGATCGCCTTACCAGACAAGTACCAAGGTAGTCG

A

CAAGAGCTCGATACTTTCCTCTTACAACTTGAGATCTACTTCCGATTCAATGAAGACAAG

TTCACTACCAAGGAATCCAAGAGCATATGGGCTGCATCATACCTCCGAGGTGAAGCAAC

C

AAATGGATTCAACCATATTTGCGCGACTATTTCGAGCATGACGATAAGGATCGCATGCAA

CCCACCCGAACAATCTTCAATAGTTTTGAAGGATTTAAGACAGAGATTCGTAGAATCTTC

GGAAATTCCAACGAGTTAGAGGTAGCGGAAGATAAGATCTTCAACCTCAAGCAGACAGG

A

TCAGCATTGAAATATGCTACGGAATTTCGAAGATATGCTGGAACAACCAAGTGGGACGA

A

ATCGCTATCATGAGTCACTACTGTAAGGGACTCAAACCAGAAGTCAGACTAGAGTTAGA

A

AGATCTGCCGAGAGTACAGATCTGAACGATCTAATTCAGGACTCCATCGAATCAGATGA

T

CGTCTCTATAGATATCGACAAAGCCAAAGATCATACAAACCCCAAGGAAACCAAAAGCA

A

GGGCCTTTACCGCAAGAATGAGGGTAGACCACGTTACAATCCACAGAGATACGGAGACCC

C

ATGGAACTAGACGCCACGCACTACACAAACGGGAACGATGACTCAGAAAAGAGACGAA

GA

CGAGAAAACAACTTATGCTTTGAATGTGGAAAAGCAGGGCACCGAGCAGTAGACTGCCG

A

AGCAAGAAGACAGGAGGAAAAAGGGGCAACTTCAAACCTAAGTTCGGCAAGGGCCAAC

TT

AACGCCACCTTTGCCATCTCAGAAAACTCAACTAAAACCGAAAATACTGAGACTTTCACC

GTTGAGGAATTTCAGCAATTACTAAAGGAATTACCACGAAATAAAGAGGGCATGAATGC

A

ATAGACTTATGGGAACAAGAGTATTACAGAACCCCAACACCCTCTGTGACAGAAGAAAG

T

CACCAGGACGAGGCAGAAGCGGACCACGCCACGATGAGCTGGACAGCTTGCTATGATGA

A

TTCTGCGGAATCCATCGATCAGATAAAGAAGCAACCGGATGGTTCCCCAAGAAAAGGAA

G

ACGAAGAACCATCAGAATAATGTAACATGCGAGGATTTAACTCCCAATATAACTTCGCA

A

GAAGTTCGCAAACTTTACCCAGCAGTTGAATGCTACGGGACAGGCAGGACAAGTGTACTG

C

AAGGTCCAGATAAATGGACACATACAATCAGCCATGATAGATTCAGGGGCTACAGGAAA

T

TTTATTGCACCAGAAGCTGCAAAGTACTTGGAAATACCACTTCAAACGAAACAACACCC

```
C
TATCGATTGCAGTTAGTTGATGGACAGCTAGCAGGGTCTGACGGAAAGATTTCGCAGGA
G
ACAATCCCAGTACGAATGGGCATAACCCAACATACAGAGGTTATACAGCTTGACGTTGT
G
CCATTGGGCCAACAACAGATCATCTTAGGAATGCCATGGTTGAAGGCACATAATCCGAA
A
ATAGATTGGGCACAAGGAATTGTGACATTTGATCAGTGCAAAAGCGGTCACAGGGACAC
G
CTAGAGGCGTCCGCGAGACGTAACACGCGCCAAGGGGAGTTGAACGCGAACAACACCG
GC
GACGTAGGACACCCAGTCCAGGGTCCTCCATTAAGAGCGAAGGCCAGTACACCTCCTCT
A
CAAATGCAGAAGCCAACGACACGGCACGAAATCGCAATCGAGGCAAAAGAAAGGCCTA
CG
ATACCAGAACAGTACAAGAAATATGAACATGTTTTCAAAGAACCAGGGATCCATGAGGC
T
TTACCGGAACACAAGCCATGGGATCATGAGATAATATTGGAGGAAGGCAAGATGCCTGT
G
CACACCCCAATTTATTCAATGTCAGCCGATGAGTTAAAAAGGCTCAGAGAATACATCGA
C
GACAATTTAGCCAAGGGATGGATCAGGGAATCCGCGTCCCAAGTGGCCAGTCCAACTAT
G
TGGGTACCCAAGAAGGATGGACCCGATAGACTAGTTGTAGACTATAGAAAGCTTAACGC
A
CTCACTAAGAAGGATCGATATCCACTTCCATTAGCTACGGAATTAAGAGATCGATTAGGC
GGAGCTACGATATTCACCAAGATGGACCTACGTAATGGTTACCACTTGATCAGAATGAA
G
GAAGGCGAAGAATGGAAAACCGCTTTCAAAACAAGATACGGGCTATACGAGTACCAAGT
T
ATGCCATTCGGGCTAACCAACGCACCAGCTACTTTCATGAGGCTTATGAACAATGTGTTG
TCACAATATTTGGATACTTGCTGTATATGCTACTTGGACGACATCCTAGTATATTCAAAC
AACAAGGTTCAACACATTAAGGACGTTAGCAACATCCTCGAAAGTCTATCCAAAGCAGA
C
TTGCTGTGCAAACCAAGCAAATGCGAATTCCATGTCACAGAAACAGAATTCTTGGGATTC
ACCGTATCAAGCCAAGGGCTCAAGATGAGCAAAGACAAGGTTAAGGCAGTGCTCGAATG
G
AAGCAGCCAACCACAATCAAGGAGGTACAATCCTTTCTAGGGTTCGTCAACTTCTACAGA
AGATTTATCAAGGGTTATTCAGGGATTACTACACCCTTGACCACGTTAACCAGAAAAGAT
CAAGGAAGCTTCGAATGGACTGCCAAAGCACAGGAGTCATTCGATACACTCAAACAAGC
```

AGTGGCAGAAGAACCAATACTGTTGACTTTTGACCCAGAGAAAGAAATCATAGTGGAAACG

GATTCCTCAGATTTCGCTATAGGAGCAGTTCTGAGCCAACCGGGCCAGAATGGAAAATAC

CAGCCAATCGCATTCTACTCCCGAAAACTATCACCAGCTGAGTTAAATTACGAGATATAT

GACAAAGAATTACTGGCAATAGTCGATGCATTTAGAGAATGGCGAGTATATTTGGAAGGA

TCGAAATACACAGTACAGGTGTATACAGATCATAAGAACTTGGTTTACTTCACCACAACG

AAGCAGTTAAACAGACGACAGGTCAGATGGTCGGAGACCATGGCCAACTACAATTTCAGA

ATTTCATATGTCAAAGGATCAGAAAACGCTAGAGCCGACGCTCTTAGCCGAAAACCAGAA

TATCAAGAAAACAAAACGTACGAGTCATACGCTATATTCAAGAAAGACGGCGAATCACTG

GTCTACAATGCACCACAGCTTGCAGCAACACACCTGTTGGAAGACAACCACCTCAGGAAA

CAGATCCAATCACACTACAACAAGGATGCTACTGCCACACGCATACGCAAGACAATAGAA

CCAGGATTCACTATAGAAGATGATACCATATACTTTCATGGAAAAGTATACATTCCGAGT

CAAATGACCAAGGAATTTGTGACGGAACAACACGGATTGCCGGCACATGGACACCAAGGA

ATTGCAAGGACATTTGCAAGAATACGGGAAATCAGTTACTTCCCACGAATGAGAACGATA

GTTGAAGAAGTTGTTGGAAATTGTGACACCTGCATACGAAACAAGTCATCACGACATGCT

CCGTATGGTCAGCTCCAGACCCCAGACATGCCTTCTCAGCCATGGAAGTCCATCACATGG

GACTTTGTGGTCAAACTACCACTCTCAAAGGATCCTACTACAGGAATTGAGTACGACGCG

ATACTCAATATAGTAGACAGGCTAACGAAATTTGCATATATGATACCATTCAAGGAAACA

TGGGATGCTGAGCAACTAGCATATGTGTTCCTAAGGGTCATAGTAAGCATACACGGAGTA

CCAGATGAGATAATCTCGGATCGAGACAAGCTCTTTACCTCGAAATTCTGGACTACCTTA

TTAGCACTTATGGGTATCAAGAGAAAGCTATCGACATCTTTCCACCCACAAACAGATGGT

CAAACAGAGAGGACCAATCAGACAATGGAAGCATATCTTAGATGCTATGTAAATTATCGA

CAAGACAATTGGGTAGAGCTATTACCCATGGCACAGTTCGCATACAATACATCGGAAACG

GAAACCACGAAAATCACCCCAGCACGAGCTAATTTTGGGTTTAATCCACAAGCGTATAA

A

ATCCCGATACCACAAGAAGTTAATGCCGAATCAGCAATAGTACAAGTCGAACAGCTGAA

A

GATCTCCAAGAGCAACTGGCTCTTGATCTAAGATTCATATCTTCCAGAACAGCAGCGTAC

TACAATACGAAACGTAGTATGGAACCTACGCTTAAAGAGGGGGATAAAGTTTATTTGCT

A

CAACGAAACATCGAAACCAAGAGACCAAGCAATAAACTCGACCACAGGAAAATAGGAC

CA

TTCAAGATTGATAAGGTAATAGGAACGGTTAATTATCGATTGAAATTACCAGACACAAT

G

AATATCCACCCAGTATTCCACATATCCTTGCTCGAACCAGCACCACCAGGAGCGCCAAAT

GCGCCATTTACAGAAATCGAACCAGTCAACCCAAACGCCATATACGACGTTGAAACAAT

A

CTAGATTGTAAATATGTCAGGGGCAAAATCAAGTATTTGATCAAATGGTTAGACTACCCA

CATTCGGAAAACACATGGGAA

SEQ ID NO: 28—*Botrytis* DCL1 promoter sequence
*B. cinerea* (B05.10) *Botrytis cinerea* supercontig 1.69 [DNA] 45790-46725-
GAAGAGGTTGTTGGCAATATTTTGAAGAAAGCTGAGGCTGATTTGAATGGAGATTAAAA

GGGGAATGAAGCTGCGGGGCCACCGATAGCACAAAAACTACTGAAGATTTAAGCACGT

TAAAATTACACTCAGGAATAAACGGATGGCAAGCTTTTCGATCGCCCAAACACGGATCT

ACGACTACGAGTTACGCACGACATGATTTAGCCTTTTGTGTGCAATGATGATTAGATAGC

ATTGCATTTCTCGAAATTGACCTGCACGACTTTTACGGGCAGATAATATCAAAGATTCCTA

GTGAGCAAGCGGTGATGATACGATGTCATTCCAAAAGTTTTTTCCTCGCGAATTTTATTTC

ATTTCGAAGGCATCTTTGCTTAGCAGCATATTCACCTTTGATGTCCTCTGTAGGGGATGG

AGTCTCTAATCTCGCGGTCACAATGAGACGTGATGCGCTGCGAAGTGGTGACAATTTCCC

TTTACTTAGAATAGATCATGCACACATGCATGATGCATAGCTAGCTAGTTTTTTATTCAAT

GATAGTTTAATGACAAACACGTATCTAGATATCCTCATTCATGTATCTGTGGGAGGTTGA

CTTAAGTTATGGCTGACTTGATAGTTTCATTATATATGTATATGTGATATCTAAGTAAAGA

TTAAAGTGAAATCGAAATGCAACGCCGAAATTCTATTAATTCCATGAAATGATGTGATAT

GGCATGACATGATATCCAAACTCCGATTTGAAATGCTCCAGCTTTCGCTTTCTAAAATTGG

TAAAAGGGACATTATTTCGTCTGGTTGTGGGTTTTCATTTCTGTGCTCCTACTAGGTGTGA

ATGATAGAGTATGCTGTGGTGTGGTGTGATCTCGGAATTTGGAAATTTGAGGGGTGTATA

TCACCTCATTTCGTGTGTCCGAATTTCTACAGACT

SEQ ID NO: 29—*Botrytis* DCL2 promoter sequence
>*B. cinerea* (B05.10) *Botrytis cinerea* supercontig 1.78 [DNA] 26792-27461-
AGAGCATTTGTAGGGGAAGGAGGAAAAATTGAGGAGGAGGATAAGATGAATTTTGATA

AATTTATTTCCTAACATCAGGTCACAATCTATGAATTACATTTGATAGTATTACGTATGCC

GGTCTGTACACAACACAACCATATAGTAAGGTATCAATCAAATGCGATGGATAGTCATTT

CAATTTCTTAGTGAATAATTACAACGAACCAGTAAAATAGCAATAACTCTGAAAAGCTTC

CGGACTGCCAAAAGGTCTCCAGGACGAGATTATTACGAAGAACCCAAGAATTCGCCTAG

GAACCAAGATAAACAAATCATCGACGTGTTGCACTTCCATCTATGCGACAATTATGCCAA

GCGAGCCGCCAGTTCTTGGGGGTGGAGCGCTAGGAATAGGGGGCCGGATTGCCATATCC

TTATCTAGATCTAGATGGTATCGATATGATAAATCAATGCAATGGAGAGTTAAAAAGTTA

TATGCCATATGATTGATAATTATTGACAATGCAGGCTATCGCGGGACAATGGTAAATGGT

TGTAAAATATGGAGTCTATTTCCTTAGCTAGCGATAAGATGGGTGGTTTAAACACATCCC

GCCTTCTCTTTATCATTCTCCTTCTCGTATTCATATATCATAATTGCAAAGTAAGGTTGTA

TTTTGGACTGTG

SEQ ID NO: 30—Verticillium DCL1 promoter sequence
>V. dahliae VdLs.17 supercont1.1 of Verticillium dahliae (VdLs.17) [DNA]
1574620-1574964-
AAGCTGTCAATTGATGCGGAGGGTGAGTGAACGTCTCGTCGGCGGGGCCCCTTGAGGCG

AGCGCCCGTTGGGGGGTGTTGTGGCACTAGGTTCTCTAGGCCGGCGGTGACTTTCATTAC

TATATTAGAAGCAAATACGGCGCCTTCATCACAATAATAAATATCGATCTCGAGTCGATT

CCAGACCCGTTATAAACCTATGTCTGTGCAACCAGTTGGGTGCTAATTTCTTGCATTATCA

TCATGGATGTTGTCTATTTGAGTCTCAGGTCCAGCTGGTGCTTATAGGTCATCTCCAGTAT

GCGACTACCTCTCTCCCTCTTTGCCATTCCTAACTGATTCTAAC

SEQ ID NO: 31—Verticillium DCL2 promoter sequence
>V. dahliae VdLs.17 supercont1.15 of Verticillium dahliae (VdLs.17) [DNA]
194566-195565 +
CTTCATCTTCCAACCGCCATTACCTCCCCCATACGCGTCCTGCCAAAGAATCATAACTGG

CTAAAACATAAGACGGGACTGGTCATCCGCTGAACCATTCCGAGCTATGTGTCCTGATTG

ACCCATCTCGGCTTATTCGCTCTCAAATACGACTGCAATCGCGTGTGGCTTGGAAACCGT

GGAATACCATCCTCATATTGTCAGCACCTGTAGCGATACAGCACAATGCTTGACGATTCG

GAATCATTTTCCGCTTCTTTGCGGAGCAGCGGATGTCCAATTGACGATGACTTGACTCCA

GAACCAACGTCCGAATCACGCGACTCAACCTCCCTACCGTATGGCCTTCAGGACGACATC

GGCCCCCTTGCTGCCACCCCGAGCCAGTCGAGTAACGTCACAATCAATGCACGGGCATA

CCAGTTGGAGATGCTGGCGGAAAGTAGGAAGAGGAATATCATTCTAGCTGTGCGAACCT

TCCCTCTTGCGCCAGTCAACCTCGATTGACACCTCCATAGATGGACACAGGCAGTGGCAA

GACCCAAGTGTACGTTCCCTGCAAGCCGAACCTGATTATTGATACTGATTTTCCCAGTGC

CGTCCTCCGAATTCGAGCAGAGCTAGAAGAAGGGGCTTCAGACAAGGTTTGACAAACTC

CACTTGGTAGCTTCGCAATCACTTACAGGGTTTTAGCTTGTATGGTTCGTGGCTCACAATG

TTGAGCTTTGCGCTCAGCAGCATTCTGTACTGCAGTCTCAGATTCCTGCAGTTCAGACCA

AGCTGCTTCTTGGCAGCGATAATGTTGATTCATGGTCCAACCAAGAGACTTGGAACGCTG

TGCTTCTCAACGTCAAATTGTGGTGTCAACCCCTCAAGTTCTCTGCGATGCCTTGAGCC

ACGGCTTTGTCCAGATGGGTTCATTATCCTTGCTTGTCTTTGATGAAGGTATTCAATCAGC

GCAGTTTATCAAGTGTTCTTGCCCTAACAACGGTGTAGCGC

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of increasing pathogen resistance in a plant or a part of a plant, the method comprising:
contacting the surface of the plant or the part of the plant with one or more of a double-stranded RNA, a set of small RNAs, or small RNA duplexes that target each dicer-like (DCL) gene of a fungal pathogen, wherein the plant or the part of the plant has increased resistance to the fungal pathogen compared to a control plant or control plant part that has not been contacted with the double-stranded RNA, set of small RNAs, or small RNA duplexes.

2. The method of claim 1, wherein the double-stranded RNA, set of small RNAs, or small RNA duplexes are sprayed onto the plant or the part of the plant.

3. The method of claim 1, wherein the plant is an ornamental plant, a fruit-producing plant, or a vegetable-producing plant.

4. The method of claim 1, wherein the part of the plant is a fruit, a vegetable, or a flower.

5. A method of increasing pathogen resistance in a fruit, a vegetable, or a flower, the method comprising:
contacting the surface of a fruit, vegetable, or flower with one or more of a double-stranded RNA, a set of small RNAs, or small RNA duplexes that target each dicer-like (DCL) genes of a fungal pathogen, wherein the fruit, vegetable, or flower has increased resistance to the fungal pathogen compared to a control fruit, vegetable, or flower that has not been contacted with the double-stranded RNA, set of small RNAs, or small RNA duplexes.

6. The method of claim 5, wherein the fruit, vegetable, or flower is from a plant that is a species of the genera Asparagus, *Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malta, Manihot, Majorana, Medicago, Nicotiana, Oryza, Panieum, Pannesetum, Persea, Pisum, Pyrus, Prunus, Raphanus, Rosa, Secale, Senecio, Sinapis, Solanum, Sorghum, Trigonella, Triticum, Vitis, Vigna,* or *Zea.*

7. The method of claim 5, wherein the fruit, vegetable, or flower is a post-harvest fruit, vegetable, or flower.

8. The method of claim 5, wherein the double-stranded RNA, set of small RNAs, or small RNA duplexes are sprayed onto the surface of the fruit, vegetable, or flower.

9. The method of claim 5, wherein the pathogen is *Botrytis* or *Verticillium.*

10. The method of claim 5, wherein the pathogen is *Botrytis* or *Verticillium.*

11. The method of claim 9, wherein the double-stranded RNA, set of small RNAs, or small RNA duplexes target any of SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:28, SEQ ID NO:29, SEQ ID NO:30, or SEQ ID NO:31 or a fragment thereof.

12. The method of claim 1, further comprising contacting the plant or the part of the plant with one or more of a double-stranded RNA, a set of small RNAs, or small RNA duplexes that target each DCL gene of a second species of fungal pathogen.

13. A method of increasing pathogen resistance to multiple pathogens in a plant or a part of a plant, the method comprising:
    contacting the surface of a plant or the part of the plant with:
    (1) a first group of one or more of a double-stranded RNA, a set of small RNAs, or small RNA duplexes that target each (DCL) gene from a first species of fungal pathogen; and
    (2) a second group of one or more of a double-stranded RNA, a set of small RNAs, or small RNA duplexes that each DCL gene from a second species of fungal pathogen, wherein the plant or the part of the plant has increased resistance to the first species of pathogen and the second species of pathogen compared to a control plant or control plant part that has not been contacted with the first and second groups of double-stranded RNAs, small RNAs, or small RNA duplexes.

14. The method of claim 13, wherein the first and second groups of double-stranded RNAs, small RNAs, or small RNA duplexes are sprayed onto the plant or the part of the plant.

15. The method of claim 13, wherein the part of the plant is a fruit, a vegetable, or a flower.

16. A method of making a plant having increased pathogen resistance to multiple pathogens, the method comprising:
    introducing into the plant a heterologous expression cassette comprising a promoter operably linked to (1) one or more polynucleotides that inhibit expression of each dicer-like (DCL) gene of a first species of fungal pathogen and (2) one or more polynucleotides that inhibit expression of each DCL gene from a second species of fungal pathogen; and
    selecting a plant comprising the expression cassette.

17. The method of claim 16, wherein the expression cassette comprises one or more polynucleotides that encode an antisense nucleic acid or inhibitory RNA (RNAi) that targets the DCL genes or a fragment thereof from the first species of fungal pathogen, and one or more polynucleotides that encode an antisense nucleic acid or RNAi that targets the DCL genes or a fragment thereof from the second species of fungal pathogen.

18. The method of claim 13, wherein the first species of fungal pathogen is a species of *Botrytis* and the second species of fungal pathogen is a species of *Verticillium*.

19. The method of claim 13, wherein the plant is a species of the genera Asparagus, *Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malta, Manihot, Majorana, Medicago, Nicotiana, Oryza, Panieum, Pannesetum, Persea, Pisum, Pyrus, Prunus, Raphanus, Rosa, Secale, Senecio, Sinapis, Solanum, Sorghum, Trigonella, Triticum, Vitis, Vigna,* or *Zea.*

20. The method of claim 13, wherein the plant is an ornamental plant, a vegetable-producing plant, or a fruit-producing plant.

21. The method of claim 10, wherein the double-stranded RNA, set of small RNAs, or small RNA duplexes target any of SEQ ID NO:1, SEQ ID NO:3, SEQ ID NO:5, SEQ ID NO:7, SEQ ID NO:9, SEQ ID NO:10, SEQ ID NO:11, SEQ ID NO:12, SEQ ID NO:28, SEQ ID NO:29, SEQ ID NO:30, or SEQ ID NO:31 or a fragment thereof.

22. The method of claim 5, further comprising contacting the fruit, vegetable, or flower with one or more of a double-stranded RNA, a set of small RNAs, or small RNA duplexes that target a second group of DCL genes of a second species of fungal pathogen.

23. The method of claim 1, wherein the pathogen is *Sclerotinia*.

* * * * *